US012098213B2

(12) United States Patent
Benz et al.

(10) Patent No.: US 12,098,213 B2
(45) Date of Patent: Sep. 24, 2024

(54) ANTIBODIES BINDING TO HLA-A2/WT1

(71) Applicant: Hoffmann-La Roche Inc., Little Falls, NJ (US)

(72) Inventors: Joerg Benz, Rheinfelden (DE); Christian Klein, Weilheim (DE); Stefan Klostermann, Neuried (DE); Ekkehard Moessner, Kreuzlingen (CH); Johannes Sam, Baden (CH); Pablo Umaña, Wollerau (CH); Lydia Jasmin Hanisch, Birmensdorf (CH); Alexander Bujotzek, Munich (DE); Wei Xu, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 124 days.

(21) Appl. No.: 17/519,436

(22) Filed: Nov. 4, 2021

(65) Prior Publication Data

US 2022/0411534 A1 Dec. 29, 2022

Related U.S. Application Data

(62) Division of application No. 16/228,102, filed on Dec. 20, 2018, now Pat. No. 11,192,957.

(30) Foreign Application Priority Data

Dec. 21, 2017 (EP) ..................... 17209205

(51) Int. Cl.
| C07K 16/30 | (2006.01) |
| A61K 35/00 | (2006.01) |
| A61P 35/00 | (2006.01) |
| C07K 16/28 | (2006.01) |
| C07K 16/32 | (2006.01) |
| A61K 39/00 | (2006.01) |

(52) U.S. Cl.
CPC .......... *C07K 16/3038* (2013.01); *A61K 35/00* (2013.01); *A61P 35/00* (2018.01); *C07K 16/2809* (2013.01); *C07K 16/2833* (2013.01); *C07K 16/32* (2013.01); *A61K 2039/505* (2013.01); *C07K 2317/31* (2013.01); *C07K 2317/33* (2013.01); *C07K 2317/34* (2013.01); *C07K 2317/52* (2013.01); *C07K 2317/54* (2013.01); *C07K 2317/55* (2013.01); *C07K 2317/565* (2013.01); *C07K 2317/73* (2013.01); *C07K 2317/92* (2013.01)

(58) Field of Classification Search
CPC ............ C07K 16/3038; C07K 16/2809; C07K 16/2833; C07K 16/32; C07K 2317/31; C07K 2317/33; C07K 2317/34; C07K 2317/52; C07K 2317/54; C07K 2317/55; C07K 2317/565; C07K 2317/73; A61K 35/00; A61K 2039/505; A61P 35/00
See application file for complete search history.

(56) References Cited

U.S. PATENT DOCUMENTS

| 4,676,980 | A | 6/1987 | Segal et al. |
| 4,737,456 | A | 4/1988 | Weng et al. |
| 4,816,567 | A | 3/1989 | Cabilly et al. |
| 5,208,020 | A | 5/1993 | Chari et al. |
| 5,500,362 | A | 3/1996 | Robinson et al. |
| 5,565,332 | A | 10/1996 | Hoogenboom et al. |
| 5,571,894 | A | 11/1996 | Wels et al. |
| 5,587,458 | A | 12/1996 | King et al. |
| 5,731,168 | A | 3/1998 | Carter et al. |
| 5,750,373 | A | 5/1998 | Garrard et al. |
| 5,770,429 | A | 6/1998 | Lonberg et al. |
| 5,821,337 | A | 10/1998 | Carter et al. |
| 5,869,046 | A | 2/1999 | Presta et al. |
| 5,959,177 | A | 9/1999 | Hein et al. |
| 5,969,108 | A | 10/1999 | McCafferty et al. |
| 6,040,498 | A | 3/2000 | Stomp et al. |
| 6,075,181 | A | 6/2000 | Kucherlapati et al. |
| 6,150,584 | A | 11/2000 | Kucherlapati et al. |
| 6,248,516 | B1 | 6/2001 | Winter et al. |
| 6,417,429 | B1 | 7/2002 | Hein et al. |
| 6,420,548 | B1 | 7/2002 | Vezina et al. |
| 6,982,321 | B2 | 1/2006 | Winter et al. |
| 7,041,870 | B2 | 5/2006 | Tomizuka et al. |
| 7,087,409 | B2 | 8/2006 | Barbas et al. |
| 7,125,978 | B1 | 10/2006 | Vezina et al. |
| 7,189,826 | B2 | 3/2007 | Rodman |

(Continued)

FOREIGN PATENT DOCUMENTS

| EP | 0 404 097 B1 | 12/1990 |
| EP | 1870459 A1 | 12/2007 |

(Continued)

OTHER PUBLICATIONS

Almagro and Fransson, "Humanization of antibodies" Front Biosci 13:1619-1633 (Jan. 1, 2008).
Asano, R., et al., "MiniReview: Development of highly functional bispecific antibodies using protein engineering" Seikagaku [J. Biochemistry-Japan] 86(4):469-473 (Aug. 1, 2014).

(Continued)

*Primary Examiner* — Nelson B Moseley, II

(74) *Attorney, Agent, or Firm* — Lawrence S. Graham

(57) ABSTRACT

The present invention generally relates to antibodies that bind to HLA-A2/WT1, including bispecific antigen binding molecules e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

40 Claims, 50 Drawing Sheets

Specification includes a Sequence Listing.

(56) References Cited

U.S. PATENT DOCUMENTS

| | | |
|---|---|---|
| 7,332,581 B2 | 2/2008 | Presta et al. |
| 7,521,541 B2 | 4/2009 | Eigenbrot et al. |
| 7,527,791 B2 | 5/2009 | Adams et al. |
| 7,695,936 B2 | 4/2010 | Carter et al. |
| 7,785,903 B2 | 8/2010 | Bond et al. |
| 7,855,275 B2 | 12/2010 | Eigenbrot et al. |
| 7,985,840 B2 | 7/2011 | Fuh et al. |
| 8,309,300 B2 | 11/2012 | Junutula et al. |
| 8,679,490 B2 | 3/2014 | Dennis et al. |
| 9,000,130 B2 | 4/2015 | Bhakta et al. |
| 9,074,000 B2 | 7/2015 | Scheinberg et al. |
| 2003/0039635 A1 | 2/2003 | Gaiger et al. |
| 2003/0157108 A1 | 8/2003 | Presta et al. |
| 2004/0093621 A1 | 5/2004 | Shitara et al. |
| 2004/0101920 A1 | 5/2004 | Radziejewski et al. |
| 2004/0110282 A1 | 6/2004 | Kanda et al. |
| 2004/0132140 A1 | 7/2004 | Satoh et al. |
| 2004/0259150 A1 | 12/2004 | Nakamura et al. |
| 2005/0031613 A1 | 2/2005 | Nakamura et al. |
| 2005/0079574 A1 | 4/2005 | Bond et al. |
| 2007/0061900 A1 | 3/2007 | Murphy et al. |
| 2007/0117126 A1 | 5/2007 | Sidhu et al. |
| 2007/0128207 A1 | 6/2007 | Sugiyama |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2013/0287777 A1 | 10/2013 | Duffy et al. |
| 2014/0024809 A1 | 1/2014 | Cheung et al. |
| 2014/0294841 A1* | 10/2014 | Scheinberg ............. A61P 35/02 435/7.1 |
| 2016/0152725 A1* | 6/2016 | Cheung ................... C07K 16/32 435/375 |
| 2016/0244515 A1 | 8/2016 | Weihofen et al. |
| 2016/0280796 A1 | 9/2016 | Scheinberg et al. |
| 2016/0369006 A1 | 12/2016 | Scheinberg et al. |
| 2017/0114141 A1 | 4/2017 | Amann et al. |
| 2017/0217281 A1 | 8/2017 | Achatz |
| 2017/0247467 A1 | 8/2017 | Amann et al. |
| 2018/0171024 A1 | 6/2018 | Peled Kamar et al. |

FOREIGN PATENT DOCUMENTS

| | | |
|---|---|---|
| RU | 2237674 C2 | 10/2004 |
| WO | 92/22653 A1 | 12/1992 |
| WO | 93/01161 A1 | 1/1993 |
| WO | 93/16185 A2 | 8/1993 |
| WO | 94/11026 A2 | 5/1994 |
| WO | 94/11026 A3 | 5/1994 |
| WO | 96/027011 A1 | 9/1996 |
| WO | 97/30087 A1 | 8/1997 |
| WO | 98/050431 A2 | 11/1998 |
| WO | 98/050431 A3 | 11/1998 |
| WO | 98/58964 A1 | 12/1998 |
| WO | 99/22764 A1 | 5/1999 |
| WO | 99/54342 A1 | 10/1999 |
| WO | 00/18795 A2 | 4/2000 |
| WO | 01/077342 A1 | 10/2001 |
| WO | 03/011878 A2 | 2/2003 |
| WO | 03/085107 A1 | 10/2003 |
| WO | 2004/056312 A2 | 7/2004 |
| WO | 2004/065540 A2 | 8/2004 |
| WO | 2004/106381 A1 | 12/2004 |
| WO | 2005/061547 A2 | 7/2005 |
| WO | 2005/100402 A1 | 10/2005 |
| WO | 2006/029879 A2 | 3/2006 |
| WO | 2006/082515 A2 | 8/2006 |
| WO | 2007/042261 A2 | 4/2007 |
| WO | 2007/110205 A2 | 10/2007 |
| WO | 2007/147901 A1 | 12/2007 |
| WO | 2008/024715 A2 | 2/2008 |
| WO | 2008/119567 A2 | 10/2008 |
| WO | 2009/080251 A1 | 7/2009 |
| WO | 2009/080252 A1 | 7/2009 |
| WO | 2009/080253 A1 | 7/2009 |
| WO | 2009/089004 A1 | 7/2009 |
| WO | 2010/112193 A1 | 10/2010 |
| WO | 2010/115589 A1 | 10/2010 |
| WO | 2010/136172 A1 | 12/2010 |
| WO | 2010/145792 A1 | 12/2010 |
| WO | 2010/129304 A2 | 2/2011 |
| WO | 2010/129304 A3 | 2/2011 |
| WO | 2011/034605 A2 | 3/2011 |
| WO | 2011/090754 A1 | 7/2011 |
| WO | 2011/090762 A1 | 7/2011 |
| WO | 2011/143545 A1 | 11/2011 |
| WO | 2012/058768 A1 | 6/2012 |
| WO | 2012/058768 A8 | 6/2012 |
| WO | 2012/109659 A1 | 8/2012 |
| WO | 2012/130831 A1 | 10/2012 |
| WO | 2012/135854 A2 | 10/2012 |
| WO | 2013/026831 A1 | 2/2013 |
| WO | 2013/026833 A1 | 2/2013 |
| WO | 2013/026839 A1 | 2/2013 |
| WO | 2013/096291 A2 | 6/2013 |
| WO | 2013/096291 A3 | 6/2013 |
| WO | 2013/120929 A1 | 8/2013 |
| WO | 2013/157953 A1 | 10/2013 |
| WO | 2013/157954 A1 | 10/2013 |
| WO | 2015/070061 A1 | 5/2015 |
| WO | 2015/070078 A1 | 5/2015 |
| WO | 2015/095392 A1 | 6/2015 |
| WO | 2015/095539 A1 | 6/2015 |
| WO | 2015/130766 A1 | 9/2015 |
| WO | 2015/150447 A1 | 10/2015 |
| WO | 2016/016299 A1 | 2/2016 |
| WO | 2016/020309 A1 | 2/2016 |
| WO | 2016/022400 A1 | 2/2016 |
| WO | 2016019940 A1 | 2/2016 |
| WO | 2016/040856 A2 | 3/2016 |
| WO | 2016/172485 A2 | 10/2016 |
| WO | 2016/174652 A1 | 11/2016 |
| WO | 2016/199140 A1 | 12/2016 |
| WO | 2016/199141 A2 | 12/2016 |
| WO | 2016/199141 A3 | 12/2016 |
| WO | 2017/060201 A1 | 4/2017 |
| WO | 2018/219299 A1 | 12/2018 |
| WO | 2019/122046 A1 | 6/2019 |

OTHER PUBLICATIONS

Ataie, N., et al., "Structure of a TCR mimic antibody with target predicts pharmacogenetics" J Mol Biol 428(1):194-205 (Jan. 16, 2016).

Atwell, S., et al., "Stable heterodimers from remodeling the domain interface of a homodimer using a phage display library" J Mol Biol 270(1):26-35 (Jul. 4, 1997).

Augsberger et al., "Targeting intracellular WT1 in AML with a novel RMF-peptide-MHC specific T-cell bispecific antibody" Blood Available Jul. 21, 2021 In Press, Journal Pre-proof http://doi.org/10.1182/blood.2020010477.

Ausubel, F., et al. Current Protocols in Molecular Biology "Percentage of Codon Synonymous Usage and Frequency of Codon Occurrence in Various Organisms" Ausubel, F., et al., eds., New York, NY-US:John Wiley & Sons, Inc., vol. 5:A.1C.1-A.1C.12 ( 1997).

Baca, M., et al., "Antibody humanization using monovalent phage display" J Biol Chem 272(16):10678-10684 (Apr. 18, 1997).

Bacac, M., et al., "CEA TCB: A novel head-to-tail 2:1 T cell bispecific antibody for treatment of CEA-positive solid tumors" Oncoimmunology 5(8 SUPPL e1203498):1-3 (Jun. 24, 2016).

Bazan, J., et al., "Phage display—a powerful technique for immunotherapy" Hum Vaccines Immuno 8(12):1817-1828 (Dec. 13, 2012).

Boerner, P., et al., "Production of antigen-specific human monoclonal antibodies from in vitro-primed human splenocytes" J Immunol 147(1):86-95 (Jul. 1, 1991).

Brennan, M. et al., "Preparation of bispecific antibodies by chemical recombination of monoclonal immunoglobulin G1 fragments" Science 229( SUPPL 4708):81-83 (Jul. 5, 1985).

Brodeur, B. et al., "Mouse-human myeloma partners for the production of heterohybridomas" Monoclonal Antibody Production Techniques and Applications (New York: Marcel Dekker, Inc.),:51-63 (1987).

(56) References Cited

OTHER PUBLICATIONS

Bruggemann, M., et al., "Comparison of the Effector Functions of Human Immunogobulins Using a Matched set of Chimeric Antibodies" J Exp Med 166(5):1351-1361 (Oct. 1, 1987).
Caldas, C., et al., "Humanization of the anti-CD18 antibody 6.7: an unexpected effect of a framework residue in binding to antigen" Mol Immunol 39(15):941-952 (May 1, 2003).
Carter, P., et al., "Bispecific human IgG by design" J Immunol Methods 248(1-2):7-15 (Feb. 1, 2001).
Carter, P., et al., "Humanization of an anti-p185 HER2 antibody for human cancer therapy" PNAS USA 89(10):4285-4289 (May 15, 1992).
Casadevall et al., "Immunoglobulin isotype influences affinity and specifity" PNA 109(31):12272-12273 (Jul. 31, 2012).
Chari, R., et al., "Immunoconjugates containing novel maytansinoids: Promising anticancer drugs" Cancer Res 52(1):127-131 (Jan. 1, 1992).
Cherf, G., et al., "Applications of yeast surface display for protein engineering" Methods Mol Biol 1319:155-175 (Jan. 1, 2015).
Chothia, C., et al., "Canonical structures for the hypervariable regions of immunoglobulins" J Mol Biol 196(4):901-917 (Aug. 20, 1987).
Clynes, R., et al., "Fc receptors are required in passive and active immunity to melanoma" PNAS USA 95(2):652-656 (Jan. 1, 1998).
Collaborative Computational Proj No. 4, "The CCP4 Suite: Programs for Protein Crystallography" Acta Crystallogr D Biol Crystallogr 50( SUPPL Pt. 5):760-763 (Sep. 1, 1994).
Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Dall'Acqua, W., et al., "Antibody humanization by framework shuffling" Methods 36(1):43-60 (Jan. 17, 2005).
Dao, T. et al., "Targeting the Intracellular WT1 Oncogene Product with a Therapeutic Human Antibody" Sci Transl Med 5(176 SUPPL 176ra33):1-11 (Mar. 13, 2013).
Dao, T., et al., "Therapeutic bispecific T-cell engager antibody targeting the intracellular oncoprotein WT1" Nat Biotechnol 33(10):1079-1086 (Oct. 1, 2015).
Du et al., "Molecular Basis of Recognition of Human Osteopontin by 23C3, a Potential Therapeutic Antibody for Treatment of Rheumatoid Arthritis" Science Direct 382:835-842 ( 2008).
Emsley, P., et al., "Features and Development of Coot" Acta Crystallogr D Biol Crystallogr D66(Pt. 4):486-501 (Apr. 1, 2010).
Ferrara, C., et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II" Biotechnol Bioeng 93(5):851-861 (Jan. 24, 2006).
Fingl, E., et al. Basis of Therapeutics "Ch. 1—General Principles" Fifth edition, New York:Macmillan Publishing Co., Inc.,:1-46 (Jan. 1, 1975).
Flatman, S., et al., "Process analytics for purification of monoclonal antibodies" J Chromatogr 848(1):79-87 (Mar. 15, 2007).
Frenzel, A., et al., "Phage display-derived human antibodies in clinical development and therapy" MABS 8(7):1177-1194 (Jul. 8, 2016).
Gazzano-Santoro, H., et al., "A non-radioactive complement-dependent cytotoxicity assay for anti-CD20 monoclonal antibody" J Immunol Methods 202(2):163-171 (Mar. 28, 1997).
Gerngross, T., "Advances in the Production of Human Therapeutic Proteins in Yeasts and Filamentous Fungi" Nat Biotechnol 22(11):1409-1414 (Nov. 22, 2004).
Graham, F., et al., "Characteristics of a Human Cell Line Transformed by DNA form Human Adenovirus Type 5" J Gen Virol 36(1):59 (Jul. 1, 1977).

Griffiths, A., et al., "Human anti-self antibodies with high specificity from phage display libraries" EMBO J 12(2):725-734 (Feb. 1, 1993).
Gruber, M. et al., "Efficient tumor cell lysis mediated by a bispecific single chain antibody expressed in *Escherichia coli*" J Immunol 152(11):5368-5374 (Jun. 1, 1994).
Hanes, J., et al., "In vitro selection and evolution of functional proteins by using ribosome display" PNAS 94(10):4937-4942 (May 1, 1997).
Harlow, E., et al. Antibodies: A Laboratory Manual Cold Spring Harbor, New York:Cold Spring Harbor Laboratory,:1-28 ( 1988).
He, M., et al., "Antibody-ribosome-mRNA (ARM) complexes as efficient selection particles for in vitro display and evolution of antibody combining sites" Nucleic Acids Res 25(24):5132-5134 (Oct. 4, 1997).
Heeley, R. et al., "Mutations Flanking the Polyglutamine Repeat in the Modulatory Domain of Rat Glucocorticoid Receptor Lead to an Increase in Affinity for Hormone" Endocr Res 28(3):217-229 (Aug. 1, 2002).
Hellstrom, I et al., "Strong antitumor activities of IgG3 antibodies to a human melanoma-associated ganglioside" PNAS USA 82(5):1499-1502 (Mar. 1, 1985).
Hellstrom, I., et al., "Antitumor effects of L6, an IgG2a antibody that reacts with most human carcinomas" PNAS USA 83(18):7059-7063 (Sep. 1, 1986).
Hinrichs, C., et al., "Reassessing target antigens for adoptive T cell therapy" Nat Biotechnol 31(11):999-1008 (Nov. 1, 2013).
Hochleitner, E. O., et al., "Characterization of a discontinuous epitope of the human immunodeficiency virus (HIV) core protein p24 by epitope excision and differential chemical modification followed by mass spectrometric peptide mapping analysis" Protein Sci 9(3):487-496 (Mar. 1, 2000).
Holliger, P., et al., "Diabodies: Small Bivalent and Bispecific Antibody Fragments" PNAS USA 90(14):6444-6448 (Jul. 15, 1993).
Holliger, P., et al., "Specific killing of lymphoma cells by cytotoxic T-cells mediated by a bispecific diabody" Protein Eng 9(3):299-305 (Mar. 1, 1996).
Hoogenboom and Winter, "By-passing immunisation. Human antibodies from synthetic repertoires of germline VH gene segments rearranged in vitro" J Mol Biol 227(2):381-388 (Sep. 20, 1992).
Hoogenboom, H., et al., "Overview of antibody phage-display technology and its applications" Methods Mol Biol 178:1-37 (Jan. 1, 2002).
Hudson, P., et al., "Engineered antibodies" Nat Med 9(1):129-134 (Jan. 1, 2003).
"International Preliminary Report on Patentability—PCT/EP2018/086055" (Report Issuance Date: Jun. 23, 2020; Chapter I),:pp. 1-11 (Jul. 2, 2020).
"International Search Report—PCT/EP2018/086055":pp. 1-7 (Jun. 28, 2019).
Johnson, S., et al., "Effector Cell Recruitment with Novel Fv-based Dual-affinity Re-targeting Protein Leads to Potent Tumor Cytolysis and in Vivo B-cell Depletion" J Mol Biol 399(3):436-449 (Jun. 11, 2010).
Junghans, R., et al., "Anti-Tac-H, a Humanized Antibody to the Interleukin 2 Receptor with New Features for Immunotherapy in Malignant and Immune Disorders" Cancer Res 50(5):1495-1502 (Mar. 1, 1990).
Kabat, E.A., et al. Sequences of Proteins of Immunological Interest: Tabulation and Analysis of Amino Acid and Nucleic Acid Sequences of Precursors, V-Regions, C-Regions, J-Chain T-Cell Receptors for Antigen, T-Cell Surface Antigens, β-2 Microglobulins, Major Histocompatibility Antigens, Thy-1, Complement, C-Reactive Protein, Thymopoietin, Integrins, Post-gamma Globulin, α2-Macroglobulins, and Other Related Proteins (NIH Publication No. 91-3242), Fifth edition, Bethesda, MD-US::647-669 (1991).
Kabsch, W., "Integration, scaling, space-group assignment and post-refinement" Acta Crystallogr D66:133-144 (Feb. 1, 2010).
Kam N., et al., "Carbon nanotubes as multifunctional biological transporters and near-infrared agents for selective cancer cell destruction" PNAS 102(33):11600-11605 (Aug 16, 2005).

(56) References Cited

OTHER PUBLICATIONS

Kanda, Y. et al., "Comparison of Cell Lines for Stable Production of Fucose-Negative Antibodies with Enhanced ADCC" Biotechnol Bioeng 94(4):680-688 (Jul. 1, 2006).
Kashmiri, S., et al., "SDR grafting—a new approach to antibody humanization" Methods 36:25-34 (Jan. 1, 2005).
Kindt et al. Antigens and Antibodies "4" (14 pages), 6th ed edition, N.Y.:W.H. Freeman and Co,:p. 91 ( 2007).
Kipriyanov, S., et al., "Bispecific Tandem Diabody for Tumor Therapy with Improved Antigen Binding and Pharmacokinetics" J Mol Biol 293(1):41-56 (Oct. 15, 1999).
Klein et al., "Targeting Intracellular WT1 in AML Utilizing a T Cell Bispecific Antibody Construct: Augmenting Efficacy through Combination with Lenalidomide" Blood 134( SUPPL 1):4450 ( 2019).
Klein, C. et al., "The use of CrossMAb technology for the generation of bi- and multispecific antibodies" MABS 8(6):1010-1020 (Aug. 31, 2016).
Klimka, A. et al., "Human anti-CD30 recombinant antibodies by guided phage antibody selection using cell panning" Brit J Cancer 83(2):252-260 (Jun. 15, 2000).
Kontermann, "Dual Targeting Strategies with Bispecific Antibodies" MAbs 4(2):182-197 (2012)
Kostelny, S., et al., "Formation of a bispecific antibody by the use of leucine zippers" J Immunol 148(5):1547-1553 (Mar. 1, 1992).
Kozbor, D., et al., "A Human Hybrid Myeloma for Production of Human Monoclonal Antibodies" J Immunol 133(6):3001-3005 (Dec. 1, 1984).
Kunik, V. et al., "Structural Consensus among Antibodies Defines the Antigen Binding Site" PLOS Computational Biology 8(2):1-12 ( 2012).
Lerner, R., "Combinatonial antibody libraries: new advances, new immunological insights" Nat Rev Immunol 16(8):498-508 (Jul. 6, 2016).
Li, H., et al., "Optimization of humanized IgGs in glycoengineered Pichia pastoris" Natt Biotechnol 24(2):210-215 (Feb. 1, 2006).
Li, J., et al., "Human antibodies for immunotherapy development generated via a human B cell hybridoma technology" PNAS USA 103(10):3557-3562 (Mar. 7, 2006).
Liljeblad, M., et al., "Analysis of agalacto-IgG in rheumatoid arthritis using surface plasmon resonance" Glycoconjugate J 17:323-329 (Jul. 14, 2000).
Linette, G., et al., "Cardiovascular toxicity and titin cross-reactivity of affinity-enhanced T cells in myeloma and melanoma" Blood 122(6):863-871 (Aug. 8, 2013).
Lonberg, N., et al., "Fully human antibodies from transgenic mouse and phage display platforms" Curr Opin Immunol 20(4):450-459 (Aug. 1, 2008).
Lonberg, N.,, "Human antibodies from transgenic animals" Nat Biotechnol 23(9):1117-1125 (Sep. 7, 2005).
MacCallum, R., et al., "Antibody-antigen Interactions: Contact Analysis and Binding Site Topography" J Mol Biol 262:732-745 (Oct. 11, 1996).
Maniatis, T., et al. Molecular Cloning: a Laboratory Manual N.Y.: Cold Spring Harbor Laboratory, Cold Spring Harbor,,,:418-419 ( 1982).
Marks and Bradbury Methods Mol Biol, Antibody Engineering "Selection of human antibodies from phage display libraries" Benny K. C. Lo,Humana Press, vol. 248:161-176 ( 2004).
Mather, J., "Establishment and characterization of two distinct mouse testicular epithelial cell lines" Biol Reprod 23(1):243-252 (Aug. 1, 1980).
Mather, J., et al., "Culture of Testicular Cells in Hormone-Supplemented Serum-Free Medium" Ann NY Acad Sci 383:44-68 (Jan. 1, 1982).
McCoy, A., et al., "Phaser crystallographic software" J Appl Cryst 40(4):658-674 (Aug. 1, 2007).
Milstein, C., et al., "Hybrid hybridomas and their use in immunohistochemistry" Nature 305(5934):537-540 (Oct. 6, 1983).
Morris, G., et al. Methods in Molec Biol "Epitope Mapping Protocols" Totowa, NJ:Humana Press, vol. 66 ( 1996).
Myszka, D.,, "Improving Biosensor Analysis" J Mol Recognit 12(5):279-284 (Sep. 30, 1999).
Nagorsen, D., et al., "Immunomodulatory therapy of cancer with T cell-engaging BiTE antibody blinatumomab" Exp Cell Res 317(9):1255-1260 (May 15, 2011).
Ni, J. et al., "Research progress and future perspectives in antibodomics and antibodomic drugs" Xiandai Mianyixue 26(4):265-268 ( 2006).
Osbourn, J. et al., "From rodent reagents to human therapeutics using antibody guided selection" Methods 36(1):61-68 (May 1, 2005).
Oshannessy, D., et al., "Determination of Rate and Equilibrium Binding Constants for Macromolecular Interactions Using Surface Plasmon Resonance: Use of Nonlinear Least Squares Analysis Methods" Anal Biochem 212(2):457-468 (Aug. 1, 1993).
Pace, C., et al., "How to measure and predict the molar absorption coefficient of a protein" Protein Sci 4(11):2411-2423 (Nov. 1, 1995).
Padlan, E. et al., "A possible procedure for reducing the immunogenicity of antibody variable domains while preserving their ligand-binding properties" Mol Immunol 28(4-5):489-498 (Apr. 30, 1991).
Pearson, W.R., et al., "Comparison of DNA Sequences with Protein Sequences" Genomics 46:24-36 (Aug. 25, 1997).
Pearson, W.R., et al., "Improved tools for biological sequence comparison" PNAS 85(8):2444-2448 (Apr. 1, 1988).
Pearson, W.R.,, "Effective Protein Sequence Comparison" Method Enzymol 266:227-258 (Jan. 1, 1996).
Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).
Pluckthun, A. et al. The Pharmacology of Monoclonal Antibodies "Antibodies from *Escherichia coli*" Rosenberg & Moore, vol. 113:269-315 ( 1994).
Polakis, P. et al., "Antibody Drug Conjugates for Cancer Therapy" Pharmacol Rev 68(1):3-19 (Jan. 1, 2016).
Presta, L., et al., "Humanization of an Antibody Directed Against IgE" J Immunol 151(5):2623-2632 (Sep. 1, 1993).
Queen, C., et al., "A humanized antibody that binds to the interleukin 2 receptor" PNAS USA 86(24):10029-10033 (Dec. 1, 1989).
Ramani, P., et al., "The Expression Pattern of Wilms' Tumour Gene (WT1) Product in Normal Tissues and Paediatric Renal Tumours" J Pathol 179(2):162-168 (Jun. 1, 1996).
Remington's Pharmaceutical Sciences, 18th edition, Easton, PA:Mack Publishing Co. pps. 1056-1286, 1449 (1990).
Ridgway, J., et al., "Knobs-into-holes' engineering of antibody CH3 domains for heavy chain heterodimerization" Protein Eng 9(7):617-621 (Jul. 1, 1996).
Riechmann, L., et al., "Reshaping human antibodies for therapy" Nature 332:323-327 (Mar. 24, 1988).
Ripka, J., et al., "Two Chinese Hamster Ovary Glycosylation Mutants Affected in the Conversion of GDP-Mannose to GDP-Fucose" Arch Biochem Biophys 249(2):533-545 (Sep. 1, 1986).
Rodrigues, M., et al., "Engineering a Humanized Bispecific F(ab')2 Fragment for Improved Binding TOT Cells" Int J Cancer 7:45-50 (Jan. 1, 1992).
Rosok, M., et al., "A combinatorial library strategy for the rapid humanization of anticarcinoma BR96 Fab" J Biol Chem 271(37):22611-22618 (Sep. 13, 1996).
Schaefer, W., et al., "Immunoglobulin domain crossover as a generic approach for the production of bispecific IgG antibodies" PNAS USA 108(27):11187-11192 (Jul. 5, 2011).
Scholler, N., Methods in Molecular Biology; Antibody Engineering: Methods and Protocols "Chapter 15: Selection of Antibody Fragments by Yeast Display" Chames, P., Second edition, New York, NY:Springer—Humana Press, vol. 907:259-280 (Jan. 1, 2012).
Seimetz, D., et al., "Development and approval of the trifunctional antibody catumaxomab (anti-EpCAM x anti-CD3) as a targeted cancer immunotherapy" Cancer Treat Rev 36(6):458-467 (Oct. 1, 2010).
Sims, M., et al., "A Humanized CD18 Antibody Can Block Function Without Cell Destruction" J Immunol 151(4):2296-2308 (Aug. 15, 1993).
Spiess, C., et al., "Alternative molecular formats and therapeutic applications for bispecific antibodies" Mol Immunol 67( SUPPL 2 Pt A):95-106 (Jan. 27, 2015).

(56) References Cited

OTHER PUBLICATIONS

Stubenrauch, K., et al., "Impact of molecular processing in the hinge region of therapeutic IgG4 antibodies on disposition profiles in cynomolgus monkeys" Drug Metab Dispos 38(1):84-91 (Jan. 1, 2010).

Takahashi et al., "Diversity of antibody production pathways and their physiological implications Righteousness" Chemistry and Biology 45(1):27-32 ( 2007).

Tutt, A., et al., "Trispecific F(ab')3 derivatives that use cooperative signaling via the TCR/CD3 complex and CD2 to activate and redirect resting cytotoxic T cells" J Immunol 147(1):60-69 (Jul. 1, 1991).

Umana, P., et al., "Engineered Glycoforms of an Antineuroblastoma IgG1 with Optimized Antibody-Dependent Cellular Cytotoxic Activity" Nat Biotechnol 17(2):176-180 (Feb. 1, 1999).

Urlaub, G., et al., "Isolation of chinese hamster cell mutants deficient in dihydrofolate reductase activity" PNAS US 77(7):4216-4220 (Jul. 1, 1980).

Van Dijk, M., et al., "Human antibodies as next generation therapeutics" Curr Opin Chem Biol 5(4):368-374 (Aug. 1, 2001).

Van Driessche, A., et al., "Active Specific Immunotherapy Targeting the Wilms' Tumor Protein 1 (WT1) for Patients with Hematological Malignancies and Solid Tumors: Lessons from Early Clinical Trials" Oncologist 17(2):250-259 (Feb. 17, 2012).

Veomett, N., et al., "Therapeutic efficacy of an Fc-enhanced TCR-like antibody to the intracellular WT1 oncoprotein" Clin Cancer Res 20(15):4036-4046 (Aug. 1, 2014).

Vitetta, E. et al., "Redesigning nature's poisons to create anti-tumor reagents" Science 238(4830):1098-1104 (Nov. 20, 1987).

Vollmers, H., et al., "The 'early birds': Natural IgM antibodies and immune surveillance" Histol Histopathol 20(3):927-937 (Jul. 1, 2005).

Vollmers, H.,, "Death by stress: natural IgM-induced apoptosis" Methods Find Exp Clin Pharmacol 27(3):185-191 (Apr. 1, 2005).

Winter, G., et al., "Making Antibodies by Phage Display Technology" Annu Rev Immunol 12:433-455 (Apr. 1, 1994).

Wright, A., et al., "Effect of Glycosylation on Antibody Function: Implications for Genetic Engineering" Trends Biotechnol 15(1):26-32 (Jan. 1, 1997).

Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).

Yazaki, P. J., et al. Methods in Molecular Biology "Expression of recombinant antibodies in mammalian cell lines" Lo, B.K.C. (ed.), Totowa, NJ:Humana Press, vol. 248:255-268 ( 2004).

Zhao, A., et al., "Phage antibody display libraries: a powerful antibody discovery platform for immunotherapy" Crit Rev Biotechnol 36(2):276-289 (Nov. 14, 2014).

Zhao, Q., et al. Methods in Molecular Biology: Therapeutic Proteins—Methods and Protocols "Chapter 5: Yeast Display of Engineered Antibody Domains" Voynov, Vladimir, ed., New York, NY:Springer, vol. 889:73-84 (Jan. 17, 2012).

Zhao, Q., et al., "Affinity maturation of T-cell receptor-like antibodies for Wilms tumor 1 peptide greatly enhances therapeutic potential" Leukemia 29(11):2238-2247 (Nov. 1, 2015).

Panka D.J. et al., "Variable region framework differences result in decreased or increased affinity of variant anti-digoxin antibodies" Proceedings of the National Academy of Sciences (PNAS) 85(9):3080-3084 (May 1, 1988).

* cited by examiner

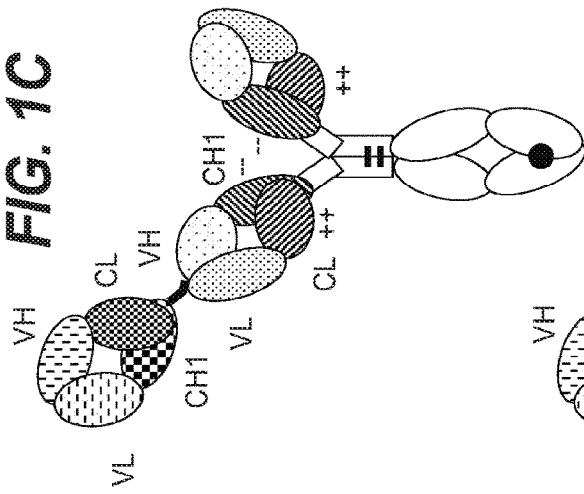
FIG. 1A  FIG. 1B  FIG. 1C
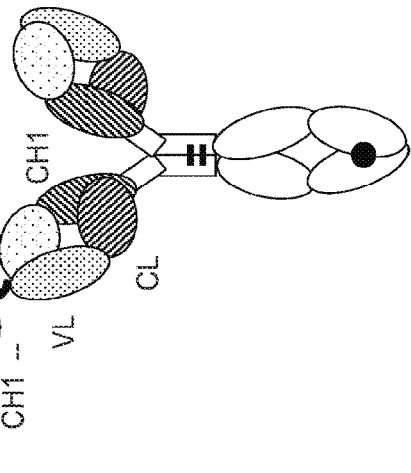
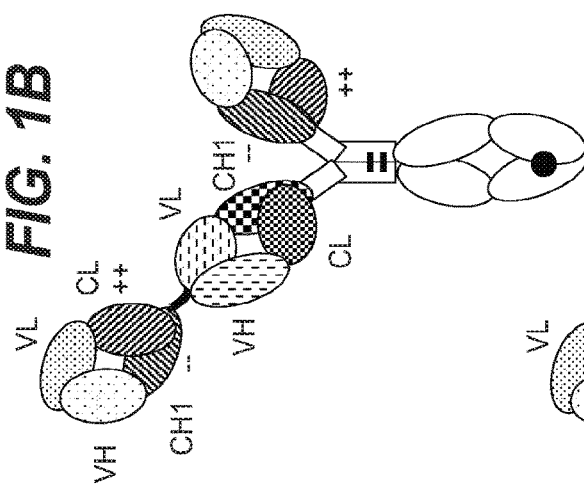
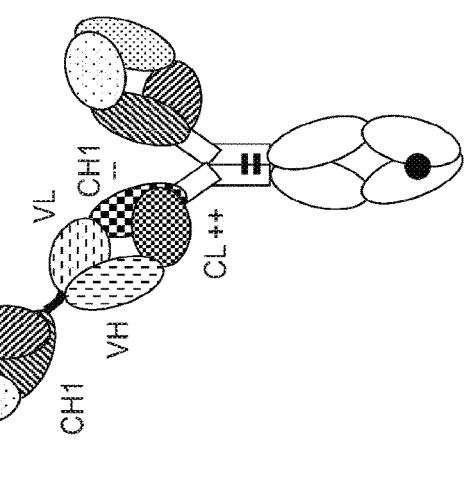
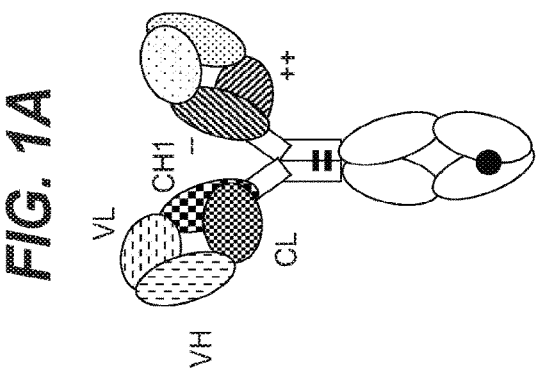
FIG. 1D
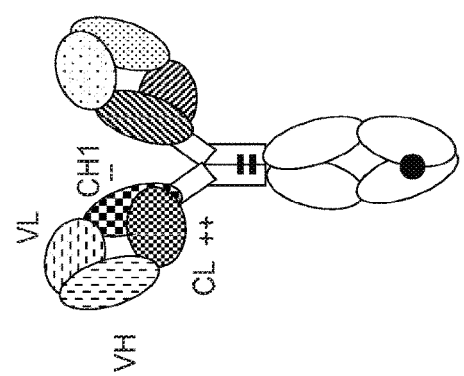
FIG. 1E  FIG. 1F

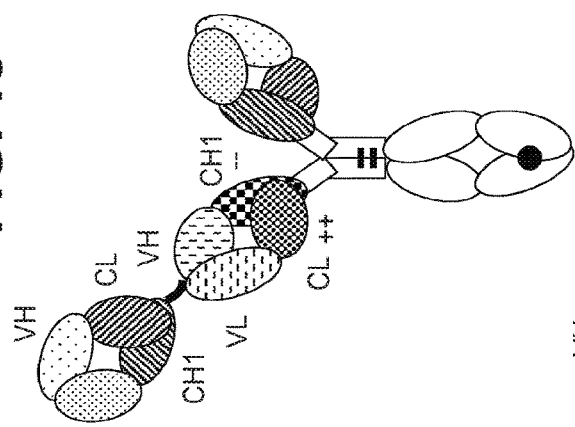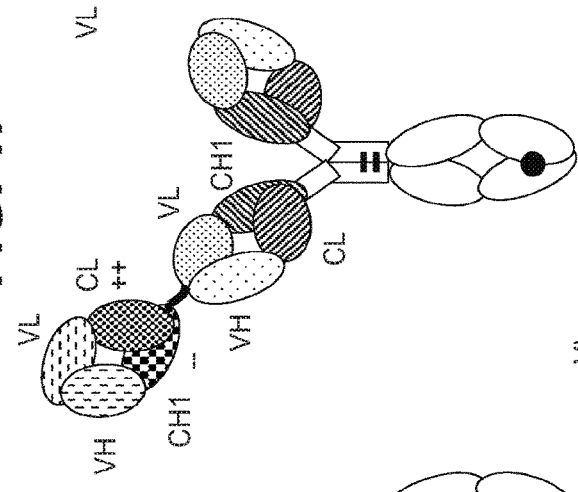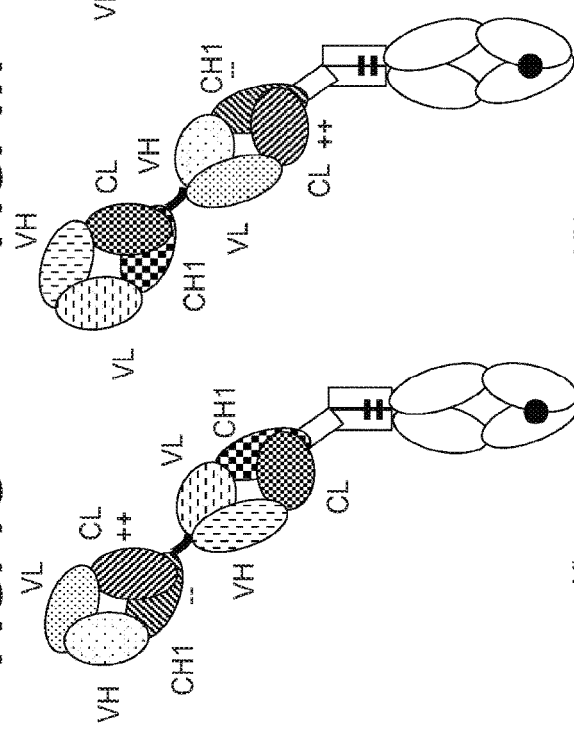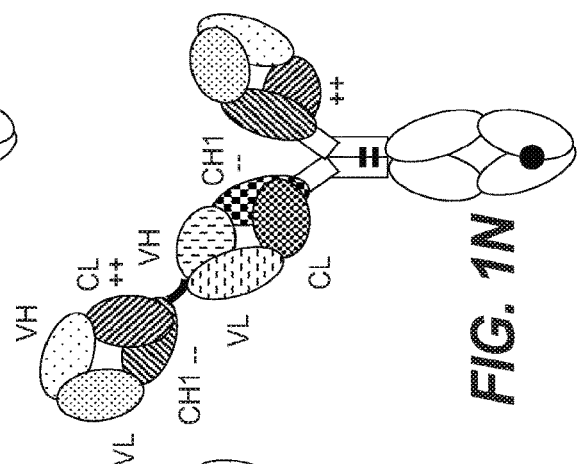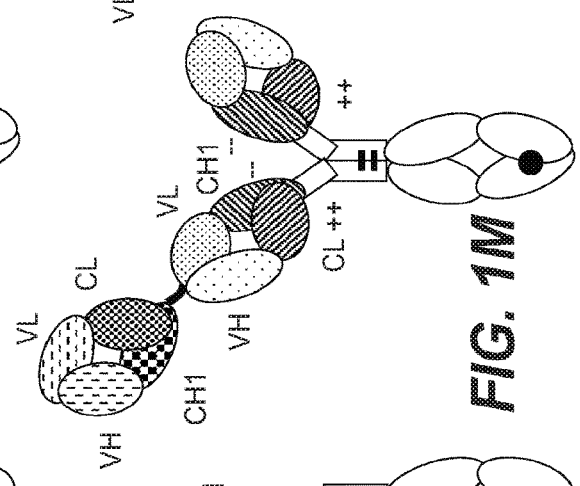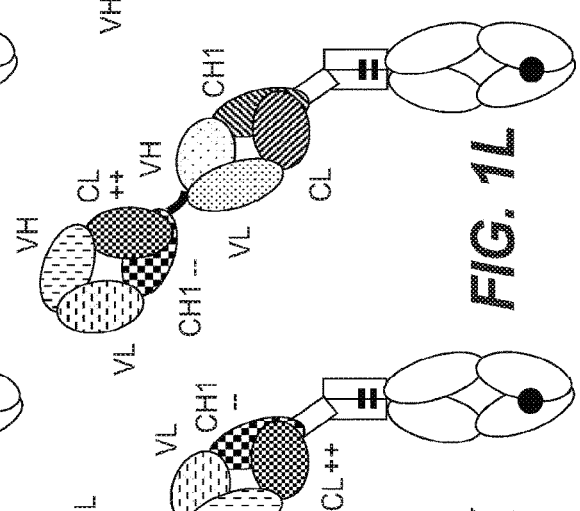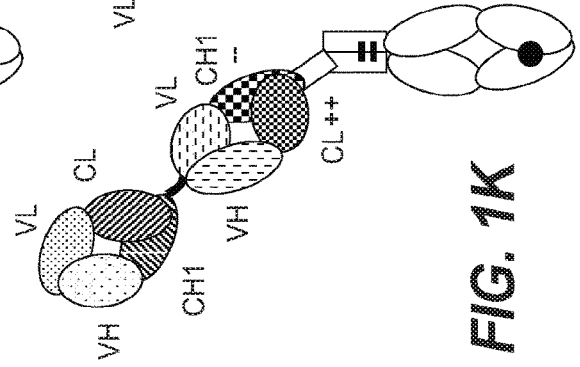

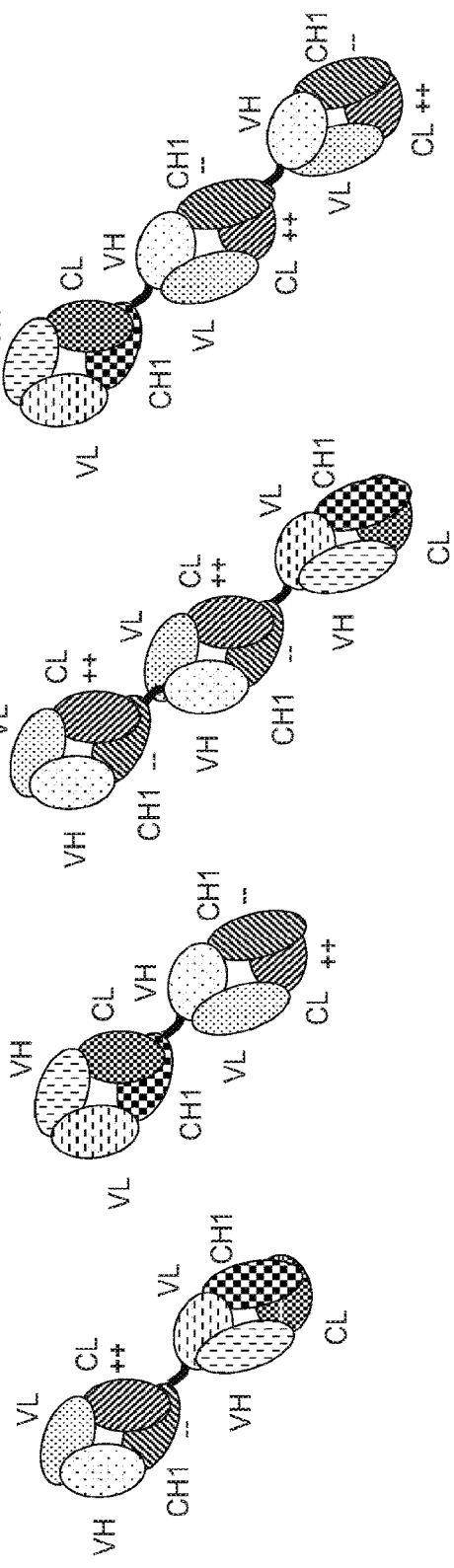
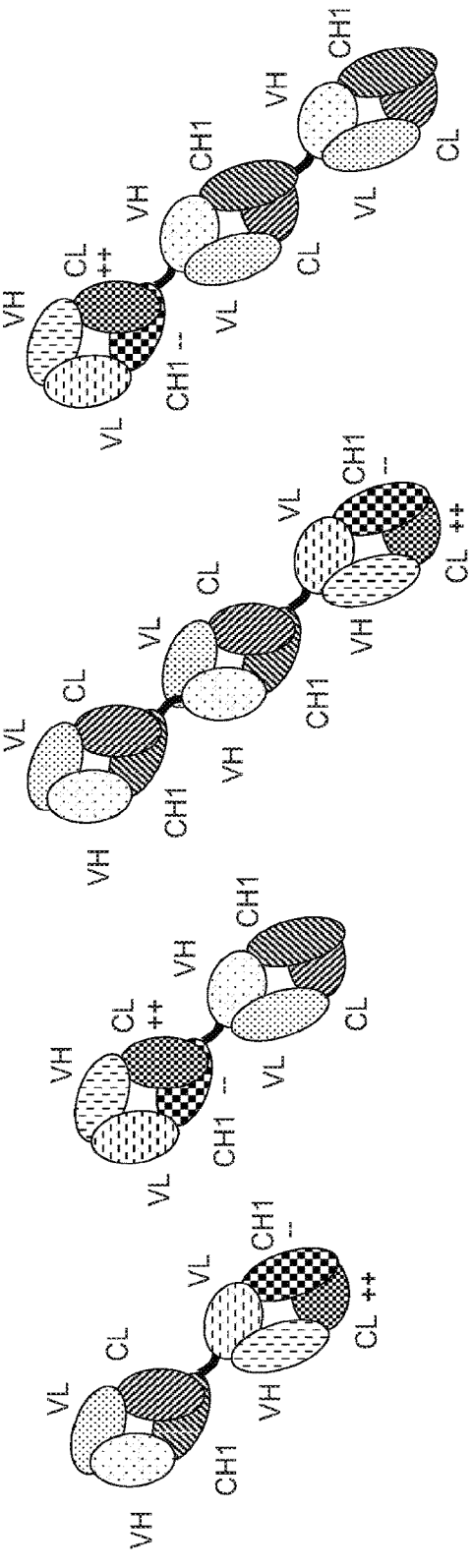
FIG. 1O  FIG. 1P  FIG. 1Q  FIG. 1R
FIG. 1S  FIG. 1T  FIG. 1U  FIG. 1V

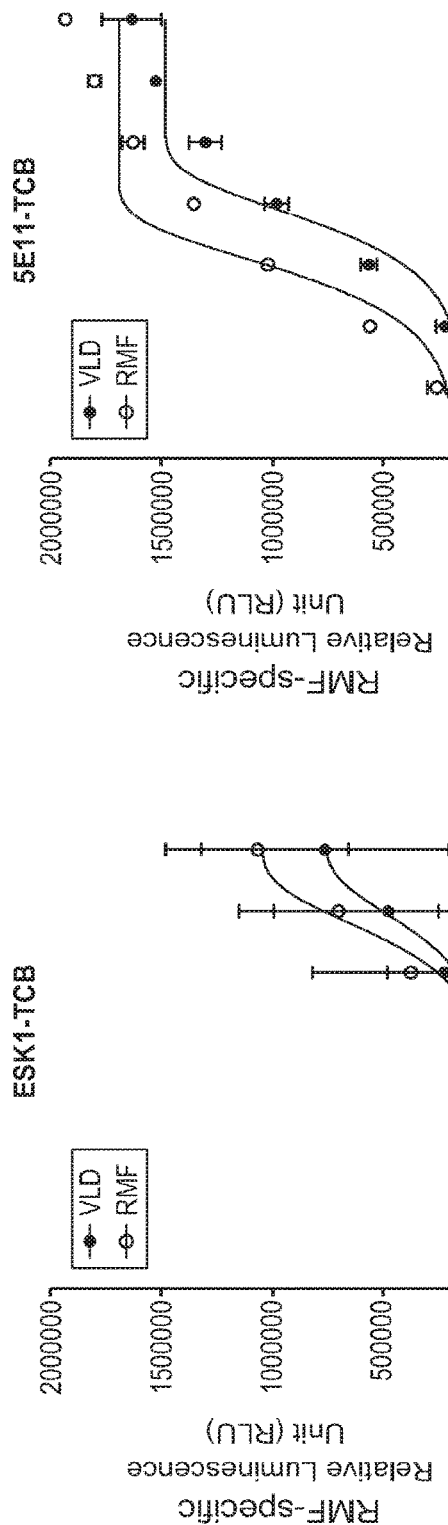
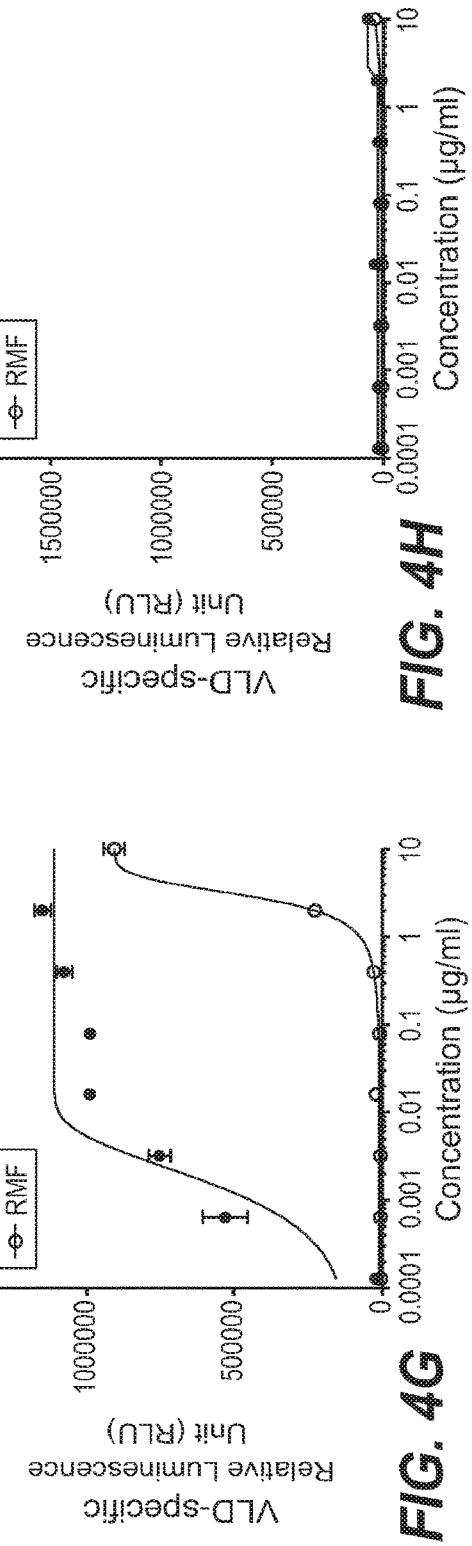

| Cell Line | HLA-A2 | WT1 (mRNA) |
|---|---|---|
| SKM-1 | + | + |
| CHO-WT1 | + | + |
| CHO-MAGE-A4 | + | - |
| BJAB | + | - |
| ARH-77 | + | - |
| K562 | - | + |

*FIG. 6A*

| Gene Name | Peptide Sequence |
|---|---|
| WT1 (Native) | RMFPNAPYL |
| MED13L | RMFPTPPSL |
| PIGQ | RMFPGEVAL |

| | |
|---|---|
| RMFPNAPYL | |
| YMFPNAPYL | |
| AMFPNAPYL | |
| RAFPNAPYL | |
| RMAPNAPYL | |
| RMFANAPYL | |
| RMFAAAPYL | |
| RMFANGPYL | |
| RMFANAAYL | |
| RMFANAPAL | |
| RMFANAPYA | |

| EC$_{50}$ Fold Change | 11D06-TCB | 33H09-TCB |
|---|---|---|
| R1Y | 69.41 | 48.87 |
| R1A | 67.46 | 33.34 |
| M2A | 49.07 | 49.14 |
| F3A | 9.86 | 31.65 |
| P4A | 1.20 | 1.38 |
| N5A | 93.26 | 110.18 |
| A6G | 90.84 | 101.61 |
| P7A | 1.55 | 2.01 |
| Y8A | 1.33 | 2.68 |
| L9A | 10.88 | 7.38 |

| | |
|---|---|
| 11D06-TCB | RMFPNAPYL |
| 33H09-TCB | RMFPNAPYL |
| ESK1-TCB | RMFPNAPYL |

| Group | No. of Animals | Compound | Dose (mg/kg) | Therapy | No. of Treatments |
|---|---|---|---|---|---|
| A | 12 | Vehicle | – | i.v. | 4 (once weekly) |
| B | 12 | WT-1-TCB (33H09) | 1 | i.v. | 4 (once weekly) |
| C | 12 | WT-1-TCB (11D06) | 1 | i.v. | 4 (once weekly) |

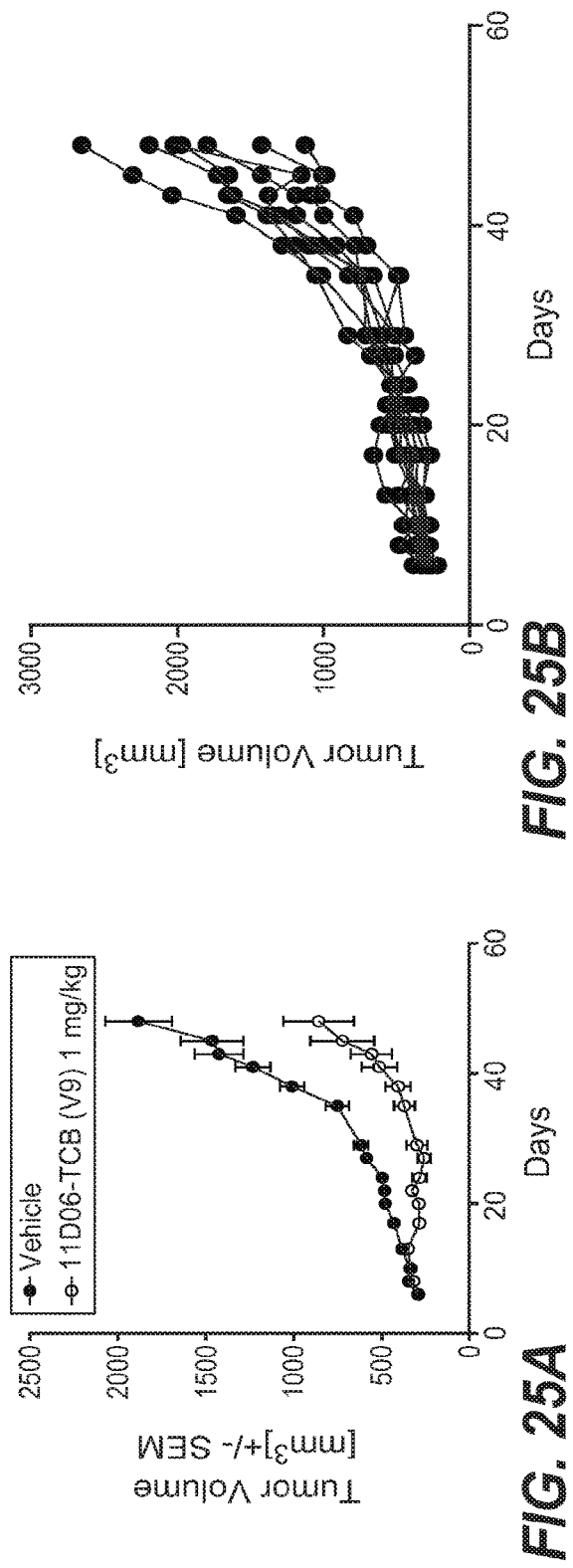
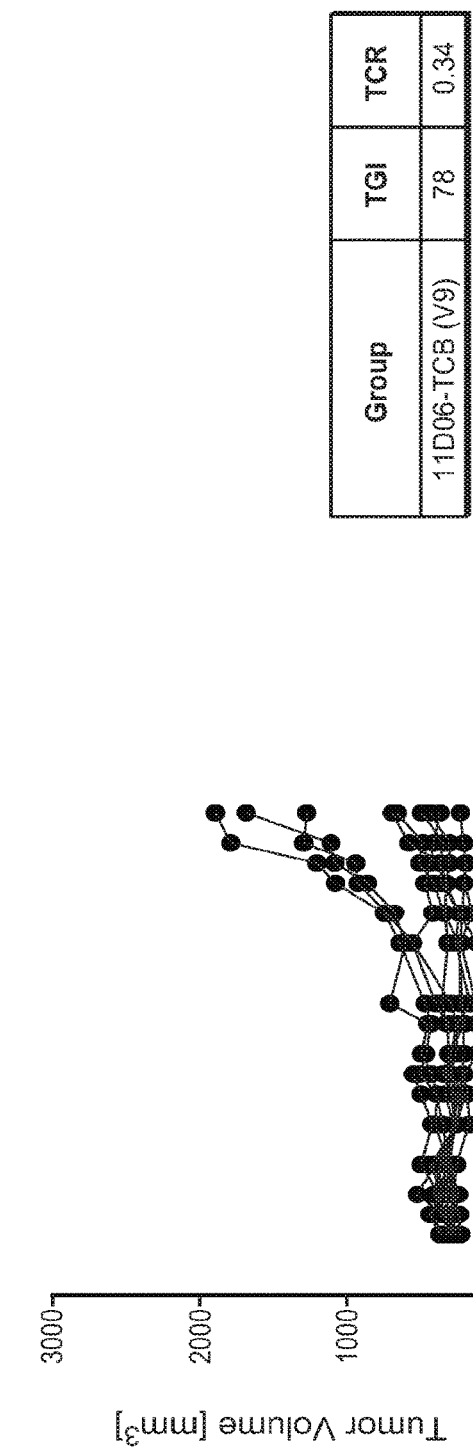
FIG. 25A
FIG. 25B
FIG. 25C
FIG. 25D

SEQUENCE LISTING

<160> NUMBER OF SEQ ID NOS: 140

<210> SEQ ID NO 1
<211> LENGTH: 5
<212> TYPE: PRT
<213> ORGANISM: Artificial Sequence
<220> FEATURE:
<223> OTHER INFORMATION: 11D06 HCDR1

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: 11D06 HCDR2

<400> SEQUENCE: 2

Gly Ile Ile Pro Ile Phe Gly Thr Ala Asn Tyr Ala Gln Lys Phe Gln
1               5                   10                  15

Gly

<210> SEQ ID NO 3

```
<211> LENGTH: 11
<212> TYPE: PRT
<213> ORGANISM: Artificial Sequence
<220> FEATURE:
<223> OTHER INFORMATION: 11D06 HCDR3

<400> SEQUENCE: 3

Ser Ile Glu Leu Trp Trp Gly Gly Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: 11D06 LCDR1

<400> SEQUENCE: 4

Arg Ala Ser Gln Ser Ile Ser Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: 11D06 LCDR2

<400> SEQUENCE: 5

Asp Ala Ser Ser Leu Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: 11D06 LCDR3

<400> SEQUENCE: 6

Gln Gln Tyr Glu Asp Tyr Thr Thr
1               5

<210> SEQ ID NO 7
<211> LENGTH: 120
<212> TYPE: PRT
<213> ORGANISM: Artificial Sequence
<220> FEATURE:
<223> OTHER INFORMATION: 11D06 VH

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Glu Leu Trp Trp Gly Gly Phe Asp Tyr Trp Gly Gln
```

Gly Thr Thr Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: 11D06 VL

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Gly Ser Leu Gln Pro
65                  70                  75                  80

Asp Asp Phe Ala Thr Tyr Tyr Cys Gln Gln Tyr Glu Asp Tyr Thr Thr
                85                  90                  95

Phe Gly Gln Gly Thr Lys Val Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: 33H09 HCDR1

<400> SEQUENCE: 9

Ser Tyr Ala Ile Ser
1               5

<210> SEQ ID NO 10
<211> LENGTH: 17
<212> TYPE: PRT
<213> ORGANISM: Artificial Sequence
<220> FEATURE:
<223> OTHER INFORMATION: 33H09 HCDR2

<400> SEQUENCE: 10

Gly Ile Ile Pro Ile Phe Gly Thr Ala Asn Tyr Ala Gln Lys Phe Gln
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: 33H09 HCDR3

<400> SEQUENCE: 11

Gly Ser Tyr Asp Leu Phe Ser Leu Asp Tyr
1               5                   10

<210> SEQ ID NO 12

```
<211> LENGTH: 11
<212> TYPE: PRT
<213> ORGANISM: Artificial Sequence
<220> FEATURE:
<223> OTHER INFORMATION: 33H09 LCDR1

<400> SEQUENCE: 12

Arg Ala Ser Gln Ser Ile Ser Ser Trp Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: 33H09 LCDR2

<400> SEQUENCE: 13

Asp Ala Ser Ser Leu Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: 33H09 LCDR3

<400> SEQUENCE: 14

Gln Gln Tyr Tyr Asp Gly Ile Thr
1               5

<210> SEQ ID NO 15
<211> LENGTH: 119
<212> TYPE: PRT
<213> ORGANISM: Artificial Sequence
<220> FEATURE:
<223> OTHER INFORMATION: 33H09 VH

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Asp Leu Phe Ser Leu Asp Tyr Trp Gly Gln Gly
                100                 105                 110

Thr Thr Val Thr Val Ser Ser
            115

<210> SEQ ID NO 16
<211> LENGTH: 106
<212> TYPE: PRT
<213> ORGANISM: Artificial Sequence
<220> FEATURE:
<223> OTHER INFORMATION: 33H09 VL
```

-continued

```
<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asp Gly Ile Thr
                85                  90                  95

Phe Gly Gln Gly Thr Lys Val Glu Ile Lys
            100                 105

<210> SEQ ID NO 17
<211> LENGTH: 5
<212> TYPE: PRT
<213> ORGANISM: Artificial Sequence
<220> FEATURE:
<223> OTHER INFORMATION: 13B04 HCDR1

<400> SEQUENCE: 17

Ser Tyr Tyr Trp Ser
1               5

<210> SEQ ID NO 18
<211> LENGTH: 16
<212> TYPE: PRT
<213> ORGANISM: Artificial Sequence
<220> FEATURE:
<223> OTHER INFORMATION: 13B04 HCDR2

<400> SEQUENCE: 18

Tyr Ile Tyr Tyr Ser Gly Ser Thr Asn Tyr Asn Pro Ser Leu Lys Ser
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: 13B04 HCDR3

<400> SEQUENCE: 19

Val Ser Tyr Asn Gly Leu Asp Tyr
1               5

<210> SEQ ID NO 20
<211> LENGTH: 11
<212> TYPE: PRT
<213> ORGANISM: Artificial Sequence
<220> FEATURE:
<223> OTHER INFORMATION: 13B04 LCDR1

<400> SEQUENCE: 20

Arg Ala Ser Gln Ser Ile Ser Ser Trp Leu Ala
1               5                   10

<210> SEQ ID NO 21
<211> LENGTH: 7
<212> TYPE: PRT
```

```
<213> ORGANISM: Artificial Sequence
<220> FEATURE:
<223> OTHER INFORMATION: 13B04 LCDR2

<400> SEQUENCE: 21

Asp Ala Ser Ser Leu Glu Ser
1               5

<210> SEQ ID NO 22
<211> LENGTH: 10
<212> TYPE: PRT
<213> ORGANISM: Artificial Sequence
<220> FEATURE:
<223> OTHER INFORMATION: 13B04 LCDR3

<400> SEQUENCE: 22

Gln Gln Tyr Asn Met Trp Asn Pro Val Thr
1               5                   10

<210> SEQ ID NO 23
<211> LENGTH: 116
<212> TYPE: PRT
<213> ORGANISM: Artificial Sequence
<220> FEATURE:
<223> OTHER INFORMATION: 13B04 VH

<400> SEQUENCE: 23

Glu Val Gln Leu Leu Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Ser Tyr Asn Gly Leu Asp Tyr Trp Gly Gln Gly Thr Leu Val
            100                 105                 110

Thr Val Ser Ser
        115

<210> SEQ ID NO 24
<211> LENGTH: 108
<212> TYPE: PRT
<213> ORGANISM: Artificial Sequence
<220> FEATURE:
<223> OTHER INFORMATION: 13B04 VL

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Asp Asp Phe Ala Thr Tyr Tyr Cys Gln Gln Tyr Asn Met Trp Asn Pro
                    85                  90                  95

Val Thr Phe Gly Gln Gly Thr Lys Val Glu Ile Lys
                100                 105

<210> SEQ ID NO 25
<211> LENGTH: 5
<212> TYPE: PRT
<213> ORGANISM: Artificial Sequence
<220> FEATURE:
<223> OTHER INFORMATION: 11B09 HCDR1

<400> SEQUENCE: 25

Ser Tyr Ala Ile Ser
1               5

<210> SEQ ID NO 26
<211> LENGTH: 17
<212> TYPE: PRT
<213> ORGANISM: Artificial Sequence
<220> FEATURE:
<223> OTHER INFORMATION: 11B09 HCDR2

<400> SEQUENCE: 26

Gly Ile Ile Pro Ile Phe Gly Thr Ala Asn Tyr Ala Gln Lys Phe Gln
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: 11B09 HCDR3

<400> SEQUENCE: 27

Val Pro Gly Arg Trp Tyr Gly Ala Met Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: 11B09 LCDR1

<400> SEQUENCE: 28

Arg Ala Ser Gln Ser Ile Ser Ser Trp Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: 11B09 LCDR2

<400> SEQUENCE: 29

Asp Ala Ser Ser Leu Glu Ser
1               5

<210> SEQ ID NO 30
<211> LENGTH: 9
<212> TYPE: PRT
```

```
<213> ORGANISM: Artificial Sequence
<220> FEATURE:
<223> OTHER INFORMATION: 11B09 LCDR3

<400> SEQUENCE: 30

Gln Gln Glu Asp Asp Tyr Pro Leu Thr
1               5

<210> SEQ ID NO 31
<211> LENGTH: 120
<212> TYPE: PRT
<213> ORGANISM: Artificial Sequence
<220> FEATURE:
<223> OTHER INFORMATION: 11B09 VH

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Pro Gly Arg Trp Tyr Gly Ala Met Asp Tyr Trp Gly Gln
            100                 105                 110

Gly Thr Thr Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: 11B09 VL

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Glu Asp Asp Tyr Pro Leu
                85                  90                  95

Thr Phe Gly Gln Gly Thr Lys Val Glu Ile Lys
            100                 105

<210> SEQ ID NO 33
<211> LENGTH: 5
<212> TYPE: PRT
<213> ORGANISM: Artificial Sequence
```

```
<220> FEATURE:
<223> OTHER INFORMATION: 33F05 HCDR1

<400> SEQUENCE: 33

Ser Tyr Tyr Trp Ser
1               5

<210> SEQ ID NO 34
<211> LENGTH: 16
<212> TYPE: PRT
<213> ORGANISM: Artificial Sequence
<220> FEATURE:
<223> OTHER INFORMATION: 33F05 HCDR2

<400> SEQUENCE: 34

Tyr Ile Tyr Tyr Ser Gly Ser Thr Asn Tyr Asn Pro Ser Leu Lys Ser
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: 33F05 HCDR3

<400> SEQUENCE: 35

Ser Tyr Tyr Glu Ala Phe Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: 33F05 LCDR1

<400> SEQUENCE: 36

Gln Gly Asp Ser Leu Arg Ser Tyr Tyr Ala Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: 33F05 LCDR2

<400> SEQUENCE: 37

Gly Lys Asn Asn Arg Pro Ser
1               5

<210> SEQ ID NO 38
<211> LENGTH: 10
<212> TYPE: PRT
<213> ORGANISM: Artificial Sequence
<220> FEATURE:
<223> OTHER INFORMATION: 33F05 LCDR3

<400> SEQUENCE: 38

Asn Ser Pro Asp Met Asn Gly Asn Ala Val
1               5                   10

<210> SEQ ID NO 39
<211> LENGTH: 116
<212> TYPE: PRT
<213> ORGANISM: Artificial Sequence
<220> FEATURE:
```

<223> OTHER INFORMATION: 33F05 VH

<400> SEQUENCE: 39

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Asn Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Ser Tyr Tyr Glu Ala Phe Asp Tyr Trp Gly Gln Gly Thr Leu Val
            100                 105                 110
Thr Val Ser Ser
            115

<210> SEQ ID NO 40
<211> LENGTH: 107
<212> TYPE: PRT
<213> ORGANISM: Artificial Sequence
<220> FEATURE:
<223> OTHER INFORMATION: 33F05 VL

<400> SEQUENCE: 40

Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Pro Ser Gly Ile Pro Asp Arg Phe Ser Gly Ser
    50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Pro Asp Met Asn Gly Asn Ala
                85                  90                  95
Val Phe Gly Gly Gly Thr Lys Leu Thr Val Leu
            100                 105

<210> SEQ ID NO 41
<211> LENGTH: 5
<212> TYPE: PRT
<213> ORGANISM: Artificial Sequence
<220> FEATURE:
<223> OTHER INFORMATION: 5E11 HCDR1

<400> SEQUENCE: 41

Ser Tyr Ala Ile Ser
1               5

<210> SEQ ID NO 42
<211> LENGTH: 17
<212> TYPE: PRT
<213> ORGANISM: Artificial Sequence
<220> FEATURE:
<223> OTHER INFORMATION: 5E11 HCDR2

<400> SEQUENCE: 42

Gly Ile Ile Pro Ile Phe Gly Thr Ala Asn Tyr Ala Gln Lys Phe Gln
1               5                   10                  15
Gly

<210> SEQ ID NO 43
<211> LENGTH: 10
<212> TYPE: PRT
<213> ORGANISM: Artificial Sequence
<220> FEATURE:
<223> OTHER INFORMATION: 5E11 HCDR3

<400> SEQUENCE: 43

Ser Ser Tyr Asp Leu Tyr Ser Phe Asp Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: 5E11 LCDR1

<400> SEQUENCE: 44

Arg Ala Ser Gln Ser Ile Ser Ser Trp Leu Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: 5E11 LCDR2

<400> SEQUENCE: 45

Asp Ala Ser Ser Leu Glu Ser
1               5

<210> SEQ ID NO 46
<211> LENGTH: 10
<212> TYPE: PRT
<213> ORGANISM: Artificial Sequence
<220> FEATURE:
<223> OTHER INFORMATION: 5E11 LCDR3

<400> SEQUENCE: 46

Gln Gln Tyr Ser Phe Pro Pro Met Ile Thr
1               5                   10

<210> SEQ ID NO 47
<211> LENGTH: 119
<212> TYPE: PRT
<213> ORGANISM: Artificial Sequence
<220> FEATURE:
<223> OTHER INFORMATION: 5E11 VH

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Asp Leu Tyr Ser Phe Asp Tyr Trp Gly Gln Gly
                100                 105                 110

Thr Thr Val Thr Val Ser Ser
        115

<210> SEQ ID NO 48
<211> LENGTH: 108
<212> TYPE: PRT
<213> ORGANISM: Artificial Sequence
<220> FEATURE:
<223> OTHER INFORMATION: 5E11 VL

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Phe Pro Pro Met
                85                  90                  95

Ile Thr Phe Gly Gln Gly Thr Lys Val Glu Ile Lys
                100                 105

<210> SEQ ID NO 49
<211> LENGTH: 5
<212> TYPE: PRT
<213> ORGANISM: Artificial Sequence
<220> FEATURE:
<223> OTHER INFORMATION: 13E08 HCDR1

<400> SEQUENCE: 49

Ser Tyr Ala Met Ser
1               5

<210> SEQ ID NO 50
<211> LENGTH: 17
<212> TYPE: PRT
<213> ORGANISM: Artificial Sequence
<220> FEATURE:
<223> OTHER INFORMATION: 13E08 HCDR2

<400> SEQUENCE: 50

Ala Ile Ser Gly Ser Gly Gly Ser Thr Tyr Tyr Ala Asp Ser Val Lys
1               5                   10                  15

Gly

<210> SEQ ID NO 51
<211> LENGTH: 10
<212> TYPE: PRT
<213> ORGANISM: Artificial Sequence

<220> FEATURE:
<223> OTHER INFORMATION: 13E08 HCDR3

<400> SEQUENCE: 51

Thr Tyr Pro Tyr Thr Gly Ser Phe Asp Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: 13E08 LCDR1

<400> SEQUENCE: 52

Arg Ala Ser Gln Ser Ile Ser Ser Trp Leu Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: 13E08 LCDR2

<400> SEQUENCE: 53

Asp Ala Ser Ser Leu Glu Ser
1               5

<210> SEQ ID NO 54
<211> LENGTH: 9
<212> TYPE: PRT
<213> ORGANISM: Artificial Sequence
<220> FEATURE:
<223> OTHER INFORMATION: 13E08 LCDR3

<400> SEQUENCE: 54

Gln Gln Asn Tyr Asn Tyr Pro Pro Thr
1               5

<210> SEQ ID NO 55
<211> LENGTH: 119
<212> TYPE: PRT
<213> ORGANISM: Artificial Sequence
<220> FEATURE:
<223> OTHER INFORMATION: 13E08 VH

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Tyr Pro Tyr Thr Gly Ser Phe Asp Tyr Trp Gly Gln Gly
            100                 105                 110

Thr Leu Val Thr Val Ser Ser

<210> SEQ ID NO 56
<211> LENGTH: 107
<212> TYPE: PRT
<213> ORGANISM: Artificial Sequence
<220> FEATURE:
<223> OTHER INFORMATION: 13E08 VL

<400> SEQUENCE: 56

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asn Tyr Asn Tyr Pro Pro
                85                  90                  95

Thr Phe Gly Gln Gly Thr Lys Val Glu Ile Lys
            100                 105

<210> SEQ ID NO 57
<211> LENGTH: 5
<212> TYPE: PRT
<213> ORGANISM: Artificial Sequence
<220> FEATURE:
<223> OTHER INFORMATION: 5C01 HCDR1

<400> SEQUENCE: 57

Ser Tyr Ala Met Ser
1               5

<210> SEQ ID NO 58
<211> LENGTH: 17
<212> TYPE: PRT
<213> ORGANISM: Artificial Sequence
<220> FEATURE:
<223> OTHER INFORMATION: 5C01 HCDR2

<400> SEQUENCE: 58

Ala Ile Ser Gly Ser Gly Gly Ser Thr Tyr Tyr Ala Asp Ser Val Lys
1               5                   10                  15

Gly

<210> SEQ ID NO 59
<211> LENGTH: 10
<212> TYPE: PRT
<213> ORGANISM: Artificial Sequence
<220> FEATURE:
<223> OTHER INFORMATION: 5C01 HCDR3

<400> SEQUENCE: 59

Gly Ser Trp Val Ser Tyr Ala Phe Asp Tyr
1               5                   10

<210> SEQ ID NO 60
<211> LENGTH: 11
<212> TYPE: PRT
<213> ORGANISM: Artificial Sequence

<220> FEATURE:
<223> OTHER INFORMATION: 5C01 LCDR1

<400> SEQUENCE: 60

Arg Ala Ser Gln Ser Ile Ser Ser Trp Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: 5C01 LCDR2

<400> SEQUENCE: 61

Asp Ala Ser Ser Leu Glu Ser
1               5

<210> SEQ ID NO 62
<211> LENGTH: 10
<212> TYPE: PRT
<213> ORGANISM: Artificial Sequence
<220> FEATURE:
<223> OTHER INFORMATION: 5C01 LCDR3

<400> SEQUENCE: 62

Gln Gln Tyr Ser Ile Trp Phe Pro Tyr Thr
1               5                   10

<210> SEQ ID NO 63
<211> LENGTH: 119
<212> TYPE: PRT
<213> ORGANISM: Artificial Sequence
<220> FEATURE:
<223> OTHER INFORMATION: 5C01 VH

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Trp Val Ser Tyr Ala Phe Asp Tyr Trp Gly Gln Gly
            100                 105                 110

Thr Leu Val Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: 5C01 VL

<400> SEQUENCE: 64

Asp Ile Gln Met Thr Gln Ser Pro Ser Thr Leu Ser Ala Ser Val Gly

```
                1               5                  10                  15
Asp Arg Val Thr Ile Thr Cys Arg Ala Ser Gln Ser Ile Ser Ser Trp
                    20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ile Trp Phe Pro
                85                  90                  95

Tyr Thr Phe Gly Gln Gly Thr Lys Val Glu Ile Lys
                100                 105

<210> SEQ ID NO 65
<211> LENGTH: 5
<212> TYPE: PRT
<213> ORGANISM: Artificial Sequence
<220> FEATURE:
<223> OTHER INFORMATION: 11G06 HCDR1

<400> SEQUENCE: 65

Ser Tyr Ala Ile Ser
1               5

<210> SEQ ID NO 66
<211> LENGTH: 17
<212> TYPE: PRT
<213> ORGANISM: Artificial Sequence
<220> FEATURE:
<223> OTHER INFORMATION: 11G06 HCDR2

<400> SEQUENCE: 66

Gly Ile Ile Pro Ile Phe Gly Thr Ala Asn Tyr Ala Gln Lys Phe Gln
1               5                   10                  15

Gly

<210> SEQ ID NO 67
<211> LENGTH: 10
<212> TYPE: PRT
<213> ORGANISM: Artificial Sequence
<220> FEATURE:
<223> OTHER INFORMATION: 11G06 HCDR3

<400> SEQUENCE: 67

Thr Gly Pro Tyr Tyr Gly Ala Phe Asp Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: 11G06 LCDR1

<400> SEQUENCE: 68

Arg Ala Ser Gln Ser Ile Ser Ser Trp Leu Ala
1               5                   10

<210> SEQ ID NO 69
<211> LENGTH: 7
<212> TYPE: PRT
<213> ORGANISM: Artificial Sequence
```

<220> FEATURE:
<223> OTHER INFORMATION: 11G06 LCDR2

<400> SEQUENCE: 69

Asp Ala Ser Ser Leu Glu Ser
1               5

<210> SEQ ID NO 70
<211> LENGTH: 8
<212> TYPE: PRT
<213> ORGANISM: Artificial Sequence
<220> FEATURE:
<223> OTHER INFORMATION: 11G06 LCDR3

<400> SEQUENCE: 70

Gln Gln Gly Phe Arg Gly Tyr Thr
1               5

<210> SEQ ID NO 71
<211> LENGTH: 119
<212> TYPE: PRT
<213> ORGANISM: Artificial Sequence
<220> FEATURE:
<223> OTHER INFORMATION: 11G06 VH

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Pro Tyr Tyr Gly Ala Phe Asp Tyr Trp Gly Gln Gly
            100                 105                 110

Thr Thr Val Thr Val Ser Ser
        115

<210> SEQ ID NO 72
<211> LENGTH: 106
<212> TYPE: PRT
<213> ORGANISM: Artificial Sequence
<220> FEATURE:
<223> OTHER INFORMATION: 11G06 VL

<400> SEQUENCE: 72

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Gly Phe Arg Gly Tyr Thr
                85                  90                  95

Phe Gly Gln Gly Thr Lys Val Glu Ile Lys
           100                 105

<210> SEQ ID NO 73
<211> LENGTH: 121
<212> TYPE: PRT
<213> ORGANISM: Artificial Sequence
<220> FEATURE:
<223> OTHER INFORMATION: ESK1 VH

<400> SEQUENCE: 73

Gln Met Gln Leu Val Gln Ser Gly Ala Glu Val Lys Glu Pro Gly Glu
1               5                   10                  15

Ser Leu Arg Ile Ser Cys Lys Gly Ser Gly Tyr Ser Phe Thr Asn Phe
            20                  25                  30

Trp Ile Ser Trp Val Arg Gln Met Pro Gly Lys Gly Leu Glu Trp Met
        35                  40                  45

Gly Arg Val Asp Pro Gly Tyr Ser Tyr Ser Tyr Ser Pro Ser Phe
    50                  55                  60

Gln Gly His Val Thr Ile Ser Ala Asp Lys Ser Thr Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Val Gln Tyr Ser Gly Tyr Tyr Asp Trp Phe Asp Pro Trp Gly
            100                 105                 110

Gln Gly Thr Leu Val Thr Val Ser Ser
        115                 120

<210> SEQ ID NO 74
<211> LENGTH: 109
<212> TYPE: PRT
<213> ORGANISM: Artificial Sequence
<220> FEATURE:
<223> OTHER INFORMATION: ESK1 VL

<400> SEQUENCE: 74

Gln Ala Trp Thr Gln Pro Pro Ser Ala Ser Gly Thr Pro Gly Gln Arg
1               5                   10                  15

Val Thr Ile Ser Cys Ser Gly Ser Ser Asn Ile Gly Ser Asn Thr
            20                  25                  30

Val Asn Trp Tyr Gln Gln Val Pro Gly Thr Ala Pro Lys Leu Leu Ile
        35                  40                  45

Tyr Ser Asn Asn Gln Arg Pro Ser Gly Val Pro Asp Arg Phe Ser Gly
    50                  55                  60

Ser Lys Ser Gly Thr Ser Ala Ser Leu Ala Ile Ser Gly Leu Gln Ser
65                  70                  75                  80

Glu Asp Glu Ala Asp Tyr Tyr Cys Ala Ala Trp Asp Asp Ser Leu Asn
                85                  90                  95

Gly Trp Val Phe Gly Gly Gly Thr Lys Leu Thr Val Leu
            100                 105

<210> SEQ ID NO 75
<211> LENGTH: 115
<212> TYPE: PRT
<213> ORGANISM: Artificial Sequence
<220> FEATURE:
<223> OTHER INFORMATION: Untargeted VH
```

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser
        115

<210> SEQ ID NO 76
<211> LENGTH: 108
<212> TYPE: PRT
<213> ORGANISM: Artificial Sequence
<220> FEATURE:
<223> OTHER INFORMATION: Untargeted VL

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 77
<211> LENGTH: 9
<212> TYPE: PRT
<213> ORGANISM: Homo sapiens

<400> SEQUENCE: 77

Val Leu Asp Phe Ala Pro Pro Gly Ala
1               5

<210> SEQ ID NO 78
<211> LENGTH: 9
<212> TYPE: PRT
<213> ORGANISM: Homo sapiens

<400> SEQUENCE: 78

Arg Met Phe Pro Asn Ala Pro Tyr Leu
1               5

```
<210> SEQ ID NO 79
<211> LENGTH: 9
<212> TYPE: PRT
<213> ORGANISM: Homo sapiens

<400> SEQUENCE: 79

Arg Met Phe Pro Thr Pro Pro Ser Leu
1               5

<210> SEQ ID NO 80
<211> LENGTH: 9
<212> TYPE: PRT
<213> ORGANISM: Homo sapiens

<400> SEQUENCE: 80

Arg Met Phe Pro Gly Glu Val Ala Leu
1               5

<210> SEQ ID NO 81
<211> LENGTH: 9
<212> TYPE: PRT
<213> ORGANISM: Homo sapiens

<400> SEQUENCE: 81

Arg Leu Phe Pro Asn Leu Pro Glu Leu
1               5

<210> SEQ ID NO 82
<211> LENGTH: 9
<212> TYPE: PRT
<213> ORGANISM: Homo sapiens

<400> SEQUENCE: 82

Arg Met Phe Pro Asn Lys Tyr Ser Leu
1               5

<210> SEQ ID NO 83
<211> LENGTH: 9
<212> TYPE: PRT
<213> ORGANISM: Homo sapiens

<400> SEQUENCE: 83

Ala Met Asp Pro Asn Ala Ala Tyr Val
1               5

<210> SEQ ID NO 84
<211> LENGTH: 9
<212> TYPE: PRT
<213> ORGANISM: Homo sapiens

<400> SEQUENCE: 84

Arg Met Gly Pro Asn Ile Tyr Glu Leu
1               5

<210> SEQ ID NO 85
<211> LENGTH: 9
<212> TYPE: PRT
<213> ORGANISM: Homo sapiens

<400> SEQUENCE: 85

Asn Met Pro Pro Asn Phe Pro Tyr Ile
1               5
```

```
<210> SEQ ID NO 86
<211> LENGTH: 9
<212> TYPE: PRT
<213> ORGANISM: Homo sapiens

<400> SEQUENCE: 86

Tyr Thr Ile Pro Asn His Pro Tyr Leu
1               5

<210> SEQ ID NO 87
<211> LENGTH: 9
<212> TYPE: PRT
<213> ORGANISM: Homo sapiens

<400> SEQUENCE: 87

Arg Leu Phe Pro Asn Ala Lys Phe Leu
1               5

<210> SEQ ID NO 88
<211> LENGTH: 9
<212> TYPE: PRT
<213> ORGANISM: Homo sapiens

<400> SEQUENCE: 88

Arg Met Val Pro Arg Ala Val Tyr Leu
1               5

<210> SEQ ID NO 89
<211> LENGTH: 9
<212> TYPE: PRT
<213> ORGANISM: Homo sapiens

<400> SEQUENCE: 89

Lys Met Val Pro Ser Ile Pro Tyr Leu
1               5

<210> SEQ ID NO 90
<211> LENGTH: 9
<212> TYPE: PRT
<213> ORGANISM: Homo sapiens

<400> SEQUENCE: 90

Arg Ile Phe Pro Ser Tyr Ser Tyr Leu
1               5

<210> SEQ ID NO 91
<211> LENGTH: 9
<212> TYPE: PRT
<213> ORGANISM: Homo sapiens

<400> SEQUENCE: 91

Arg Leu Phe Pro Asn Ser Lys Phe Leu
1               5

<210> SEQ ID NO 92
<211> LENGTH: 9
<212> TYPE: PRT
<213> ORGANISM: Homo sapiens

<400> SEQUENCE: 92

Lys Met Thr Pro Cys Ile Pro Tyr Leu
1               5

<210> SEQ ID NO 93
<211> LENGTH: 9
```

```
<212> TYPE: PRT
<213> ORGANISM: Homo sapiens

<400> SEQUENCE: 93

Ser Met Phe Pro Ser Leu Lys Tyr Leu
1               5

<210> SEQ ID NO 94
<211> LENGTH: 9
<212> TYPE: PRT
<213> ORGANISM: Homo sapiens

<400> SEQUENCE: 94

Arg Leu Leu Pro Ser Ala Pro Thr Leu
1               5

<210> SEQ ID NO 95
<211> LENGTH: 9
<212> TYPE: PRT
<213> ORGANISM: Homo sapiens

<400> SEQUENCE: 95

Arg Leu Arg Pro His Val Pro Tyr Leu
1               5

<210> SEQ ID NO 96
<211> LENGTH: 9
<212> TYPE: PRT
<213> ORGANISM: Homo sapiens

<400> SEQUENCE: 96

Arg Met Asn Pro Asn Ser Pro Ser Ile
1               5

<210> SEQ ID NO 97
<211> LENGTH: 9
<212> TYPE: PRT
<213> ORGANISM: Homo sapiens

<400> SEQUENCE: 97

Arg Val Phe Asn Asn Arg Trp Tyr Leu
1               5

<210> SEQ ID NO 98
<211> LENGTH: 9
<212> TYPE: PRT
<213> ORGANISM: Homo sapiens

<400> SEQUENCE: 98

Arg Leu Gln Leu Asn Asn Pro Tyr Leu
1               5

<210> SEQ ID NO 99
<211> LENGTH: 9
<212> TYPE: PRT
<213> ORGANISM: Homo sapiens

<400> SEQUENCE: 99

Arg Met Phe Phe Asn Gly Arg Tyr Ile
1               5

<210> SEQ ID NO 100
<211> LENGTH: 9
<212> TYPE: PRT
<213> ORGANISM: Homo sapiens
```

```
<400> SEQUENCE: 100

Arg Leu Ser Pro Asn Arg Pro Pro Leu
1               5

<210> SEQ ID NO 101
<211> LENGTH: 9
<212> TYPE: PRT
<213> ORGANISM: Homo sapiens

<400> SEQUENCE: 101

Glu Thr Phe Pro Asn Ser Trp Tyr Leu
1               5

<210> SEQ ID NO 102
<211> LENGTH: 9
<212> TYPE: PRT
<213> ORGANISM: Homo sapiens

<400> SEQUENCE: 102

Gly Leu Lys Pro Asn Ala Ile Tyr Leu
1               5

<210> SEQ ID NO 103
<211> LENGTH: 9
<212> TYPE: PRT
<213> ORGANISM: Homo sapiens

<400> SEQUENCE: 103

Arg Gln Phe Pro Asn Ala Ser Leu Ile
1               5

<210> SEQ ID NO 104
<211> LENGTH: 9
<212> TYPE: PRT
<213> ORGANISM: Homo sapiens

<400> SEQUENCE: 104

Tyr Ile Phe Pro Asn Cys Pro Phe Leu
1               5

<210> SEQ ID NO 105
<211> LENGTH: 9
<212> TYPE: PRT
<213> ORGANISM: Homo sapiens

<400> SEQUENCE: 105

Arg Leu Arg Ile Asn Phe Pro Tyr Leu
1               5

<210> SEQ ID NO 106
<211> LENGTH: 449
<212> TYPE: PRT
<213> ORGANISM: Homo sapiens

<400> SEQUENCE: 106

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
```

```
            50                  55                  60
Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                     85                  90                  95

Ser Gly Gln Phe Thr Gly Thr Ala Gly Ala Cys Arg Tyr Gly Pro Phe
                    100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                    165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
                290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
                435                 440                 445

Leu
```

<210> SEQ ID NO 107
<211> LENGTH: 207

```
<212> TYPE: PRT
<213> ORGANISM: Homo sapiens

<400> SEQUENCE: 107

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Ile
        195                 200                 205

<210> SEQ ID NO 108
<211> LENGTH: 198
<212> TYPE: PRT
<213> ORGANISM: Macaca fascicularis

<400> SEQUENCE: 108

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Leu Val Tyr Tyr Trp Ser Lys
    130                 135                 140
```

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
            195

<210> SEQ ID NO 109
<211> LENGTH: 225
<212> TYPE: PRT
<213> ORGANISM: Homo sapiens

<400> SEQUENCE: 109

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro
225

<210> SEQ ID NO 110
<211> LENGTH: 10
<212> TYPE: PRT
<213> ORGANISM: Artificial Sequence
<220> FEATURE:
<223> OTHER INFORMATION: linker

<400> SEQUENCE: 110

Gly Gly Gly Gly Ser Gly Gly Gly Gly Ser
1               5                   10

```
<210> SEQ ID NO 111
<211> LENGTH: 11
<212> TYPE: PRT
<213> ORGANISM: Artificial Sequence
<220> FEATURE:
<223> OTHER INFORMATION: linker

<400> SEQUENCE: 111

Asp Gly Gly Gly Gly Ser Gly Gly Gly Gly Ser
1               5                   10

<210> SEQ ID NO 112
<211> LENGTH: 107
<212> TYPE: PRT
<213> ORGANISM: Homo sapiens

<400> SEQUENCE: 112

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 113
<211> LENGTH: 105
<212> TYPE: PRT
<213> ORGANISM: Homo sapiens

<400> SEQUENCE: 113

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105

<210> SEQ ID NO 114
<211> LENGTH: 328
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Lys
```

-continued

```
  1               5                  10                 15
Ser Thr Ser Gly Gly Thr Ala Ala Leu Gly Cys Leu Val Lys Asp Tyr
             20                 25                 30
Phe Pro Glu Pro Val Thr Val Ser Trp Asn Ser Gly Ala Leu Thr Ser
             35                 40                 45
Gly Val His Thr Phe Pro Ala Val Leu Gln Ser Ser Gly Leu Tyr Ser
             50                 55                 60
Leu Ser Ser Val Val Thr Val Pro Ser Ser Leu Gly Thr Gln Thr
 65                 70                 75                 80
Tyr Ile Cys Asn Val Asn His Lys Pro Ser Asn Thr Lys Val Asp Lys
                 85                 90                 95
Lys Val Glu Pro Lys Ser Cys Asp Lys Thr His Thr Cys Pro Pro Cys
            100                105                110
Pro Ala Pro Glu Leu Leu Gly Gly Pro Ser Val Phe Leu Phe Pro Pro
            115                120                125
Lys Pro Lys Asp Thr Leu Met Ile Ser Arg Thr Pro Glu Val Thr Cys
130                135                140
Val Val Val Asp Val Ser His Glu Asp Pro Glu Val Lys Phe Asn Trp
145                150                155                160
Tyr Val Asp Gly Val Glu Val His Asn Ala Lys Thr Lys Pro Arg Glu
                165                170                175
Glu Gln Tyr Asn Ser Thr Tyr Arg Val Val Ser Val Leu Thr Val Leu
                180                185                190
His Gln Asp Trp Leu Asn Gly Lys Glu Tyr Lys Cys Lys Val Ser Asn
            195                200                205
Lys Ala Leu Pro Ala Pro Ile Glu Lys Thr Ile Ser Lys Ala Lys Gly
210                215                220
Gln Pro Arg Glu Pro Gln Val Tyr Thr Leu Pro Pro Ser Arg Asp Glu
225                230                235                240
Leu Thr Lys Asn Gln Val Ser Leu Thr Cys Leu Val Lys Gly Phe Tyr
                245                250                255
Pro Ser Asp Ile Ala Val Glu Trp Glu Ser Asn Gly Gln Pro Glu Asn
            260                265                270
Asn Tyr Lys Thr Thr Pro Pro Val Leu Asp Ser Asp Gly Ser Phe Phe
            275                280                285
Leu Tyr Ser Lys Leu Thr Val Asp Lys Ser Arg Trp Gln Gln Gly Asn
            290                295                300
Val Phe Ser Cys Ser Val Met His Glu Ala Leu His Asn His Tyr Thr
305                310                315                320
Gln Lys Ser Leu Ser Leu Ser Pro
                325
```

<210> SEQ ID NO 115
<211> LENGTH: 5
<212> TYPE: PRT
<213> ORGANISM: Artificial Sequence
<220> FEATURE:
<223> OTHER INFORMATION: CD3 HCDR1

<400> SEQUENCE: 115

```
Thr Tyr Ala Met Asn
 1               5
```

<210> SEQ ID NO 116
<211> LENGTH: 19
<212> TYPE: PRT

```
<213> ORGANISM: Artificial Sequence
<220> FEATURE:
<223> OTHER INFORMATION: CD3 HCDR2

<400> SEQUENCE: 116

Arg Ile Arg Ser Lys Tyr Asn Asn Tyr Ala Thr Tyr Tyr Ala Asp Ser
1               5                   10                  15

Val Lys Gly

<210> SEQ ID NO 117
<211> LENGTH: 14
<212> TYPE: PRT
<213> ORGANISM: Artificial Sequence
<220> FEATURE:
<223> OTHER INFORMATION: CD3 HCDR3

<400> SEQUENCE: 117

His Gly Asn Phe Gly Asn Ser Tyr Val Ser Trp Phe Ala Tyr
1               5                   10

<210> SEQ ID NO 118
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 118

Gly Ser Ser Thr Gly Ala Val Thr Thr Ser Asn Tyr Ala Asn
1               5                   10

<210> SEQ ID NO 119
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 119

Gly Thr Asn Lys Arg Ala Pro
1               5

<210> SEQ ID NO 120
<211> LENGTH: 9
<212> TYPE: PRT
<213> ORGANISM: Artificial Sequence
<220> FEATURE:
<223> OTHER INFORMATION: CD3 LCDR3

<400> SEQUENCE: 120

Ala Leu Trp Tyr Ser Asn Leu Trp Val
1               5

<210> SEQ ID NO 121
<211> LENGTH: 125
<212> TYPE: PRT
<213> ORGANISM: Artificial Sequence
<220> FEATURE:
<223> OTHER INFORMATION: CD3 VH

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30
```

```
Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 122
<211> LENGTH: 109
<212> TYPE: PRT
<213> ORGANISM: Artificial Sequence
<220> FEATURE:
<223> OTHER INFORMATION: CD3 VL

<400> SEQUENCE: 122

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 123
<211> LENGTH: 448
<212> TYPE: PRT
<213> ORGANISM: Artificial Sequence
<220> FEATURE:
<223> OTHER INFORMATION: WT1 11D06 VH-CH1(EE)-Fc(hole, PGLALA)

<400> SEQUENCE: 123

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Glu Leu Trp Trp Gly Gly Phe Asp Tyr Trp Gly Gln
                100                 105                 110
```

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 124
<211> LENGTH: 673
<212> TYPE: PRT
<213> ORGANISM: Artificial Sequence
<220> FEATURE:
<223> OTHER INFORMATION: WT1 11D06 VH-CH1(EE)-CD3 VL-CH1-Fc(knob,
      PGLALA)

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr 20                  25                  30
Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Ile Glu Leu Trp Trp Gly Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Glu Lys Val Glu Pro Lys Ser Cys Asp
        210                 215                 220

Gly Gly Gly Gly Ser Gly Gly Gly Gly Ser Gln Ala Val Val Thr Gln
225                 230                 235                 240

Glu Pro Ser Leu Thr Val Ser Pro Gly Gly Thr Val Thr Leu Thr Cys
                245                 250                 255

Gly Ser Ser Thr Gly Ala Val Thr Thr Ser Asn Tyr Ala Asn Trp Val
                260                 265                 270

Gln Glu Lys Pro Gly Gln Ala Phe Arg Gly Leu Ile Gly Gly Thr Asn
            275                 280                 285

Lys Arg Ala Pro Gly Thr Pro Ala Arg Phe Ser Gly Ser Leu Leu Gly
        290                 295                 300

Gly Lys Ala Ala Leu Thr Leu Ser Gly Ala Gln Pro Glu Asp Glu Ala
305                 310                 315                 320

Glu Tyr Tyr Cys Ala Leu Trp Tyr Ser Asn Leu Trp Val Phe Gly Gly
                325                 330                 335

Gly Thr Lys Leu Thr Val Leu Ser Ser Ala Ser Thr Lys Gly Pro Ser
            340                 345                 350

Val Phe Pro Leu Ala Pro Ser Ser Lys Ser Thr Ser Gly Gly Thr Ala
                355                 360                 365

Ala Leu Gly Cys Leu Val Lys Asp Tyr Phe Pro Glu Pro Val Thr Val
            370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Lys Lys Val Glu Pro Lys Ser Cys
        435                 440                 445

```
Asp Lys Thr His Thr Cys Pro Cys Pro Ala Pro Glu Ala Ala Gly
        450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
        515                 520                 525

Arg Val Val Ser Val Leu Thr Val Leu His Gln Asp Trp Leu Asn Gly
    530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Cys Arg Asp Glu Leu Thr Lys Asn Gln Val Ser
            580                 585                 590

Leu Trp Cys Leu Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
    610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Pro

<210> SEQ ID NO 125
<211> LENGTH: 213
<212> TYPE: PRT
<213> ORGANISM: Artificial Sequence
<220> FEATURE:
<223> OTHER INFORMATION: WT1 11D06 VL-CL(RK)

<400> SEQUENCE: 125

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Gly Ser Leu Gln Pro
65                  70                  75                  80

Asp Asp Phe Ala Thr Tyr Tyr Cys Gln Gln Tyr Glu Asp Tyr Thr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125
```

```
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                    165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
                    195                 200                 205
Asn Arg Gly Glu Cys
    210
```

<210> SEQ ID NO 126
<211> LENGTH: 447
<212> TYPE: PRT
<213> ORGANISM: Artificial Sequence
<220> FEATURE:
<223> OTHER INFORMATION: WT1 33H09 VH-CH1(EE)-Fc(hole, PGLALA)

<400> SEQUENCE: 126

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Ser Tyr Asp Leu Phe Ser Leu Asp Tyr Trp Gly Gln Gly
                100                 105                 110
Thr Thr Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
    130                 135                 140
Gly Cys Leu Val Glu Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Glu Lys Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
            325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 127
<211> LENGTH: 672
<212> TYPE: PRT
<213> ORGANISM: Artificial Sequence
<220> FEATURE:
<223> OTHER INFORMATION: WT1 33H09 VH-CH1(EE)-CD3 VL-CH1-Fc(knob,
      PGLALA)

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Ser Tyr Asp Leu Phe Ser Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
            275                 280                 285

Arg Ala Pro Gly Thr Pro Ala Arg Phe Ser Gly Ser Leu Leu Gly Gly
            290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
            355                 360                 365

Leu Gly Cys Leu Val Lys Asp Tyr Phe Pro Glu Pro Val Thr Val Ser
        370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
            435                 440                 445

Lys Thr His Thr Cys Pro Pro Cys Pro Ala Pro Glu Ala Ala Gly Gly
            450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605
```

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
                660                 665                 670

<210> SEQ ID NO 128
<211> LENGTH: 213
<212> TYPE: PRT
<213> ORGANISM: Artificial Sequence
<220> FEATURE:
<223> OTHER INFORMATION: WT1 33H09 VL-CL(RK)

<400> SEQUENCE: 128

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asp Gly Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 129
<211> LENGTH: 232
<212> TYPE: PRT
<213> ORGANISM: Artificial Sequence
<220> FEATURE:
<223> OTHER INFORMATION: CD3 VH-CL

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

```
Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ala Ser Val
                    115                 120                 125

Ala Ala Pro Ser Val Phe Ile Phe Pro Pro Ser Asp Glu Gln Leu Lys
            130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                    165                 170                 175

Ser Gln Glu Ser Val Thr Glu Gln Asp Ser Lys Asp Ser Thr Tyr Ser
                    180                 185                 190

Leu Ser Ser Thr Leu Thr Leu Ser Lys Ala Asp Tyr Glu Lys His Lys
                    195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 130
<211> LENGTH: 5
<212> TYPE: PRT
<213> ORGANISM: Artificial Sequence
<220> FEATURE:
<223> OTHER INFORMATION: CD3 HCDR1 (V9)

<400> SEQUENCE: 130

Gly Tyr Thr Met Asn
1               5

<210> SEQ ID NO 131
<211> LENGTH: 17
<212> TYPE: PRT
<213> ORGANISM: Artificial Sequence
<220> FEATURE:
<223> OTHER INFORMATION: CD3 HCDR2 (V9)

<400> SEQUENCE: 131

Leu Ile Asn Pro Tyr Lys Gly Val Ser Thr Tyr Asn Gln Lys Phe Lys
1               5                   10                  15

Asp

<210> SEQ ID NO 132
<211> LENGTH: 13
<212> TYPE: PRT
<213> ORGANISM: Artificial Sequence
<220> FEATURE:
<223> OTHER INFORMATION: CD3 HCDR3 (V9)

<400> SEQUENCE: 132

Ser Gly Tyr Tyr Gly Asp Ser Asp Trp Tyr Phe Asp Val
```

<210> SEQ ID NO 133
<211> LENGTH: 11
<212> TYPE: PRT
<213> ORGANISM: Artificial Sequence
<220> FEATURE:
<223> OTHER INFORMATION: CD3 LCDR1 (V9)

<400> SEQUENCE: 133

Arg Ala Ser Gln Asp Ile Arg Asn Tyr Leu Asn
1               5                   10

<210> SEQ ID NO 134
<211> LENGTH: 7
<212> TYPE: PRT
<213> ORGANISM: Artificial Sequence
<220> FEATURE:
<223> OTHER INFORMATION: CD3 LCDR2 (V9)

<400> SEQUENCE: 134

Tyr Thr Ser Arg Leu Glu Ser
1               5

<210> SEQ ID NO 135
<211> LENGTH: 9
<212> TYPE: PRT
<213> ORGANISM: Artificial Sequence
<220> FEATURE:
<223> OTHER INFORMATION: CD3 LCDR3 (V9)

<400> SEQUENCE: 135

Gln Gln Gly Asn Thr Leu Pro Trp Thr
1               5

<210> SEQ ID NO 136
<211> LENGTH: 122
<212> TYPE: PRT
<213> ORGANISM: Artificial Sequence
<220> FEATURE:
<223> OTHER INFORMATION: CD3 VH (V9)

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 137
<211> LENGTH: 107
<212> TYPE: PRT

<213> ORGANISM: Artificial Sequence
<220> FEATURE:
<223> OTHER INFORMATION: CD3 VL (V9)

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 138
<211> LENGTH: 275
<212> TYPE: PRT
<213> ORGANISM: Homo sapiens

<400> SEQUENCE: 138

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

```
Phe Gln Lys Trp Ala Ala Val Val Pro Ser Gly Gln Glu Gln Arg
            245                 250                 255

Tyr Thr Cys His Val Gln His Glu Gly Leu Pro Lys Pro Leu Thr Leu
            260                 265                 270

Arg Trp Glu
        275

<210> SEQ ID NO 139
<211> LENGTH: 671
<212> TYPE: PRT
<213> ORGANISM: Artificial Sequence
<220> FEATURE:
<223> OTHER INFORMATION: WT1 11D06 VH-CH1(EE)-CD3 (V9) VL-CH1-Fc(knob,
      PGLALA)

<400> SEQUENCE: 139

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Glu Leu Trp Trp Gly Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Glu Pro Lys Ser Cys Asp
            210                 215                 220

Gly Gly Gly Gly Ser Gly Gly Gly Ser Asp Ile Gln Met Thr Gln
225                 230                 235                 240

Ser Pro Ser Ser Leu Ser Ala Ser Val Gly Asp Arg Val Thr Ile Thr
            245                 250                 255

Cys Arg Ala Ser Gln Asp Ile Arg Asn Tyr Leu Asn Trp Tyr Gln Gln
            260                 265                 270

Lys Pro Gly Lys Ala Pro Lys Leu Leu Ile Tyr Tyr Thr Ser Arg Leu
            275                 280                 285

Glu Ser Gly Val Pro Ser Arg Phe Ser Gly Ser Gly Ser Gly Thr Asp
            290                 295                 300

Tyr Thr Leu Thr Ile Ser Ser Leu Gln Pro Glu Asp Phe Ala Thr Tyr
```

```
            305                 310                 315                 320
Tyr Cys Gln Gln Gly Asn Thr Leu Pro Trp Thr Phe Gly Gln Gly Thr
                325                 330                 335
Lys Val Glu Ile Lys Ser Ser Ala Ser Thr Lys Gly Pro Ser Val Phe
                340                 345                 350
Pro Leu Ala Pro Ser Ser Lys Ser Thr Ser Gly Gly Thr Ala Ala Leu
                355                 360                 365
Gly Cys Leu Val Lys Asp Tyr Phe Pro Glu Pro Val Thr Val Ser Trp
            370                 375                 380
Asn Ser Gly Ala Leu Thr Ser Gly Val His Thr Phe Pro Ala Val Leu
385                 390                 395                 400
Gln Ser Ser Gly Leu Tyr Ser Leu Ser Ser Val Val Thr Val Pro Ser
                405                 410                 415
Ser Ser Leu Gly Thr Gln Thr Tyr Ile Cys Asn Val Asn His Lys Pro
                420                 425                 430
Ser Asn Thr Lys Val Asp Lys Lys Val Glu Pro Lys Ser Cys Asp Lys
                435                 440                 445
Thr His Thr Cys Pro Pro Cys Pro Ala Pro Glu Ala Ala Gly Gly Pro
            450                 455                 460
Ser Val Phe Leu Phe Pro Pro Lys Pro Lys Asp Thr Leu Met Ile Ser
465                 470                 475                 480
Arg Thr Pro Glu Val Thr Cys Val Val Val Asp Val Ser His Glu Asp
                485                 490                 495
Pro Glu Val Lys Phe Asn Trp Tyr Val Asp Gly Val Glu Val His Asn
                500                 505                 510
Ala Lys Thr Lys Pro Arg Glu Glu Gln Tyr Asn Ser Thr Tyr Arg Val
            515                 520                 525
Val Ser Val Leu Thr Val Leu His Gln Asp Trp Leu Asn Gly Lys Glu
                530                 535                 540
Tyr Lys Cys Lys Val Ser Asn Lys Ala Leu Gly Ala Pro Ile Glu Lys
545                 550                 555                 560
Thr Ile Ser Lys Ala Lys Gly Gln Pro Arg Glu Pro Gln Val Tyr Thr
                565                 570                 575
Leu Pro Pro Cys Arg Asp Glu Leu Thr Lys Asn Gln Val Ser Leu Trp
                580                 585                 590
Cys Leu Val Lys Gly Phe Tyr Pro Ser Asp Ile Ala Val Glu Trp Glu
            595                 600                 605
Ser Asn Gly Gln Pro Glu Asn Asn Tyr Lys Thr Thr Pro Pro Val Leu
610                 615                 620
Asp Ser Asp Gly Ser Phe Phe Leu Tyr Ser Lys Leu Thr Val Asp Lys
625                 630                 635                 640
Ser Arg Trp Gln Gln Gly Asn Val Phe Ser Cys Ser Val Met His Glu
                645                 650                 655
Ala Leu His Asn His Tyr Thr Gln Lys Ser Leu Ser Leu Ser Pro
            660                 665                 670

<210> SEQ ID NO 140
<211> LENGTH: 229
<212> TYPE: PRT
<213> ORGANISM: Artificial Sequence
<220> FEATURE:
<223> OTHER INFORMATION: CD3 (V9) VH-CL

<400> SEQUENCE: 140

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
            50                  55                  60

Lys Asp Arg Phe Thr Ile Ser Val Asp Lys Ser Lys Asn Thr Ala Tyr
65                      70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Ala Ser Val Ala Ala Pro
                115                 120                 125

Ser Val Phe Ile Phe Pro Pro Ser Asp Glu Gln Leu Lys Ser Gly Thr
                130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
                180                 185                 190

Thr Leu Thr Leu Ser Lys Ala Asp Tyr Glu Lys His Lys Val Tyr Ala
                195                 200                 205

Cys Glu Val Thr His Gln Gly Leu Ser Ser Pro Val Thr Lys Ser Phe
210                 215                 220

Asn Arg Gly Glu Cys
225
```

ANTIBODIES BINDING TO HLA-A2/WT1

CROSS REFERENCE TO RELATED APPLICATIONS

This application claims priority to European Patent Application No. EP 17209205.8, filed Dec. 21, 2017, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Dec. 13, 2018, is named P34563-US_ST25.txt and is 95,833 bytes in size.

FIELD OF THE INVENTION

The present invention generally relates to antibodies that bind to HLA-A2/WT1, including bispecific antigen binding molecules e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

WT1 (Wilms tumor 1, Wilms tumor protein) is an oncogenic transcription factor involved in cell proliferation, differentiation, as well as apoptosis and organ development, whose expression in normal adult tissue is rare (Hinrichs and Restifo, Nat Biotechnol (2013) 31, 999-1008). WT1 is, however, reported to be overexpressed in several types of haematological maligancies and a wide range of solid tumors (Van Driessche et al., Oncologist (2012) 17, 250-259). WT1 is a nuclear protein, localized intracellularly. Intracellular protein can be degraded in the proteasome, processed and presented on the cell surface by major histocompatibility complex (MHC) I as T cell epitopes, and recognized by T cell receptors (TCR). As such, WT1-derived peptides such as $WT1_{RMF}$ (RMFPNAPYL) and $WT1_{VLD}$ (VLDFAPPGA) are presented in the context of HLA-A2 on the cell surface and can trigger T cell recognition.

Several approaches have been taken to exploit WT1 as target for cancer (immuno) therapy, including the development of cancer vaccines based on WT1-derived peptide and adoptive T cell transfer or WT1-specific T cells. TCR-like antibodies against the HLA-A2/$WT1_{RMF}$ complex, including bispecific derivatives thereof, have also been generated (Dao et al., Sci Transl Med (2013) 5, 176ra33; WO2012/135854; Dao et al., Nat Biotechnol (2015) 33, 1079-1086; WO 2015/070061; WO 2017/060201).

Bispecific antibodies that bind to a surface antigen on target cells and an activating T cell antigen such as CD3 on T-cells (also called herein T cell bispecific antibodies or "TCBs") hold great promise for the treatment of various cancers. The simultaneous binding of such an antibody to both of its targets will force a temporary interaction between target cell and T cell, causing crosslinking of the T cell receptor and subsequent activation of any cytotoxic T cell and subsequent lysis of the target cell. Given their potency in target cell killing, the choice of target and the specificity of the targeting antibody is of utmost importance for T cell bispecific antibodies to avoid on- and off-target toxicities. Intracellular proteins such as WT1 represent attractive targets, but are only accessible to T cell receptor (TCR)-like antibodies that bind major histocompatibility complex (MHC) presenting peptide antigens derived from the intracellular protein on the cell surface. An inherent issue of TCR-like antibodies is potential cross-reactivity with MHC molecules per se, or MHC molecules presenting peptides other than the desired one, which could compromise organ or tissue selectivity.

SUMMARY OF THE INVENTION

The present invention provides novel antibodies, including bispecific antibodies, that bind HLA-A2/WT1 and have particularly favorable properties for therapeutic purposes.

The present inventors have developed novel antibodies with unexpected, improved properties, that bind to HLA-A2/WT1. In particular, the antibody binds HLA-A2/WT1 with good affinity and remarkable specificity. Furthermore, the inventors have developed bispecific antigen binding molecules that bind to HLA-A2/WT1 and an activating T cell antigen, incorporating the novel HLA-A2/WT1 antibody and combine good efficacy and produceability with low toxicity and favorable pharmacokinetic properties.

In a first aspect the present invention provides an antibody that binds to HLA-A2/WT1, wherein the antibody comprises (i) a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;

(ii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(iii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;

0 (iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(v) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;

(vi) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;

(vii) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;

(viii) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62; or (ix) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70.

In one embodiment, the antibody comprises (i) a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8;

(ii) a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16;

(iii) a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24;

(iv) a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32;

(v) a VH comprising an amino acid sequence that is at least about 95%, 96%, 97%, 98%, 99% or 100% identical to the amino acid sequence of SEQ ID NO: 39, and a VL comprising an amino acid sequence that is at least about 95%, 96%, 97%, 98%, 99% or 100% identical to the amino acid sequence of SEQ ID NO: 40;

(vi) a VH comprising an amino acid sequence that is at least about 95%, 96%, 97%, 98%, 99% or 100% identical to the amino acid sequence of SEQ ID NO: 47, and a VL comprising an amino acid sequence that is at least about 95%, 96%, 97%, 98%, 99% or 100% identical to the amino acid sequence of SEQ ID NO: 48;

(vii) a VH comprising an amino acid sequence that is at least about 95%, 96%, 97%, 98%, 99% or 100% identical to the amino acid sequence of SEQ ID NO: 55, and a VL comprising an amino acid sequence that is at least about 95%, 96%, 97%, 98%, 99% or 100% identical to the amino acid sequence of SEQ ID NO: 56;

(viii) a VH comprising an amino acid sequence that is at least about 95%, 96%, 97%, 98%, 99% or 100% identical to the amino acid sequence of SEQ ID NO: 63, and a VL comprising an amino acid sequence that is at least about 95%, 96%, 97%, 98%, 99% or 100% identical to the amino acid sequence of SEQ ID NO: 64; or (ix) a VH comprising an amino acid sequence that is at least about 95%, 96%, 97%, 98%, 99% or 100% identical to the amino acid sequence of SEQ ID NO: 71, and a VL comprising an amino acid sequence that is at least about 95%, 96%, 97%, 98%, 99% or 100% identical to the amino acid sequence of SEQ ID NO: 72.

In one embodiment, the antibody is an IgG, particularly an IgG$_1$, antibody. In one embodiment, the antibody is a full-length antibody. In another embodiment, the antibody is an antibody fragment selected from the group of an Fv molecule, a scFv molecule, a Fab molecule, and a F(ab')$_2$ molecule. In one embodiment, the antibody is a multispecific antibody.

The invention also provides a bispecific antigen binding molecule, comprising (a) a first antigen binding moiety that binds to a first antigen, wherein the first antigen is HLA-A2/WT1 and the first antigen binding moiety comprises (i) a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;

(ii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(iii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;

(iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(v) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;

(vi) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;

(vii) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;

(viii) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62; or (ix) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70; and (b) a second antigen binding moiety which specifically binds to a second antigen.

In one embodiment, the first antigen binding moiety comprises
  (i) a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8;
  (ii) a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16;
  (iii) a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24;
  (iv) a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32;
  (v) a VH comprising an amino acid sequence that is at least about 95%, 96%, 97%, 98%, 99% or 100% identical to the amino acid sequence of SEQ ID NO: 39, and a VL comprising an amino acid sequence that is at least about 95%, 96%, 97%, 98%, 99% or 100% identical to the amino acid sequence of SEQ ID NO: 40;
  (vi) a VH comprising an amino acid sequence that is at least about 95%, 96%, 97%, 98%, 99% or 100% identical to the amino acid sequence of SEQ ID NO: 47, and a VL comprising an amino acid sequence that is at least about 95%, 96%, 97%, 98%, 99% or 100% identical to the amino acid sequence of SEQ ID NO: 48;
  (vii) a VH comprising an amino acid sequence that is at least about 95%, 96%, 97%, 98%, 99% or 100% identical to the amino acid sequence of SEQ ID NO: 55, and a VL comprising an amino acid sequence that is at least about 95%, 96%, 97%, 98%, 99% or 100% identical to the amino acid sequence of SEQ ID NO: 56;
  (viii) a VH comprising an amino acid sequence that is at least about 95%, 96%, 97%, 98%, 99% or 100% identical to the amino acid sequence of SEQ ID NO: 63, and a VL comprising an amino acid sequence that is at least about 95%, 96%, 97%, 98%, 99% or 100% identical to the amino acid sequence of SEQ ID NO: 64; or
  (ix) a VH comprising an amino acid sequence that is at least about 95%, 96%, 97%, 98%, 99% or 100% identical to the amino acid sequence of SEQ ID NO: 71, and a VL comprising an amino acid sequence that is at least about 95%, 96%, 97%, 98%, 99% or 100% identical to the amino acid sequence of SEQ ID NO: 72.

In one embodiment, the second antigen is CD3, particularly CD3ε. In one embodiment, the second antigen binding moiety comprises a VH comprising a HCDR 1 of SEQ ID NO: 115, a HCDR 2 of SEQ ID NO: 116, and a HCDR 3 of SEQ ID NO: 117, and a VL comprising a LCDR 1 of SEQ ID NO: 118, a LCDR 2 of SEQ ID NO: 119 and a LCDR 3 of SEQ ID NO: 120. In one embodiment, the VH of the second antigen binding moiety comprises an amino acid sequence that is at least about 95%, 96%, 97%, 98%, 99% or 100% identical to the amino acid sequence of SEQ ID NO: 121, and the VL of the second antigen binding moiety comprises an amino acid sequence that is at least about 95%, 96%, 97%, 98%, 99% or 100% identical to the amino acid sequence of SEQ ID NO: 122. In one embodiment, the first and/or the second antigen binding moiety is a Fab molecule. In one embodiment, the second antigen binding moiety is a Fab molecule wherein the variable domains VL and VH or the constant domains CL and CH1, particularly the variable domains VL and VH, of the Fab light chain and the Fab heavy chain are replaced by each other.

In one embodiment, the first antigen binding moiety is a Fab molecule wherein in the constant domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index). In one embodiment, the first and the second antigen binding moiety are fused to each other, optionally via a peptide linker. In one embodiment, the first and the second antigen binding moiety are each a Fab molecule and either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety. In one embodiment, the bispecific antigen binding molecule comprises a third antigen binding moiety. In one embodiment, the third antigen moiety is identical to the first antigen binding moiety. In one embodiment, the bispecific antigen binding molecule comprises an Fc domain composed of a first and a second subunit. In one embodiment, the first, the second and, where present, the third antigen binding moiety are each a Fab molecule; and either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and the third antigen binding moiety, where present, is fused at the C-terminus of the Fab heavy chain to the N-terminus of the second subunit of the Fc domain. In one embodiment, the Fc domain is an IgG, particularly an IgG$_1$, Fc domain. In one embodiment, the Fc domain is a human Fc domain. In one embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. In one embodiment, the Fc domain comprises one or more amino acid substitution that reduces binding to an Fc receptor and/or effector function.

According to another aspect of the invention there is provided one or more isolated polynucleotide(s) encoding an antibody or bispecific antigen binding molecule of the invention. The invention further provides one or more expression vector(s) comprising the isolated polynucleotide(s) of the invention, and a host cell comprising the isolated polynucleotide(s) or the expression vector(s) of the invention. In some embodiments the host cell is a eukaryotic cell, particularly a mammalian cell.

In another aspect is provided a method of producing an antibody that binds to HLA-A2/WT1, comprising the steps of a) culturing the host cell of the invention under conditions suitable for the expression of the antibody and b) recovering the antibody. The invention also encompasses an antibody that binds to HLA-A2/WT1 produced by the method of the invention.

The invention further provides a pharmaceutical composition comprising the antibody or bispecific antigen binding molecule of the invention and a pharmaceutically acceptable carrier. Also encompassed by the invention are methods of using the antibody, bispecific antigen binding molecule and pharmaceutical composition of the invention. In one aspect the invention provides an antibody, bispecific antigen binding molecule or pharmaceutical composition according to the invention for use as a medicament. In one aspect is provided an antibody, bispecific antigen binding molecule or pharmaceutical composition according to the invention for use in the treatment of a disease. In a specific embodiment the disease is cancer.

Also provided is the use of an antibody or bispecific antigen binding molecule according to the invention in the manufacture of a medicament for the treatment of a disease; as well as a method of treating a disease in an individual, comprising administering to said individual a therapeutically effective amount of a composition comprising the antibody or bispecific antigen binding molecule according to the invention in a pharmaceutically acceptable form. In a specific embodiment the disease is cancer. In any of the above embodiments the individual preferably is a mammal, particularly a human.

BRIEF DESCRIPTION OF THE DRAWINGS

FIGS. 4A-H. Activation of T cells by HLA-A2/WT1 x CD3 bispecific antibodies (TCBs) upon binding to peptide-pulsed T2 cells (NFAT reporter assay). (A) 11D06-TCB, (B) 33H09-TCB, (C) 11B09-TCB, (D) 13B04-TCB, (E) ESK1-TCB, (F) 5E11-TCB. (G) 5C01-TCB, (H) DP47GS-TCB.

FIGS. 6A-G. Killing of HLA-A2+WT1+ tumor cell lines mediated by HLA-A2/WT1 x CD3 bispecific antibodies (TCBs). (A) Overview of cell lines. (B-E) Killing of cell lines by (B) 11D06-TCB, (C) 33H09-TCB, (D) 11B09-TCB, (E) 13B04-TCB. (F) Killing of SKM-1 cells by different TCBs. (G) Killing of BJAB cells by different TCBs.

FIG. 16. Interface and interaction matrix of 5C01 Fab residues (rows) with HLA-A2/WT1VLD pMHC residues (columns). N=near/neighboring, H=H-bond, Pi=Pi interactions, SB=salt bridge. Interface residues defined as residues that undergo a change in solvent-accessible surface area in absence/presence of the interaction partner.

FIG. 18. Interface and interaction matrix of 11D06 Fab residues (rows) with HLA-A2/WT1$_{RMF}$ pMHC residues (columns). N=near/neighboring, H=H-bond, Pi=Pi interactions, SB=salt bridge. Interface residues defined as residues that undergo a change in solvent-accessible surface area in absence/presence of the interaction partner.

Figure 20:
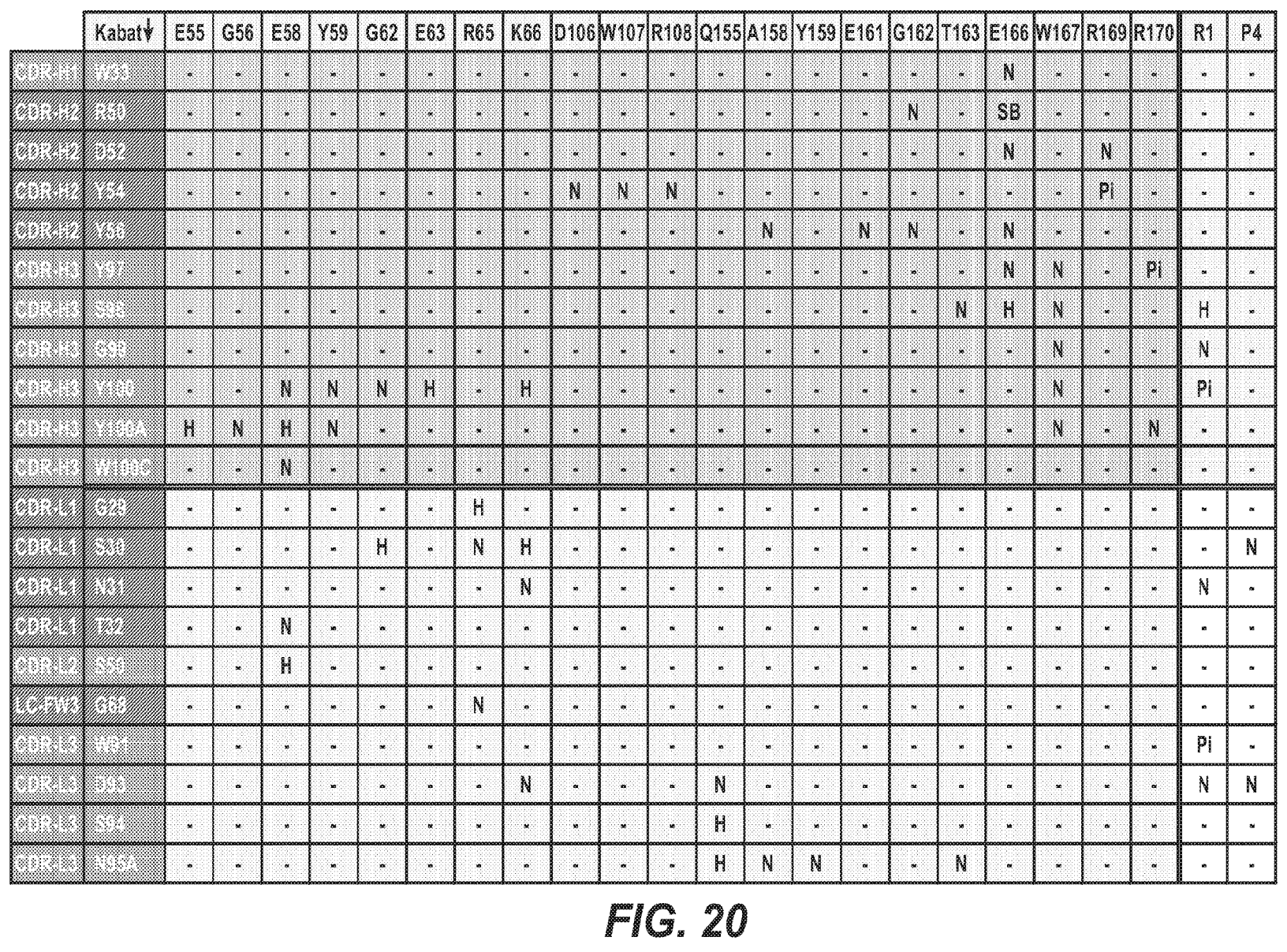

FIG. 20. Interface and interaction matrix of ESK1 Fab residues (rows) with HLA-A2/WT1$_{RMF}$ pMHC residues (columns). N=near/neighboring, H=H-bond, Pi=Pi interactions, SB=salt bridge. Interface residues defined as residues that undergo a change in solvent-accessible surface area in absence/presence of the interaction partner.

FIGS. 25A-D. Efficacy study with HLA-A2/WT1 x CD3 bispecific antibody 11D06-TCB (V9) in SKM-1 xenograft in humanized mice. (A) Tumor growth kinetics (mean) in all treatment groups. (B) Single tumor growth kinetics in the vehicle group. (C) Single tumor growth kinetics in the 11D06-TCB (V9) group. (D) Statistics. Calculations based on day 48 (vehicle as control group). Tumor growth inhibition (TGI): TGI>100→tumor regression, TGI=100→tumor stasis. Treatment to control ratio (TCR): TCR=1→no effect, TCR=0→complete regression.

DETAILED DESCRIPTION OF THE INVENTION

Definitions

Figure 1X:
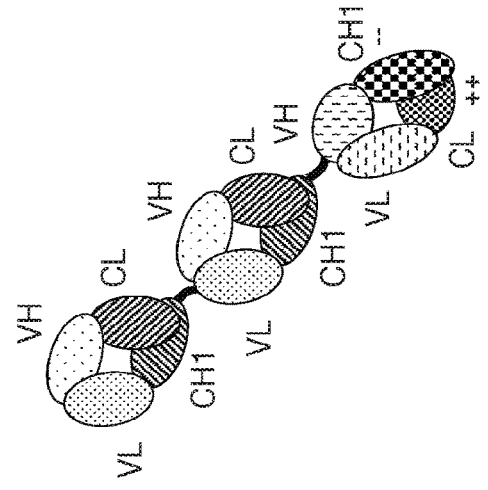
FIGS. 1A-Z. Exemplary configurations of the bispecific antigen binding molecules of the invention. (A, D) Illustration of the "1+1 CrossMab" molecule. (B, E) Illustration of the "2+1 IgG Crossfab" molecule with alternative order of Crossfab and Fab components ("inverted"). (C, F) Illustration of the "2+1 IgG Crossfab" molecule. (G, K) Illustration of the "1+1 IgG Crossfab" molecule with alternative order of Crossfab and Fab components ("inverted"). (H, L) Illustration of the "1+1 IgG Crossfab" molecule. (I, M) Illustration of the "2+1 IgG Crossfab" molecule with two CrossFabs. (J, N) Illustration of the "2+1 IgG Crossfab" molecule with two CrossFabs and alternative order of Crossfab and Fab components ("inverted"). (O, S) Illustration of the "Fab-Crossfab" molecule. (P, T) Illustration of the "Crossfab-Fab" molecule. (Q, U) Illustration of the "(Fab)$_2$-Crossfab" molecule. (R, V) Illustration of the "Crossfab-(Fab)$_2$" molecule. (W, Y) Illustration of the "Fab-(Crossfab)$_2$" molecule. (X, Z) Illustration of the "(Crossfab)$_2$-Fab" molecule. Black dot: optional modification in the Fc domain promoting heterodimerization. ++, −−: amino acids of opposite charges optionally introduced in the CH1 and CL domains. Crossfab molecules are depicted as comprising an exchange of VH and VL regions, but may—in embodiments wherein no charge modifications are introduced in CH1 and CL domains—alternatively comprise an exchange of the CH1 and CL domains.

Terms are used herein as generally used in the art, unless otherwise defined in the following. As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" or "antigen" refers to a site on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM).

The term "epitope" denotes the site on an antigen, either proteinaceous or non-proteinaceous, to which an antigen binding moiety binds. Epitopes can be formed both from contiguous amino acid stretches (linear epitope) or comprise non-contiguous amino acids (conformational epitope), e.g. coming in spatial proximity due to the folding of the antigen, i.e. by the tertiary folding of a proteinaceous antigen. Linear epitopes are typically still bound by an antigen binding moiety after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation. "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no. P07766 (version 189), or NCBI (www.ncbi.nlm.nih.gov/) RefSeq NP_000724.1. See also SEQ ID NO: 107. The amino acid sequence of cynomolgus [Macaca fascicularis] CD3ε is shown in NCBI GenBank no. BAB71849.1. See also SEQ ID NO: 108.

"WT1", also known as "Wilms tumor 1" or "Wilms tumor protein", refers to any native WT1 from any vertebrate source, including mammals such as primates (e.g. humans), non-human primates (e.g. cynomolgus monkeys) and rodents (e.g. mice and rats), unless otherwise indicated. The term encompasses "full-length," unprocessed WT1 as well as any form of WT1 that results from processing in the cell. The term also encompasses naturally occurring variants of WT1, e.g., splice variants or allelic variants. In one embodiment, WT1 is human WT1, particularly the protein of SEQ ID NO: 106. Human WT1 is described in UniProt (www.uniprot.org) accession no. P19544 (entry version 215), and an amino acid sequence of human WT1 is also shown in SEQ ID NO: 106.

By "VLD", "VLD peptide" or "WT1$_{VLD}$" is meant the WT1 derived peptide having the amino acid sequence VLD-FAPPGA (SEQ ID NO: 77; position 37-45 of the WT1 protein of SEQ ID NO: 106). By "RMF", "RMF peptide" or "WT1$_{RMF}$" is meant the WT1 derived peptide having the amino acid sequence RMFRNAPYL (SEQ ID NO: 78; position 126-134 of the WT1 protein of SEQ ID NO: 106).

"HLA-A2", "HLA-A*02", "HLA-A02", or "HLA-A*2" (used interchangeably) refers to a human leukocyte antigen serotype in the HLA-A serotype group. The HLA-A2 protein (encoded by the respective HLA gene) constitutes the α chain of the respective class I MHC (major histocompatibility complex) protein, which further comprises a β2 microglobulin subunit. A specific HLA-A2 protein is HLA-A201 (also referred to as HLA-A0201, HLA-A02.01, or HLA-A*02:01). In specific embodiments, the HLA-A2 protein described herein is HLA-A201 "HLA-A2/WT1" refers to a complex of a HLA-A2 molecule and a WT1 derived peptide (also referred to herein as a "WT1 peptide"), specifically the RMF or VLD peptide ("HLA-A2/WT1$_{RMF}$" and "HLA-A2/WT1$_{VLD}$", respectively). The antibody or bispecific antigen binding molecule of the present invention specifically binds to either the HLA-A2/WT1$_{RMF}$ or the HLA-A2/WT1$_{VLD}$ complex.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed e.g. on a BIAcore instrument) (Liljeblad et al., Glyco J 17, 323-329 (2000)), and traditional binding assays (Heeley, Endocr Res 28, 217-229 (2002)). Suitable assays for determining the specificity of the antibody and bispecific antigen binding molecule of the present invention are described herein, e.g. in Examples 4, 9 and 10 hereinbelow. In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3, particularly the epsilon subunit of CD3 (see UniProt no. P07766 (version 189), NCBI RefSeq no. NP_000724.1, SEQ ID NO: 107 for the human sequence; or UniProt no. Q95LI5 (version 49), NCBI GenBank no. BAB71849.1, SEQ ID NO: 108 for the cynomolgus [Macaca fascicularis] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "target cell antigen" as used herein refers to an antigenic determinant presented on the surface of a target cell, for example a cell in a tumor such as a cancer cell or a cell of the tumor stroma. In a particular embodiment, the target cell antigen is HLA-A2/WT1, particularly HLA-A2/WT1$_{RMF}$ or HLA-A2/WT1$_{VLD}$, most particularly HLA-A2/WT1$_{RMF}$.

As used herein, the terms "first", "second" or "third" with respect to Fab molecules etc., are used for convenience of distinguishing when there is more than one of each type of moiety. Use of these terms is not intended to confer a specific order or orientation of the bispecific antigen binding molecule unless explicitly so stated.

By "fused" is meant that the components (e.g. a Fab molecule and an Fc domain subunit) are linked by peptide bonds, either directly or via one or more peptide linkers.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH—CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment, i.e. that is not in its natural milieu. No particular level of purification is required. For example, an isolated antibody can be removed from its native or natural environment. Recombinantly produced antibodies expressed in host cells are considered isolated for the purpose of the invention, as are native or recombinant antibodies which have been separated, fractionated, or partially or substantially purified by any suitable technique. As such, the antibodies and bispecific antigen binding molecules of the present invention are isolated. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007). The terms "full length antibody," "intact antibody," and "whole antibody" are used herein interchangeably to refer to an antibody having a structure substantially similar to a native antibody structure.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869, 046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity. As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, MD (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The term "hypervariable region" or "HVR", as used herein, refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs; three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following order in VH (or VL): FR1-H1(L1)-FR2-H2(L2)-FR3-H3(L3)-FR4.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some embodiments, some FR residues in a humanized antibody are substituted with corresponding residues from a non-human antibody (e.g., the antibody from which the HVR residues are derived), e.g., to restore or improve antibody specificity or affinity. A "humanized form" of an antibody, e.g. of a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain embodiments, a human antibody is derived from a non-human transgenic mammal, for example a mouse, a rat, or a rabbit. In certain embodiments, a human antibody is derived from a hybridoma cell line. Antibodies or antibody fragments isolated from human antibody libraries are also considered human antibodies or human antibody fragments herein.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain.

However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in an antibody or bispecific antigen binding molecule according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in an antibody or bispecific antigen binding molecule according to the invention, comprises an additional C-terminal glycine residue (G446, numbering according to EU index of Kabat). Compositions of the invention, such as the pharmaceutical compositions described herein, comprise a population of antibodies or bispecific antigen binding molecules of the invention. The population of antibodies or bispecific antigen binding molecules may comprise molecules having a full-length heavy chain and molecules having a cleaved variant heavy chain. The population of antibodies or bispecific antigen binding molecules may consist of a mixture of molecules having a full-length heavy chain and molecules having a cleaved variant heavy chain, wherein at least 50%, at least 60%, at least 70%, at least 80% or at least 90% of the antibodies or bispecific antigen binding molecules have a cleaved variant heavy chain. In one embodiment of the invention a composition comprising a population of antibodies or bispecific antigen binding molecules of the invention comprises an antibody or bispecific antigen binding molecule comprising a heavy chain including a subunit of an Fc domain as specified herein with an additional C-terminal glycine-lysine dipeptide (G446 and K447, numbering according to EU index of Kabat). In one embodiment of the invention a composition comprising a population of antibodies or bispecific antigen binding molecules of the invention comprises an antibody or bispecific antigen binding molecule comprising a heavy chain including a subunit of an Fc domain as specified herein with an additional C-terminal glycine residue (G446, numbering according to EU index of Kabat). In one embodiment of the invention such a composition comprises a population of antibodies or bispecific antigen binding molecules comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, G329, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36, and is publicly available from http://fasta.bioch.virginia.edu/fasta_www2/fasta_down.shtml. Alternatively, a public server accessible at http://fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

"Isolated polynucleotide (or nucleic acid) encoding [e.g. an antibody or bispecific antigen binding molecule of the invention]" refers to one or more polynucleotide molecules encoding antibody heavy and light chains (or fragments thereof), including such polynucleotide molecule(s) in a single vector or separate vectors, and such nucleic acid molecule(s) present at one or more locations in a host cell.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette comprises polynucleotide sequences that encode antibodies or bispecific antigen binding molecules of the invention or fragments thereof.

The term "vector" or "expression vector" refers to a DNA molecule that is used to introduce and direct the expression of a specific gene to which it is operably associated in a cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the cell, the ribonucleic acid molecule or protein that is encoded by the gene is produced by the cellular transcription and/or translation machinery. In one embodiment, the expression vector of the invention comprises an expression cassette that comprises polynucleotide sequences that encode antibodies or bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies or bispecific antigen binding molecules of the present invention. Host cells include cultured cells, e.g. mammalian cultured cells, such as HEK cells, CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative. As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The invention provides antibodies and bispecific antigen binding molecules that bind HLA-A2/WT1, particularly HLA-A2/WT1$_{RMF}$ or HLA-A2/WT1$_{VLD}$, most particularly HLA-A2/WT1$_{RMF}$, and have good affinity and specificity as required for therapeutic purposes. In addition, the molecules have also other favorable properties for therapeutic application, e.g. with respect to efficacy and/or safety as well as produceability.

HLA-A2/WT1 Antibody

The present inventors have developed novel antibodies that bind to HLA-A2/WT1 with particularly good affinity and specificity. For instance, as shown in the Examples, the inventors have developed antibodies that are remarkably selective for HLA-A2/WT1 (specifically HLA-A2/WT1$_{RMF}$) over complexes of HLA-A2 with other, structurally similar peptides.

Thus, in certain aspects, the invention provides an antibody that binds to HLA-A2/WT1 and has any of the following features.

In one embodiment, the antibody has a monovalent affinity to HLA-A2/WT1 with a dissociation constant ($K_D$) of lower than about 100 nM, lower than about 75 nM, or lower than about 50 nM. In one embodiment, the antibody has a bivalent affinity (avidity) to HLA-A2/WT1 with an apparent $K_D$ of lower than about 1.5 nM, lower than about 1 nM, or lower than about 0.75 nM. In one embodiment, the bivalent affinity (avidity) of the antibody is at 10-fold, at least 20-fold, at least 50-fold, or at least 100-fold higher than the monovalent affinity of the antibody in terms of (apparent) $K_D$.

In one embodiment, the affinity is determined by Surface Plasmon Resonance (SPR) at 25° C. In one embodiment, the monovalent affinity is determined in a Fab molecule format of the antibody. In one embodiment, the bivalent affinity (avidity) is determined in an IgG molecule format of the antibody.

In a specific embodiment, the affinity of the antibody is determined as follows: Experiments are performed at 25° C. using PBST as running buffer (10 mM PBS, PH 7.4 and 0.005% (v/v) Tween 20). A ProteOn XPR36 biosensor equipped with GLC and GLM sensor chips and coupling reagents (10 mM sodium acetate pH 4.5, sulfo-N-hydroxysuccinimide [sulfo-NHS], 1-ethyl-3-(3-dimethylaminpropyl)-carbodiimide hydrochloride [EDC] and ethanolamine) from BioRad Inc. (Hercules, CA) is used. Immobilizations are performed at 30 µl/min on a GLM chip. pAb (goat) anti human IgG, F(ab)2 specific antibody (Jackson ImmunoResearch) is coupled in vertical direction using a standard amine-coupling procedure: all six ligand channels are activated for 5 min with a mixture of EDC (200 mM) and sulfo-NHS (50 mM). Immediately after the surfaces are activated, pAb (goat) anti human IgG, F(ab)2 specific antibody (50 µg/ml, 10 mM sodium acetate, pH 5) is injected across all six channels for 5 min. Finally, channels are blocked with a 5 min injection of 1 M ethanolamine-HCl (pH 8.5). The Fab variants are captured from *E. coli* supernatants by simultaneous injection along five of the separate horizontal channels (30 µl/min) for 5 min. Conditioned medium is injected along the sixth channel to provide an 'in-line' blank for double referencing purposes. One-shot kinetic measurements are performed by injection of a dilution series of HLA-WT1 (e.g. HLA-A2/WT1$_{RMF}$ or HLA-A2/WT1$_{VLD}$) (100, 50, 25, 12.5, 6.25, 0 nM, 50 µl/min) for 2 min along the vertical channels. Dissociation is monitored for 3 min. Kinetic data is analyzed in ProteOn Manager v. 2.1. Processing of the reaction spot data involves applying an interspot-reference and a double-reference step using an inline buffer blank (Myszka, J Mol Recognit (1999) 12, 279-284). The processed data from replicate one-shot injections are fit to a simple 1:1 Langmuir binding model without mass transport (O'Shannessy et al., Anal Biochem (1993) 212, 457-468).

The antibody of the invention specifically binds to HLA-A2/WT1 (i.e. a complex of a HLA-A2 molecule and a WT1-derived peptide). In some embodiments, the antibody of the invention specifically binds to HLA-A2/WT1RMF (i.e. a complex of a HLA-A2 molecule and the WT1$_{RMF}$ peptide). In a more specific embodiment, the antibody specifically binds to HLA-A201/WT1$_{RMF}$ (i.e. a complex of a HLA-A201 molecule and the WT1$_{RMF}$ peptide). Antibodies of the invention that bind to HLA-A2/WT1$_{RMF}$ include antibodies 11D06, 33H09 and 5E11 described herein. In other embodiments, the antibody of the invention specifically binds to HLA-A2/WT1$_{VLD}$ (i.e. a complex of a HLA-A2 molecule and the WT1$_{VLD}$ peptide). In a more specific embodiment, the antibody specifically binds to HLA-A201/WT1$_{VLD}$ (i.e. a complex of a HLA-A201 molecule and the WT1$_{VLD}$ peptide). Antibodies of the invention that bind to HLA-A2/WT1$_{VLD}$ include antibodies 11B09, 13B04 and 5C01 described herein.

In one embodiment, specific binding of the antibody is determined by flow cytometry using HLA-A2/peptide (e.g. WT1$_{RMF}$ or WT1$_{VLD}$ peptide)-expressing cells, particularly peptide-pulsed T2 cells.

In a specific embodiment, specific binding of the antibody is determined as follows:

T2 cells are prepared as a cell suspension at $10^6$ cells/ml in IMDM medium (Gibco by Life Technologies, Cat No. 31980-048), supplemented with 10% FBS (Gibco, Cat No. 16140-071)+1% Penicillin-Streptomycin (Gibco, Cat No. 15070-063) (complete medium). Cells are kept in a total volume of 10 ml in a tube, and incubated with 10 µl of peptide (e.g. WT1 VLD peptide (SEQ ID NO: 77), or RMF peptide (SEQ ID NO: 78)) at $10^{-2}$ M (final concentration of the peptide: $10^{-5}$M) for 2 hours at 37° C. with 5% $CO_2$. After washing, cells are suspended in cold PBS and incubated with titrated concentration of antibody in IgG format (e.g. 10 µg/ml to 0.00064 µg/ml) for 1 hour at 4° C., followed by incubation with a secondary anti-human IgG-Fc phycoerythrin (PE)-conjugated antibody (Jackson Laboratories, Cat No. 109-116-098) for 30 min. Cells are acquired on FACS LSR II (BD), and data are presented as mean fluorescence intensity (MFI) of PE in Graphpad Prism.

In one embodiment, the antibody of the invention does not significantly bind to HLA-A2 alone (i.e. without a peptide) or HLA-A2 with a peptide other than a WT1-derived peptide such as WT1$_{RMF}$ or WT1$_{VLD}$.

In one embodiment, the antibody does not significantly bind to HLA-A2 in the absence of a WT1-derived peptide, particularly WT1$_{RMF}$ or WT1$_{VLD}$. In one embodiment, the antibody binds to HLA-A2/WT1 (specifically HLA-A2/WT1$_{RMF}$ Or HLA-A2/WT1$_{VLD}$) with an $EC_{50}$ that is at least 5, at least 10, at least 15, at least 20, at least 25, at least 50, at least 75 or at least 100 times lower than the EC50 for binding to HLA-A2 in the absence of a WT1-derived peptide (specifically WT1$_{RMF}$ or WT1$_{VLD}$).

In one embodiment, the antibody binds to HLA-A2/WT1 (specifically HLA-A2/WT1$_{RMF}$ or HLA-A2/WT1$_{VLD}$), but does not significantly bind to HLA-A2 with a peptide selected from the peptides in Table 5 (the peptides of SEQ ID NOs 79-105). In one embodiment, the antibody binds to HLA-A2/WT1 (specifically HLA-A2/WT1$_{RMF}$ or HLA-A2/WT1$_{VLD}$), but does not significantly bind to HLA-A2 with any of the peptides in Table 5 (the peptides of SEQ ID NOs 79-105).

In one embodiment, the antibody binds to HLA-A2/WT1 (specifically HLA-A2/WT1$_{RMF}$ or HLA-A2/WT1$_{VLD}$) with an EC50 that is at least 5, at least 10, at least 15, at least 20, at least 25, at least 50, at least 75 or at least 100 times lower than the EC50 for binding to HLA-A2 with a peptide selected from the peptides in Table 5 (the peptides of SEQ ID NOs 79-105). In one embodiment, the antibody binds to HLA-A2/WT1 (specifically HLA-A2/WT1$_{RMF}$ or HLA-A2/WT1$_{VLD}$) with an EC50 that is at least 5, at least 10, at least 15, at least 20, at least 25, at least 50, at least 75 or at least 100 times lower than the EC50 for binding to HLA-A2 with any of the peptides in Table 5 (the peptides of SEQ ID NOs 79-105).

In one embodiment, the EC50 is determined flow cytometry using HLA-A2/peptide (e.g. WT1$_{RMF}$ or WT1$_{VLD}$ peptide)-expressing cells, particularly peptide-pulsed T2 cells.

In a specific embodiment, the EC50 is determined as follows:

T2 cells (ATCC, Cat. No. CRL-1992) are prepared as a cell suspension at $10^6$ cells/ml in IMDM medium (Gibco by Life Technologies, Cat No. 31980-048), supplemented with 10% FBS (Gibco, Cat No. 16140-071)+1% Penicillin-Streptomycin (Gibco, Cat No. 15070-063) (complete medium). Cells are kept in a total volume of 10 ml in a tube, and incubated with 10 µl of peptide (e.g. WT1 VLD peptide (SEQ ID NO: 77), or RMF peptide (SEQ ID NO: 78)) at $10^{-2}$ M (final concentration of the peptide: $10^{-5}$ M) for 2 hours at 37° C. with 5% $CO_2$. After washing, cells are suspended in cold PBS and incubated with titrated concentration of antibody in IgG format (e.g. 10 µg/ml to 0.00064 µg/ml) for 1 hour at 4° C., followed by incubation with a secondary anti-human IgG-Fc phycoerythrin (PE)-conjugated antibody (Jackson Laboratories, Cat No. 109-116-098) for 30 min. Cells are acquired on FACS LSR II (BD), and data are presented as mean fluorescence intensity (MFI) of PE in Graphpad Prism. EC50 values are calculated in Microsoft® Excel using the XLfit® add-on (ID Business Solutions, Guildford, UK).

In one aspect, the invention provides an antibody that competes for binding to HLA-A2/WT1, particularly HLA-A201/WT1$_{RMF}$, with an antibody comprising a heavy chain variable region (VH) sequence of SEQ ID NO: 7, and a light chain variable region (VL) sequence of SEQ ID NO: 8. Competition assays may be used to identify an antibody that competes with the antibody comprising the VH sequence of SEQ ID NO: 7 and the VL sequence of SEQ ID NO: 8 (the reference antibody) for binding to HLA-A2/WT1. In certain embodiments, such a competing antibody binds to the same epitope (e.g., a linear or a conformational epitope) that is bound by the reference antibody. Detailed exemplary methods for mapping an epitope to which an antibody binds are provided in Morris (1996) "Epitope Mapping Protocols", in Methods in Molecular Biology vol. 66 (Humana Press, Totowa, NJ) and are also described in the Examples herein. In an exemplary competition assay, immobilized HLA-A2/WT1 is incubated in a solution comprising a first labeled antibody that binds to HLA-A2/WT1 (e.g., the antibody comprising the VH sequence of SEQ ID NO: 7 and the VL sequence of SEQ ID NO: 8) and a second unlabeled antibody that is being tested for its ability to compete with the first antibody for binding to HLA-A2/WT1. The second antibody may be present in a hybridoma supernatant. As a control, immobilized HLA-A2/WT1 is incubated in a solution comprising the first labeled antibody but not the second unlabeled antibody. After incubation under conditions permissive for binding of the first antibody to HLA-A2/WT1, excess unbound antibody is removed, and the amount of label associated with immobilized HLA-A2/WT1 is measured. If the amount of label associated with immobilized HLA-A2/WT1 is substantially reduced in the test sample relative to the control sample, then that indicates that the second antibody is competing with the first antibody for binding to HLA-A2/WT1. See Harlow and Lane (1988) *Antibodies: A Laboratory Manual* ch. 14 (Cold Spring Harbor Laboratory, Cold Spring Harbor, NY).

In one aspect, the invention provides an antibody that binds to the same epitope of HLA-A2/WT1, particularly HLA-A2/WT1$_{RMF}$, as an antibody comprising a heavy chain variable region (VH) sequence of SEQ ID NO: 7, and a light chain variable region (VL) sequence of SEQ ID NO: 8. Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies", Harlow and Lane (Cold Spring Harbor Press, Cold Spring Harb., NY).

Antigen Structure-based Antibody Profiling (ASAP), also known as Modification-Assisted Profiling (MAP), allows to bin a multitude of monoclonal antibodies specifically binding to HLA-A2/WT1 based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

Also competitive binding can be used to easily determine whether an antibody binds to the same epitope of HLA-A2/WT1 as, or competes for binding with, a reference anti HLA-A2/WT1 antibody. For example, an "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Also for example, to determine if an antibody binds to the same epitope of HLA-A2/WT1 as a reference antibody, the reference antibody is allowed to bind to HLA-A2/WT1 under saturating conditions. After removal of the excess of the reference antibody, the ability of an anti HLA-A2/WT1 antibody in question to bind to HLA-A2/WT1 is assessed. If the antibody is able to bind to HLA-A2/WT1 after saturation binding of the reference antibody, it can be concluded that the antibody in question binds to a different epitope than the reference antibody. But, if the antibody in question is not able to bind to HLA-A2/WT1 after saturation binding of the reference antibody, then the antibody in question may bind to the same epitope as the epitope bound by the reference antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to HLA-A2/WT1, then it can be concluded that the anti-HLA-A2/WT1 antibody in question and the reference anti-HLA-A2/WT1 antibody compete for binding to HLA-A2/WT1.

In some embodiments two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., Cancer Res. 50 (1990) 1495-1502).

In some embodiments two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

In one aspect, the invention provides an antibody that binds to HLA-A2/WT1, wherein the antibody binds to an epitope of HLA-A2/WT1, particularly HLA-A2/WT1$_{RMF}$, according to any of the following embodiments. The epitope may particularly be determined by crystal structure analysis.

In one embodiment, said epitope comprises at least three amino acid residues of the WT1 peptide, particularly the WT1$_{RMF}$ peptide shown in SEQ ID NO: 78.

In one embodiment, said epitope comprises at least four amino acid residues of the WT1 peptide, particularly the WT1$_{RMF}$ peptide shown in SEQ ID NO: 78.

In one embodiment, said epitope comprises at least five amino acid residues of the WT1 peptide, particularly the WT1$_{RMF}$ peptide shown in SEQ ID NO: 78.

In one embodiment, said epitope comprises at least six amino acid residues of the WT1 peptide, particularly the WT1$_{RMF}$ peptide shown in SEQ ID NO: 78.

In one embodiment, said epitope comprises at least three amino acid residues of the WT1 peptide, wherein said at least three amino acid residues are selected from the amino acid residues corresponding to amino acid residues R1, M2, P4, N5, A6 and Y8 of the WT1$_{RMF}$ peptide shown in SEQ ID NO: 78.

In one embodiment, said epitope comprises at least four amino acid residues of the WT1 peptide, wherein said at least four amino acid residues are selected from the amino acid residues corresponding to amino acid residues R1, M2, P4, N5, A6 and Y8 of the WT1$_{RMF}$ peptide shown in SEQ ID NO: 78.

In one embodiment, said epitope comprises at least five amino acid residues of the WT1 peptide, wherein said at least five amino acid residues are selected from the amino acid residues corresponding to amino acid residues R1, M2, P4, N5, A6 and Y8 of the WT1$_{RMF}$ peptide shown in SEQ ID NO: 78.

In one embodiment, said epitope comprises at least six amino acid residues of the WT1 peptide, wherein said at least six amino acid residues are selected from the amino acid residues corresponding to amino acid residues R1, M2, P4, N5, A6 and Y8 of the WT1$_{RMF}$ peptide shown in SEQ ID NO: 78.

In one embodiment, said epitope comprises amino acid residues corresponding to amino acid residues R1, N5 and A6 of the WT1$_{RMF}$ peptide shown in SEQ ID NO: 78.

In one embodiment, said epitope comprises amino acid residues corresponding to amino acid residues R1, M2, P4, N5, A6 and Y8 of the WT1$_{RMF}$ peptide shown in SEQ ID NO: 78.

In one embodiment, said epitope comprises amino acid residues corresponding to amino acid residues E58, R65, K66 and Q155 of the HLA-A2 sequence shown in SEQ ID NO: 138.

In one embodiment, said epitope comprises amino acid residues corresponding to amino acid residues E58, R65, K66 and Q155 of the HLA-A2 sequence shown in SEQ ID NO: 138, and amino acid residues corresponding to amino acid residues R1, N5 and A6 of the WT1$_{RMF}$ peptide shown in SEQ ID NO: 78.

In one embodiment, said epitope comprises amino acid residues corresponding to amino acid residues E58, R65, K66, Q155 and D61 of the HLA-A2 sequence shown in SEQ ID NO: 138. In one embodiment, said epitope comprises amino acid residues corresponding to amino acid residues E58, R65, K66, Q155 and A69 of the HLA-A2 sequence shown in SEQ ID NO: 138. In one embodiment, said epitope comprises amino acid residues corresponding to amino acid residues E58, R65, K66, Q155 and A150 of the HLA-A2 sequence shown in SEQ ID NO: 138.

In one embodiment, said epitope comprises amino acid residues corresponding to amino acid residues E58, R65, K66, Q155, and one or more of D61, A69 and A150 of the HLA-A2 sequence shown in SEQ ID NO: 138, and amino acid residues corresponding to amino acid residues R1, M2, P4, N5, A6 and/or Y8 of the WT1$_{RMF}$ peptide shown in SEQ ID NO: 78.

In one embodiment, said epitope comprises amino acid residues corresponding to amino acid residues E58, D61, G62, R65, K66, A69, A150, Q155, A158, T163, E166, W167 and R170 of the HLA-A2 sequence shown in SEQ ID NO: 138.

In one embodiment, said epitope comprises amino acid residues corresponding to amino acid residues E58, D61, G62, R65, K66, A69, A150, Q155, A158, T163, E166, W167 and R170 of the HLA-A2 sequence shown in SEQ ID NO: 138, and amino acid residues corresponding to amino acid residues R1, M2, P4, N5, A6 and/or Y8 of the WT1$_{RMF}$ peptide shown in SEQ ID NO: 78.

In one embodiment, said epitope does not comprise amino acid residues corresponding to amino acid residues G56, D106, W107, R108, E161, G162 and/or R169 of the HLA-A2 sequence shown in SEQ ID NO: 138.

In a further aspect the present invention provides an antibody that binds to HLA-A2/WT1, wherein the antibody comprises (i) a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;

(ii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(iii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;

(iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(v) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;

(vi) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;

(vii) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;

(viii) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62; or (ix) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70.

In a particular embodiment, the antibody comprises a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6.

In another embodiment, the antibody comprises a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14.

In a further embodiment, the antibody comprises a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22.

In still a further embodiment, the antibody comprises a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30.

In some embodiments, the antibody is a human antibody. In one embodiment, the VH is a human VH and/or the VL is a human VL. In one embodiment, the antibody comprises CDRs as in any of the above embodiments, and further comprises a human framework, e.g. a human immunoglobulin framework.

In one embodiment, the antibody comprises (i) a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8;

(ii) a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16;

(iii) a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24;

(iv) a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32;

(v) a VH comprising an amino acid sequence that is at least about 95%, 96%, 97%, 98%, 99% or 100% identical to the amino acid sequence of SEQ ID NO: 39, and a VL comprising an amino acid sequence that is at least about 95%, 96%, 97%, 98%, 99% or 100% identical to the amino acid sequence of SEQ ID NO: 40;

(vi) a VH comprising an amino acid sequence that is at least about 95%, 96%, 97%, 98%, 99% or 100% identical to the amino acid sequence of SEQ ID NO: 47, and a VL comprising an amino acid sequence that is at least about 95%, 96%, 97%, 98%, 99% or 100% identical to the amino acid sequence of SEQ ID NO: 48;

(vii) a VH comprising an amino acid sequence that is at least about 95%, 96%, 97%, 98%, 99% or 100% identical to the amino acid sequence of SEQ ID NO: 55, and a VL comprising an amino acid sequence that is at least about 95%, 96%, 97%, 98%, 99% or 100% identical to the amino acid sequence of SEQ ID NO: 56;

(viii) a VH comprising an amino acid sequence that is at least about 95%, 96%, 97%, 98%, 99% or 100% identical to the amino acid sequence of SEQ ID NO: 63, and a VL comprising an amino acid sequence that is at least about 95%, 96%, 97%, 98%, 99% or 100% identical to the amino acid sequence of SEQ ID NO: 64; or (ix) a VH comprising an amino acid sequence that is at least about 95%, 96%, 97%, 98%, 99% or 100% identical to the amino acid sequence of SEQ ID NO: 71, and a VL comprising an amino acid sequence that is at least about 95%, 96%, 97%, 98%, 99% or 100% identical to the amino acid sequence of SEQ ID NO: 72.

In a particular embodiment, the antibody comprises a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8.

In another embodiment, the antibody comprises a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16.

In a further embodiment, the antibody comprises a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24.

In still a further embodiment, the antibody comprises a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32.

In one embodiment, the antibody comprises
(i) a VH sequence that is at least about 95%, 96%, 97%, 98%, 99% or 100% identical to the amino acid sequence of SEQ ID NO: 7, and a VL sequence that is at least about 95%, 96%, 97%, 98%, 99% or 100% identical to the amino acid sequence of SEQ ID NO: 8;
(ii) a VH sequence that is at least about 95%, 96%, 97%, 98%, 99% or 100% identical to the amino acid sequence of SEQ ID NO: 15, and a VL sequence that is at least about 95%, 96%, 97%, 98%, 99% or 100% identical to the amino acid sequence of SEQ ID NO: 16;
(iii) a VH sequence that is at least about 95%, 96%, 97%, 98%, 99% or 100% identical to the amino acid sequence of SEQ ID NO: 23, and a VL sequence that is at least about 95%, 96%, 97%, 98%, 99% or 100% identical to the amino acid sequence of SEQ ID NO: 24;
(iv) a VH sequence that is at least about 95%, 96%, 97%, 98%, 99% or 100% identical to the amino acid sequence of SEQ ID NO: 31, and a VL sequence that is at least about 95%, 96%, 97%, 98%, 99% or 100% identical to the amino acid sequence of SEQ ID NO: 32;
(v) a VH sequence that is at least about 95%, 96%, 97%, 98%, 99% or 100% identical to the amino acid sequence of SEQ ID NO: 39, and a VL sequence that is at least about 95%, 96%, 97%, 98%, 99% or 100% identical to the amino acid sequence of SEQ ID NO: 40;
(vi) a VH sequence that is at least about 95%, 96%, 97%, 98%, 99% or 100% identical to the amino acid sequence of SEQ ID NO: 47, and a VL sequence that is at least about 95%, 96%, 97%, 98%, 99% or 100% identical to the amino acid sequence of SEQ ID NO: 48;
(vii) a VH sequence that is at least about 95%, 96%, 97%, 98%, 99% or 100% identical to the amino acid sequence of SEQ ID NO: 55, and a VL sequence that is at least about 95%, 96%, 97%, 98%, 99% or 100% identical to the amino acid sequence of SEQ ID NO: 56;
(viii) a VH sequence that is at least about 95%, 96%, 97%, 98%, 99% or 100% identical to the amino acid sequence of SEQ ID NO: 63, and a VL sequence that is at least about 95%, 96%, 97%, 98%, 99% or 100% identical to the amino acid sequence of SEQ ID NO: 64; or
(ix) a VH sequence that is at least about 95%, 96%, 97%, 98%, 99% or 100% identical to the amino acid sequence of SEQ ID NO: 71, and a VL sequence that is at least about 95%, 96%, 97%, 98%, 99% or 100% identical to the amino acid sequence of SEQ ID NO: 72.

In a particular embodiment, the antibody comprises a VH sequence that is at least about 95%, 96%, 97%, 98%, 99% or 100% identical to the amino acid sequence of SEQ ID NO: 7, and a VL sequence that is at least about 95%, 96%, 97%, 98%, 99% or 100% identical to the amino acid sequence of SEQ ID NO: 8.

In another embodiment, the antibody comprises a VH sequence that is at least about 95%, 96%, 97%, 98%, 99% or 100% identical to the amino acid sequence of SEQ ID NO: 15, and a VL sequence that is at least about 95%, 96%, 97%, 98%, 99% or 100% identical to the amino acid sequence of SEQ ID NO: 16.

In a further embodiment, the antibody comprises a VH sequence that is at least about 95%, 96%, 97%, 98%, 99% or 100% identical to the amino acid sequence of SEQ ID NO: 23, and a VL sequence that is at least about 95%, 96%, 97%, 98%, 99% or 100% identical to the amino acid sequence of SEQ ID NO: 24.

In still a further embodiment, the antibody comprises a VH sequence that is at least about 95%, 96%, 97%, 98%, 99% or 100% identical to the amino acid sequence of SEQ ID NO: 31, and a VL sequence that is at least about 95%, 96%, 97%, 98%, 99% or 100% identical to the amino acid sequence of SEQ ID NO: 32.

In certain embodiments, a VH or VL sequence having at least 95%, 96%, 97%, 98%, or 99% identity contains substitutions (e.g., conservative substitutions), insertions, or deletions relative to the reference sequence, but an antibody comprising that sequence retains the ability to bind to HLA-A2/WT1. In certain embodiments, a total of 1 to 10 amino acids have been substituted, inserted and/or deleted in the VH (SEQ ID NO: 7, 15, 23, 31, 39, 47, 55, 63 or 71) and/or a total of 1 to 10 amino acids have been substituted, inserted and/or deleted in the VL (SEQ ID NO: 8, 16, 24, 32, 40, 48, 56, 64 or 72). In certain embodiments, substitutions, insertions, or deletions occur in regions outside the HVRs (i.e., in the FRs). Optionally, the antibody comprises the VH sequence and/or the VL sequence indicated above, including post-translational modifications of that sequence.

In one embodiment, the antibody comprises
(i) a VH comprising the amino acid sequence of SEQ ID NO: 7, and a VL comprising the amino acid sequence of SEQ ID NO: 8;
(ii) a VH comprising the amino acid sequence of SEQ ID NO: 15, and a VL comprising the amino acid sequence of SEQ ID NO: 16;
(iii) a VH comprising the amino acid sequence of SEQ ID NO: 23, and a VL comprising the amino acid sequence of SEQ ID NO: 24;
(iv) a VH comprising the amino acid sequence of SEQ ID NO: 31, and a VL comprising the amino acid sequence of SEQ ID NO: 32;
(v) a VH comprising the amino acid sequence of SEQ ID NO: 39, and a VL comprising the amino acid sequence of SEQ ID NO: 40;
(vi) a VH comprising the amino acid sequence of SEQ ID NO: 47, and a VL comprising the amino acid sequence of SEQ ID NO: 48;
(vii) a VH comprising the amino acid sequence of SEQ ID NO: 55, and a VL comprising the amino acid sequence of SEQ ID NO: 56;
(viii) a VH comprising the amino acid sequence of SEQ ID NO: 63, and a VL comprising the amino acid sequence of SEQ ID NO: 64; or
(ix) a VH comprising the amino acid sequence of SEQ ID NO: 71, and a VL comprising the amino acid sequence of SEQ ID NO: 72.

In one embodiment, the antibody comprises
(i) the VH sequence of SEQ ID NO: 7, and the VL sequence of SEQ ID NO: 8;
(ii) the VH sequence of SEQ ID NO: 15, and the VL sequence of SEQ ID NO: 16;

(iii) the VH sequence of SEQ ID NO: 23, and the VL sequence of SEQ ID NO: 24;
(iv) the VH sequence of SEQ ID NO: 31, and the VL sequence of SEQ ID NO: 32;
(v) the VH sequence of SEQ ID NO: 39, and the VL sequence of SEQ ID NO: 40;
(vi) the VH sequence of SEQ ID NO: 47, and the VL sequence of SEQ ID NO: 48;
(vii) the VH sequence of SEQ ID NO: 55, and the VL sequence of SEQ ID NO: 56;
(viii) the VH sequence of SEQ ID NO: 63, and the VL sequence of SEQ ID NO: 64; or
(ix) the VH sequence of SEQ ID NO: 71, and the VL sequence of SEQ ID NO: 72.

In a particular embodiment, the antibody comprises a VH comprising the amino acid sequence of SEQ ID NO: 7 and a VL comprising the amino acid sequence of SEQ ID NO: 8.

In another embodiment, the antibody comprises a VH comprising the amino acid sequence of SEQ ID NO: 15 and a VL comprising the amino acid sequence of SEQ ID NO: 16.

In a further embodiment, the antibody comprises a VH comprising the amino acid sequence of SEQ ID NO: 23 and a VL comprising the amino acid sequence of SEQ ID NO: 24.

In still a further embodiment, the antibody comprises a VH comprising the amino acid sequence of SEQ ID NO: 31 and a VL comprising the amino acid sequence of SEQ ID NO: 32.

In a particular embodiment, the antibody comprises the VH sequence of SEQ ID NO: 7 and the VL sequence of SEQ ID NO: 8.

In another embodiment, the antibody comprises the VH sequence of SEQ ID NO: 15 and the VL sequence of SEQ ID NO: 16.

In a further embodiment, the antibody comprises the VH sequence of SEQ ID NO: 23 and the VL sequence of SEQ ID NO: 24.

In still a further embodiment, the antibody comprises the VH sequence of SEQ ID NO: 31 and the VL sequence of SEQ ID NO: 32.

In one embodiment, the antibody comprises a human constant region. In one embodiment, the antibody is an immunoglobulin molecule comprising a human constant region, particularly an IgG class immunoglobulin molecule comprising a human CH1, CH2, CH3 and/or CL domain. Exemplary sequences of human constant domains are given in SEQ ID NOs 112 and 113 (human kappa and lambda CL domains, respectively) and SEQ ID NO: 114 (human IgG1 heavy chain constant domains CH1-CH2-CH3). In some embodiments, the antibody comprises a light chain constant region comprising an amino acid sequence that is at least about 95%, 96%, 97%, 98%, 99% or 100% identical to the amino acid sequence of SEQ ID NO: 112 or SEQ ID NO: 113, particularly the amino acid sequence of SEQ ID NO: 112. In some embodiments, the antibody comprises a heavy chain constant region comprising an amino acid sequence that is at least about 95%, 96%, 97%, 98%, 99% or 100% identical to the amino acid sequence of SEQ ID NO: 114.

Particularly, the heavy chain constant region may comprise amino acid mutations in the Fc domain as described herein.

In one embodiment, the antibody is a monoclonal antibody.

In one embodiment, the antibody is an IgG, particularly an IgG$_1$, antibody. In one embodiment, the antibody is a full-length antibody.

In one embodiment, the antibody comprises an Fc domain, particularly an IgG Fc domain, more particularly an IgG1 Fc domain. In one embodiment the Fc domain is a human Fc domain. The Fc domain of the antibody may incorporate any of the features, singly or in combination, described herein in relation to the Fc domain of the bispecific antigen binding molecule of the invention.

In another embodiment, the antibody is an antibody fragment selected from the group of an Fv molecule, a scFv molecule, a Fab molecule, and a F(ab')$_2$ molecule; particularly a Fab molecule. In another embodiment, the antibody fragment is a diabody, a triabody or a tetrabody.

In a further aspect, the antibody according to any of the above embodiments may incorporate any of the features, singly or in combination, as described in the sections below.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one embodiment, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e.g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO2003/085107), or cells with reduced or abolished activity of a GDP-fucose synthesis or transporter protein (see, e.g., US2004259150, US2005031613, US2004132140, US2004110282).

In a further embodiment, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,300,930, 7,855,275, 9,000,130, or WO2016040856.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Immunoconjugates

The invention also provides immunoconjugates comprising an anti-HLA-A2/WT1 antibody as described herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

Multispecific Antibodies

In certain embodiments, an antibody provided herein is a multispecific antibody, e.g. a bispecific antibody. Multispecific antibodies are monoclonal antibodies that have binding specificities for at least two different sites, i.e., different epitopes on different antigens or different epitopes on the same antigen. In certain embodiments, the multispecific antibody has three or more binding specificities. In certain embodiments, one of the binding specificities is for HLA-A2/WT1 and the other (two or more) specificity is for any other antigen. In certain embodiments, bispecific antibodies may bind to two (or more) different epitopes of HLA-A2/WT1. Multispecific (e.g., bispecific) antibodies may also be used to localize cytotoxic agents or cells to cells which express HLA-A2/WT1. Multispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more antigen binding sites, including for example, "Octopus antibodies," or DVD-Ig are also included herein (see, e.g. WO 2001/77342 and WO 2008/024715). Other examples of multispecific antibodies with three or more antigen binding sites can be found in WO 2010/115589, WO 2010/112193, WO 2010/136172, WO2010/145792, and WO 2013/026831. The bispecific antibody or antigen binding fragment thereof also includes a "Dual Acting FAb" or "DAF" comprising an antigen binding site that binds to HLA-A2/WT1 as well as another different antigen, or two different epitopes of HLA-A2/WT1 (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

A particular type of multispecific antibodies, also included herein, are bispecific antibodies designed to simultaneously bind to a surface antigen on a target cell, e.g., a tumor cell, and to an activating, invariant component of the T cell receptor (TCR) complex, such as CD3, for retargeting of T cells to kill target cells. Hence, in certain embodiments, an antibody provided herein is a multispecific antibody, particularly a bispecific antibody, wherein one of the binding specificities is for HLA-A2/WT1 and the other is for CD3.

Examples of bispecific antibody formats that may be useful for this purpose include, but are not limited to, the so-called "BiTE" (bispecific T cell engager) molecules wherein two scFv molecules are fused by a flexible linker (see, e.g., WO2004/106381, WO2005/061547, WO2007/042261, and WO2008/119567, Nagorsen and Bäuerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO2013/026839, WO 2016/020309; Bacac et al., Oncoimmunology 5(8) (2016) e1203498.

Bispecific Antigen Binding Molecules that Bind to HLA-A2/WT1 and a Second Antigen The invention also provides a bispecific antigen binding molecule, i.e. an antigen binding molecule that comprises at least two antigen binding moieties capable of specific binding to two distinct antigenic determinants (a first and a second antigen).

Based on the HLA-A2/WT1 antibodies they developed, the present inventors have developed bispecific antigen binding molecules that bind to HLA-A2/WT1 and a further antigen, particularly an activating T cell antigen such as CD3.

As shown in the Examples, these bispecific antigen binding molecules have a number of remarkable properties, including good efficacy and low toxicity.

Thus, in certain aspects, the invention provides a bispecific antigen binding molecule, comprising (a) a first antigen binding moiety that binds to a first antigen, wherein the first antigen is HLA-A2/WT1, and (b) a second antigen binding moiety which specifically binds to a second antigen, wherein the bispecific antigen binding molecule has any of the following features.

The bispecific antigen binding molecule of the invention specifically induces T-cell mediated killing of cells expressing HLA-A2/WT1 (i.e. a complex of a HLA-A2 molecule and a WT1-derived peptide). In some embodiments, the bispecific antigen binding molecule of the invention specifically induces T-cell mediated killing of cells expressing HLA-A2/WT1$_{RMF}$ (i.e. a complex of a HLA-A2 molecule and the WT1$_{RMF}$ peptide). In a more specific embodiment, the bispecific antigen binding molecule specifically induces T-cell mediated killing of cells expressing HLA-A2.01/WT1$_{RMF}$ (i.e. a complex of a HLA-A201 molecule and the WT1$_{RMF}$ peptide).

In one embodiment, induction of T-cell mediated killing by the bispecific antigen binding molecule is determined using HLA-A2/peptide (e.g. WT1$_{RMF}$ or WT1$_{VLD}$ peptide)-expressing cells, particularly peptide-pulsed T2 cells, and measuring lactate dehydrogenase (LDH) release from said cells after incubation with the bispecific antigen binding molecule in the presence of T cells. In a specific embodiment, induction of T-cell mediated killing by the bispecific antigen binding molecule is determined as follows:

T2 cells (ATCC, Cat. No. CRL-1992) are prepared as a cell suspension at $10^6$ cells/ml in IMDM medium (Gibco by Life Technologies, Cat No. 31980-048), supplemented with 10% FBS (Gibco, Cat No. 16140-071)+1% Penicillin-Streptomycin (Gibco, Cat No. 15070-063) (complete medium). Cells are kept in a total volume of 10 ml in a tube, and incubated with 10 µl of peptide (e.g. WT1 VLD peptide (SEQ ID NO: 77), or RMF peptide (SEQ ID NO: 78)) at $10^{-2}$ M (final concentration of the peptide: 105M) for 2 hours at 37° C. with 5% $CO_2$. Pan CD3$^+$ cells are purified from PBMCs isolated from buffy coat by Ficoll (GE Healthcare, Cat. No. 17-1440-03) gradient centrifugation. Total CD3$^+$ T cells are purified by MACS (Miltenyi Biotec) using a Human Pan T cell Isolation Kit (Miltenyi Biotec, Cat. No. 130-096-535). The cytotoxicity assay is performed as follows: The peptide-pulsed cells (100 µl) are seeded into a 96 well microtiter round bottom plate ($3\times10^5$ cells/ml), co-cultured with 50 µl of T cells ($6\times10^6$ cells/ml), and with 50 µl of titrated bispecific antigen binding molecule (e.g. at 40 µg/ml to 0.00004 µg/ml) in complete medium for 18 hours at 37° C. with 5% $CO_2$. Thereafter, 50 µl of supernatant are transferred into a new white plate, and 25 µl per well of CytoTox-Glo Luciferase Assay (Promega, Cat. No. G9291) are added for incubation at room temperature (RT) for 15 minutes. The luminescence signal (for measurement of LDH release as indicative of cell death) is read by EnVision (PerkinElmer). Data are presented as Relative Luminescence Unit (RLU).

The bispecific antigen binding molecule of the invention specifically activates T cells in the presence of cells expressing HLA-A2/WT1 (i.e. a complex of a HLA-A2 molecule and a WT1-derived peptide). In some embodiments, the bispecific antigen binding molecule of the invention specifically activates T cells in the presence of cells expressing HLA-A2/WT1$_{RMF}$ (i.e. a complex of a HLA-A2 molecule and the WT1$_{RMF}$ peptide). In a more specific embodiment, the bispecific antigen binding molecule specifically activates T cells in the presence of cells expressing HLA-A201/WT1$_{RMF}$ (i.e. a complex of a HLA-A201 molecule and the WT1$_{RMF}$ peptide).

In one embodiment, activation of T cells by the bispecific antigen binding molecule is determined by measuring, particularly by flow cytometry, expression of CD25 and/or CD69 by T cells after incubation with the bispecific antigen binding molecule in the presence of HLA-A2/peptide (e.g. WT1$_{RMF}$ or WT1$_{VLD}$ peptide)-expressing cells, particularly peptide-pulsed T2 cells.

In a specific embodiment, activation of T cells by the bispecific antigen binding molecule is determined as follows:

T2 cells (ATCC, Cat. No. CRL-1992) are prepared as a cell suspension at $10^6$ cells/ml in IMDM medium (Gibco by Life Technologies, Cat No. 31980-048), supplemented with 10% FBS (Gibco, Cat No. 16140-071)+1% Penicillin-Streptomycin (Gibco, Cat No. 15070-063) (complete medium). Cells are kept in a total volume of 10 ml in a tube, and incubated with 10 µl of peptide (e.g. WT1 VLD peptide (SEQ ID NO: 77), or RMF peptide (SEQ ID NO: 78)) at $10^{-2}$ M (final concentration of the peptide: 105M) for 2 hours at 37° C. with 5% $CO_2$. Pan CD3$^+$ cells are purified from PBMCs isolated from buffy coat by Ficoll (GE Healthcare, Cat. No. 17-1440-03) gradient centrifugation. Total CD3$^+$ T cells are purified by MACS (Miltenyi Biotec) using a Human Pan T cell Isolation Kit (Miltenyi Biotec, Cat. No. 130-096-535). The cytotoxicity assay is performed as follows: The peptide-pulsed cells (100 µl) are seeded into a 96 well microtiter round bottom plate ($3\times10^5$ cells/ml), co-cultured with 50 µl of T cells ($6\times10^6$ cells/ml), and with 50 µl of titrated bispecific antigen binding moelcule (e.g. at 40 µg/ml to 0.00004 g/ml) in complete medium for 18 hours at 37° C. with 5% $CO_2$. Cells are harvested after 18 hours of co-incubation, and stained with antibodies against CD3 (Biolegend Cat. No. 300321), CD25 (Biolegend Cat. No. 302606) and CD69 (Biolegend Cat. No. 310914) to measure T cell activation by flow cytometry.

In another embodiment, activation of T cells by the bispecific antigen binding molecule is determined using HLA-A2/peptide (e.g. WT1$_{RMF}$ or WT1$_{VLD}$ peptide)-expressing cells, particularly peptide-pulsed T2 cells, and a reporter T cell line, particularly a Jurkat T cell line that expresses a luciferase reporter driven by an NFAT (nuclear factor of activated T cells) response element.

In a specific embodiment, activation of T cells by the bispecific antigen binding molecule is determined as follows:

T2 cells (ATCC, Cat. No. CRL-1992) are prepared as a cell suspension at $10^6$ cells/ml in IMDM medium (Gibco by Life Technologies, Cat No. 31980-048), supplemented with 10% FBS (Gibco, Cat No. 16140-071)+1% Penicillin-Streptomycin (Gibco, Cat No. 15070-063) (complete medium). Cells are kept in a total volume of 10 ml in a tube, and incubated with 10 µl of peptide (e.g. WT1 VLD peptide (SEQ ID NO: 77), or RMF peptide (SEQ ID NO: 78)) at $10^{-2}$ M (final concentration of the peptide: $10^{-5}$ M) for 2 hours at 37° C. with 5% $CO_2$. After washing, 90 µl of the peptide-pulsed cells in a cell suspension of $2.2\times10^5$ cells/ml are seeded into a 96 well microtiter round bottom plate (20,000 cells/well, TPP, Cat. No. 92097), co-cultured with 50 µl of Jurkat cells that express luciferase under the promoter of NFAT (Jurkat-NFAT; Promega, Cat. No. CS176501) (cell suspension of $2\times10^6$ cells/ml), and with 10 µl of titrated bispecific antigen binding molecule (e.g. at 100 µg/ml to 0.0064 µg/ml in PBS) for 16 hours at 37° C. with 5% $CO_2$. Thereafter, 50 µl of supernatant are removed, and replaced with 100 µl per well of Bright-Glo Luciferase Assay (Promega, Cat. No. F2620) for incubation at room temperature (RT). Five minutes later, 180 µl of supernatant are transferred into a new white plate to measure luminescence signal by En Vision (PerkinElmer). Data are presented as Relative Luminescence Unit (RLU).

In one embodiment, the bispecific antigen binding molecule of the invention does not significantly induce T cell mediated killing of, or activate T cells in the presence of, cells expressing HLA-A2 alone (i.e. without a peptide) or HLA-A2 with a peptide other than a WT1-derived peptide such as WT1$_{RMF}$ or WT1$_{VLD}$.

In one embodiment, the bispecific antigen binding does not significantly induce T cell mediated killing of, or activate T cells in the presence of, cells expressing HLA-A2 in the absence of a WT1-derived peptide, particularly WT1$_{RMF}$ or WT1$_{VLD}$. In one embodiment, the bispecific antigen binding molecule induces T cell mediated killing of, and/or activates T cells in the presence of, cells expressing HLA-A2/WT1 (specifically HLA-A2/WT1$_{RMF}$ or HLA-A2/WT1$_{VLD}$) with an EC50 that is at least 5, at least 10, at least 15, at least 20, at least 25, at least 50, at least 75 or at least 100 times lower than the EC50 for induction of T cell mediated killing of, or activation of T cells in the presence of, cells expressing HLA-A2 in the absence of a WT1-derived peptide (specifically WT1$_{RMF}$ or WT1$_{VLD}$).

In one embodiment, the bispecific antigen binding molecule induces T cell mediated killing of, and/or activates T cells in the presence of, cells expressing HLA-A2/WT1 (specifically HLA-A2/WT1$_{RMF}$ or HLA-A2/WT1$_{VLD}$), but does not significantly induce T cell mediated killing of, or activate T cells in the presence of, cells expressing to HLA-A2 with a peptide selected from the peptides in Table 5 (the peptides of SEQ ID NOs 79-105). In one embodiment, the bispecific antigen binding molecule induces T cell mediated killing of, and/or activates T cells in the presence of, cells expressing to HLA-A2/WT1 (specifically HLA-A2/WT1$_{RMF}$ Or HLA-A2/WT1$_{VLD}$), but does not significantly induce T cell mediated killing of, or activate T cells in the presence of, cells expressing to HLA-A2 with any of the peptides in Table 5 (the peptides of SEQ ID NOs 79-10$^5$). In one embodiment, the bispecific antigen binding molecule induces T cell mediated killing of, and/or activates T cells in the presence of, cells expressing HLA-A2/WT1 (specifically HLA-A2/WT1$_{RMF}$ or HLA-A2/WT1$_{VLD}$) with an EC50 that is at least 5, at least 10, at least 15, at least 20, at least 25, at least 50, at least 75 or at least 100 times lower than the EC50 for induction of T cell mediated killing of, and/or activation of T cells in the presence of, cells expressing to HLA-A2 with a peptide selected from the peptides in Table 5 (the peptides of SEQ ID NOs 79-10$^5$). In one embodiment, the bispecific antigen binding molecule induces T cell mediated killing of, and/or activates T cells in the presence of, cells expressing HLA-A2/WT1 (specifically HLA-A2/WT1$_{RMF}$ or HLA-A2/WT1$_{VLD}$) with an EC50 that is at least 5, at least 10, at least 15, at least 20, at least 25, at least 50, at least 75 or at least 100 times lower than the EC50 for induction of T cell mediated killing of, and/or activation of T cells in the presence of, cells expressing to HLA-A2 with any of the peptides in Table 5 (the peptides of SEQ ID NOs 79-105).

In one embodiment, induction of T cell mediated killing and/or activation of T cells is determined as described above, and the EC50 is calculated in Microsoft® Excel using the XLfit® add-on (ID Business Solutions, Guildford, UK).

According to particular embodiments of the invention, the antigen binding moieties comprised in the bispecific antigen binding molecule are Fab molecules (i.e. antigen binding domains composed of a heavy and a light chain, each comprising a variable and a constant domain). In one embodiment, the first and/or the second antigen binding moiety is a Fab molecule. In one embodiment, said Fab molecule is human. In a particular embodiment, said Fab molecule is humanized. In yet another embodiment, said Fab molecule comprises human heavy and light chain constant domains.

Preferably, at least one of the antigen binding moieties is a crossover Fab molecule. Such modification reduces mispairing of heavy and light chains from different Fab molecules, thereby improving the yield and purity of the bispecific antigen binding molecule of the invention in recombinant production. In a particular crossover Fab molecule useful for the bispecific antigen binding molecule of the invention, the variable domains of the Fab light chain and the Fab heavy chain (VL and VH, respectively) are exchanged. Even with this domain exchange, however, the preparation of the bispecific antigen binding molecule may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired bispecific antigen binding molecule, charged amino acids with opposite charges may be introduced at specific amino acid positions in the CH1 and CL domains of either the Fab molecule(s) binding to the first antigen (HLA-A2/WT1), or the Fab molecule binding to the second antigen (e.g. an activating T cell antigen such as CD3), as further described herein. Charge modifications are made either in the conventional Fab molecule(s) comprised in the bispecific antigen binding molecule (such as shown e.g. in FIGS. 1A-C, G-J), or in the VH/VL crossover Fab molecule(s) comprised in the bispecific antigen binding molecule (such as shown e.g. in FIGS. 1 D-F, K-N) (but not in both). In particular embodiments, the charge modifications are made in the conventional Fab molecule(s) comprised in the bispecific antigen binding molecule (which in particular embodiments bind(s) to the first antigen, i.e. HLA-A2/WT1).

In a particular embodiment according to the invention, the bispecific antigen binding molecule is capable of simultaneous binding to the first antigen (i.e. HLA-A2/WT1), and the second antigen (e.g. an activating T cell antigen, particularly CD3). In one embodiment, the bispecific antigen binding molecule is capable of crosslinking a T cell and a target cell by simultaneous binding HLA-A2/WT1 and an activating T cell antigen. In an even more particular embodiment, such simultaneous binding results in lysis of the target cell, particularly a HLA-A2/WT1 expressing tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the bispecific antigen binding molecule to the activating T cell antigen, particularly CD3, without simultaneous binding to HLA-A2/WT1 does not result in T cell activation.

In one embodiment, the bispecific antigen binding molecule is capable of re-directing cytotoxic activity of a T cell to a target cell. In a particular embodiment, said re-direction is independent of MHC-mediated peptide antigen presentation by the target cell and and/or specificity of the T cell. Particularly, a T cell according to any of the embodiments of the invention is a cytotoxic T cell. In some embodiments the T cell is a CD4$^+$ or a CD8$^+$ T cell, particularly a CD8$^+$ T cell.

First Antigen Binding Moiety

The bispecific antigen binding molecule of the invention comprises at least one antigen binding moiety, particularly a Fab molecule, that binds to HLA-A2/WT1 (first antigen). In certain embodiments, the bispecific antigen binding molecule comprises two antigen binding moieties, particularly Fab molecules, which bind to HLA-A2/WT1. In a particular such embodiment, each of these antigen binding moieties binds to the same antigenic determinant. In an even more particular embodiment, all of these antigen binding moieties are identical, i.e. they comprise the same amino acid sequences including the same amino acid substitutions in the CH1 and CL domain as described herein (if any). In one embodiment, the bispecific antigen binding molecule comprises not more than two antigen binding moieties, particularly Fab molecules, which bind to HLA-A2/WT1.

In particular embodiments, the antigen binding moiety(ies) which bind to HLA-A2/WT1 is/are a conventional Fab molecule. In such embodiments, the antigen binding moiety(ies) that binds to a second antigen is a crossover Fab molecule as described herein, i.e. a Fab molecule wherein the variable domains VH and VL or the constant domains CH1 and CL of the Fab heavy and light chains are exchanged/replaced by each other.

In alternative embodiments, the antigen binding moiety(ies) which bind to HLA-A2/WT1 is/are a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) that binds a second antigen is a conventional Fab molecule.

The HLA-A2/WT1 binding moiety is able to direct the bispecific antigen binding molecule to a target site, for example to a specific type of tumor cell that expresses HLA-A2/WT1.

The first antigen binding moiety of the bispecific antigen binding molecule may incorporate any of the features, singly or in combination, described herein in relation to the antibody that binds HLA-A2/WT1, unless scientifically clearly unreasonable or impossible.

Thus, in one aspect, the invention provides a bispecific antigen binding molecule, comprising (a) a first antigen binding moiety that binds to a first antigen, wherein the first antigen is HLA-A2/WT1 and the first antigen binding moiety comprises
  (i) a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;
  (ii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;
  (iii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;
  (iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;
  (v) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;
  (vi) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;
  (vii) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;
  (viii) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62; or
  (ix) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70, and
  (b) a second antigen binding moiety that binds to a second antigen.

In a particular embodiment, the first antigen binding moiety comprises a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6.

In another embodiment, the first antigen binding moiety comprises a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14.

In a further embodiment, the first antigen binding moiety comprises a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22.

In still a further embodiment, the first antigen binding moiety comprises a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30.

In some embodiments, the first antigen binding moiety is (derived from) a human antibody. In one embodiment, the VH is a human VH and/or the VL is a human VL. In one embodiment, the first antigen binding moiety comprises CDRs as in any of the above embodiments, and further comprises a human framework, e.g. a human immunoglobulin framework.

In one embodiment, the first antigen binding moiety comprises
  (i) a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8;
(ii) a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16;
(iii) a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24;
(iv) a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32;
(v) a VH comprising an amino acid sequence that is at least about 95%, 96%, 97%, 98%, 99% or 100% identical to the amino acid sequence of SEQ ID NO: 39, and a VL comprising an amino acid sequence that is at least about 95%, 96%, 97%, 98%, 99% or 100% identical to the amino acid sequence of SEQ ID NO: 40;
(vi) a VH comprising an amino acid sequence that is at least about 95%, 96%, 97%, 98%, 99% or 100% identical to the amino acid sequence of SEQ ID NO: 47, and a VL comprising an amino acid sequence that is at least about 95%, 96%, 97%, 98%, 99% or 100% identical to the amino acid sequence of SEQ ID NO: 48;
(vii) a VH comprising an amino acid sequence that is at least about 95%, 96%, 97%, 98%, 99% or 100% identical to the amino acid sequence of SEQ ID NO: 55, and a VL comprising an amino acid sequence that is at least about 95%, 96%, 97%, 98%, 99% or 100% identical to the amino acid sequence of SEQ ID NO: 56;
(viii) a VH comprising an amino acid sequence that is at least about 95%, 96%, 97%, 98%, 99% or 100% identical to the amino acid sequence of SEQ ID NO: 63, and a VL comprising an amino acid sequence that is at least about 95%, 96%, 97%, 98%, 99% or 100% identical to the amino acid sequence of SEQ ID NO: 64; or
(ix) a VH comprising an amino acid sequence that is at least about 95%, 96%, 97%, 98%, 99% or 100% identical to the amino acid sequence of SEQ ID NO: 71, and a VL comprising an amino acid sequence that is at least about 95%, 96%, 97%, 98%, 99% or 100% identical to the amino acid sequence of SEQ ID NO: 72.

In a particular embodiment, the first antigen binding moiety comprises a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8.

In another embodiment, the first antigen binding moiety comprises a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16.

In a further embodiment, the first antigen binding moiety comprises a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24.

In still a further embodiment, the first antigen binding moiety comprises a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32. In one embodiment, the first antigen binding moiety comprises
(i) a VH sequence that is at least about 95%, 96%, 97%, 98%, 99% or 100% identical to the amino acid sequence of SEQ ID NO: 7, and a VL sequence that is at least about 95%, 96%, 97%, 98%, 99% or 100% identical to the amino acid sequence of SEQ ID NO: 8;
(ii) a VH sequence that is at least about 95%, 96%, 97%, 98%, 99% or 100% identical to the amino acid sequence of SEQ ID NO: 15, and a VL sequence that is at least about 95%, 96%, 97%, 98%, 99% or 100% identical to the amino acid sequence of SEQ ID NO: 16;
(iii) a VH sequence that is at least about 95%, 96%, 97%, 98%, 99% or 100% identical to the amino acid sequence of SEQ ID NO: 23, and a VL sequence that is at least about 95%, 96%, 97%, 98%, 99% or 100% identical to the amino acid sequence of SEQ ID NO: 24;
(iv) a VH sequence that is at least about 95%, 96%, 97%, 98%, 99% or 100% identical to the amino acid sequence of SEQ ID NO: 31, and a VL sequence that is at least about 95%, 96%, 97%, 98%, 99% or 100% identical to the amino acid sequence of SEQ ID NO: 32;
(v) a VH sequence that is at least about 95%, 96%, 97%, 98%, 99% or 100% identical to the amino acid sequence of SEQ ID NO: 39, and a VL sequence that is at least about 95%, 96%, 97%, 98%, 99% or 100% identical to the amino acid sequence of SEQ ID NO: 40;
(vi) a VH sequence that is at least about 95%, 96%, 97%, 98%, 99% or 100% identical to the amino acid sequence of SEQ ID NO: 47, and a VL sequence that is at least about 95%, 96%, 97%, 98%, 99% or 100% identical to the amino acid sequence of SEQ ID NO: 48;
(vii) a VH sequence that is at least about 95%, 96%, 97%, 98%, 99% or 100% identical to the amino acid sequence of SEQ ID NO: 55, and a VL sequence that is at least about 95%, 96%, 97%, 98%, 99% or 100% identical to the amino acid sequence of SEQ ID NO: 56;
(viii) a VH sequence that is at least about 95%, 96%, 97%, 98%, 99% or 100% identical to the amino acid sequence of SEQ ID NO: 63, and a VL sequence that is at least about 95%, 96%, 97%, 98%, 99% or 100% identical to the amino acid sequence of SEQ ID NO: 64; or (ix) a VH sequence that is at least about 95%, 96%, 97%, 98%, 99% or 100% identical to the amino acid sequence of SEQ ID NO: 71, and a VL sequence that is at least about 95%, 96%, 97%, 98%, 99% or 100% identical to the amino acid sequence of SEQ ID NO: 72.

In a particular embodiment, the first antigen binding moiety comprises a VH sequence that is at least about 95%, 96%, 97%, 98%, 99% or 100% identical to the amino acid sequence of SEQ ID NO: 7, and a VL sequence that is at least about 95%, 96%, 97%, 98%, 99% or 100% identical to the amino acid sequence of SEQ ID NO: 8.

In another embodiment, the first antigen binding moiety comprises a VH sequence that is at least about 95%, 96%, 97%, 98%, 99% or 100% identical to the amino acid sequence of SEQ ID NO: 15, and a VL sequence that is at least about 95%, 96%, 97%, 98%, 99% or 100% identical to the amino acid sequence of SEQ ID NO: 16.

In a further embodiment, the first antigen binding moiety comprises a VH sequence that is at least about 95%, 96%, 97%, 98%, 99% or 100% identical to the amino acid sequence of SEQ ID NO: 23, and a VL sequence that is at least about 95%, 96%, 97%, 98%, 99% or 100% identical to the amino acid sequence of SEQ ID NO: 24.

In still a further embodiment, the first antigen binding moiety comprises a VH sequence that is at least about 95%, 96%, 97%, 98%, 99% or 100% identical to the amino acid sequence of SEQ ID NO: 31, and a VL sequence that is at least about 95%, 96%, 97%, 98%, 99% or 100% identical to the amino acid sequence of SEQ ID NO: 32.

In one embodiment, the first antigen binding moiety comprises
(i) a VH comprising the amino acid sequence of SEQ ID NO: 7, and a VL comprising the amino acid sequence of SEQ ID NO: 8;
(ii) a VH comprising the amino acid sequence of SEQ ID NO: 15, and a VL comprising the amino acid sequence of SEQ ID NO: 16;
(iii) a VH comprising the amino acid sequence of SEQ ID NO: 23, and a VL comprising the amino acid sequence of SEQ ID NO: 24;
(iv) a VH comprising the amino acid sequence of SEQ ID NO: 31, and a VL comprising the amino acid sequence of SEQ ID NO: 32;
(v) a VH comprising the amino acid sequence of SEQ ID NO: 39, and a VL comprising the amino acid sequence of SEQ ID NO: 40;
(vi) a VH comprising the amino acid sequence of SEQ ID NO: 47, and a VL comprising the amino acid sequence of SEQ ID NO: 48;
(vii) a VH comprising the amino acid sequence of SEQ ID NO: 55, and a VL comprising the amino acid sequence of SEQ ID NO: 56;
(viii) a VH comprising the amino acid sequence of SEQ ID NO: 63, and a VL comprising the amino acid sequence of SEQ ID NO: 64; or
(ix) a VH comprising the amino acid sequence of SEQ ID NO: 71, and a VL comprising the amino acid sequence of SEQ ID NO: 72.

In one embodiment, the first antigen binding moiety comprises
(i) the VH sequence of SEQ ID NO: 7, and the VL sequence of SEQ ID NO: 8;
(ii) the VH sequence of SEQ ID NO: 15, and the VL sequence of SEQ ID NO: 16;
(iii) the VH sequence of SEQ ID NO: 23, and the VL sequence of SEQ ID NO: 24;
(iv) the VH sequence of SEQ ID NO: 31, and the VL sequence of SEQ ID NO: 32;
(v) the VH sequence of SEQ ID NO: 39, and the VL sequence of SEQ ID NO: 40;
(vi) the VH sequence of SEQ ID NO: 47, and the VL sequence of SEQ ID NO: 48;
(vii) the VH sequence of SEQ ID NO: 55, and the VL sequence of SEQ ID NO: 56;
(viii) the VH sequence of SEQ ID NO: 63, and the VL sequence of SEQ ID NO: 64; or
(ix) the VH sequence of SEQ ID NO: 71, and the VL sequence of SEQ ID NO: 72.

In a particular embodiment, the first antigen binding moiety comprises a VH comprising the amino acid sequence of SEQ ID NO: 7 and a VL comprising the amino acid sequence of SEQ ID NO: 8. In another embodiment, the first antigen binding moiety comprises a VH comprising the amino acid sequence of SEQ ID NO: 15 and a VL comprising the amino acid sequence of SEQ ID NO: 16.

In a further embodiment, the first antigen binding moiety comprises a VH comprising the amino acid sequence of SEQ ID NO: 23 and a VL comprising the amino acid sequence of SEQ ID NO: 24.

In still a further embodiment, the first antigen binding moiety comprises a VH comprising the amino acid sequence of SEQ ID NO: 31 and a VL comprising the amino acid sequence of SEQ ID NO: 32.

In a particular embodiment, the first antigen binding moiety comprises the VH sequence of SEQ ID NO: 7 and the VL sequence of SEQ ID NO: 8.

In another embodiment, the first antigen binding moiety comprises the VH sequence of SEQ ID NO: 15 and the VL sequence of SEQ ID NO: 16.

In a further embodiment, the first antigen binding moiety comprises the VH sequence of SEQ ID NO: 23 and the VL sequence of SEQ ID NO: 24.

In still a further embodiment, the first antigen binding moiety comprises the VH sequence of SEQ ID NO: 31 and the VL sequence of SEQ ID NO: 32.

In one embodiment, the first antigen binding moiety comprises a human constant region. In one embodiment, the first antigen binding moiety is a Fab molecule comprising a human constant region, particularly a human CH1 and/or CL domain. Exemplary sequences of human constant domains are given in SEQ ID NOs 112 and 113 (human kappa and lambda CL domains, respectively) and SEQ ID NO: 114 (human IgG) heavy chain constant domains CH1-CH2-CH3). In some embodiments, the first antigen binding moiety comprises a light chain constant region comprising an amino acid sequence that is at least about 95%, 96%, 97%, 98%, 99% or 100% identical to the amino acid sequence of SEQ ID NO: 112 or SEQ ID NO: 113, particularly the amino acid sequence of SEQ ID NO: 112. Particularly, the light chain constant region may comprise amino acid mutations as described herein under "charge modifications" and/or may comprise deletion or substitutions of one or more (particularly two) N-terminal amino acids if in a crossover Fab molecule. In some embodiments, the first antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 114. Particularly, the heavy chain constant region (specifically CH1 domain) may comprise amino acid mutations as described herein under "charge modifications".

Second Antigen Binding Moiety

The bispecific antigen binding molecule of the invention comprises at least one antigen binding moiety, particularly a Fab molecule, that binds to a second antigen (different from HLA-A2/WT1). In particular embodiments, the antigen binding moiety that binds the second antigen is a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) that binds to the first antigen (i.e. HLA-A2/WT1) is preferably a conventional Fab molecule. In embodiments where there is more than one antigen binding moiety, particularly Fab molecule, that binds to HLA-A2/WT1 comprised in the bispecific antigen binding molecule, the antigen binding moiety that binds to the second antigen preferably is a crossover Fab molecule and the antigen binding moieties that bind to HLA-A2/WT1 are conventional Fab molecules.

In alternative embodiments, the antigen binding moiety that binds to the second antigen is a conventional Fab molecule. In such embodiments, the antigen binding moiety(ies) that binds to the first antigen (i.e. HLA-A2/WT1) is a crossover Fab molecule as described herein, i.e. a Fab molecule wherein the variable domains VH and VL or the constant domains CH1 and CL of the Fab heavy and light chains are exchanged/replaced by each other. In embodiments where there is more than one antigen binding moiety, particularly Fab molecule, that binds to a second antigen comprised in the bispecific antigen binding molecule, the antigen binding moiety that binds to HLA-A2/WT1 preferably is a crossover Fab molecule and the antigen binding moieties that bind to the second antigen are conventional Fab molecules.

In some embodiments, the second antigen is an activating T cell antigen (also referred to herein as an "activating T cell antigen binding moiety, or activating T cell antigen binding Fab molecule"). In a particular embodiment, the bispecific antigen binding molecule comprises not more than one antigen binding moiety capable of specific binding to an activating T cell antigen. In one embodiment the bispecific antigen binding molecule provides monovalent binding to the activating T cell antigen.

In particular embodiments, the second antigen is CD3, particularly human CD3 (SEQ ID NO: 107) or cynomolgus CD3 (SEQ ID NO: 108), most particularly human CD3. In one embodiment the second antigen binding moiety is cross-reactive for (i.e. specifically binds to) human and cynomolgus CD3. In some embodiments, the second antigen is the epsilon subunit of CD3 (CD3 epsilon).

In one embodiment, the second antigen binding moiety comprises a HCDR 1 of SEQ ID NO: 115, a HCDR 2 of SEQ ID NO: 116, a HCDR 3 of SEQ ID NO: 117, a LCDR 1 of SEQ ID NO: 118, a LCDR 2 of SEQ ID NO: 119 and a LCDR 3 of SEQ ID NO: 120.

In one embodiment, the second antigen binding moiety comprises a VH comprising a HCDR 1 of SEQ ID NO: 115, a HCDR 2 of SEQ ID NO: 116, and a HCDR 3 of SEQ ID NO: 117, and a VL comprising a LCDR 1 of SEQ ID NO: 118, a LCDR 2 of SEQ ID NO: 119 and a LCDR 3 of SEQ ID NO: 120.

In some embodiments, the second antigen binding moiety is (derived from) a humanized antibody. In one embodiment, the VH is a humanized VH and/or the VL is a humanized VL. In one embodiment, the second antigen binding moiety comprises CDRs as in any of the above embodiments, and further comprises an acceptor human framework, e.g. a human immunoglobulin framework or a human consensus framework.

In one embodiment, the second antigen binding moiety comprises a VH sequence that is at least about 95%, 96%, 97%, 98%, 99% or 100% identical to the amino acid sequence of SEQ ID NO: 121. In one embodiment, the second antigen binding moiety comprises a VL sequence that is at least about 95%, 96%, 97%, 98%, 99% or 100% identical to the amino acid sequence of SEQ ID NO: 122.

In one embodiment, the second antigen binding moiety comprises a VH sequence that is at least about 95%, 96%, 97%, 98%, 99% or 100% identical to the amino acid sequence of SEQ ID NO: 121, and a VL sequence that is at least about 95%, 96%, 97%, 98%, 99% or 100% identical to the amino acid sequence of SEQ ID NO: 122.

In one embodiment, the VH of the second antigen binding moiety comprises an amino acid sequence that is at least about 95%, 96%, 97%, 98%, 99% or 100% identical to the amino acid sequence of SEQ ID NO: 121, and the VL of the second antigen binding moiety comprises an amino acid sequence that is at least about 95%, 96%, 97%, 98%, 99% or 100% identical to the amino acid sequence of SEQ ID NO: 122.

In one embodiment, the second antigen binding moiety comprises a VH comprising the amino acid sequence of SEQ ID NO: 121, and a VL comprising the amino acid sequence of SEQ ID NO: 122. In one embodiment, the second antigen binding moiety comprises the VH sequence of SEQ ID NO: 121, and the VL sequence of SEQ ID NO: 122.

In a particular embodiment, the second antigen binding moiety comprises a HCDR 1 of SEQ ID NO: 130, a HCDR 2 of SEQ ID NO: 131, a HCDR 3 of SEQ ID NO: 132, a LCDR 1 of SEQ ID NO: 133, a LCDR 2 of SEQ ID NO: 134 and a LCDR 3 of SEQ ID NO: 135.

In another particular embodiment, the second antigen binding moiety comprises a VH comprising a HCDR 1 of SEQ ID NO: 130, a HCDR 2 of SEQ ID NO: 131, and a HCDR 3 of SEQ ID NO: 132, and a VL comprising a LCDR 1 of SEQ ID NO: 133, a LCDR 2 of SEQ ID NO: 134 and a LCDR 3 of SEQ ID NO: 135.

In some embodiments, the second antigen binding moiety is (derived from) a humanized antibody. In one embodiment, the VH is a humanized VH and/or the VL is a humanized VL. In one embodiment, the second antigen binding moiety comprises CDRs as in any of the above embodiments, and further comprises an acceptor human framework, e.g. a human immunoglobulin framework or a human consensus framework.

In one embodiment, the second antigen binding moiety comprises a VH sequence that is at least about 95%, 96%, 97%, 98%, 99% or 100% identical to the amino acid sequence of SEQ ID NO: 136. In one embodiment, the second antigen binding moiety comprises a VL sequence that is at least about 95%, 96%, 97%, 98%, 99% or 100% identical to the amino acid sequence of SEQ ID NO: 137.

In a particular embodiment, the second antigen binding moiety comprises a VH sequence that is at least about 95%, 96%, 97%, 98%, 99% or 100% identical to the amino acid sequence of SEQ ID NO: 136, and a VL sequence that is at least about 95%, 96%, 97%, 98%, 99% or 100% identical to the amino acid sequence of SEQ ID NO: 137.

In another particular embodiment, the VH of the second antigen binding moiety comprises an amino acid sequence that is at least about 95%, 96%, 97%, 98%, 99% or 100% identical to the amino acid sequence of SEQ ID NO: 136, and the VL of the second antigen binding moiety comprises an amino acid sequence that is at least about 95%, 96%, 97%, 98%, 99% or 100% identical to the amino acid sequence of SEQ ID NO: 137.

In one embodiment, the second antigen binding moiety comprises a VH comprising the amino acid sequence of SEQ ID NO: 136, and a VL comprising the amino acid sequence of SEQ ID NO: 137. In one embodiment, the second antigen binding moiety comprises the VH sequence of SEQ ID NO: 136, and the VL sequence of SEQ ID NO: 137.

In one embodiment, the second antigen binding moiety comprises a human constant region. In one embodiment, the second antigen binding moiety is a Fab molecule comprising a human constant region, particularly a human CH1 and/or CL domain. Exemplary sequences of human constant domains are given in SEQ ID NOs 112 and 113 (human kappa and lambda CL domains, respectively) and SEQ ID NO: 114 (human IgG$_1$ heavy chain constant domains CH1-CH2-CH3). In some embodiments, the second antigen binding moiety comprises a light chain constant region comprising an amino acid sequence that is at least about 95%, 96%, 97%, 98%, 99% or 100% identical to the amino acid sequence of SEQ ID NO: 112 or SEQ ID NO: 113, particularly the amino acid sequence of SEQ ID NO: 112. Particularly, the light chain constant region may comprise amino acid mutations as described herein under "charge modifications" and/or may comprise deletion or substitutions of one or more (particularly two) N-terminal amino acids if in a crossover Fab molecule. In some embodiments, the second antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 114. Particularly, the heavy chain constant region (specifically CH1 domain) may comprise amino acid mutations as described herein under "charge modifications". In some embodiments, the second antigen binding moiety is a Fab molecule wherein the variable domains VL and VH or the constant domains CL and CH1, particularly the variable domains VL and VH, of the Fab light chain and the Fab heavy chain are replaced by each other (i.e. according to such embodiment, the second antigen binding moiety is a crossover Fab molecule wherein the variable or constant domains of the Fab light chain and the Fab heavy chain are exchanged). In one such embodiment, the first (and the third, if any) antigen binding moiety is a conventional Fab molecule.

In one embodiment, not more than one antigen binding moiety that binds to the second antigen (e.g. an activating T cell antigen such as CD3) is present in the bispecific antigen binding molecule (i.e. the bispecific antigen binding molecule provides monovalent binding to the second antigen).

Charge Modifications

The bispecific antigen binding molecules of the invention may comprise amino acid substitutions in Fab molecules comprised therein which are particularly efficient in reducing mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired bispecific antigen binding molecule compared to undesired side products, in particular Bence Jones-type side products occurring in bispecific antigen binding molecules with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some embodiments wherein the first and the second antigen binding moiety of the bispecific antigen binding molecule are both Fab molecules, and in one of the antigen binding moieties (particularly the second antigen binding moiety) the variable domains VL and VH of the Fab light chain and the Fab heavy chain are replaced by each other, i) in the constant domain CL of the first antigen binding moiety the amino acid at position 124 is substituted by a positively charged amino acid (numbering according to Kabat), and wherein in the constant domain CH1 of the first antigen binding moiety the amino acid at position 147 or the amino acid at position 213 is substituted by a negatively charged amino acid (numbering according to Kabat EU index); or ii) in the constant domain CL of the second antigen binding moiety the amino acid at position 124 is substituted by a positively charged amino acid (numbering according to Kabat), and wherein in the constant domain CH1 of the second antigen binding moiety the amino acid at position 147 or the amino acid at position 213 is substituted by a negatively charged amino acid (numbering according to Kabat EU index).

The bispecific antigen binding molecule does not comprise both modifications mentioned under i) and ii). The constant domains CL and CH1 of the antigen binding moiety having the VH/VL exchange are not replaced by each other (i.e. remain unexchanged).

In a more specific embodiment, i) in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index); or ii) in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In one such embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index).

In a further embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index).

In a particular embodiment, in the constant domain CL of the first antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first antigen binding moiety the amino acid at position 124 is substituted by lysine (K) (numbering according to Kabat) and the amino acid at position 123 is substituted by lysine (K) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first antigen binding moiety the amino acid at position 124 is substituted by lysine (K) (numbering according to Kabat) and the amino acid at position 123 is substituted by arginine (R) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In particular embodiments, if amino acid substitutions according to the above embodiments are made in the constant domain CL and the constant domain CH1 of the first antigen binding moiety, the constant domain CL of the first antigen binding moiety is of kappa isotype.

Alternatively, the amino acid substitutions according to the above embodiments may be made in the constant domain CL and the constant domain CH1 of the second antigen binding moiety instead of in the constant domain CL and the constant domain CH1 of the first antigen binding moiety. In particular such embodiments, the constant domain CL of the second antigen binding moiety is of kappa isotype.

Accordingly, in one embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In a further embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index).

In still another embodiment, in the constant domain CL of the second antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one embodiment, in the constant domain CL of the second antigen binding moiety the amino acid at position 124 is substituted by lysine (K) (numbering according to Kabat) and the amino acid at position 123 is substituted by lysine (K) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index). In another embodiment, in the constant domain CL of the second antigen binding moiety the amino acid at position 124 is substituted by lysine (K) (numbering according to Kabat) and the amino acid at position 123 is substituted by arginine (R) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In a particular embodiment, the bispecific antigen binding molecule of the invention comprises
(a) a first antigen binding moiety that binds to a first antigen, wherein the first antigen is HLA-A2/WT1, specifically HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6, and
(b) a second antigen binding moiety that binds to a second antigen, wherein the second antigen binding moiety is a Fab molecule wherein the variable domains VL and VH of the Fab light chain and the Fab heavy chain are replaced by each other;
wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In another particular embodiment, the bispecific antigen binding molecule of the invention comprises
(a) a first antigen binding moiety that binds to a first antigen, wherein the first antigen is HLA-A2/WT1, specifically HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

Bispecific Antigen Binding Molecule Formats

Figure 1Z:
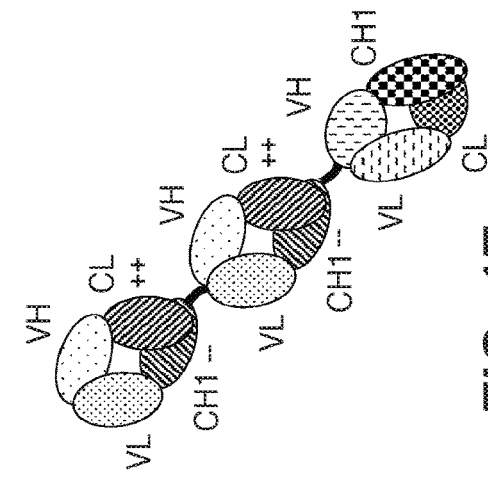
Figure 1W:
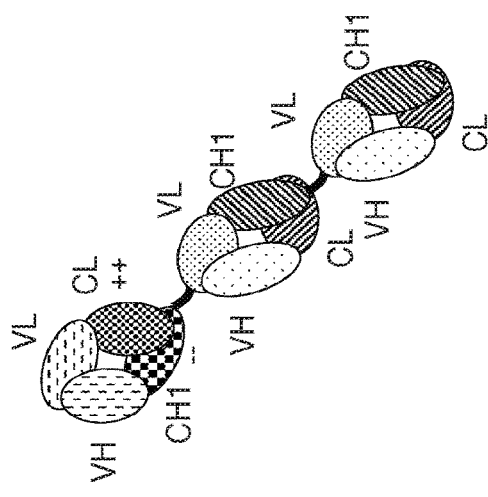
Figure 1Y:
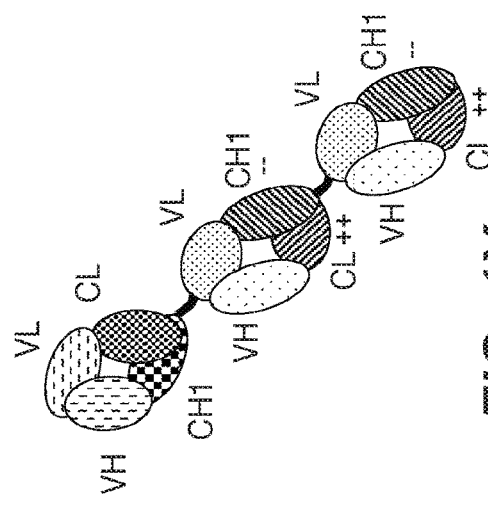

The components of the bispecific antigen binding molecule according to the present invention can be fused to each other in a variety of configurations. Exemplary configurations are depicted in FIGS. 1A-Z.

In particular embodiments, the antigen binding moieties comprised in the bispecific antigen binding molecule are Fab molecules. In such embodiments, the first, second, third etc. antigen binding moiety may be referred to herein as first, second, third etc. Fab molecule, respectively.

In one embodiment, the first and the second antigen binding moiety of the bispecific antigen binding molecule are fused to each other, optionally via a peptide linker. In particular embodiments, the first and the second antigen binding moiety are each a Fab molecule. In one such embodiment, the second antigen binding moiety is fused at the C-terminus of the Fab heavy chain to the N-terminus of the Fab heavy chain of the first antigen binding moiety. In another such embodiment, the first antigen binding moiety is fused at the C-terminus of the Fab heavy chain to the N-terminus of the Fab heavy chain of the second antigen binding moiety. In embodiments wherein either (i) the second antigen binding moiety is fused at the C-terminus of the Fab heavy chain to the N-terminus of the Fab heavy chain of the first antigen binding moiety or (ii) the first antigen binding moiety is fused at the C-terminus of the Fab heavy chain to the N-terminus of the Fab heavy chain of the second antigen binding moiety, additionally the Fab light chain of the first antigen binding moiety and the Fab light chain of the second antigen binding moiety may be fused to each other, optionally via a peptide linker.

A bispecific antigen binding molecule with a single antigen binding moiety (such as a Fab molecule) capable of specific binding to a target cell antigen such as HLA-A2/WT1 (for example as shown in FIGS. 1A, D, G, H, K, L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In other cases, however, it will be advantageous to have a bispecific antigen binding molecule comprising two or more antigen binding moieties (such as Fab molecules) specific for a target cell antigen (see examples shown in FIG. 1B, 1C, 1E, 1F, 1I, 1J, 1M or 1N), for example to optimize targeting to the target site or to allow crosslinking of target cell antigens.

Accordingly, in particular embodiments, the bispecific antigen binding molecule according to the present invention comprises a third antigen binding moiety.

In one embodiment, the third antigen binding moiety binds to the first antigen, i.e. HLA-A2/WT1.

In one embodiment, the third antigen binding moiety is a Fab molecule.

In particular embodiments, the third antigen moiety is identical to the first antigen binding moiety. The third antigen binding moiety of the bispecific antigen binding molecule may incorporate any of the features, singly or in combination, described herein in relation to the first antigen binding moiety and/or the antibody that binds HLA-A2/WT1, unless scientifically clearly unreasonable or impossible.

In one embodiment, the third antigen binding moiety comprises (i) a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;

(ii) a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14;

(iii) a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22;

(iv) a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30;

(v) a VH comprising a HCDR 1 of SEQ ID NO: 33, a HCDR 2 of SEQ ID NO: 34, and a HCDR 3 of SEQ ID NO: 35, and a VL comprising a LCDR 1 of SEQ ID NO: 36, a LCDR 2 of SEQ ID NO: 37 and a LCDR 3 of SEQ ID NO: 38;

(vi) a VH comprising a HCDR 1 of SEQ ID NO: 41, a HCDR 2 of SEQ ID NO: 42, and a HCDR 3 of SEQ ID NO: 43, and a VL comprising a LCDR 1 of SEQ ID NO: 44, a LCDR 2 of SEQ ID NO: 45 and a LCDR 3 of SEQ ID NO: 46;

(vii) a VH comprising a HCDR 1 of SEQ ID NO: 49, a HCDR 2 of SEQ ID NO: 50, and a HCDR 3 of SEQ ID NO: 51, and a VL comprising a LCDR 1 of SEQ ID NO: 52, a LCDR 2 of SEQ ID NO: 53 and a LCDR 3 of SEQ ID NO: 54;

(viii) a VH comprising a HCDR 1 of SEQ ID NO: 57, a HCDR 2 of SEQ ID NO: 58, and a HCDR 3 of SEQ ID NO: 59, and a VL comprising a LCDR 1 of SEQ ID NO: 60, a LCDR 2 of SEQ ID NO: 61 and a LCDR 3 of SEQ ID NO: 62; or (ix) a VH comprising a HCDR 1 of SEQ ID NO: 65, a HCDR 2 of SEQ ID NO: 66, and a HCDR 3 of SEQ ID NO: 67, and a VL comprising a LCDR 1 of SEQ ID NO: 68, a LCDR 2 of SEQ ID NO: 69 and a LCDR 3 of SEQ ID NO: 70.

In a particular embodiment, the third antigen binding moiety comprises a VH comprising a HCDR 1 of SEQ ID NO: 1, a HCDR 2 of SEQ ID NO: 2, and a HCDR 3 of SEQ ID NO: 3, and a VL comprising a LCDR 1 of SEQ ID NO: 4, a LCDR 2 of SEQ ID NO: 5 and a LCDR 3 of SEQ ID NO: 6.

In another embodiment, the third antigen binding moiety comprises a VH comprising a HCDR 1 of SEQ ID NO: 9, a HCDR 2 of SEQ ID NO: 10, and a HCDR 3 of SEQ ID NO: 11, and a VL comprising a LCDR 1 of SEQ ID NO: 12, a LCDR 2 of SEQ ID NO: 13 and a LCDR 3 of SEQ ID NO: 14.

In a further embodiment, the third antigen binding moiety comprises a VH comprising a HCDR 1 of SEQ ID NO: 17, a HCDR 2 of SEQ ID NO: 18, and a HCDR 3 of SEQ ID NO: 19, and a VL comprising a LCDR 1 of SEQ ID NO: 20, a LCDR 2 of SEQ ID NO: 21 and a LCDR 3 of SEQ ID NO: 22.

In still a further embodiment, the third antigen binding moiety comprises a VH comprising a HCDR 1 of SEQ ID NO: 25, a HCDR 2 of SEQ ID NO: 26, and a HCDR 3 of SEQ ID NO: 27, and a VL comprising a LCDR 1 of SEQ ID NO: 28, a LCDR 2 of SEQ ID NO: 29 and a LCDR 3 of SEQ ID NO: 30.

In some embodiments, the third antigen binding moiety is (derived from) a human antibody. In one embodiment, the VH is a human VH and/or the VL is a human VL. In one embodiment, the third antigen binding moiety comprises CDRs as in any of the above embodiments, and further comprises a human framework, e.g. a human immunoglobulin framework.

In one embodiment, the third antigen binding moiety comprises (i) a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8;

(ii) a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16;

(iii) a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24;

(iv) a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32;

(v) a VH comprising an amino acid sequence that is at least about 95%, 96%, 97%, 98%, 99% or 100% identical to the amino acid sequence of SEQ ID NO: 39, and a VL comprising an amino acid sequence that is at least about 95%, 96%, 97%, 98%, 99% or 100% identical to the amino acid sequence of SEQ ID NO: 40;

(vi) a VH comprising an amino acid sequence that is at least about 95%, 96%, 97%, 98%, 99% or 100% identical to the amino acid sequence of SEQ ID NO: 47, and a VL comprising an amino acid sequence that is at least about 95%, 96%, 97%, 98%, 99% or 100% identical to the amino acid sequence of SEQ ID NO: 48;

(vii) a VH comprising an amino acid sequence that is at least about 95%, 96%, 97%, 98%, 99% or 100% identical to the amino acid sequence of SEQ ID NO: 55, and a VL comprising an amino acid sequence that is at least about 95%, 96%, 97%, 98%, 99% or 100% identical to the amino acid sequence of SEQ ID NO: 56;

(viii) a VH comprising an amino acid sequence that is at least about 95%, 96%, 97%, 98%, 99% or 100% identical to the amino acid sequence of SEQ ID NO: 63, and a VL comprising an amino acid sequence that is at least about 95%, 96%, 97%, 98%, 99% or 100% identical to the amino acid sequence of SEQ ID NO: 64; or (ix) a VH comprising an amino acid sequence that is at least about 95%, 96%, 97%, 98%, 99% or 100% identical to the amino acid sequence of SEQ ID NO: 71, and a VL comprising an amino acid sequence that is at least about 95%, 96%, 97%, 98%, 99% or 100% identical to the amino acid sequence of SEQ ID NO: 72.

In a particular embodiment, the third antigen binding moiety comprises a VH comprising an amino acid sequence that is at least about 95%, 96%, 97%, 98%, 99% or 100% identical to the amino acid sequence of SEQ ID NO: 7, and a VL comprising an amino acid sequence that is at least about 95%, 96%, 97%, 98%, 99% or 100% identical to the amino acid sequence of SEQ ID NO: 8.

In another embodiment, the third antigen binding moiety comprises a VH comprising an amino acid sequence that is at least about 95%, 96%, 97%, 98%, 99% or 100% identical to the amino acid sequence of SEQ ID NO: 15, and a VL comprising an amino acid sequence that is at least about 95%, 96%, 97%, 98%, 99% or 100% identical to the amino acid sequence of SEQ ID NO: 16.

In a further embodiment, the third antigen binding moiety comprises a VH comprising an amino acid sequence that is at least about 95%, 96%, 97%, 98%, 99% or 100% identical to the amino acid sequence of SEQ ID NO: 23, and a VL comprising an amino acid sequence that is at least about 95%, 96%, 97%, 98%, 99% or 100% identical to the amino acid sequence of SEQ ID NO: 24.

In still a further embodiment, the third antigen binding moiety comprises a VH comprising an amino acid sequence that is at least about 95%, 96%, 97%, 98%, 99% or 100% identical to the amino acid sequence of SEQ ID NO: 31, and a VL comprising an amino acid sequence that is at least about 95%, 96%, 97%, 98%, 99% or 100% identical to the amino acid sequence of SEQ ID NO: 32.

In one embodiment, the third antigen binding moiety comprises
- (i) a VH sequence that is at least about 95%, 96%, 97%, 98%, 99% or 100% identical to the amino acid sequence of SEQ ID NO: 7, and a VL sequence that is at least about 95%, 96%, 97%, 98%, 99% or 100% identical to the amino acid sequence of SEQ ID NO: 8;
- (ii) a VH sequence that is at least about 95%, 96%, 97%, 98%, 99% or 100% identical to the amino acid sequence of SEQ ID NO: 15, and a VL sequence that is at least about 95%, 96%, 97%, 98%, 99% or 100% identical to the amino acid sequence of SEQ ID NO: 16;
- (iii) a VH sequence that is at least about 95%, 96%, 97%, 98%, 99% or 100% identical to the amino acid sequence of SEQ ID NO: 23, and a VL sequence that is at least about 95%, 96%, 97%, 98%, 99% or 100% identical to the amino acid sequence of SEQ ID NO: 24;
- (iv) a VH sequence that is at least about 95%, 96%, 97%, 98%, 99% or 100% identical to the amino acid sequence of SEQ ID NO: 31, and a VL sequence that is at least about 95%, 96%, 97%, 98%, 99% or 100% identical to the amino acid sequence of SEQ ID NO: 32;
- (v) a VH sequence that is at least about 95%, 96%, 97%, 98%, 99% or 100% identical to the amino acid sequence of SEQ ID NO: 39, and a VL sequence that is at least about 95%, 96%, 97%, 98%, 99% or 100% identical to the amino acid sequence of SEQ ID NO: 40;
- (vi) a VH sequence that is at least about 95%, 96%, 97%, 98%, 99% or 100% identical to the amino acid sequence of SEQ ID NO: 47, and a VL sequence that is at least about 95%, 96%, 97%, 98%, 99% or 100% identical to the amino acid sequence of SEQ ID NO: 48;
- (vii) a VH sequence that is at least about 95%, 96%, 97%, 98%, 99% or 100% identical to the amino acid sequence of SEQ ID NO: 55, and a VL sequence that is at least about 95%, 96%, 97%, 98%, 99% or 100% identical to the amino acid sequence of SEQ ID NO: 56;
- (viii) a VH sequence that is at least about 95%, 96%, 97%, 98%, 99% or 100% identical to the amino acid sequence of SEQ ID NO: 63, and a VL sequence that is at least about 95%, 96%, 97%, 98%, 99% or 100% identical to the amino acid sequence of SEQ ID NO: 64; or
- (ix) a VH sequence that is at least about 95%, 96%, 97%, 98%, 99% or 100% identical to the amino acid sequence of SEQ ID NO: 71, and a VL sequence that is at least about 95%, 96%, 97%, 98%, 99% or 100% identical to the amino acid sequence of SEQ ID NO: 72.

In a particular embodiment, the third antigen binding moiety comprises a VH sequence that is at least about 95%, 96%, 97%, 98%, 99% or 100% identical to the amino acid sequence of SEQ ID NO: 7, and a VL sequence that is at least about 95%, 96%, 97%, 98%, 99% or 100% identical to the amino acid sequence of SEQ ID NO: 8.

In another embodiment, the third antigen binding moiety comprises a VH sequence that is at least about 95%, 96%, 97%, 98%, 99% or 100% identical to the amino acid sequence of SEQ ID NO: 15, and a VL sequence that is at least about 95%, 96%, 97%, 98%, 99% or 100% identical to the amino acid sequence of SEQ ID NO: 16.

In a further embodiment, the third antigen binding moiety comprises a VH sequence that is at least about 95%, 96%, 97%, 98%, 99% or 100% identical to the amino acid sequence of SEQ ID NO: 23, and a VL sequence that is at least about 95%, 96%, 97%, 98%, 99% or 100% identical to the amino acid sequence of SEQ ID NO: 24.

In still a further embodiment, the third antigen binding moiety comprises a VH sequence that is at least about 95%, 96%, 97%, 98%, 99% or 100% identical to the amino acid sequence of SEQ ID NO: 31, and a VL sequence that is at least about 95%, 96%, 97%, 98%, 99% or 100% identical to the amino acid sequence of SEQ ID NO: 32.

In one embodiment, the third antigen binding moiety comprises
- (i) a VH comprising the amino acid sequence of SEQ ID NO: 7, and a VL comprising the amino acid sequence of SEQ ID NO: 8;
- (ii) a VH comprising the amino acid sequence of SEQ ID NO: 15, and a VL comprising the amino acid sequence of SEQ ID NO: 16;
- (iii) a VH comprising the amino acid sequence of SEQ ID NO: 23, and a VL comprising the amino acid sequence of SEQ ID NO: 24;
- (iv) a VH comprising the amino acid sequence of SEQ ID NO: 31, and a VL comprising the amino acid sequence of SEQ ID NO: 32;
- (v) a VH comprising the amino acid sequence of SEQ ID NO: 39, and a VL comprising the amino acid sequence of SEQ ID NO: 40;
- (vi) a VH comprising the amino acid sequence of SEQ ID NO: 47, and a VL comprising the amino acid sequence of SEQ ID NO: 48;
- (vii) a VH comprising the amino acid sequence of SEQ ID NO: 55, and a VL comprising the amino acid sequence of SEQ ID NO: 56;
- (viii) a VH comprising the amino acid sequence of SEQ ID NO: 63, and a VL comprising the amino acid sequence of SEQ ID NO: 64; or
- (ix) a VH comprising the amino acid sequence of SEQ ID NO: 71, and a VL comprising the amino acid sequence of SEQ ID NO: 72.

In one embodiment, the third antigen binding moiety comprises
- (i) the VH sequence of SEQ ID NO: 7, and the VL sequence of SEQ ID NO: 8;
- (ii) the VH sequence of SEQ ID NO: 15, and the VL sequence of SEQ ID NO: 16;
- (iii) the VH sequence of SEQ ID NO: 23, and the VL sequence of SEQ ID NO: 24;
- (iv) the VH sequence of SEQ ID NO: 31, and the VL sequence of SEQ ID NO: 32;
- (v) the VH sequence of SEQ ID NO: 39, and the VL sequence of SEQ ID NO: 40;
- (vi) the VH sequence of SEQ ID NO: 47, and the VL sequence of SEQ ID NO: 48;
- (vii) the VH sequence of SEQ ID NO: 55, and the VL sequence of SEQ ID NO: 56;
- (viii) the VH sequence of SEQ ID NO: 63, and the VL sequence of SEQ ID NO: 64; or
- (ix) the VH sequence of SEQ ID NO: 71, and the VL sequence of SEQ ID NO: 72.

In a particular embodiment, the third antigen binding moiety comprises a VH comprising the amino acid sequence of SEQ ID NO: 7 and a VL comprising the amino acid sequence of SEQ ID NO: 8.

In another embodiment, the third antigen binding moiety comprises a VH comprising the amino acid sequence of SEQ ID NO: 15 and a VL comprising the amino acid sequence of SEQ ID NO: 16.

In a further embodiment, the third antigen binding moiety comprises a VH comprising the amino acid sequence of SEQ ID NO: 23 and a VL comprising the amino acid sequence of SEQ ID NO: 24.

In still a further embodiment, the third antigen binding moiety comprises a VH comprising the amino acid sequence of SEQ ID NO: 31 and a VL comprising the amino acid sequence of SEQ ID NO: 32.

In a particular embodiment, the third antigen binding moiety comprises the VH sequence of SEQ ID NO: 7 and the VL sequence of SEQ ID NO: 8.

In another embodiment, the third antigen binding moiety comprises the VH sequence of SEQ ID NO: 15 and the VL sequence of SEQ ID NO: 16.

In a further embodiment, the third antigen binding moiety comprises the VH sequence of SEQ ID NO: 23 and the VL sequence of SEQ ID NO: 24.

In still a further embodiment, the third antigen binding moiety comprises the VH sequence of SEQ ID NO: 31 and the VL sequence of SEQ ID NO: 32.

In one embodiment, the third antigen binding moiety comprises a human constant region. In one embodiment, the third antigen binding moiety is a Fab molecule comprising a human constant region, particularly a human CH1 and/or CL domain. Exemplary sequences of human constant domains are given in SEQ ID NOs 112 and 113 (human kappa and lambda CL domains, respectively) and SEQ ID NO: 114 (human IgG$_1$ heavy chain constant domains CH1-CH2-CH3). In some embodiments, the third antigen binding moiety comprises a light chain constant region comprising an amino acid sequence that is at least about 95%, 96%, 97%, 98%, 99% or 100% identical to the amino acid sequence of SEQ ID NO: 112 or SEQ ID NO: 113, particularly the amino acid sequence of SEQ ID NO: 112. Particularly, the light chain constant region may comprise amino acid mutations as described herein under "charge modifications" and/or may comprise deletion or substitutions of one or more (particularly two) N-terminal amino acids if in a crossover Fab molecule. In some embodiments, the third antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 114. Particularly, the heavy chain constant region (specifically CH1 domain) may comprise amino acid mutations as described herein under "charge modifications". In particular embodiments, the third and the first antigen binding moiety are each a Fab molecule and the third antigen binding moiety is identical to the first antigen binding moiety. Thus, in these embodiments the first and the third antigen binding moiety comprise the same heavy and light chain amino acid sequences and have the same arrangement of domains (i.e. conventional or crossover)). Furthermore, in these embodiments, the third antigen binding moiety comprises the same amino acid substitutions, if any, as the first antigen binding moiety. For example, the amino acid substitutions described herein as "charge modifications" will be made in the constant domain CL and the constant domain CH1 of each of the first antigen binding moiety and the third antigen binding moiety. Alternatively, said amino acid substitutions may be made in the constant domain CL and the constant domain CH1 of the second antigen binding moiety (which in particular embodiments is also a Fab molecule), but not in the constant domain CL and the constant domain CH1 of the first antigen binding moiety and the third antigen binding moiety.

Like the first antigen binding moiety, the third antigen binding moiety particularly is a conventional Fab molecule. Embodiments wherein the first and the third antigen binding moieties are crossover Fab molecules (and the second antigen binding moiety is a conventional Fab molecule) are, however, also contemplated. Thus, in particular embodiments, the first and the third antigen binding moieties are each a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other embodiments, the first and the third antigen binding moieties are each a crossover Fab molecule and the second antigen binding moiety is a conventional Fab molecule.

If a third antigen binding moiety is present, in a particular embodiment the first and the third antigen moiety bind to HLA-A2/WT1, and the second antigen binding moiety binds to a second antigen, particularly an activating T cell antigen, more particularly CD3, most particularly CD3 epsilon.

In particular embodiments, the bispecific antigen binding molecule comprises an Fc domain composed of a first and a second subunit. The first and the second subunit of the Fc domain are capable of stable association.

The bispecific antigen binding molecule according to the invention can have different configurations, i.e. the first, second (and optionally third) antigen binding moiety may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some embodiments, the first and the second antigen binding moiety are each a Fab molecule and the second antigen binding moiety is fused at the C-terminus of the Fab heavy chain to the N-terminus of the first or the second subunit of the Fc domain. In such embodiments, the first antigen binding moiety may be fused at the C-terminus of the Fab heavy chain to the N-terminus of the Fab heavy chain of the second antigen binding moiety or to the N-terminus of the other one of the subunits of the Fc domain. In particular such embodiments, said first antigen binding moiety is a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other such embodiments, said first Fab molecule is a crossover Fab molecule and the second Fab molecule is a conventional Fab molecule.

In one embodiment, the first and the second antigen binding moiety are each a Fab molecule, the second antigen binding moiety is fused at the C-terminus of the Fab heavy chain to the N-terminus of the first or the second subunit of the Fc domain, and the first antigen binding moiety is fused at the C-terminus of the Fab heavy chain to the N-terminus of the Fab heavy chain of the second antigen binding moiety. In a specific embodiment, the bispecific antigen binding molecule essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIGS. 1G and 1K (with the second antigen binding domain in these examples being a VH/VL crossover Fab molecule). Optionally, the Fab light chain of the first Fab molecule and the Fab light chain of the second Fab molecule may additionally be fused to each other.

In another embodiment, the first and the second antigen binding moiety are each a Fab molecule and the first and the second antigen binding moiety are each fused at the C-terminus of the Fab heavy chain to the N-terminus of one of the subunits of the Fc domain. In a specific embodiment, the bispecific antigen binding molecule essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIGS. 1A and 1D (in these examples with the second antigen binding domain being a VH/VL crossover Fab molecule and the first antigen binding moiety being a conventional Fab molecule). The first and the second Fab molecule may be fused to the Fc domain directly or through a peptide linker. In a particular embodiment the first and the second Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain.

In some embodiments, the first and the second antigen binding moiety are each a Fab molecule and the first antigen binding moiety is fused at the C-terminus of the Fab heavy chain to the N-terminus of the first or the second subunit of the Fc domain. In such embodiments, the second antigen binding moiety may be fused at the C-terminus of the Fab heavy chain to the N-terminus of the Fab heavy chain of the second antigen binding moiety or (as described above) to the N-terminus of the other one of the subunits of the Fc domain. In particular such embodiments, said first antigen binding moiety is a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other such embodiments, said first Fab molecule is a crossover Fab molecule and the second Fab molecule is a conventional Fab molecule.

In one embodiment, the first and the second antigen binding moiety are each a Fab molecule, the first antigen binding moiety is fused at the C-terminus of the Fab heavy chain to the N-terminus of the first or the second subunit of the Fc domain, and the second antigen binding moiety is fused at the C-terminus of the Fab heavy chain to the N-terminus of the Fab heavy chain of the first antigen binding moiety. In a specific embodiment, the bispecific antigen binding molecule essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIGS. 1H and 1L (in these examples with the second antigen binding domain being a VH/VL crossover Fab molecule and the first antigen binding moiety being a conventional Fab molecule). Optionally, the Fab light chain of the first Fab molecule and the Fab light chain of the second Fab molecule may additionally be fused to each other.

In some embodiments, a third antigen binding moiety, particularly a third Fab molecule, is fused at the C-terminus of the Fab heavy chain to the N-terminus of the first or second subunit of the Fc domain. In particular such embodiments, said first and third Fab molecules are each a conventional Fab molecule, and the second Fab molecule is a crossover Fab molecule as described herein, i.e. a Fab molecule wherein the variable domains VH and VL or the constant domains CL and CH1 of the Fab heavy and light chains are exchanged/replaced by each other. In other such embodiments, said first and third Fab molecules are each a crossover Fab molecule and the second Fab molecule is a conventional Fab molecule.

In a particular such embodiment, the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second Fab molecule. In a specific embodiment, the bispecific antigen binding molecule essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1B and 1E (in these examples with the second antigen binding moiety being a VH/VL crossover Fab molecule, and the first and the third antigen binding moiety being a conventional Fab molecule), and FIGS. 1J and 1N (in these examples with the second antigen binding moiety being a conventional Fab molecule, and the first and the third antigen binding moiety being a VH/VL crossover Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In another such embodiment, the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. In a specific embodiment, the bispecific antigen binding molecule essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1C and 1F (in these examples with the second antigen binding moiety being a VH/VL crossover Fab molecule, and the first and the third antigen binding moiety being a conventional Fab molecule) and in FIGS. 1I and 1M (in these examples with the second antigen binding moiety being a conventional Fab molecule, and the first and the third antigen binding moiety being a VH/VL crossover Fab molecule). The first and the third Fab molecule may be fused to the Fc domain directly or through a peptide linker. In a particular embodiment the first and the third Fab molecule are each fused to the Fc domain through an immunoglobulin hinge region. In a specific embodiment, the immunoglobulin hinge region is a human IgG, hinge region, particularly where the Fc domain is an $IgG_1$ Fc domain. Optionally, the Fab light chain of the first Fab molecule and the Fab light chain of the second Fab molecule may additionally be fused to each other.

In configurations of the bispecific antigen binding molecule wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment the immunoglobulin is an $IgG_1$ subclass immunoglobulin. In another embodiment the immunoglobulin is an $IgG_4$ subclass immunoglobulin. In a further particular embodiment the immunoglobulin is a human immunoglobulin. In other embodiments the immunoglobulin is a chimeric immunoglobulin or a humanized immunoglobulin. In one embodiment, the immunoglobulin comprises a human constant region, particularly a human Fc region.

In some of the bispecific antigen binding molecule of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the bispecific antigen binding molecules of the invention.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence $(D)-(G_4S)_2$ (SEQ ID NOs 110 and 111). Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VL_{(2)}$-$CH1_{(2)}$-CH2-CH3(-CH4)), and a polypeptide wherein the Fab heavy chain of the first Fab molecule shares a carboxy-terminal peptide bond with an Fc domain subunit ($VH_{(1)}$-$CH1_{(1)}$-CH2-CH3(-CH4)). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In certain embodiments the polypeptides are covalently linked, e.g., by a disulfide bond.

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit ($VH_{(2)}$-$CL_{(2)}$-CH2-CH3(-CH4)), and a polypeptide wherein the Fab heavy chain of the first Fab molecule shares a carboxy-terminal peptide bond with an Fc domain subunit ($VH_{(1)}$-$CH1_{(1)}$-CH2-CH3(-CH4)). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In certain embodiments the polypeptides are covalently linked, e.g., by a disulfide bond.

In some embodiments, the bispecific antigen binding molecule comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit ($VL_{(2)}$-$CH1_{(2)}$-$VH_{(1)}$-$CH1_{(1)}$-CH2-CH3(-CH4)). In other embodiments, the bispecific antigen binding molecule comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VH_{(1)}$-$CH1_{(1)}$-$VL_{(2)}$-$CH1_{(2)}$-CH2-CH3(-CH4)).

In some of these embodiments the bispecific antigen binding molecule further comprises a crossover Fab light chain polypeptide of the second Fab molecule, wherein the Fab heavy chain variable region of the second Fab molecule shares a carboxy-terminal peptide bond with the Fab light chain constant region of the second Fab molecule ($VH_{(2)}$-$CL_{(2)}$), and the Fab light chain polypeptide of the first Fab molecule ($VL_{(1)}$-$CL_{(1)}$). In others of these embodiments the bispecific antigen binding molecule further comprises a polypeptide wherein the Fab heavy chain variable region of the second Fab molecule shares a carboxy-terminal peptide bond with the Fab light chain constant region of the second Fab molecule which in turn shares a carboxy-terminal peptide bond with the Fab light chain polypeptide of the first Fab molecule ($VH_{(2)}$-$CL_{(2)}$-$VL_{(1)}$-$CL_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule ($VL_{(1)}$-$CL_{(1)}$-$VH_{(2)}$-$CL_{(2)}$), as appropriate.

The bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain embodiments the polypeptides are covalently linked, e.g., by a disulfide bond.

In some embodiments, the bispecific antigen binding molecule comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with an Fc domain subunit ($VH_{(2)}$-$CL_{(2)}$-$VH_{(1)}$-$CH1_{(1)}$-CH2-CH3(-CH4)). In other embodiments, the bispecific antigen binding molecule comprises a polypeptide wherein the Fab heavy chain of the first Fab molecule shares a carboxy-terminal peptide bond with the Fab heavy chain variable region of the second Fab molecule which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit ($VH_{(1)}$-$CH1_{(1)}$-$VH_{(2)}$-$CL_{(2)}$-CH2-CH3(-CH4)).

In some of these embodiments the bispecific antigen binding molecule further comprises a crossover Fab light chain polypeptide of the second Fab molecule, wherein the Fab light chain variable region of the second Fab molecule shares a carboxy-terminal peptide bond with the Fab heavy chain constant region of the second Fab molecule ($VL_{(2)}$-$CH1_{(2)}$), and the Fab light chain polypeptide of the first Fab molecule ($VL_{(1)}$-$CL_{(1)}$). In others of these embodiments the bispecific antigen binding molecule further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule ($VL_{(2)}$-$CH1_{(2)}$-$VL_{(1)}$-$CL_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule ($VL_{(1)}$-$CL_{(1)}$-$VH_{(2)}$-$CL_{(2)}$), as appropriate.

The bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain embodiments the polypeptides are covalently linked, e.g., by a disulfide bond.

In certain embodiments, the bispecific antigen binding molecule does not comprise an Fc domain. In particular such embodiments, said first and, if present third Fab molecules are each a conventional Fab molecule, and the second Fab molecule is a crossover Fab molecule as described herein, i.e. a Fab molecule wherein the variable domains VH and VL or the constant domains CL and CH1 of the Fab heavy and light chains are exchanged/replaced by each other. In other such embodiments, said first and, if present third Fab molecules are each a crossover Fab molecule and the second Fab molecule is a conventional Fab molecule.

Figure 10A:
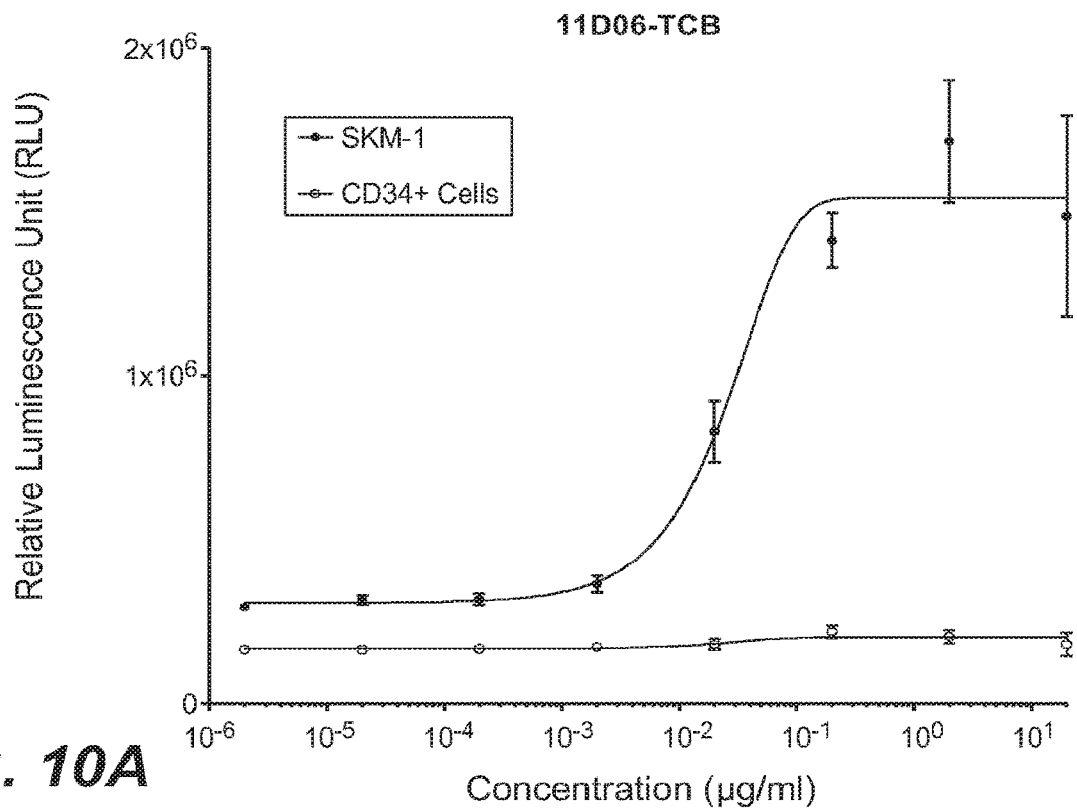
FIGS. 10A-B. No killing of normal bone marrow-derived CD34+ stem cells mediated by selected HLA-A2/WT1 x CD3 bispecific antibodies (TCBs). (A) 11D06-TCB, (B) 33H09-TCB.
Figure 10B:
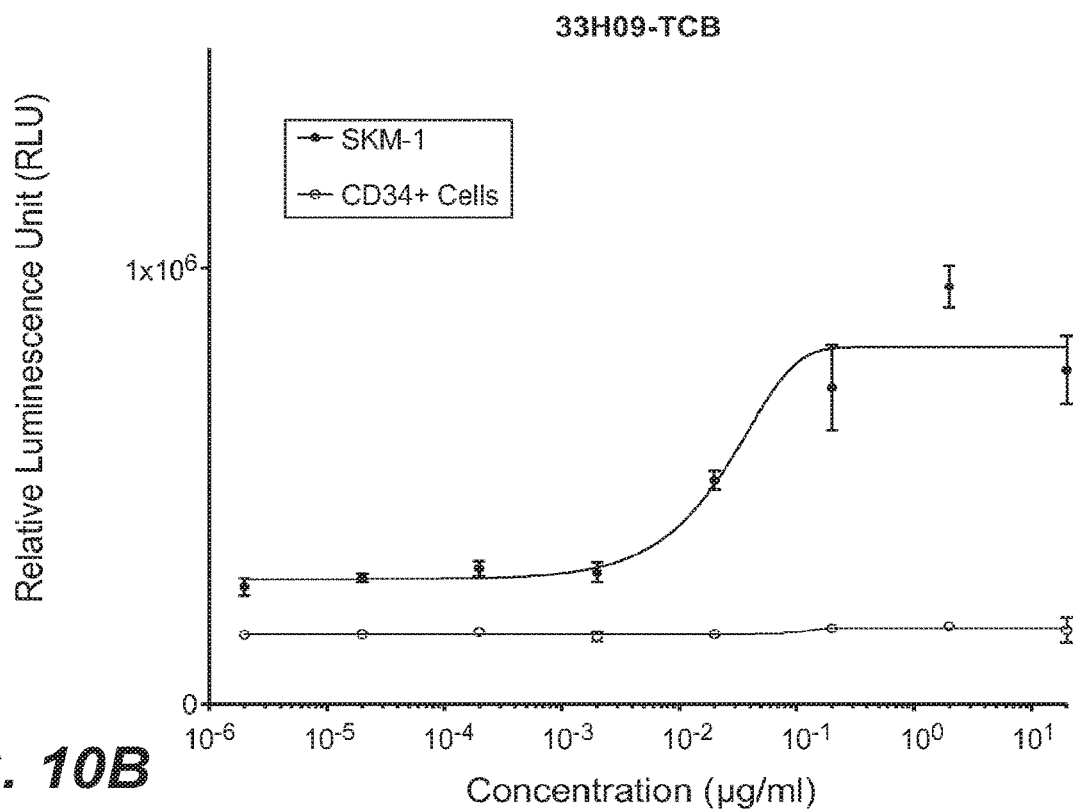

In one such embodiment, the bispecific antigen binding molecule essentially consists of the first and the second antigen binding moiety, and optionally one or more peptide linkers, wherein the first and the second antigen binding moiety are both Fab molecules and the first antigen binding moiety is fused at the C-terminus of the Fab heavy chain to the N-terminus of the Fab heavy chain of the second antigen binding moiety. Such a configuration is schematically depicted in FIGS. 10A-B and 1S (in these examples with the second antigen binding domain being a VH/VL crossover Fab molecule and the first antigen binding moiety being a conventional Fab molecule). In another such embodiment, the bispecific antigen binding molecule essentially consists of the first and the second antigen binding moiety, and optionally one or more peptide linkers, wherein the first and the second antigen binding moiety are both Fab molecules and the second antigen binding moiety is fused at the C-terminus of the Fab heavy chain to the N-terminus of the Fab heavy chain of the first antigen binding moiety. Such a configuration is schematically depicted in FIGS. 1P and 1T (in these examples with the second antigen binding domain being a VH/VL crossover Fab molecule and the first antigen binding moiety being a conventional Fab molecule). In some embodiments, the first Fab molecule is fused at the C-terminus of the Fab heavy chain to the N-terminus of the Fab heavy chain of the second Fab molecule, and the bispecific antigen binding molecule further comprises a third antigen binding moiety, particularly a third Fab molecule, wherein said third Fab molecule is fused at the C-terminus of the Fab heavy chain to the N-terminus of the Fab heavy chain of the first Fab molecule. In certain such embodiments, the bispecific antigen binding molecule essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the C-terminus of the Fab heavy chain to the N-terminus of the Fab heavy chain of the first Fab molecule. Such a configuration is schematically depicted in FIGS. 1Q and 1U (in these examples with the second antigen binding domain being a VH/VL crossover Fab molecule and the first and the antigen binding moiety each being a conventional Fab molecule), or FIGS. 1X and 1Z (in these examples with the second antigen binding domain being a conventional Fab molecule and the first and the third antigen binding moiety each being a VH/VL crossover Fab molecule).

In some embodiments, the second Fab molecule is fused at the C-terminus of the Fab heavy chain to the N-terminus of the Fab heavy chain of the first Fab molecule, and the bispecific antigen binding molecule further comprises a third antigen binding moiety, particularly a third Fab molecule, wherein said third Fab molecule is fused at the N-terminus of the Fab heavy chain to the C-terminus of the Fab heavy chain of the first Fab molecule. In certain such embodiments, the bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIGS. 1R and 1V (in these examples with the second antigen binding domain being a VH/VL crossover Fab molecule and the first and the antigen binding moiety each being a conventional Fab molecule), or FIGS. 1W and 1Y (in these examples with the second antigen binding domain being a conventional Fab molecule and the first and the third antigen binding moiety each being a VH/VL crossover Fab molecule).

In certain embodiments the bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(2)}$-$CL_{(2)}$-$VH_{(1)}$-$CH1_{(1)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-$CH1_{(3)}$-$VH_{(1)}$-$CH1_{(1)}$-$VL_{(2)}$-$CH1_{(2)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) (VH$_{(3)}$-CH1$_{(3)}$-VH$_{(1)}$-CH1$_{(1)}$-VH$_{(2)}$-CL$_{(2)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$ and the Fab light chain polypeptide of the first Fab molecule (VL$_{(1)}$-CL$_{(1)}$). In some embodiments the bispecific antigen binding molecule further comprises the Fab light chain polypeptide of a third Fab molecule (VL$_{(3)}$-CL$_{(3)}$).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule (VL$_{(2)}$-CH1$_{(2)}$-VH$_{(1)}$-CH1$_{(1)}$-VH$_{(3)}$-CH1$_{(3)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some embodiments the bispecific antigen binding molecule further comprises the Fab light chain polypeptide of a third Fab molecule (VL$_{(3)}$-CL$_{(3)}$).

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule (VH$_{(2)}$-CL$_{(2)}$-VH$_{(1)}$-CH1$_{(1)}$-VH$_{(3)}$-CH1$_{(3)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In some embodiments the bispecific antigen binding molecule further comprises the Fab light chain polypeptide of a third Fab molecule (VL$_{(3)}$-CL$_{(3)}$).

In certain embodiments the bispecific antigen binding molecule according to the invention comprises a polypeptide wherein the Fab heavy chain of the second Fab molecule shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) (VH$_{(2)}$-CH1$_{(2)}$-VL$_{(1)}$-CH1$_{(1)}$-VL$_{(3)}$-CH1$_{(3)}$). In some embodiments the bispecific antigen binding molecule further comprises a polypeptide wherein the Fab heavy chain variable region of the first Fab molecule shares a carboxy-terminal peptide bond with the Fab light chain constant region of the first Fab molecule (VH$_{(1)}$-CL$_{(1)}$) and the Fab light chain polypeptide of the second Fab molecule (VL$_{(2)}$-CL$_{(2)}$). In some embodiments the bispecific antigen binding molecule further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain embodiments the bispecific antigen binding molecule according to the invention comprises a polypeptide wherein the Fab heavy chain of the second Fab molecule shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) (VH$_{(2)}$-CH1$_{(2)}$-VH$_{(1)}$-CL$_{(1)}$-VH$_{(3)}$-CL$_{(3)}$). In some embodiments the bispecific antigen binding molecule further comprises a polypeptide wherein the Fab light chain variable region of the first Fab molecule shares a carboxy-terminal peptide bond with the Fab heavy chain constant region of the first Fab molecule (VL$_{(1)}$-CH1$_{(1)}$) and the Fab light chain polypeptide of the second Fab molecule (VL$_{(2)}$-CL$_{(2)}$). In some embodiments the bispecific antigen binding molecule further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In certain embodiments the bispecific antigen binding molecule according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule (VL$_{(3)}$-CH1$_{(3)}$-VL$_{(1)}$-CH1$_{(1)}$-VH$_{(2)}$-CH1$_{(2)}$). In some embodiments the bispecific antigen binding molecule further comprises a polypeptide wherein the Fab heavy chain variable region of the first Fab molecule shares a carboxy-terminal peptide bond with the Fab light chain constant region of the first Fab molecule (VH$_{(1)}$-CL$_{(1)}$) and the Fab light chain polypeptide of the second Fab molecule (VL$_{(2)}$-CL$_{(2)}$). In some embodiments the bispecific antigen binding molecule further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain embodiments the bispecific antigen binding molecule according to the invention comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule (VH$_{(3)}$-CL$_{(3)}$-VH$_{(1)}$-CL$_{(1)}$-VH$_{(2)}$-CH1$_{(2)}$). In some embodiments the bispecific antigen binding molecule further comprises a polypeptide wherein the Fab light chain variable region of the first Fab molecule shares a carboxy-terminal peptide bond with the Fab heavy chain constant region of the first Fab molecule (VL$_{(1)}$-CH1$_{(1)}$) and the Fab light chain polypeptide of the second Fab molecule (VL$_{(2)}$-CL$_{(2)}$). In some embodiments the bispecific antigen binding molecule further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In one embodiment, the invention provides a bispecific antigen binding molecule comprising
  a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;
  b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other;
  c) an Fc domain composed of a first and a second subunit; wherein
    (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or
    (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising
  a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;
  b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other;
  c) a third antigen binding moiety that binds to the first antigen and is identical to the first antigen binding moiety; and
  d) an Fc domain composed of a first and a second subunit; wherein
    (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or
    (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising
  a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;
b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other;
c) an Fc domain composed of a first and a second subunit; wherein
(i) the first antigen binding moiety under a) and the second antigen binding moiety under b) are each fused at the C-terminus of the Fab heavy chain to the N-terminus of one of the subunits of the Fc domain under c).

In one embodiment, the invention provides a bispecific antigen binding molecule comprising
a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14;
b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other;
c) an Fc domain composed of a first and a second subunit; wherein
(i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or
(ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising
a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14;
b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other; c) a third antigen binding moiety that binds to the first antigen and is identical to the first antigen binding moiety; and
d) an Fc domain composed of a first and a second subunit; wherein
(i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or
(ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising
a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14;
b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other;
c) an Fc domain composed of a first and a second subunit; wherein
(i) the first antigen binding moiety under a) and the second antigen binding moiety under b) are each fused at the C-terminus of the Fab heavy chain to the N-terminus of one of the subunits of the Fc domain under c).

In all of the different configurations of the bispecific antigen binding molecule according to the invention, the amino acid substitutions described herein, if present, may either be in the CH1 and Cl domains of the first and (if present) the third antigen binding moiety/Fab molecule, or in the CH1 and CL domains of the second antigen binding moiety/Fab molecule. Preferably, they are in the CH1 and CL domains of the first and (if present) the third antigen binding moiety/Fab molecule. In accordance with the concept of the invention, if amino acid substitutions as described herein are made in the first (and, if present, the third) antigen binding moiety/Fab molecule, no such amino acid substitutions are made in the second antigen binding moiety/Fab molecule. Conversely, if amino acid substitutions as described herein are made in the second antigen binding moiety/Fab molecule, no such amino acid substitutions are made in the first (and, if present, the third) antigen binding moiety/Fab molecule. Amino acid substitutions are particularly made in bispecific antigen binding molecules comprising a Fab molecule wherein the variable domains VL and VH1 of the Fab light chain and the Fab heavy chain are replaced by each other.

In particular embodiments of the bispecific antigen binding molecule according to the invention, particularly wherein amino acid substitutions as described herein are made in the first (and, if present, the third) antigen binding moiety/Fab molecule, the constant domain CL of the first (and, if present, the third) Fab molecule is of kappa isotype. In other embodiments of the bispecific antigen binding molecule according to the invention, particularly wherein amino acid substitutions as described herein are made in the second antigen binding moiety/Fab molecule, the constant domain CL of the second antigen binding moiety/Fab molecule is of kappa isotype. In some embodiments, the constant domain CL of the first (and, if present, the third) antigen binding moiety/Fab molecule and the constant domain CL of the second antigen binding moiety/Fab molecule are of kappa isotype.

In one embodiment, the invention provides a bispecific antigen binding molecule comprising a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;
  b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;
  c) an Fc domain composed of a first and a second subunit;
  wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and
  wherein
  (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or
  (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising
  a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;
  b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;
  c) a third antigen binding moiety that binds to the first antigen and is identical to the first antigen binding moiety; and
  d) an Fc domain composed of a first and a second subunit;
  wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and
  wherein
  (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or
  (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising
  a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;

c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

In one embodiment, the invention provides a bispecific antigen binding molecule comprising a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;

c) an Fc domain composed of a first and a second subunit; wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;

c) a third antigen binding moiety that binds to the first antigen and is identical to the first antigen binding moiety; and d) an Fc domain composed of a first and a second subunit; wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising
a) a first antigen binding moiety that binds to a first antigen, wherein the first antigen is HLA-A2/WT1, particularly HLA-A2/WT1$_{RMF}$, and the first antigen binding moiety is a Fab molecule comprising a heavy chain variable region (VH) comprising a heavy chain complementary determining region (HCDR) 1 of SEQ ID NO: 9, a HCDR 2 of SEQ ID NO: 10, and a HCDR 3 of SEQ ID NO: 11, and a light chain variable region (VL) comprising a light chain complementarity determining region (LCDR) 1 of SEQ ID NO: 12, a LCDR 2 of SEQ ID NO: 13 and a LCDR 3 of SEQ ID NO: 14;
b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;
c) an Fc domain composed of a first and a second subunit;
wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and
wherein the first antigen binding moiety under a) and the second antigen binding moiety under b) are each fused at the C-terminus of the Fab heavy chain to the N-terminus of one of the subunits of the Fc domain under c).

According to any of the above embodiments, components of the bispecific antigen binding molecule (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, (G$_4$S)$_n$, (SG$_4$)$_n$, (G$_4$S)$_n$ or G$_4$(SG$_4$)$_n$ peptide linkers, wherein n is generally an integer from 1 to 10, typically from 2 to 4.

In a particular aspect, the invention provides a bispecific antigen binding molecule comprising
a) a first and a third antigen binding moiety that binds to a first antigen; wherein the first antigen is HLA-A2/WT1, particularly HLA-A2/WT1$_{RMF}$, and wherein the first and the second antigen binding moiety are each a (conventional) Fab molecule comprising a heavy chain variable region comprising the amino acid sequence of SEQ ID NO: 7 and a light chain variable region comprising the amino acid sequence of SEQ ID NO: 8;
b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising (i) a heavy chain variable region comprising the amino acid sequence of SEQ ID NO: 121 and a light chain variable region comprising the amino acid sequence of SEQ ID NO: 122, or (ii) a heavy chain variable region comprising the amino acid sequence of SEQ ID NO: 136 and a light chain variable region comprising the amino acid sequence of SEQ ID NO: 137 (particularly a a heavy chain variable region comprising the amino acid sequence of SEQ ID NO: 136 and a light chain variable region comprising the amino acid sequence of SEQ ID NO: 137);
c) an Fc domain composed of a first and a second subunit;
wherein
in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index);
and wherein further
the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In a further aspect, the invention provides a bispecific antigen binding molecule comprising
a) a first and a third antigen binding moiety that binds to a first antigen; wherein the first antigen is HLA-A2/WT1, particularly HLA-A2/WT1$_{RMF}$, and wherein the first and the second antigen binding moiety are each a (conventional) Fab molecule comprising a heavy chain variable region comprising the amino acid sequence of SEQ ID NO: 15 and a light chain variable region comprising the amino acid sequence of SEQ ID NO: 16;
b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising (i) a heavy chain variable region comprising the amino acid sequence of SEQ ID NO: 121 and a light chain variable region comprising the amino acid sequence of SEQ ID NO: 122, or (ii) a heavy chain variable region comprising the amino acid sequence of SEQ ID NO: 136 and a light chain variable region comprising the amino acid sequence of SEQ ID NO: 137 (particularly a heavy chain variable region comprising the amino acid sequence of SEQ ID NO: 136 and a light chain variable region comprising the amino acid sequence of SEQ ID NO: 137);
c) an Fc domain composed of a first and a second subunit;
wherein
in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index);

and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In one embodiment according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further embodiment according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further embodiment according to these aspects of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further embodiment according to these aspects of the invention, the Fc domain is a human IgG$_1$ Fc domain.

In particular specific embodiment, the bispecific antigen binding molecule comprises a polypeptide comprising an amino acid sequence that is at least 95%, 96%, 97%, 98%, or 99% identical to the sequence of SEQ ID NO: 123, a polypeptide comprising an amino acid sequence that is at least 95%, 96%, 97%, 98%, or 99% identical to the sequence of SEQ ID NO: 125, a polypeptide comprising an amino acid sequence that is at least 95%, 96%, 97%, 98%, or 99% identical to the sequence of SEQ ID NO: 139, and a polypeptide comprising an amino acid sequence that is at least 95%, 96%, 97%, 98%, or 99% identical to the sequence of SEQ ID NO: 140. In a further particular specific embodiment, the bispecific antigen binding molecule comprises a polypeptide comprising the amino acid sequence of SEQ ID NO: 123, a polypeptide comprising the amino acid sequence of SEQ ID NO: 125, a polypeptide comprising the amino acid sequence of SEQ ID NO: 139 and a polypeptide comprising the amino acid sequence of SEQ ID NO: 140.

In another specific embodiment, the bispecific antigen binding molecule comprises a polypeptide comprising an amino acid sequence that is at least 95%, 96%, 97%, 98%, or 99% identical to the sequence of SEQ ID NO: 123, a polypeptide comprising an amino acid sequence that is at least 95%, 96%, 97%, 98%, or 99% identical to the sequence of SEQ ID NO: 124, a polypeptide comprising an amino acid sequence that is at least 95%, 96%, 97%, 98%, or 99% identical to the sequence of SEQ ID NO: 125, and a polypeptide comprising an amino acid sequence that is at least 95%, 96%, 97%, 98%, or 99% identical to the sequence of SEQ ID NO: 129. In a further particular specific embodiment, the bispecific antigen binding molecule comprises a polypeptide comprising the amino acid sequence of SEQ ID NO: 123, a polypeptide comprising the amino acid sequence of SEQ ID NO: 124, a polypeptide comprising the amino acid sequence of SEQ ID NO: 125 and a polypeptide comprising the amino acid sequence of SEQ ID NO: 129.

In another specific embodiment, the bispecific antigen binding molecule comprises a polypeptide comprising an amino acid sequence that is at least 95%, 96%, 97%, 98%, or 99% identical to the sequence of SEQ ID NO: 126, a polypeptide comprising an amino acid sequence that is at least 95%, 96%, 97%, 98%, or 99% identical to the sequence of SEQ ID NO: 127, a polypeptide comprising an amino acid sequence that is at least 95%, 96%, 97%, 98%, or 99% identical to the sequence of SEQ ID NO: 128, and a polypeptide comprising an amino acid sequence that is at least 95%, 96%, 97%, 98%, or 99% identical to the sequence of SEQ ID NO: 129. In a further specific embodiment, the bispecific antigen binding molecule comprises a polypeptide comprising the amino acid sequence of SEQ ID NO: 126, a polypeptide comprising the amino acid sequence of SEQ ID NO: 127, a polypeptide comprising the amino acid sequence of SEQ ID NO: 128 and a polypeptide comprising the amino acid sequence of SEQ ID NO: 129.

Fc Domain

In particular embodiments, the bispecific antigen binding molecule of the invention comprises an Fc domain composed of a first and a second subunit. It is understood, that the features of the Fc domain described herein in relation to the bispecific antigen binding molecule can equally apply to an Fc domain comprised in an antibody of the invention.

The Fc domain of the bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment, the bispecific antigen binding molecule of the invention comprises not more than one Fc domain.

In one embodiment, the Fc domain of the bispecific antigen binding molecule is an IgG Fc domain. In a particular embodiment, the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat EU index numbering), particularly the amino acid substitution S228P. This amino acid substitution reduces in vivo Fab arm exchange of IgG$_4$ antibodies (see Stubenrauch et al., Drug Metabolism and Disposition 38, 84-91 (2010)). In a further particular embodiment, the Fc domain is a human Fc domain. In an even more particular embodiment, the Fc domain is a human IgG$_1$ Fc domain. An exemplary sequence of a human IgG$_1$ Fc region is given in SEQ ID NO: 109.

Fc Domain Modifications Promoting Heterodimerization

Bispecific antigen binding molecules according to the invention comprise different antigen binding moieties, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of bispecific antigen binding molecules in recombinant production, it will thus be advantageous to introduce in the Fc domain of the bispecific antigen binding molecule a modification promoting the association of the desired polypeptides.

Accordingly, in particular embodiments, the Fc domain of the bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the bispecific antigen binding molecule which reduce heavy/light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In a particular embodiment the antigen binding moiety that binds to the second antigen (e.g. an activating T cell antigen) is fused (optionally via the first antigen binding moiety, which binds to HLA-A2/WT1, and/or a peptide linker) to the first subunit of the Fc domain (comprising the "knob" modification). Without wishing to be bound by theory, fusion of the antigen binding moiety that binds a second antigen, such as an activating T cell antigen, to the knob-containing subunit of the Fc domain will (further) minimize the generation of antigen binding molecules comprising two antigen binding moieties that bind to an activating T cell antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment, the heterodimerization approach described in EP 1870459, is used alternatively. This approach is based on the introduction of charged amino acids with opposite charges at specific amino acid positions in the CH3/CH3 domain interface between the two subunits of the Fc domain. One preferred embodiment for the bispecific antigen binding molecule of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment, the bispecific antigen binding molecule of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment, the bispecific antigen binding molecule of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said bispecific antigen binding molecule comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment, the heterodimerization approach described in WO 2013/157953 is used alternatively. In one embodiment, a first CH3 domain comprises amino acid mutation T366K and a second CH3 domain comprises amino acid mutation 1.351D (numberings according to Kabat EU index). In a further embodiment, the first CH3 domain comprises further amino acid mutation L351K. In a further embodiment, the second CH3 domain comprises further an amino acid mutation selected from Y349E, Y349D and L368E (preferably L368E) (numberings according to Kabat EU index).

In one embodiment, the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment, a first CH3 domain comprises amino acid mutation Y407A and a second CH3 domain comprises amino acid mutations T366A, K409F. In a further embodiment, the second CH3 domain further comprises amino acid mutations K392E, T411E, D399R and S400R (numberings according to Kabat EU index).

In one embodiment, the heterodimerization approach described in WO 2011/143545 is used alternatively, e.g. with the amino acid modification at a position selected from the group consisting of 368 and 409 (numbering according to Kabat EU index).

In one embodiment, the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment, a first CH3 domain comprises amino acid mutation T366Y and a second CH3 domain comprises amino acid mutation Y407T (numberings according to Kabat EU index).

In one embodiment, the bispecific antigen binding molecule or its Fc domain is of $IgG_2$ subclass and the heterodimerization approach described in WO 2010/129304 is used alternatively. In an alternative embodiment, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment, a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment, the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment, the heterodimerization approach described in WO 2007/147901 is used alternatively. In one embodiment, a first CH3 domain comprises amino acid mutations K253E, D282K, and K322D and a second CH3 domain comprises amino acid mutations D239K, E240K, and K292D (numberings according to Kabat EU index).

In still another embodiment, the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to the bispecific antigen binding molecule (or the antibody) favorable pharmacokinetic properties, including a long serum half-life which contributes to good accumulation in the target tissue and a favorable tissue-blood distribution ratio. At the same time it may, however, lead to undesirable targeting of the bispecific antigen binding molecule (or the antibody) to cells expressing Fc receptors rather than to the preferred antigen-bearing cells. Moreover, the co-activation of Fc receptor signaling pathways may lead to cytokine release which, in combination with the T cell activating properties (e.g. in embodiments of the bispecific antigen binding molecule wherein the second antigen binding moiety binds to an activating T cell antigen) and the long half-life of the bispecific antigen binding molecule, results in excessive activation of cytokine receptors and severe side effects upon systemic administration. Activation of (Fc receptor-bearing) immune cells other than T cells may even reduce efficacy of the bispecific antigen binding molecule (particularly a bispecific antigen binding molecule wherein the second antigen binding moiety binds to an activating T cell antigen) due to the potential destruction of T cells e.g. by NK cells.

Accordingly, in particular embodiments, the Fc domain of the bispecific antigen binding molecule according to the invention exhibits reduced binding affinity to an Fc receptor and/or reduced effector function, as compared to a native IgG$_1$ Fc domain. In one such embodiment the Fc domain (or the bispecific antigen binding molecule comprising said Fc domain) exhibits less than 50%, preferably less than 20%, more preferably less than 10% and most preferably less than 5% of the binding affinity to an Fc receptor, as compared to a native IgG$_1$ Fc domain (or a bispecific antigen binding molecule comprising a native IgG Fc domain), and/or less than 50%, preferably less than 20%, more preferably less than 10% and most preferably less than 5% of the effector function, as compared to a native IgG$_1$ Fc domain domain (or a bispecific antigen binding molecule comprising a native IgG: Fc domain). In one embodiment, the Fc domain domain (or the bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment, the effector function is ADCC. In one embodiment, the Fc domain domain exhibits substantially similar binding affinity to neonatal Fc receptor (FcRn), as compared to a native IgG$_1$ Fc domain domain. Substantially similar binding to FcRn is achieved when the Fc domain (or the bispecific antigen binding molecule comprising said Fc domain) exhibits greater than about 70%, particularly greater than about 80%, more particularly greater than about 90% of the binding affinity of a native IgG$_1$ Fc domain (or the bispecific antigen binding molecule comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment, the amino acid mutation reduces the binding affinity of the Fc domain to an Fc receptor. In one embodiment, the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the bispecific antigen binding molecule comprising an engineered Fc domain exhibits less than 20%, particularly less than 10%, more particularly less than 5% of the binding affinity to an Fc receptor as compared to a bispecific antigen binding molecule comprising a non-engineered Fc domain. In a particular embodiment, the Fc receptor is an Fcγ receptor. In some embodiments, the Fc receptor is a human Fc receptor. In some embodiments, the Fc receptor is an activating Fc receptor. In a specific embodiment, the Fc receptor is an activating human Fcγ receptor, more specifically human FcγRIIIa, FcγRI or FcγRIIa, most specifically human FcγRIIIa. Preferably, binding to each of these receptors is reduced. In some embodiments, binding affinity to a complement component, specifically binding affinity to C1q, is also reduced. In one embodiment, binding affinity to neonatal Fc receptor (FcRn) is not reduced. Substantially similar binding to FcRn, i.e. preservation of the binding affinity of the Fc domain to said receptor, is achieved when the Fc domain (or the bispecific antigen binding molecule comprising said Fc domain) exhibits greater than about 70% of the binding affinity of a non-engineered form of the Fc domain (or the bispecific antigen binding molecule comprising said non-engineered form of the Fc domain) to FcRn. The Fc domain, or bispecific antigen binding molecules of the invention comprising said Fc domain, may exhibit greater than about 80% and even greater than about 90% of such affinity. In certain embodiments, the Fc domain of the bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced cross-linking of target-bound antibodies, reduced dendritic cell maturation, or reduced T cell priming. In one embodiment, the reduced effector function is one or more selected from the group of reduced CDC, reduced ADCC, reduced ADCP, and reduced cytokine secretion. In a particular embodiment, the reduced effector function is reduced ADCC. In one embodiment the reduced ADCC is less than 20% of the ADCC induced by a non-engineered Fc domain (or a bispecific antigen binding molecule comprising a non-engineered Fc domain).

In one embodiment, the amino acid mutation that reduces the binding affinity of the Fc domain to an Fc receptor and/or effector function is an amino acid substitution. In one embodiment, the Fc domain comprises an amino acid substitution at a position selected from the group of E233, L234, L235, N297, P331 and P329 (numberings according to Kabat EU index). In a more specific embodiment, the Fc domain comprises an amino acid substitution at a position selected from the group of L234, L235 and P329 (numberings according to Kabat EU index). In some embodiments, the Fc domain comprises the amino acid substitutions L234A and L235A (numberings according to Kabat EU index). In one such embodiment, the Fc domain is an IgG$_1$ Fc domain, particularly a human IgG$_1$ Fc domain. In one embodiment, the Fc domain comprises an amino acid substitution at position P329. In a more specific embodiment, the amino acid substitution is P329A or P329G, particularly P329G (numberings according to Kabat EU index). In one embodiment, the Fc domain comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain comprises amino acid substitutions at positions P329, L234 and L235 (numberings according to Kabat EU index). In more particular embodiments, the Fc domain comprises the amino acid mutations L234A, L235A and P329G ("P329G LALA", "PGLALA" or "LALAPG"). Specifically, in particular embodiments, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such embodiment, the Fc domain is an IgG: Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments, the Fc domain of the bispecific antigen binding molecules of the invention is an IgG$_4$ Fc domain, particularly a human IgG$_4$ Fc domain. In one embodiment, the IgG$_4$ Fc domain comprises amino acid substitutions at position S228, specifically the amino acid substitution S228P (numberings according to Kabat EU index). To further reduce its binding affinity to an Fc receptor and/or its effector function, in one embodiment, the IgG$_4$ Fc domain comprises an amino acid substitution at position L235, specifically the amino acid substitution L235E (numberings according to Kabat EU index). In another embodiment, the IgG$_4$ Fc domain comprises an amino acid substitution at position P329, specifically the amino acid substitution P329G (numberings according to Kabat EU index). In a particular embodiment, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety.

In a particular embodiment, the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain embodiments, N-glycosylation of the Fc domain has been eliminated. In one such embodiment, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or bispecific antigen binding molecules comprising an Fc domain for Fc receptors may be evaluated using cell lines known to express particular Fc receptors, such as human NK cells expressing FcγIIIa receptor.

Effector function of an Fc domain, or a bispecific antigen binding molecule comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or the bispecific antigen binding molecule comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

FcRn binding and in vivo clearance/half life determinations can also be performed using methods known in the art (see, e.g., Petkova, S. B. et al., *Int'l. Immunol.* 18(12): 1759-1769 (2006); WO 2013/120929).

Polynucleotides

The invention further provides isolated polynucleotides encoding an antibody or bispecific antigen binding molecule as described herein or a fragment thereof. In some embodiments, said fragment is an antigen binding fragment.

The polynucleotides encoding antibodies or bispecific antigen binding molecules of the invention may be expressed as a single polynucleotide that encodes the entire antibody or bispecific antigen binding molecule or as multiple (e.g., two or more) polynucleotides that are co-expressed. Polypeptides encoded by polynucleotides that are co-expressed may associate through, e.g., disulfide bonds or other means to form a functional antibody or bispecific antigen binding molecule. For example, the light chain portion of an antibody or bispecific antigen binding molecule may be encoded by a separate polynucleotide from the portion of the antibody or bispecific antigen binding molecule comprising the heavy chain of the antibody or bispecific antigen binding molecule. When co-expressed, the heavy chain polypeptides will associate with the light chain polypeptides to form the antibody or bispecific antigen binding molecule. In another example, the portion of the antibody or bispecific antigen binding molecule comprising one of the two Fc domain subunits and optionally (part of) one or more Fab molecules could be encoded by a separate polynucleotide from the portion of the antibody or bispecific antigen binding molecule comprising the the other of the two Fc domain subunits and optionally (part of) a Fab molecule.

When co-expressed, the Fc domain subunits will associate to form the Fc domain.

In some embodiments, the isolated polynucleotide encodes the entire antibody or bispecific antigen binding molecule according to the invention as described herein. In other embodiments, the isolated polynucleotide encodes a polypeptide comprised in the antibody or bispecific antigen binding molecule according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Antibodies or bispecific antigen binding molecules of the invention may be obtained, for example, by solid-state peptide synthesis (e.g. Merrifield solid phase synthesis) or recombinant production. For recombinant production one or more polynucleotide encoding the antibody or bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an antibody or bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody or bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody or bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or bispecific antigen binding molecule is desired, DNA encoding a signal sequence may be placed upstream of the nucleic acid encoding an antibody or bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody or bispecific antigen binding molecule may be included within or at the ends of the antibody or bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) one or more vector comprising one or more polynucleotide that encodes (part of) an antibody or bispecific antigen binding molecule of the invention. As used herein, the term "host cell" refers to any kind of cellular system which can be engineered to generate the antibody or bispecific antigen binding molecule of the invention or fragments thereof. Host cells suitable for replicating and for supporting expression of antibodies or bispecific antigen binding molecules are well known in the art. Such cells may be transfected or transduced as appropriate with the particular expression vector and large quantities of vector containing cells can be grown for seeding large scale fermenters to obtain sufficient quantities of the antibody or bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CVI line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain. In one embodiment, a method of producing an antibody or bispecific antigen binding molecule according to the invention is provided, wherein the method comprises culturing a host cell comprising a polynucleotide encoding the antibody or bispecific antigen binding molecule, as provided herein, under conditions suitable for expression of the antibody or bispecific antigen binding molecule, and optionally recovering the antibody or bispecific antigen binding molecule from the host cell (or host cell culture medium).

The components of the bispecific antigen binding molecule (or the antibody) of the invention may be genetically fused to each other. The bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of bispecific antigen binding molecules are provided herein. Additional sequences may also be included to incorporate a cleavage site to separate the individual components of the fusion if desired, for example an endopeptidase recognition sequence.

The antibody or bispecific antigen binding molecule of the invention generally comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region may be used in the antibody or bispecific antigen binding molecule of the invention. Non-limiting antibodies, antibody fragments, antigen binding domains or variable regions useful in the present invention can be of murine, primate, or human origin. If the antibody or bispecific antigen binding molecule is intended for human use, a chimeric form of antibody may be used wherein the constant regions of the antibody are from a human. A humanized or fully human form of the antibody can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human antibodies can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3): 927-937

(2005) and Vollmers and Brandlein, *Methods and Findings in Experimental and Clinical Pharmacology,* 27(3):185-91 (2005).

Human antibodies may also be generated by isolation from human antibody libraries, as described herein.

Antibodies useful in the invention may be isolated by screening combinatorial libraries for antibodies with the desired activity or activities. Methods for screening combinatorial libraries are reviewed, e.g., in Lerner et al. in *Nature Reviews* 16:498-508 (2016). For example, a variety of methods are known in the art for generating phage display libraries and screening such libraries for antibodies possessing the desired binding characteristics. Such methods are reviewed, e.g., in Frenzel et al. in mAbs 8:1177-1194 (2016); Bazan et al. in *Human Vaccines and Immunotherapeutics* 8:1817-1828 (2012) and Zhao et al. in *Critical Reviews in Biotechnology* 36:276-289 (2016) as well as in Hoogenboom et al. in *Methods in Molecular Biology* 178: 1-37 (O'Brien et al., ed., Human Press, Totowa, N J, 2001) and in Marks and Bradbury in *Methods in Molecular Biology* 248:161-175 (Lo, ed., Human Press, Totowa, N J, 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in *EMBO Journal* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319:155-175 (2015) as well as in the Zhao et al. in *Methods in Molecular Biology* 889:73-84 (2012). Methods for ribosome display are described, e.g., in He et al. in *Nucleic Acids Research* 25:5132-5134 (1997) and in Hanes et al. in *PNAS* 94:4937-4942 (1997).

Antibodies or bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody or bispecific antigen binding molecule binds. For example, for affinity chromatography purification of antibodies or bispecific antigen binding molecules of the invention, a matrix with protein A or protein G may be used. Sequential Protein A or G affinity chromatography and size exclusion chromatography can be used to isolate an antibody or bispecific antigen binding molecule essentially as described in the Examples. The purity of the antibody or bispecific antigen binding molecule can be determined by any of a variety of well known analytical methods including gel electrophoresis, high pressure liquid chromatography, and the like.

Compositions, Formulations, and Routes of Administration

In a further aspect, the invention provides pharmaceutical compositions comprising any of the antibodies or bispecific antigen binding molecules provided herein, e.g., for use in any of the below therapeutic methods. In one embodiment, a pharmaceutical composition comprises any of the antibodies or bispecific antigen binding molecules provided herein and a pharmaceutically acceptable carrier. In another embodiment, a pharmaceutical composition comprises any of the antibodies or bispecific antigen binding molecules provided herein and at least one additional therapeutic agent, e.g., as described below.

Further provided is a method of producing an antibody or bispecific antigen binding molecule of the invention in a form suitable for administration in vivo, the method comprising (a) obtaining an antibody or bispecific antigen binding molecule according to the invention, and (b) formulating the antibody or bispecific antigen binding molecule with at least one pharmaceutically acceptable carrier, whereby a preparation of antibody or bispecific antigen binding molecule is formulated for administration in vivo.

Pharmaceutical compositions of the present invention comprise a therapeutically effective amount of antibody or bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody or bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. An antibody or bispecific antigen binding moelcule of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies or bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the antibodies or bispecific antigen binding molecules may be in powder form for constitution with a suitable vehicle, e.g., sterile pyrogen-free water, before use. Sterile injectable solutions are prepared by incorporating the antibodies or bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the antibodies or bispecific antigen binding molecules may also be formulated as a depot preparation. Such long acting formulations may be administered by implantation (for example subcutaneously or intramuscularly) or by intramuscular injection. Thus, for example, the antibodies or bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies or bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen. The antibodies or bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

Pharmaceutical salts tend to be more soluble in aqueous and other protic solvents than are the corresponding free base forms.

Therapeutic Methods and Compositions

Any of the antibodies or bispecific antigen binding molecules provided herein may be used in therapeutic methods. Antibodies or bispecific antigen binding molecules of the invention may be used as immunotherapeutic agents, for example in the treatment of cancers.

For use in therapeutic methods, antibodies or bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies or bispecific antigen binding molecules of the invention for use as a medicament are provided. In further aspects, antibodies or bispecific antigen binding molecules of the invention for use in treating a disease are provided. In certain embodiments, antibodies or bispecific antigen binding molecules of the invention for use in a method of treatment are provided. In one embodiment, the invention provides an antibody or bispecific antigen binding molecule as described herein for use in the treatment of a disease in an individual in need thereof. In certain embodiments, the invention provides an antibody or bispecific antigen binding molecule for use in a method of treating an individual having a disease comprising administering to the individual a therapeutically effective amount of the antibody or bispecific antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides an antibody or bispecific antigen binding molecule as described herein for use in inducing lysis of a target cell, particularly a tumor cell. In certain embodiments, the invention provides an antibody or bispecific antigen binding molecule for use in a method of inducing lysis of a target cell, particularly a tumor cell, in an individual comprising administering to the individual an effective amount of the antibody or bispecific antigen binding molecule to induce lysis of a target cell. An "individual" according to any of the above embodiments is a mammal, preferably a human.

In a further aspect, the invention provides for the use of an antibody or bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of an antibody or bispecific antigen binding molecule of the invention. In one embodiment a composition is administered to said individual, comprising the antibody or bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with an antibody or bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of an antibody or bispecific antigen binding molecule to induce lysis of a target cell. In one embodiment, an "individual" is a human.

In certain embodiments the disease to be treated is a proliferative disorder, particularly cancer. Non-limiting examples of cancers include haematological cancer such as leukemia, bladder cancer, brain cancer, head and neck cancer, pancreatic cancer, biliary cancer, thyroid cancer, lung cancer, breast cancer, ovarian cancer, uterine cancer, cervical cancer, endometrial cancer, esophageal cancer, colon cancer, colorectal cancer, rectal cancer, gastric cancer, prostate cancer, skin cancer, squamous cell carcinoma, sarcoma, bone cancer, and kidney cancer. Other cell proliferation disorders that may be treated using an antibody or bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases.

In certain embodiments the cancer is chosen from the group consisting of haematological cancer (such as leukemia), kidney cancer, bladder cancer, skin cancer, lung cancer, colorectal cancer, breast cancer, brain cancer, head and neck cancer and prostate cancer. In one embodiment, the cancer is a haematological cancer, particularly leukemia, most particularly acute lymphoblastic leukemia (ALL) or acute myelogenous leukemia (AML). A skilled artisan readily recognizes that in many cases the antibody or bispecific antigen binding molecule may not provide a cure but may only provide partial benefit. In some embodiments, a physiological change having some benefit is also considered therapeutically beneficial. Thus, in some embodiments, an amount of antibody or bispecific antigen binding molecule that provides a physiological change is considered an "effective amount" or a "therapeutically effective amount". The subject, patient, or individual in need of treatment is typically a mammal, more specifically a human.

In some embodiments, an effective amount of an antibody or bispecific antigen binding molecule of the invention is administered to a cell. In other embodiments, a therapeutically effective amount of an antibody or bispecific antigen binding molecule of the invention is administered to an individual for the treatment of disease.

For the prevention or treatment of disease, the appropriate dosage of an antibody or bispecific antigen binding molecule of the invention (when used alone or in combination with one or more other additional therapeutic agents) will depend on the type of disease to be treated, the route of administration, the body weight of the patient, the type of antibody or bispecific antigen binding molecule, the severity and course of the disease, whether the antibody or bispecific antigen binding molecule is administered for preventive or therapeutic purposes, previous or concurrent therapeutic interventions, the patient's clinical history and response to the antibody or bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The antibody or bispecific antigen binding molecule is suitably administered to the patient at one time or over a series of treatments. Depending on the type and severity of the disease, about 1 μg/kg to 15 mg/kg (e.g. 0.1 mg/kg-10 mg/kg) of antibody or bispecific antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody or bispecific antigen binding molecule). An initial higher loading dose, followed by one or more lower doses may be administered. However, other dosage regimens may be useful. The progress of this therapy is easily monitored by conventional techniques and assays.

The antibodies or bispecific antigen binding molecules of the invention will generally be used in an amount effective to achieve the intended purpose. For use to treat or prevent a disease condition, the antibodies or bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the antibodies or bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the antibodies or bispecific antigen binding molecules may not be related to plasma concentration. One having skill in the art will be able to optimize therapeutically effective local dosages without undue experimentation.

A therapeutically effective dose of the antibodies or bispecific antigen binding molecules described herein will generally provide therapeutic benefit without causing substantial toxicity. Toxicity and therapeutic efficacy of an antibody or bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies or bispecific antigen binding molecules that exhibit large therapeutic indices are preferred. In one embodiment, the antibody or bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies or bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The antibodies and bispecific antigen binding molecules of the invention may be administered in combination with one or more other agents in therapy. For instance, an antibody or bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. Such other agents are suitably present in combination in amounts that are effective for the purpose intended. The effective amount of such other agents depends on the amount of antibody or bispecific antigen binding molecule used, the type of disorder or treatment, and other factors discussed above. The antibodies or bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody or bispecific antigen binding molecule of the invention can occur prior to, simultaneously, and/or following, administration of the additional therapeutic agent and/or adjuvant. Antibodies or bispecific antigen binding molecules of the invention may also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or bispecific antigen binding molecule of the invention. The label or package insert indicates that the composition is used for treating the condition of choice. Moreover, the article of manufacture may comprise (a) a first container with a composition contained therein, wherein the composition comprises an antibody or bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Methods and Compositions for Diagnostics and Detection

In certain embodiments, any of the anti-HLA-A2/WT1 antibodies provided herein is useful for detecting the presence of HLA-A2/WT1 in a biological sample. The term "detecting" as used herein encompasses quantitative or qualitative detection. In certain embodiments, a biological sample comprises a cell or tissue, such as prostate tissue.

In one embodiment, an anti-HLA-A2/WT1 antibody for use in a method of diagnosis or detection is provided. In a further aspect, a method of detecting the presence of HLA-A2/WT1 in a biological sample is provided. In certain embodiments, the method comprises contacting the biological sample with an anti-HLA-A2/WT1 antibody as described herein under conditions permissive for binding of the anti-HLA-A2/WT1 antibody to HLA-A2/WT1, and detecting whether a complex is formed between the anti-HLA-A2/WT1 antibody and HLA-A2/WT1. Such method may be an in vitro or in vivo method. In one embodiment, an anti-HLA-A2/WT1 antibody is used to select subjects eligible for therapy with an anti-HLA-A2/WT1 antibody, e.g. where HLA-A2/WT1 is a biomarker for selection of patients.

Exemplary disorders that may be diagnosed using an antibody of the invention include cancer, particularly prostate cancer.

In certain embodiments, labeled anti-HLA-A2/WT1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

EXAMPLES

The following are examples of methods and compositions of the invention. It is understood that various other embodiments may be practiced, given the general description provided above.

Example 1. Generation of Fab Binders to HLA-A2/WT1

Selection and Screening of Anti-HLA-A2/WT1 Fabs

Anti-HLA-A2/WT1 Fabs were selected by phage display from synthetic Fab libraries based on entirely human frameworks with sequence diversity in CDR3 of VL (3 different lengths) and VH domains (6 different lengths).

Selection rounds (biopanning) were performed in solution according to the following protocol: 1. pre-clearing of ~$10^{12}$ phagemid particles per library pool on neutravidin coated 96 well plates coated with 500 nM of an unrelated biotinylated HLA-A2/WT1$_{VLD}$ complex, 2. incubation of the non-HLA-A2/WT1$_{VLD}$-binding phagemid particles with 100 nM biotinylated HLA-A2/WT1$_{RMF}$ complex for 0.5 h in a total volume of 800 µl, 3. capture of biotinylated HLA-A2/WT1$_{RMF}$ and specifically binding phage by adding 80 µl of streptavidin-coated magnetic particles for 20 min on a shaker, 4. washing of respective magnetic particles 5-10× with 1 ml PBS/Tween 20 and 5-10× with 1 ml PBS using a magnetic particle separator, 5. elution of phage particles by addition of 1 ml 100 mM triethylamine (TEA) for 5-10 min and neutralization by addition of an ½ volume of 1 M Tris/HCl pH 7.4, 6. re-infection of log-phase E. coli TG1 cells with the eluted phage particles, infection with helperphage VCSM13, incubation on a shaker at 30° C. over night and subsequent PEG/NaCl precipitation of phagemid particles to be used in the next selection round.

Selections were carried out over 3 to 4 rounds using constant antigen concentrations of 100 nM.

In addition to selection campaigns with constant antigen concentrations, further selection campaigns were carried out with decreasing antigen concentrations of 100 nM, 50 nM, 10 nM and 5 nM in order to select for antibodies with lower affinities.

HLA-A2/WT1 Binding Assays: Sandwich ELISA for Characterisation of Fabs Obtained by Phage Display Individual clones were bacterially expressed as 1 ml cultures in 96-well format and supernatants were subjected to a screening by ELISA. Specific binders were defined as having signals higher than 5× background for HLA-A2/WT1$_{RMF}$ and signals lower than 3× background for HLA-A2/WT1$_{VLD}$. More precisely, neutravidin 96 well strip plates (Thermo Fisher) were coated with 10 nM of HLA-A2/WT1$_{RMF}$ or 50 nM HLA-A2/WT1$_{VLD}$ at 37° C. for 30 min, followed by blocking of the plate with 2% (w/v) milk-phosphate-buffered saline (MPBS) (200 µl/well) for 1 h at room temperature. The plate was washed 3 times with PBS, then Fab containing bacterial supernatants were added and the plate was incubated at room temperature for 1h. After another 3 washing steps with PBS, anti-FLAG-HRP secondary antibody (Sigma, Cat. No. A8592) ((1:4000) was added and the plate was incubated on a shaker for 1 h at room temperature. The plate was washed 3 times with PBS and developed by adding 100 µl/well BM Blue POD (Roche). The enzymatic reaction was stopped by adding 50 µl/well 1 M H$_2$SO$_4$. The OD was read at 450 nm (reference at 650 nm) for a final read-out of OD$_{450\ 650}$. ELISA-positive clones were subjected to the kinetic screening experiment described below.

HLA-A2/WT1 Binding Assays: Surface Plasmon Resonance for Kinetic Characterisation of Fabs Obtained by Phage Display Specific binders were identified by surface plasmon resonance-screening of Fab-containing bacterial culture supernatants using a ProteOn XPR36 biosensor (BioRad). In brief, after infection of log-phase E. coli TG1 cells with the eluted phage particles, single colony forming units (cfu) were plated and picked for inoculation of 1 ml expression cultures in 96-deep well plates.

All experiments were performed at 25° C. using PBST as running buffer (10 mM PBS, pH 7.4 and 0.005% (v/v) Tween 20). A ProteOn XPR36 biosensor equipped with GLC and GLM sensor chips and coupling reagents (10 mM sodium acetate pH 4.5, sulfo-N-hydroxysuccinimide [sulfo-NHS], 1-ethyl-3-(3-dimethylaminpropyl)-carbodiimide hydrochloride [EDC] and ethanolamine) from BioRad Inc. (Hercules, CA) were used.

Immobilizations were performed at 30 µl/min on a GLM chip. pAb (goat) anti human IgG, F(ab)2 specific antibody (Jackson ImmunoResearch) was coupled in vertical direction using a standard amine-coupling procedure: all six ligand channels were activated for 5 min with a mixture of EDC (200 mM) and sulfo-NHS (50 mM). Immediately after the surfaces were activated, pAb (goat) anti human IgG, F(ab)2 specific antibody (50 µg/ml, 10 mM sodium acetate, pH 5) was injected across all six channels for 5 min. Finally, channels were blocked with a 5 min injection of 1 M ethanolamine-HCl (pH 8.5). Final immobilization levels were similar on all channels, ranging from 11000 to 11500 RU. The Fab variants were captured from E. coli supernatants by simultaneous injection along five of the separate horizontal channels (30 µl/min) for 5 min and resulted in levels ranging from 200 to 900 RU, depending on the concentration of Fab in supernatant. Conditioned medium was injected along the sixth channel to provide an 'in-line' blank for double referencing purposes. One-shot kinetic measurements were performed by injection of a dilution series of HLA-A2/WT1$_{RMF}$ or HLA-A2/WT1$_{VLD}$ (100, 50, 25, 12.5, 6.25, 0 nM, 50 µl/min) for 2 min along the vertical channels. Dissociation was monitored for 3 min. Kinetic data were analyzed in ProteOn Manager v. 2.1. Processing of the reaction spot data involved applying an interspot-reference and a double-reference step using an inline buffer blank (Myszka, J Mol Recognit (1999) 12, 279-284). The processed data from replicate one-shot injections were fit to a simple 1:1 Langmuir binding model without mass transport (O'Shannessy et al., Anal Biochem (1993) 212, 457-468).

For measurements of IgG from supernatants of HEK productions in 6-well format, the IgG variants were captured from HEK293 supernatants by simultaneous injection along five of the separate horizontal channels (30 µl/min) for 5 min and resulted in levels ranging from 200 to 400 RU. Conditioned medium was injected along the sixth channel to provide an 'in-line' blank for double referencing purposes. One-shot kinetic measurements were performed by injection of a dilution series of HLA-A2/WT1$_{RMF}$ or HLA-A2/

WT1$_{VLD}$ (100, 50, 25, 12.5, 6.25, 0 nM, 50 μl/min) for 3 min along the vertical channels. Dissociation was monitored for 5 min. Kinetic data were analyzed as described above.

Based on binding profile and measured specificity to bind to the antigen, binders were shortlisted and measured in cell binding assays.

Sequences of all selected binders (11D06, 33H09, 13B04, 11B09, 33F05, 5E11, 13E08, 5C01, 11G$_{06}$) are provided in the sequence listing included herein and summarized in Table 1 below.

TABLE 1

Amino acid sequences of selected HLA-A2/WT1 binders.

| Binder | SEQ ID NO | | | | | | | |
|---|---|---|---|---|---|---|---|---|
| | HCDR1 | HCDR2 | HCDR3 | VH | LCDR1 | LCDR2 | LCDR3 | VL |
| 11D06 | 1 | 2 | 3 | 7 | 4 | 5 | 6 | 8 |
| 33H09 | 9 | 10 | 11 | 15 | 12 | 13 | 14 | 16 |
| 13B04 | 17 | 18 | 19 | 23 | 20 | 21 | 22 | 24 |
| 11B09 | 25 | 26 | 27 | 31 | 28 | 29 | 30 | 32 |
| 33F05 | 33 | 34 | 35 | 39 | 36 | 37 | 38 | 40 |
| 5E11 | 41 | 42 | 43 | 47 | 44 | 45 | 46 | 48 |
| 13E08 | 49 | 50 | 51 | 55 | 52 | 53 | 54 | 56 |
| 5C01 | 57 | 58 | 59 | 63 | 60 | 61 | 62 | 64 |
| 11G06 | 65 | 66 | 67 | 71 | 68 | 69 | 70 | 72 |

Example 2. Preparation of HLA-A2/WT1 IgG and HLA-A2/WT1 x CD3 Bispecific Antibodies Cloning The cDNAs encoding the proteins were cloned into a vector system (Evitria) using conventional (non-PCR based) cloning techniques. The vector plasmids were gene synthesized. Plasmid DNA was prepared under low-endotoxin conditions based on anion exchange chromatography. DNA concentration was determined by measuring the absorption at a wavelength of 260 nm. Correctness of the sequences was verified with Sanger sequencing (with up to two sequencing reactions per plasmid depending on the size of the cDNA).

Production

IgG antibodies and bispecific antibodies were generated by transient transfection of HEK293 EBNA cells (cultivated in suspension serum free in Excell culture medium). Cells were centrifuged and medium replaced by pre-warmed CD CHO medium. Expression vectors were mixed in CD CHO medium, polyethyleneimine (PEI) was added, the solution vortexed and incubated for 10 minutes at room temperature. Afterwards, cells were mixed with the DNA/PEI solution, transferred to shake flask and incubated for 3 hours at 37° C. in an incubator with a 5% CO$_2$ atmosphere. After the incubation, Excell medium with supplements was added. One day after transfection supplements were added. Cell supernatants were harvested after 7 days and purified by standard methods.

Alternatively, suspension-adapted CHO K1 cells (originally from ATCC and adapted to serum-free growth in suspension culture) were used for production. The seed was grown in eviGrow medium, a chemically defined, animal-component free, serum-free medium. Cells were transfected with eviFect transfection reagent, and cells were grown after transfection in eviMake2, an animal-component free, serum-free medium. Supernatant was harvested by centrifugation and subsequent filtration (0.2 μm filter).

Purification

Proteins were purified from filtered cell culture supernatants referring to standard protocols. In brief, Fc containing proteins were purified from cell culture supernatants by affinity chromatography using Protein A (HiTrap ProteinA HP column, GE Healthcare). Elution was achieved at pH 3.0 followed by immediate neutralization of the sample. The protein was concentrated and aggregated protein was separated from monomeric protein by size exclusion chromatography (HiLoad Superdex 200 column, GE Healthcare) in 20 mM histidine, 140 mM sodium chloride, pH 6.0.

Analytics

The concentration of purified proteins was determined by measuring the optical density (OD) at 280 nm, using the molar extinction coefficient calculated on the basis of the amino acid sequence according to Pace et al. (Protein Science, 1995, 4, 2411-1423). Purity and molecular weight of the proteins were analyzed by CE-SDS in the presence and absence of a reducing agent using a LabChipGXII system (Caliper Lifescience). Determination of the aggregate content was performed by HPLC chromatography using analytical size-exclusion column (TSKgel G3000 SW XL, Tosoh) equilibrated in a 25 mM K$_2$HPO$_4$, 125 mM NaCl, 200 mM L-arginine monohydrocloride, pH 6.7 running buffer at 25° C.

Figure 2:
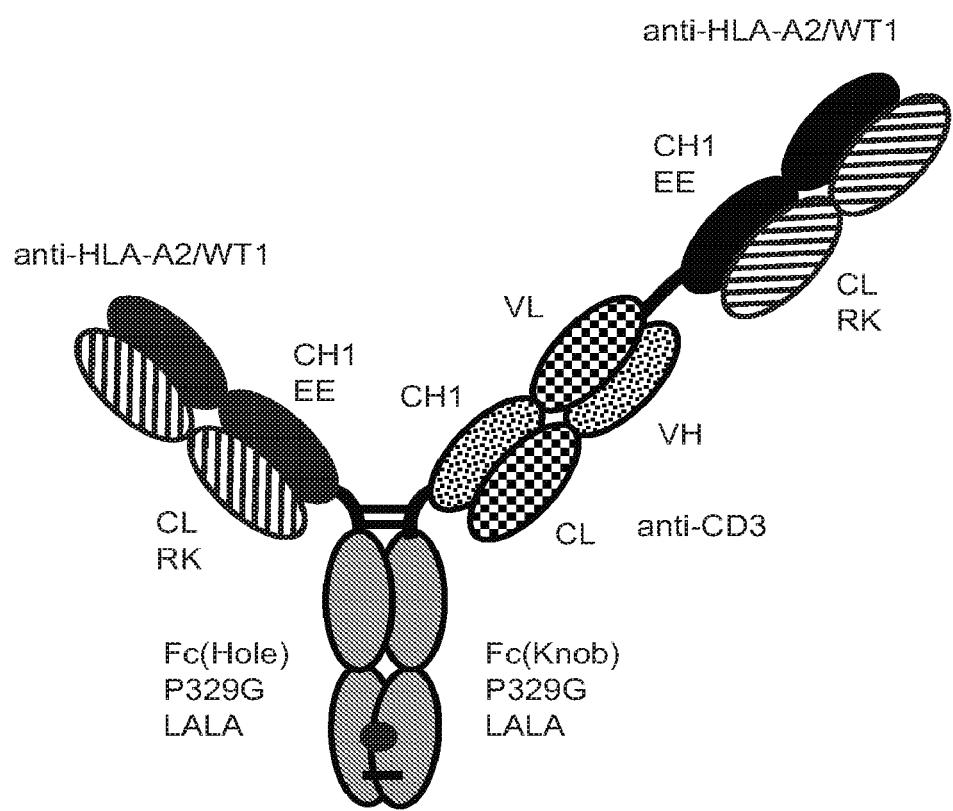
FIG. 2. Illustration of the T-cell bispecific (TCB) antibody molecules prepared in the Examples. All tested TCB antibody molecules were produced as "2+1 IgG CrossFab, inverted" with charge modifications (VH/VL exchange in CD3 binder, charge modifications in WT1 binders, EE=147E, 213E; RK=123R, 124K).
Figure 3B:
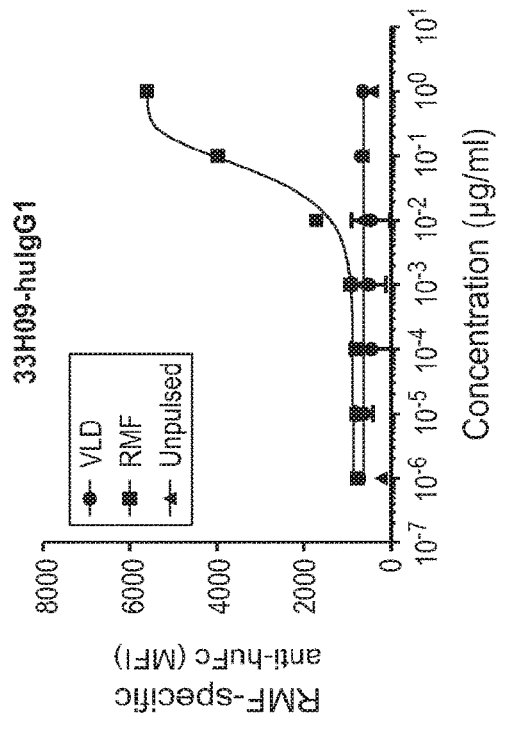
FIGS. 3A-G. Binding of HLA-A2/WT1 IgG antibodies to peptide-pulsed T2 cells. (A) 11D06 IgG, (B) 33H09-IgG, (C) 11B09-IgG, (D) 13B04-IgG, (E) 5E11-IgG, (F) 5C01-IgG, (G) 11G06-IgG.
Figure 3D:
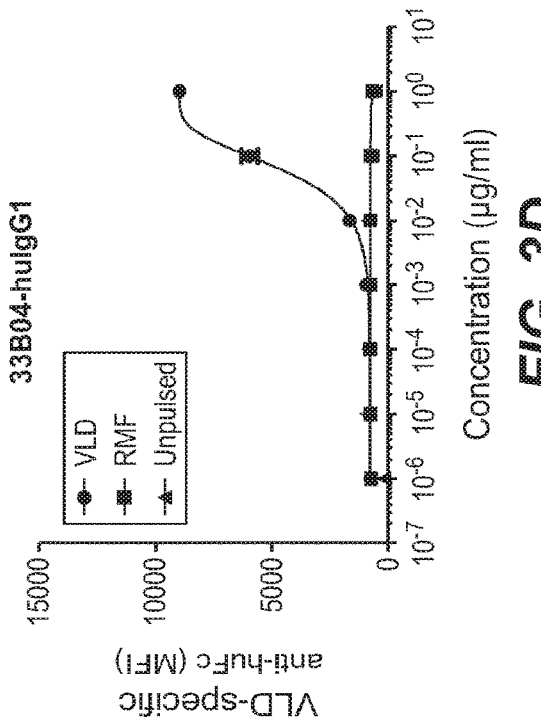
Figure 3A:
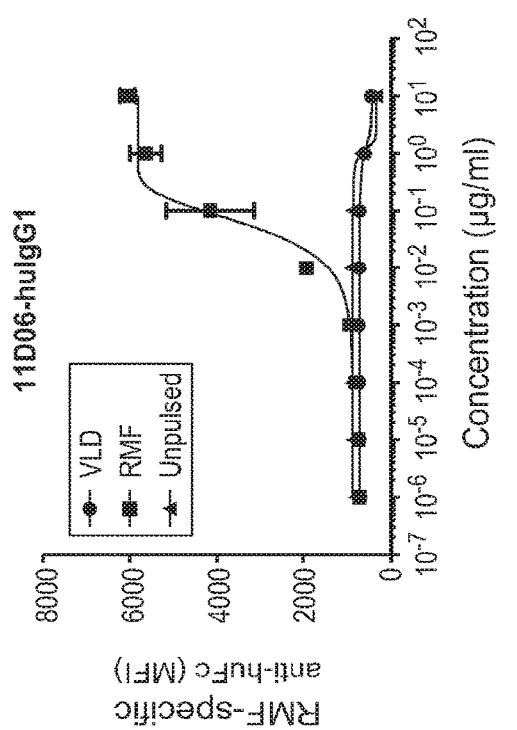
Figure 3C:
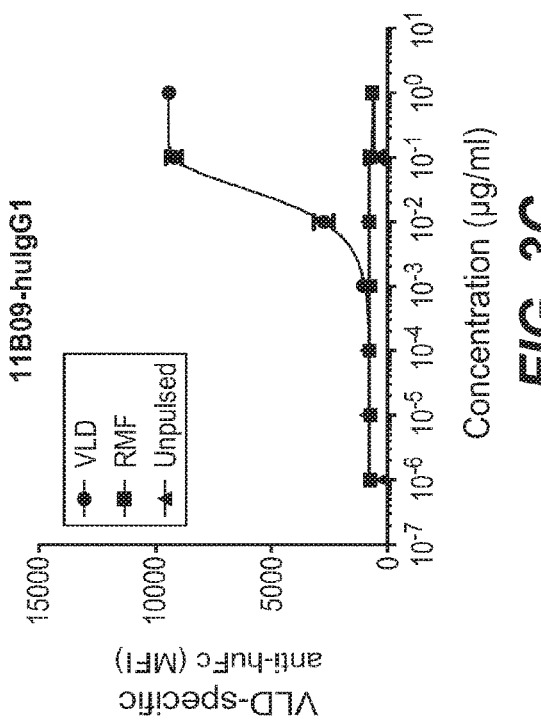
Figure 3E:
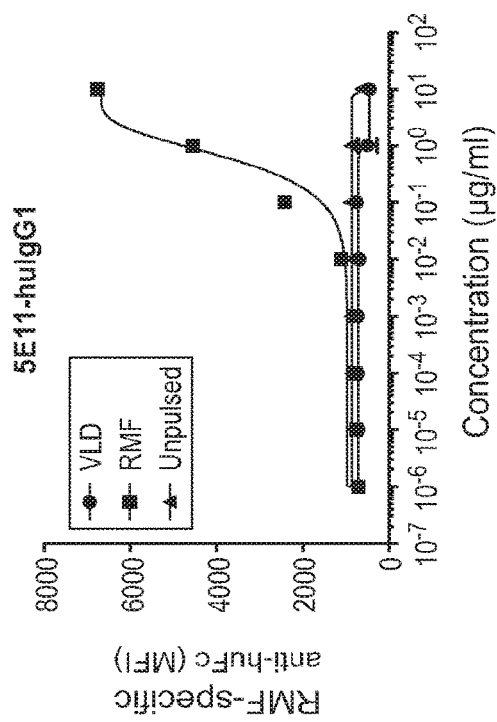
Figure 3G:
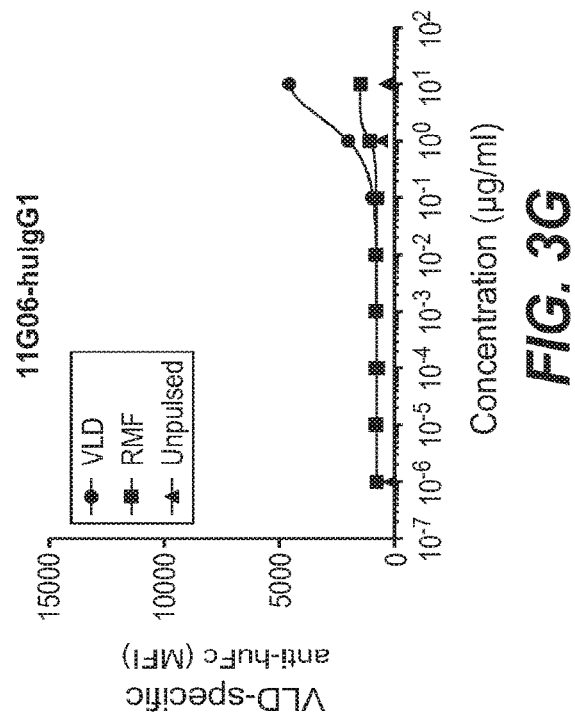
Figure 3F:
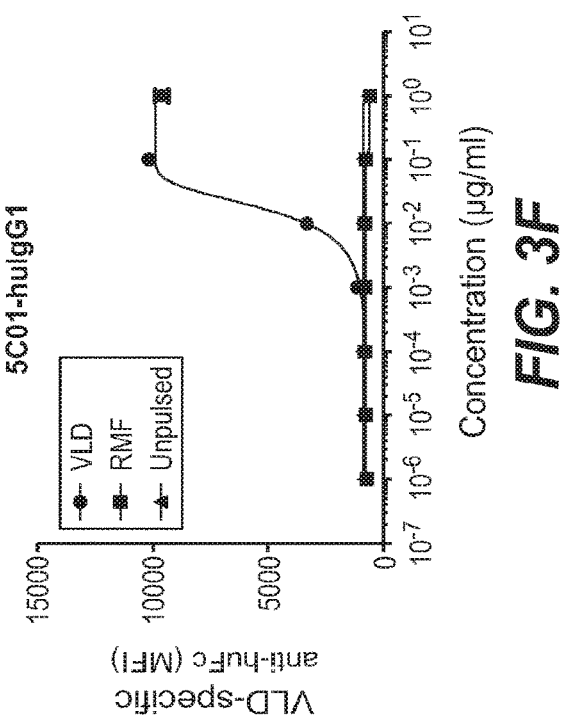
Figure 4A:
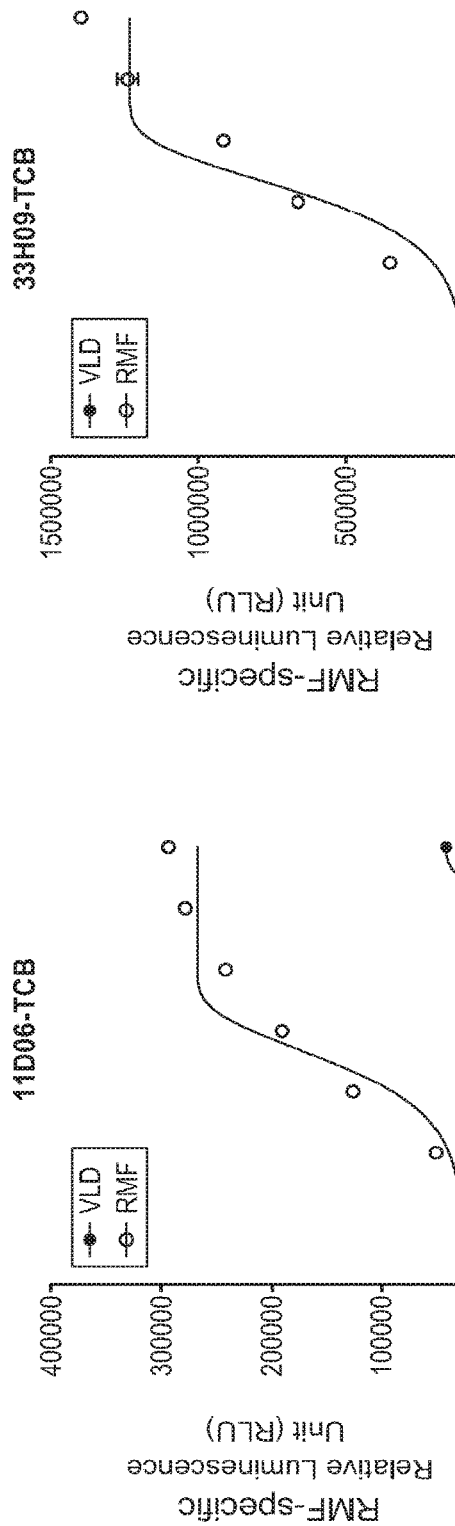
Figure 4B:
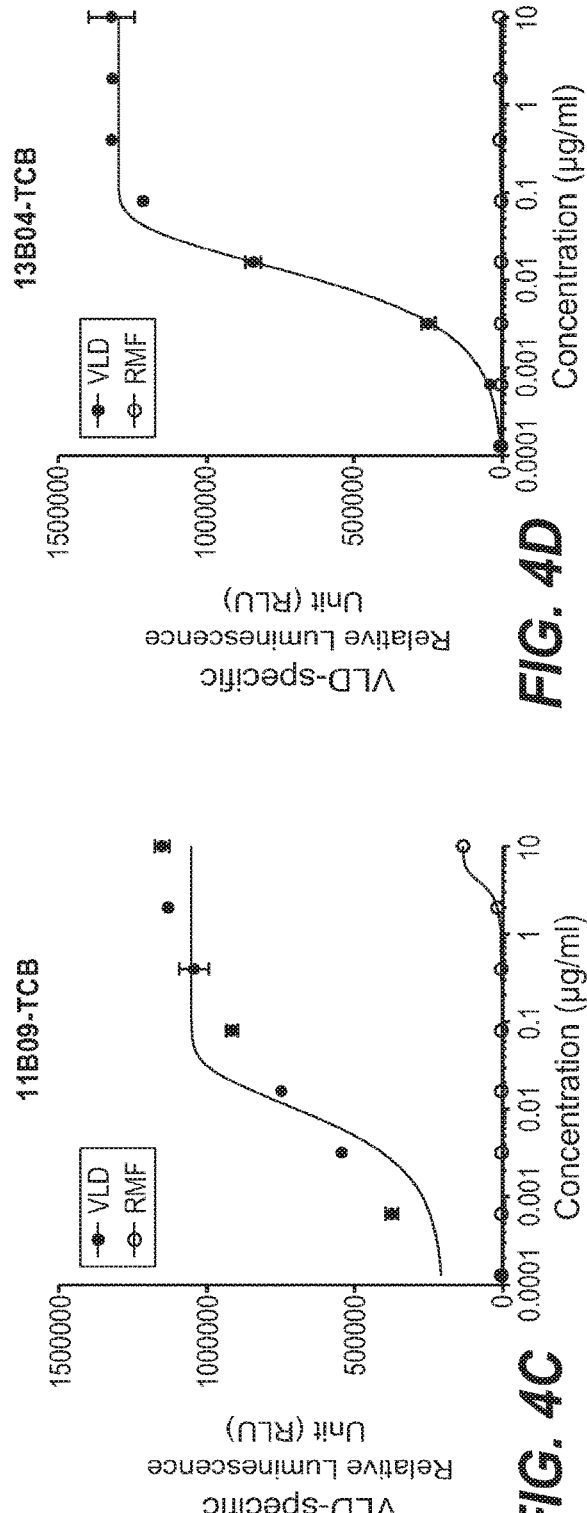
Figure 4C:
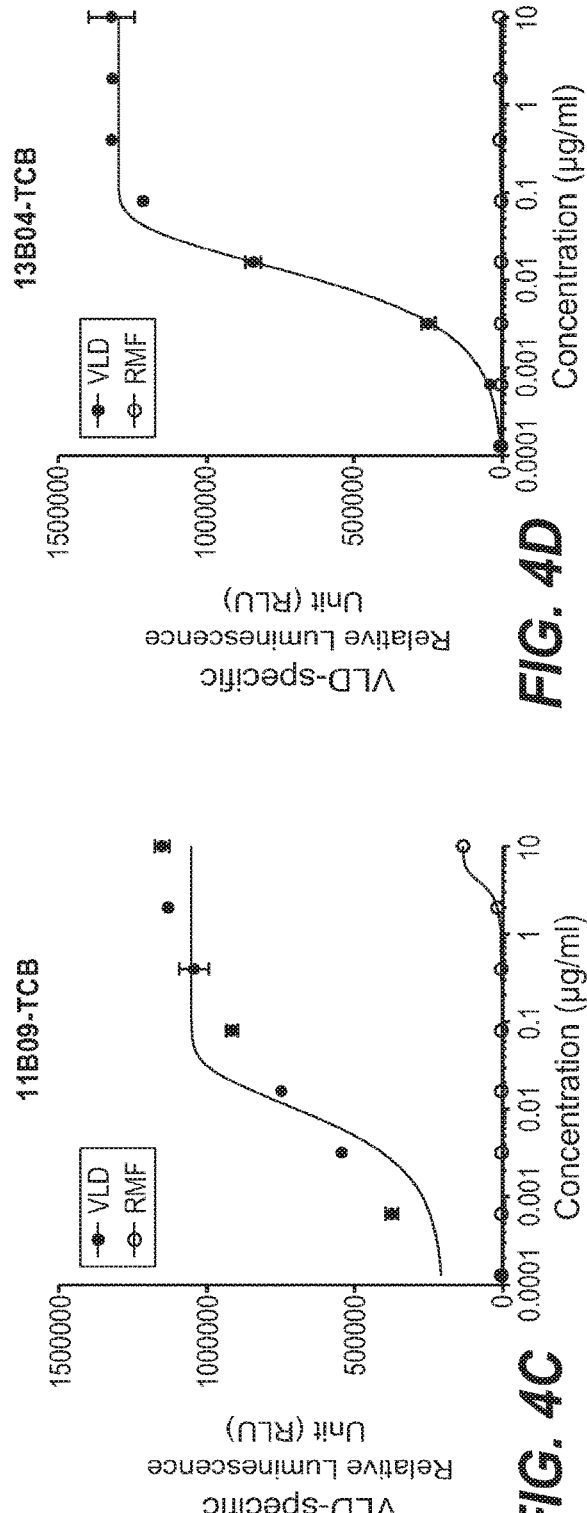
Figure 4D:
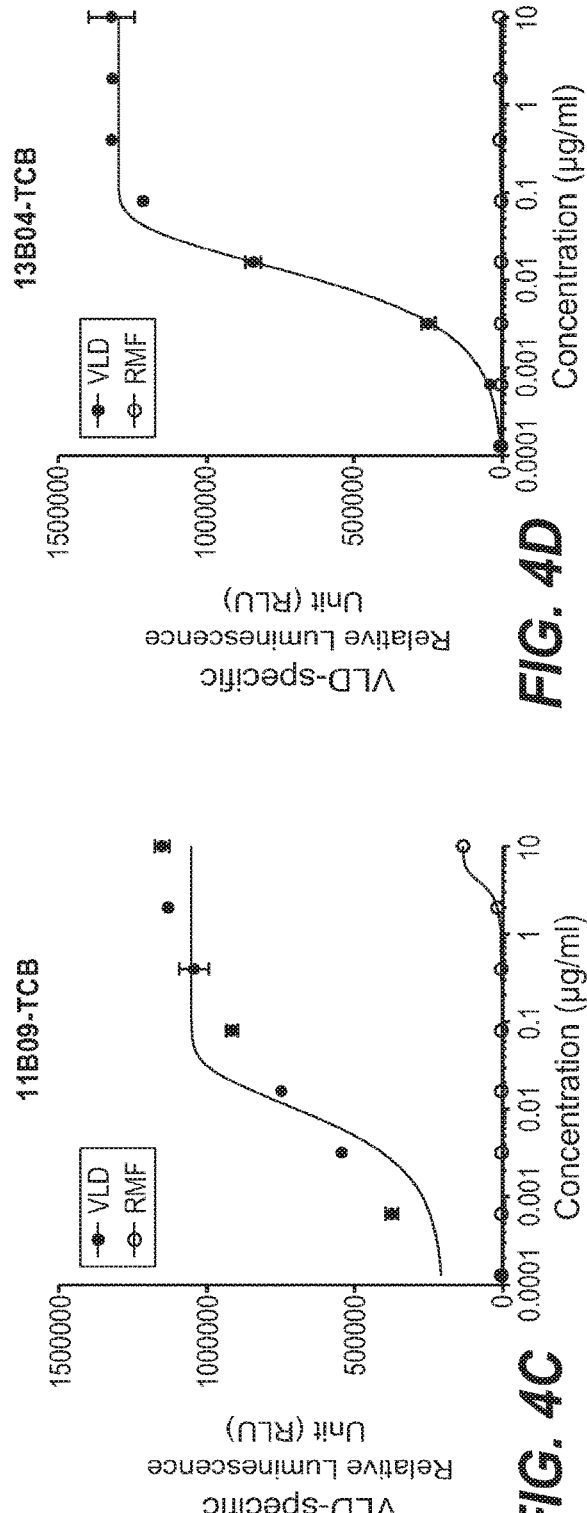
Figure 5A:
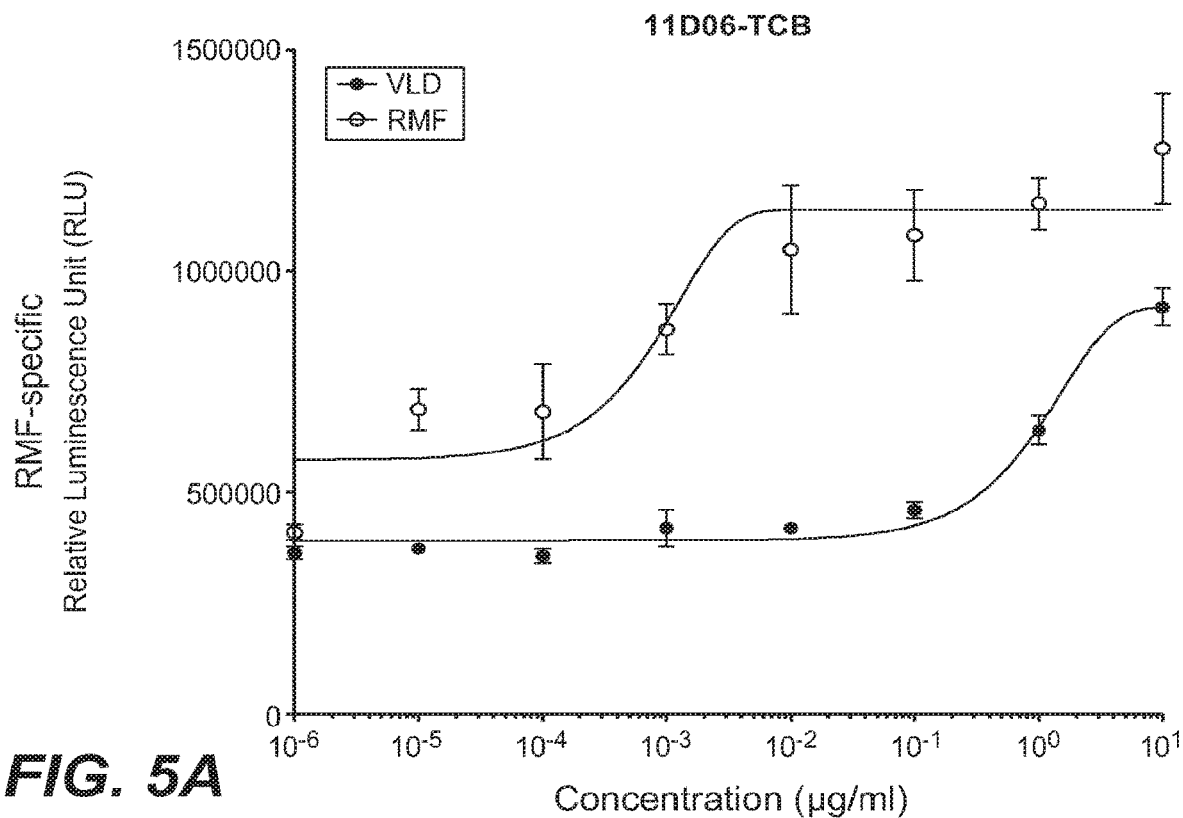
FIGS. 5A-F. Killing of peptide-pulsed T2 cells mediated by HLA-A2/WT1 x CD3 bispecific antibodies (TCBs). (A) 11D06-TCB, (B) 33H09-TCB, (C) 13B04-TCB, (D) 11B09-TCB, (E) 33F05-TCB, (F) 5C01-TCB.
Figure 5B:
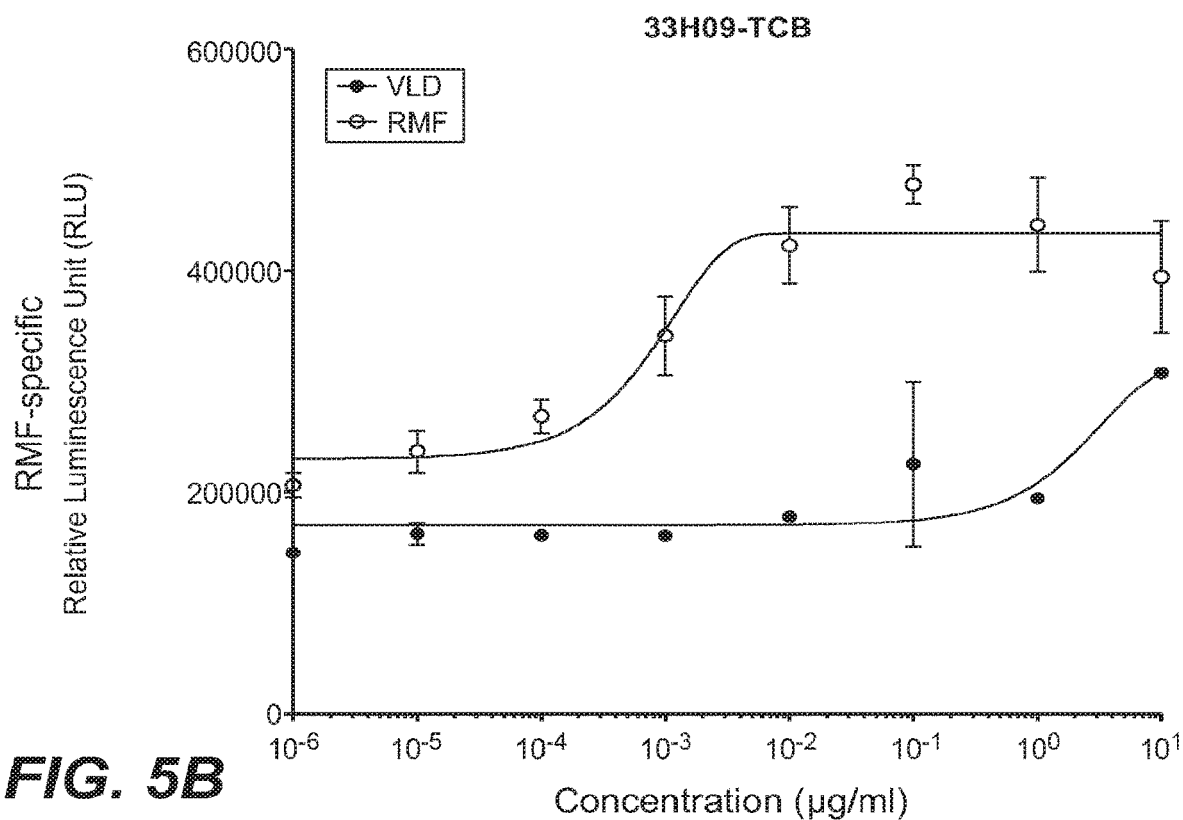
Figure 5C:
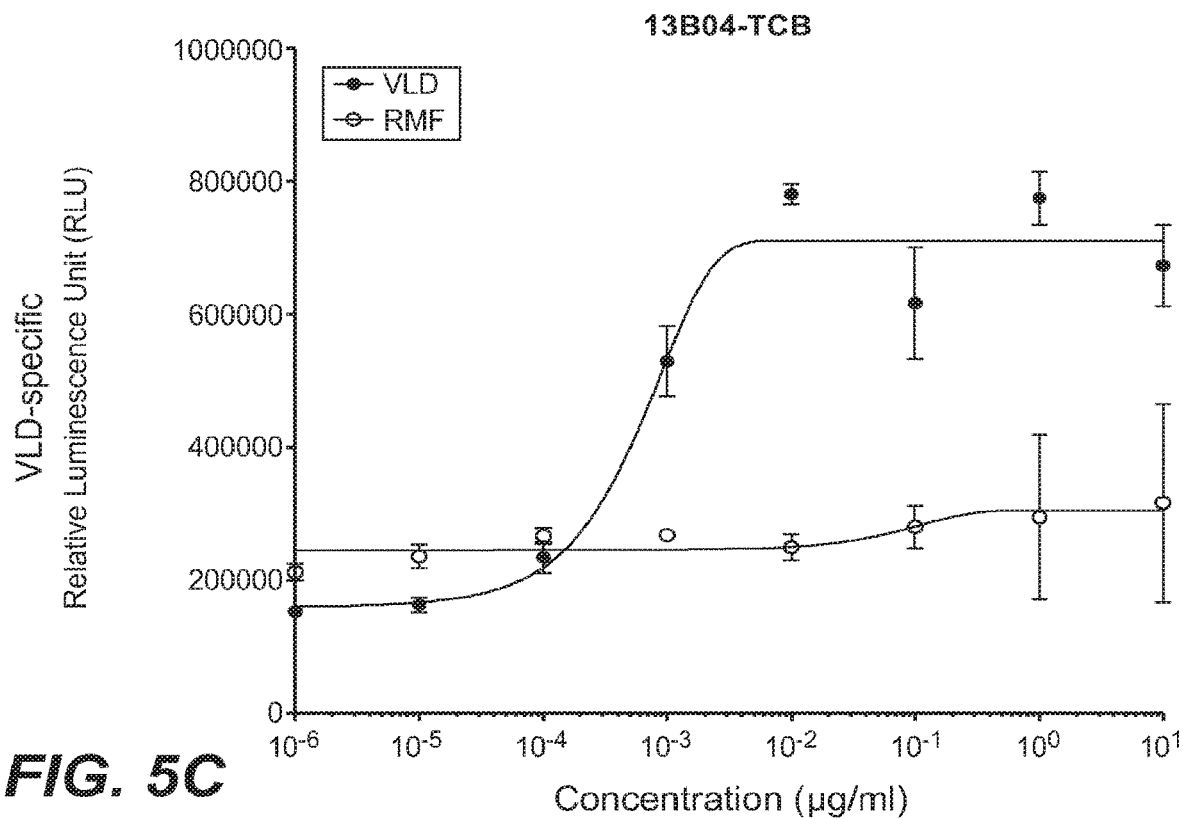
Figure 5D:
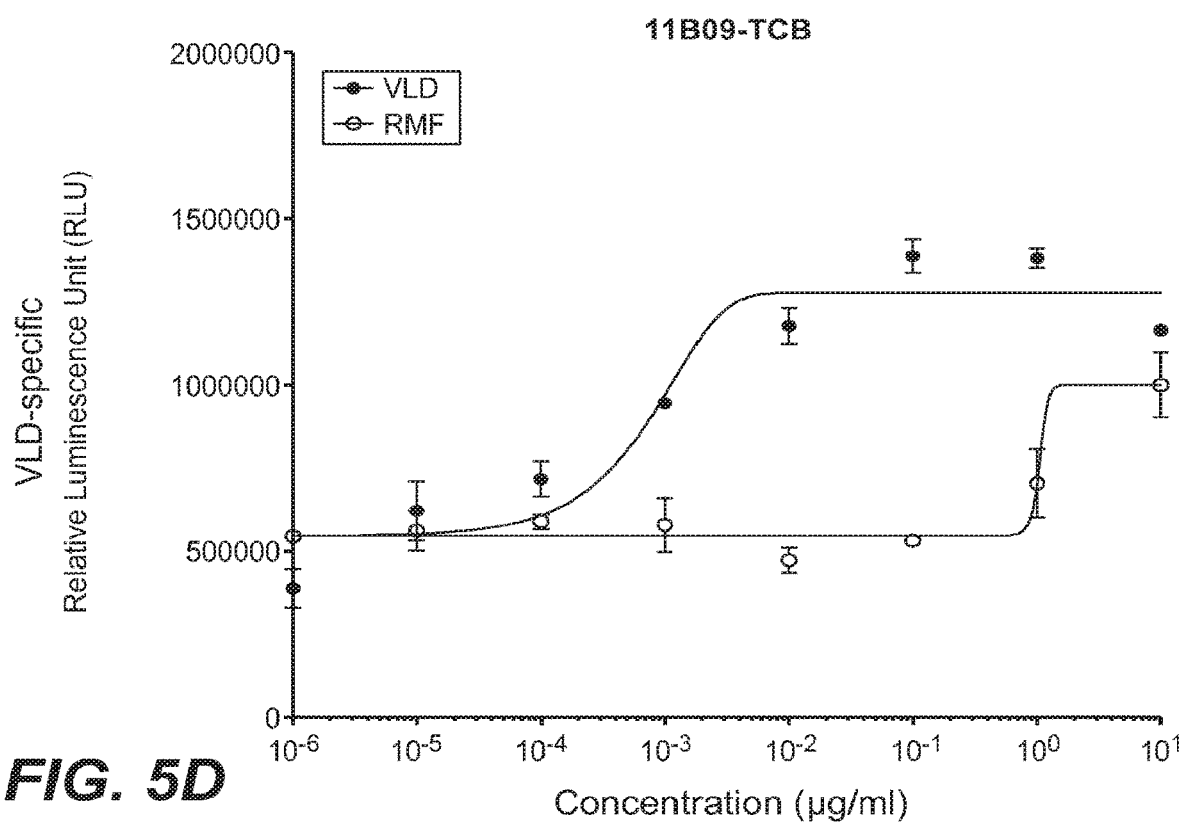
Figure 5E:
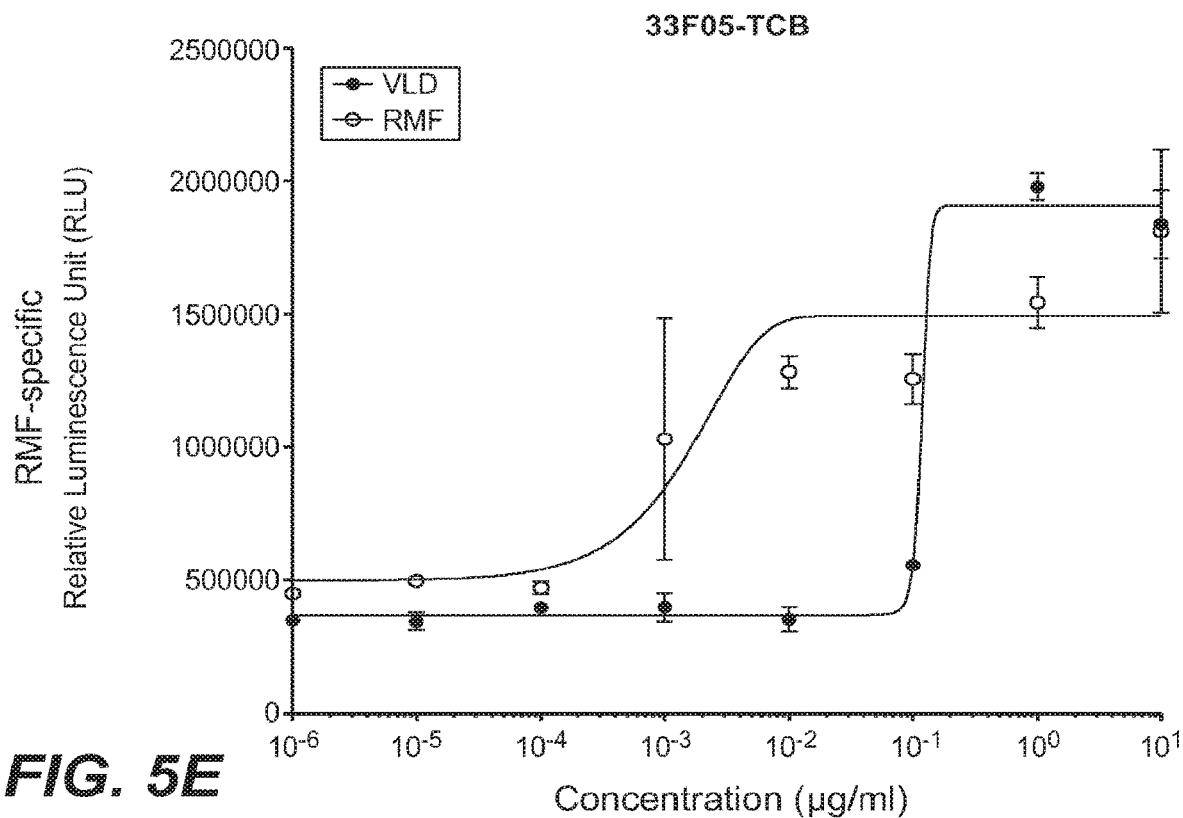
Figure 5F:
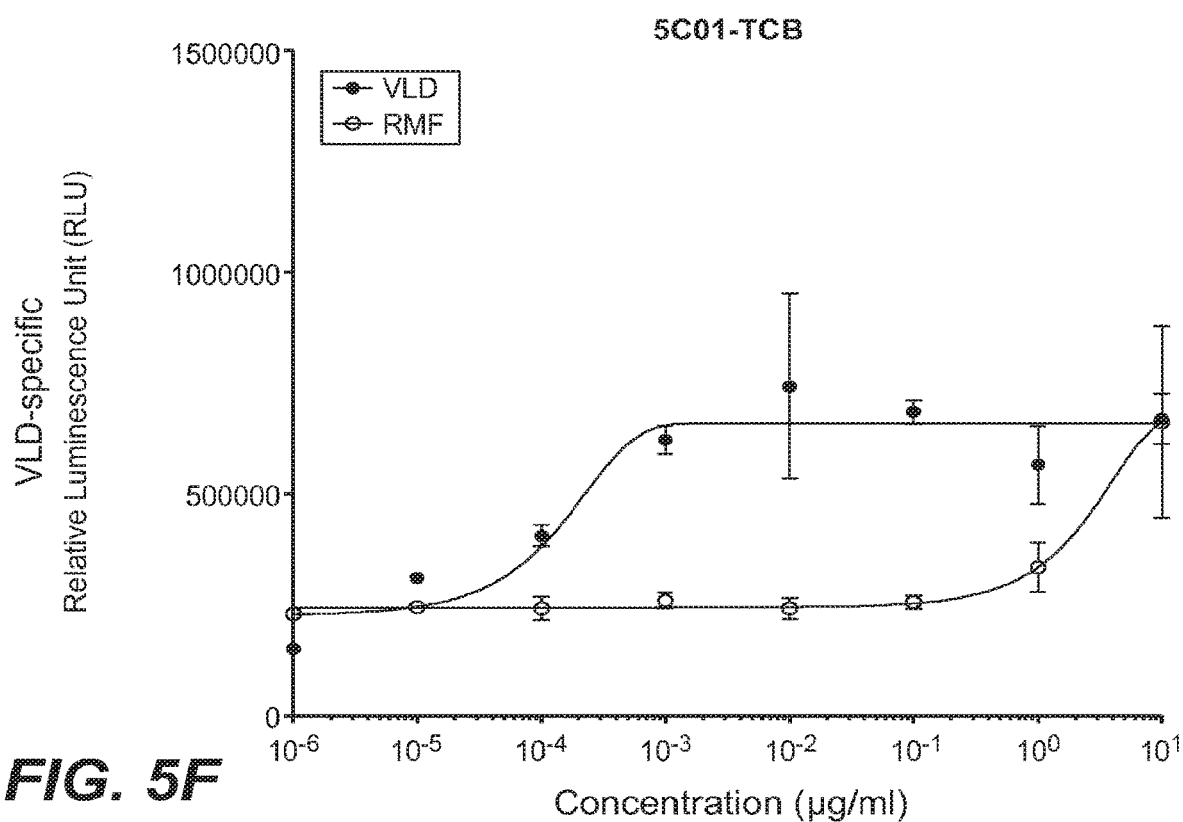

CD3 bispecific antibodies are also referred to herein a "T cell bispecific antibodies" or "TCBs". A schematic illustration of the bispecific antibodies prepared in this example is given in FIG. 2.

Exemplary sequences of TCBs are given in SEQ ID NOs 123, 124, 125 and 129 (11D06 TCB) and SEQ ID NOs 126, 127, 128 and 129 (33H09-TCB). Other TCBs were constructed in an analogous manner, using the VH and VL sequences of the corresponding HLA-A2/WT1 binders.

As controls, a HLA-A2/WT1 x CD3 bispecific antibody (TCB) based on a binder similar to antibody ESK1 (Dao et al., Sci Transl Med (2013) 5, 176ra33; WO2012/135854)—referred to herein as "ESK1-TCB" (see SEQ ID NOs 73 and 74 for the variable region sequences)—as well as an untargeted TCB (see SEQ ID NOs 75 and 76 for the variable region sequences) were prepared.

All molecules were produced and purified following the same method. The final quality was very good for all molecules with almost 100% monomer content and 100% purity on CE-SDS.

Example 3. Biochemical Analysis of Affinity and Avidity of HLA-A2/WT1 x CD3 Bispecific Antibodies For determination of affinity of HLA-A2/WT1 x CD3 bispecific antibodies to HLA-A2/WT1$_{RMF}$, surface plasmon resonance (SPR) experiments were performed at 25° C. on a Biacore T200 with HBS-EP as running buffer (0.01 M HEPES pH 7.4, 0.15 M NaCl, 0.005% Surfactant P20 (GE Healthcare)). Anti-human Fc specific antibody (GE Healthcare, Cat. No. BR-1008-39) was directly immobilized by amine coupling on a CM5 chip (GE Healthcare). The bispecific constructs were captured for 30 s at 5 nM. A three-fold dilution series of the HLA-A2/WT1$_{RMF}$ complex in HBS-EP (1.03 to 250 nM) was passed over the ligand at 30 µl/min for 120 sec to record the association phase. The dissociation phase was monitored for 120 s and triggered by switching from the sample solution to HBS-EP. The chip surface was regenerated after every cycle using an injection of 3M MgCl$_2$ at 10 µl/min for 30 sec. Bulk refractive index differences were corrected for by subtracting the response obtained on the reference flow cell which contains the anti-human Fc antibody, but without bispecific construct captured on it. The affinity constants were derived from the kinetic rate constants by fitting to a 1:1 Langmuir binding using the BIAeval software (GE Healthcare).

For determination of avidity and specificity of the HLA-A2/WT1 x CD3 bispecific antibodies to HLA-A2/WT1$_{RMF}$, SPR experiments were again performed at 25° C. on a Biacore T200 with HBS-EP as running buffer (0.01 M HEPES pH 7.4, 0.15 M NaCl, 0.005% Surfactant P20 (GE Healthcare)). Anti-His antibody (Penta His, Qiagen Cat. No. 34660) was directly immobilized by amine coupling on a CM5 chip (GE Healthcare). The HLA-A2/WT1$_{RMF}$ Or HLA-A2/WT1$_{VLD}$ was captured for 30 sec and 10 µl/min at 5 or 10 nM (for the bispecific antibody or IgG measurement, respectively). A 3-fold dilution series of the bispecific constructs in HBS-EP (1.23 to 100 nM) were passed over the ligand at 30 µl/min for 120 sec to record the association phase. The dissociation phase was monitored for 240 sec and triggered by switching from the sample solution to HBS-EP. The chip surface was regenerated after every cycle using an injection of 10 mM glycine pH 2 for 60 sec. Bulk refractive index differences were corrected for by subtracting the response obtained on the reference flow cell (which contains the anti-His antibody, but without HLA-A2/WT1$_{RMF}$ captured on it). Even though it is a 2:1 interaction (analyte is bivalent) the affinity constants were derived from the kinetic rate constants by fitting to a 1:1 Langmuir binding using the BIAeval software (GE Healthcare). This results in an apparent K$_D$ representing the avidity of the interaction.

The results of these experiments are summarized in Table 2 below. Both tested HLA-A2/WT1 antibodies bind to HLA-A2/WT1$_{RMF}$ with double-digit nanomolar (monovalent) affinity/three-digit picomolar (bivalent) affinity (avidity), and keep the same affinity/avidity when converted from IgG to bispecific format. While the affinity of the two tested antibodies differs by about a factor two, avidity of both molecules is in the same range.

No binding of the tested HLA-A2/WT1 antibodies to HLA-A2/WT1$_{VLD}$ was detected (data not shown).

TABLE 2

Summary of affinity and avidity data as determined by SPR for selected HLA-A2/WT1 IgG and HLA-A2/WT1 x CD3 bispecific antibodies ("TCBs") to HLA-A2/WT1$_{RMF}$.

| Analyte | ligand | Affinity ka (1/Ms) | Affinity kd (1/s) | Affinity KD | Avidity ka (1/Ms) average stdev | Avidity kd (1/s) average stdev | Avidity Apparent KD (pM) average stdev |
|---|---|---|---|---|---|---|---|
| 33H09-huIgG1 | RMF | 1.67 10$^6$ | 1.16 10$^{-1}$ | 70 nM | 4.74 10$^6$ | 3.57 10$^{-3}$ | 750 |
|  |  | 1.8 10$^6$ | 1.24 10$^{-1}$ | 69 nM | 6.5 10$^4$ | 2.35 10$^{-4}$ | 50 |
| 33H09-TCB | RMF | 2.67 10$^6$ | 1.85 10$^{-1}$ | 70 nM | 3.3 10$^7$ | 1.81 10$^{-2}$ | 540 |
|  |  | 2.32 10$^6$ | 1.61 10$^{-1}$ | 69 nM | 5.85 10$^6$ | 6.45 10$^{-3}$ | 110 |
| 11D06-huIgG1 | RMF | 1.08 10$^6$ | 3.78 10$^{-2}$ | 35 nM | 2.97 10$^6$ | 1.81 10$^{-3}$ | 610 |
|  |  | 1.04 10$^6$ | 3.57 10$^{-2}$ | 34 nM | 1.01 10$^6$ | 1.28 10$^{-4}$ | 20 |
| 11D06-TCB | RMF | 1.07 10$^6$ | 3.85 10$^{-2}$ | 36 nM | 7.05 10$^6$ | 4.98 10$^{-3}$ | 710 |
|  |  | 1.12 10$^6$ | 3.82 10$^{-2}$ | 34 nM | 1.87 10$^6$ | 1.39 10$^{-3}$ | 80 |

For determination of affinity of HLA-A2/WT1 x CD3 bispecific antibodies to CD3, surface plasmon resonance (SPR) experiments were performed at 25° C. on a Biacore T200 with HBS-EP as running buffer (0.01 M HEPES pH 7.4, 0.15 M NaCl, 0.005% Surfactant P20 (GE Healthcare)). Anti-human Fab specific antibody (GE Healthcare, Cat. No. 28-9583-25) was directly immobilized by amine coupling on a CM5 chip (GE Healthcare). The bispecific constructs were captured for 40 s at 5 nM. A three-fold dilution series of the CD3εδ-Fc fusion molecule in HBS-EP (12.35 to 3000 nM) was passed over the bispecific antibodies at 30 µl/min for 240 sec to record the association phase. The dissociation phase was monitored for 240 s and triggered by switching from the sample solution to HBS-EP. The chip surface was regenerated after every cycle using a double injection of 10 mM glycine-HCl pH 2.1 at 30 µl/min for 60 sec. Bulk refractive index differences were corrected for by subtracting the response obtained on the reference flow cell (which contains the anti-human Fab antibody, but without bispecific construct captured on it). The affinity constants were derived from the kinetic rate constants by fitting to a 1:1 Langmuir binding using the BIAeval software (GE Healthcare).

The results are summarized in Table 3. Since the CD3 binder is identical in both tested bispecific molecule, as expected their affinity to CD3 is essentially the same.

TABLE 3

Summary of affinity data as determined by SPR for selected HLA-A2/WT1 x CD3 bispecific antibodies ("TCBs") to CD3.

| | | Affinity | | |
|---|---|---|---|---|
| Analyte | ligand | ka (1/Ms) | kd (1/s) | KD |
| 33H09-TC8 | huCD3-Fc | $2.74\ 10^4$ | $2.93\ 10^{-3}$ | 110 nM |
| | | $2.66\ 10^4$ | $2.77\ 10^{-3}$ | 100 nM |
| 11D06-TCB | huCD3-Fc | $2.59\ 10^4$ | $3.01\ 10^{-3}$ | 120 nM |
| | | $2.53\ 10^4$ | $2.82\ 10^{-3}$ | 110 nM |

Example 4. Selection of IgG Binders for Specificity for HLA-A2/WT1 Peptide RMF or VLD We first measured the binding specificity on peptide-pulsed T2 cells by the IgG binders generated from phage display by flow cytometry. Briefly, T2 cells were prepared as a cell suspension at $10^6$ cells/ml in IMDM medium (Gibco by Life Technologies, Cat No. 31980-048), supplemented with 10% FBS (Gibco, Cat No. 16140-071)+1% Penicillin-Streptomycin (Gibco, Cat No. 15070-063) (complete medium). Cells were kept in a total volume of 10 ml in a tube, and incubated with 10 μl of peptide (WT1 p37-45 VLD peptide (SEQ ID NO: 77), or p126-134 RMF peptide (SEQ ID NO: 78)) at $10^{-2}$ M (final concentration of the peptide: $10^{-5}$ M) for 2 hours at 37° C. with 5% $CO_2$. After washing, cells were suspended in cold PBS and incubated with titrated concentration of IgG binders (10 μg/ml to 0.00064 μg/ml) for 1 hour at 4° C., followed by incubation with a secondary anti-human IgG-Fc phycoerythrin (PE)-conjugated antibody (Jackson Laboratories, Cat No. 109-116-098) for 30 min. Cells were acquired on FACS LSR II (BD), and data are presented as mean fluorescence intensity (MFI) of PE in Graphpad Prism.

As shown in FIGS. 3A-G, 11D06-IgG, 33H09-IgG and 5E11-IgG all bind to RMF-peptide pulsed T2 cells, but not to unpulsed or VLD peptide-pulsed T2 cells. In contrast, 11B09-IgG, 13B04-IgG and 5C01-IgG (but not 11G06-IgG) all bind specifically to VLD-peptide, but not to RMF-peptide. Based on these data binders for conversion to CD3 bispecific antibodies (TCBs) were selected.

Example 5. Activation of T Cells in a NFAT-Jurkat Reporter Assay Upon Binding of HLA-A2/WT1 x CD3 Bispecific Antibodies ("TCBs") to Peptide-Pulsed T2 Cells To check the specificity of the HLA-A2/WT1 x CD3 bispecific antibodies ("TCBs"), a reporter cell line, Jurkat cells that express luciferase under the promoter of NFAT (Jurkat-NFAT; Promega Cat. No. CS176501), was used to measure activation of T cells when TCBs bind to peptide-pulsed T2 cells (ATCC, Cat. No. CRL-1992). Briefly, T2 cells were prepared as a cell suspension at $10^6$ cells/ml in IMDM medium (Gibco by Life Technologies, Cat. No. 31980-048), supplemented with 10% FBS (Gibco, Cat. No. 16140-071)+1% Penicillin-Streptomycin (Gibco, Cat. No. 15070-063) (complete medium). Cells were kept in a total volume of 10 ml in a tube, and incubated with 10 μl of peptide (WT1 p37-45 VLD peptide, or p126-134 RMF peptide) at $10^{-2}$ M (final concentration of the peptide: $10^{-5}$ M) for 2 hours at 37° C. with 5% $CO_2$. After washing, 90 μl of the peptide-pulsed cells in a cell suspension of $2.2 \times 10^5$ cells/ml were seeded into a 96 well microtiter round bottom plate (20,000 cells/well, TPP, Cat. No. 92097), co-cultured with 50 μl of Jurkat-NFAT (cell suspension of $2 \times 10^6$ cells/ml), and with 10 μl of titrated TCB (at 100 μg/ml to 0.0064 μg/ml in PBS) for 16 hours at 37° C. with 5% $CO_2$. Thereafter, 50 μl of supernatant were removed, and replaced with 100 μl per well of Bright-Glo Luciferase Assay (Promega, Cat. No. E2620) for incubation at room temperature (RT). Five minutes later, 180 μl of supernatant were transferred into a new white plate to measure luminescence signal by EnVision (PerkinElmer). Data are presented as Relative Luminescence Unit (RLU).

As shown in FIGS. 4A-H, the TCBs based on the 11D06 and the 33H09 binder (11D06-TCB and 33H09-TCB, respectively) specifically recognize the HLA-A2/WT1$_{RMF}$ complex and activate NFAT on reporter Jurkat cells only in the presence of T2 cells pulsed with the RMF peptide. In contrast thereto, the control TCB based on the ESK1-like binder (ESK1-TCB) did not show specificity for RMF peptide. Also the TCB based on the 5E11 binder (5E11-TCB) showed activation of NFAT reporter T cells in the presence of both RMF and VLD peptide-pulsed T2 cells, thus this TCB was eliminated for the next round of screening. There were also some VLD peptide-specific TCBs identified such as the ones based on the 11B09 and the 13B04 binder (11B09-TCB and 13B04-TCB, respectively). As a negative control, untargeted TCB (DP47GS-TCB) was used in the assay, which did not activate NFAT on reporter Jurkat cells in the presence of RMF- or VLD-peptide pulsed T2 cells. 5C01-TCB showed recognition of VLD peptide, but cross-reacted with RMF peptide at higher concentrations.

Example 6. T Cell Cytotoxicity Mediated by HLA-A2/WT1 x CD3 Bispecific Antibodies ("TCBs") Upon Binding to Peptide-Pulsed T2 Cells Next, we measured the cytotoxicity of the TCBs. The target cells were peptide-pulsed T2 cells as described in Example 5. The effector cells were pan CD3$^+$ cells purified from PBMCs isolated from buffy coat by Ficoll (GE Healthcare, Cat. No. 17-1440-03) gradient centrifugation. Total CD3$^+$ T cells were purified by MACS (Miltenyi Biotec) using a Human Pan T cell Isolation Kit (Miltenyi Biotec, Cat. No. 130-096-535). The cytotoxicity assay was performed as follows: The peptide-pulsed cells (100 μl) were seeded into a 96 well microtiter round bottom plate ($3 \times 10^5$ cells/ml), co-cultured with 50 μl of T cells ($6 \times 10^6$ cells/ml), and with 50 μl of titrated TCB (at 40 μg/ml to 0.00004 μg/ml) in complete medium for 18 hours at 37° C. with 5% $CO_2$. Thereafter, 50 μl of supernatant were transferred into a new white plate, and 25 μl per well of CytoTox-Glo Luciferase Assay (Promega, Cat. No. G9291) were added for incubation at room temperature (RT) for 15 minutes. The luminescence signal (for measurement of LDH release as indicative of cell death) was read by EnVision (PerkinElmer). Data are presented as Relative Luminescence Unit (RLU).

FIGS. 5A-F shows the TCB-mediated specific T cell killing of RMF- or VLD-expressing target cells. We found that both 11D06-TCB and 33H09-TCB showed specific killing on RMF peptide-pulsed T2 cells. 33F05-TCB did not mediate specific killing of RMF or VLD peptide-pulsed cells. In addition, 13B04-TCB and 11B09-TCB mediated potent killing on VLD peptide-pulsed T2 cells. 5C01-TCB showed killing of VLD-pulsed T2 cells, but also of RMF-pulsed cells at higher concentration, consistent with the observations in the NFAT reporter assay (FIGS. 4A-H).

Figure 6B:
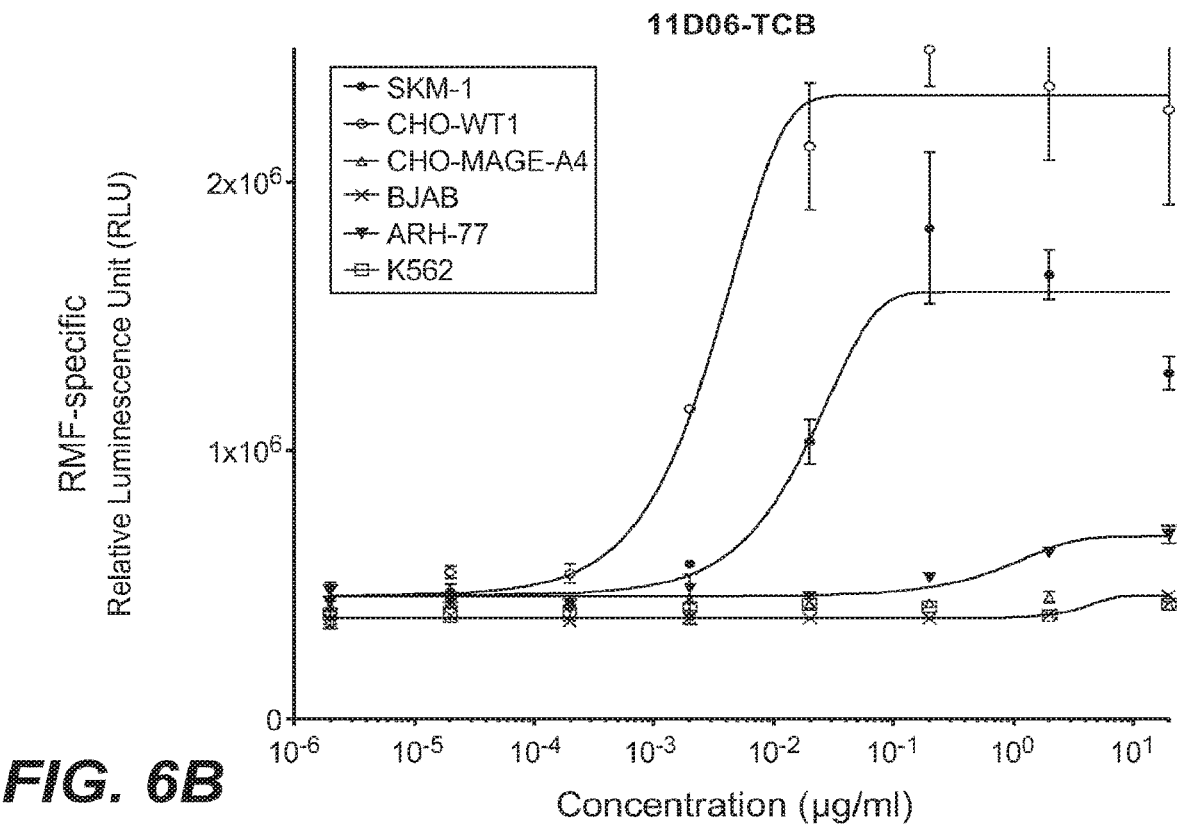
Figure 6C:
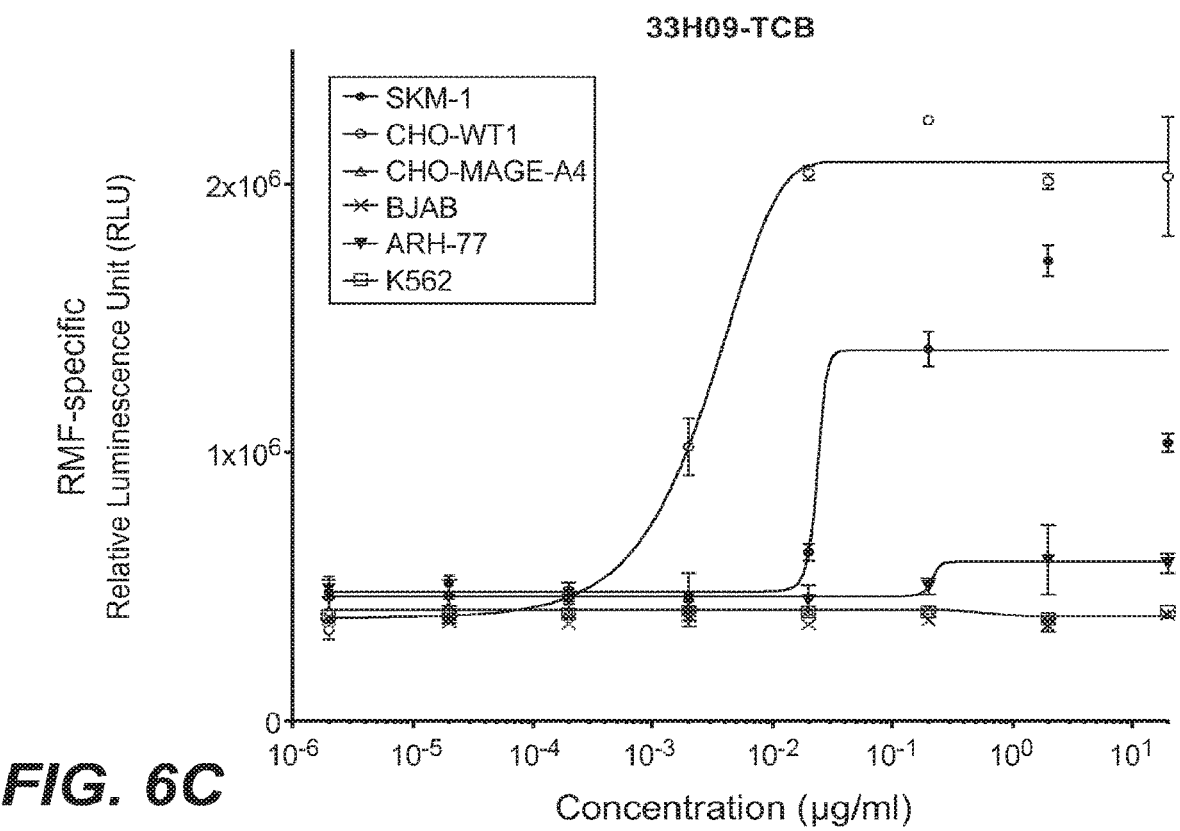
Figure 6D:
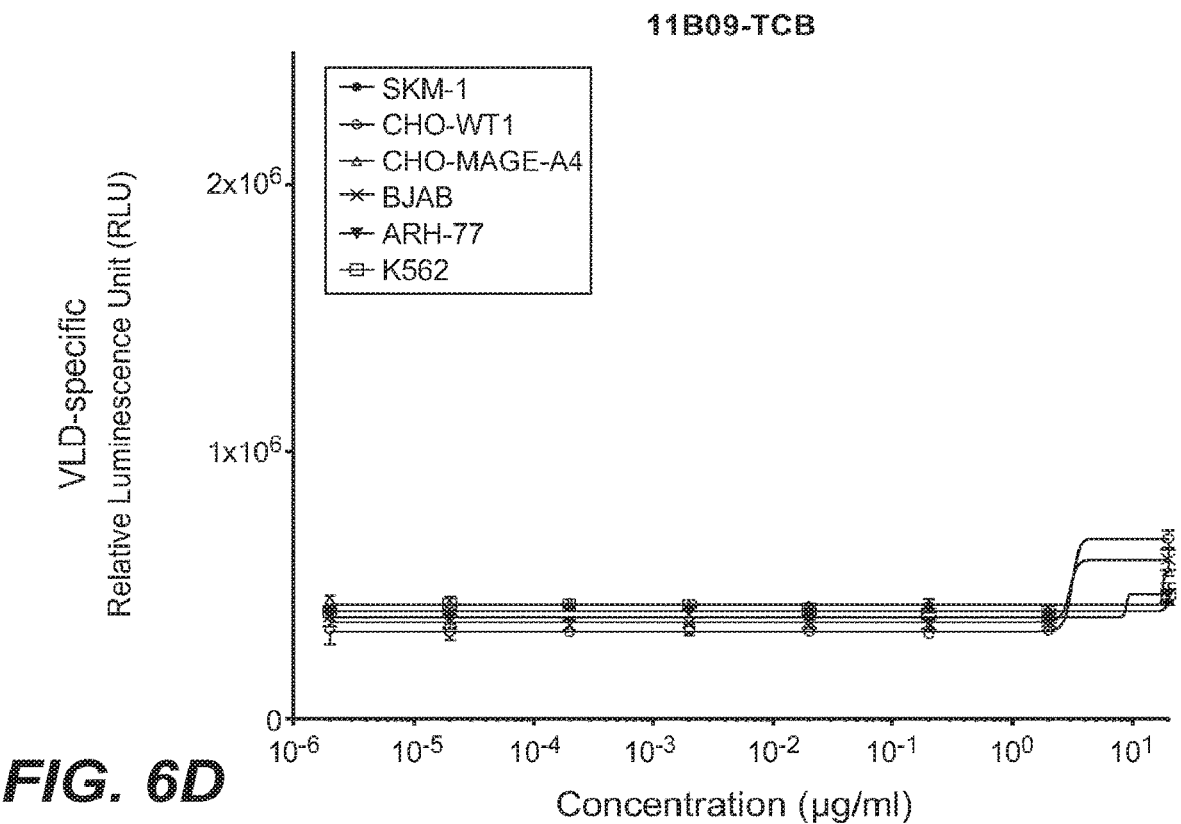
Figure 6E:
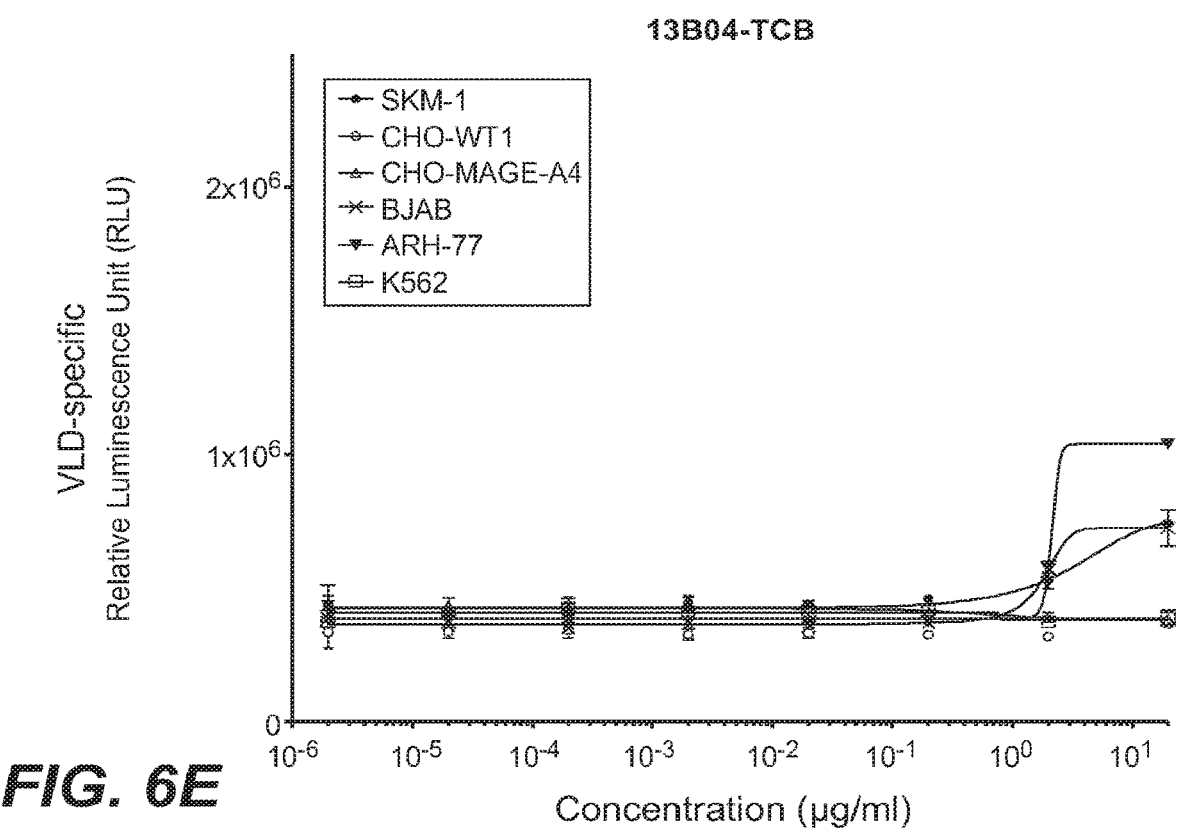

Example 7. T Cell Cytotoxicity Mediated by HLA-A2/WT1 x CD3 Bispecific Antibodies ("TCBs") Upon Binding to WT1$^+$ Cell Lines To confirm the specific killing by the TCBs, we performed the cytotoxicity assay on WT1$^+$ tumor cell lines. The HLA-A2$^+$WT1$^+$ cell lines were SKM-1 cells (DZMZ No. ACC 547), and CHO cells transfected with HLA-A2/WT1$_{RMF}$ complex (CHO-WT1) (in-house). The negative controls were HLA-A2$^+$WT1$^-$ cells: BJAB (DZMZ No. ACC 757), ARH-77 (DZMZ No. ACC 512), and CHO cells transfected with HLA-A2/MAGE-A4 complex (CHO-MAGEA4) (in-house), as well as a HLA-A2$^-$WT1$^+$ cell line: K562 (ATCC No. CLL-243) (FIG. 6A). The cytotoxicity assay was performed as described in Example 6. Both 11D06-TCB and 33H09-TCB showed potent killing on SKM-1 and CHO-WT1 cells, but not on any HLA-A2+WT1$^-$ cells and HLA-A2$^-$WT1$^+$ cells, indicating that these two TCBs have specificity for WT1 peptide RMF (FIGS. 6 B, 6C). In contrast thereto, none of the VLD peptide-specific TCBs showed killing on HLA-A2$^+$WT1$^+$ cell lines, and if they showed low potency killing at high concentration (10 µg/ml) on the WT1$^+$ cell lines, the same degree of killing was seen on WT1 cell lines as well (FIGS. 6 D, 6E). Based on these functional data, we selected 11D06-TCB and 33H09-TCB for further evaluation.

Figure 6F:
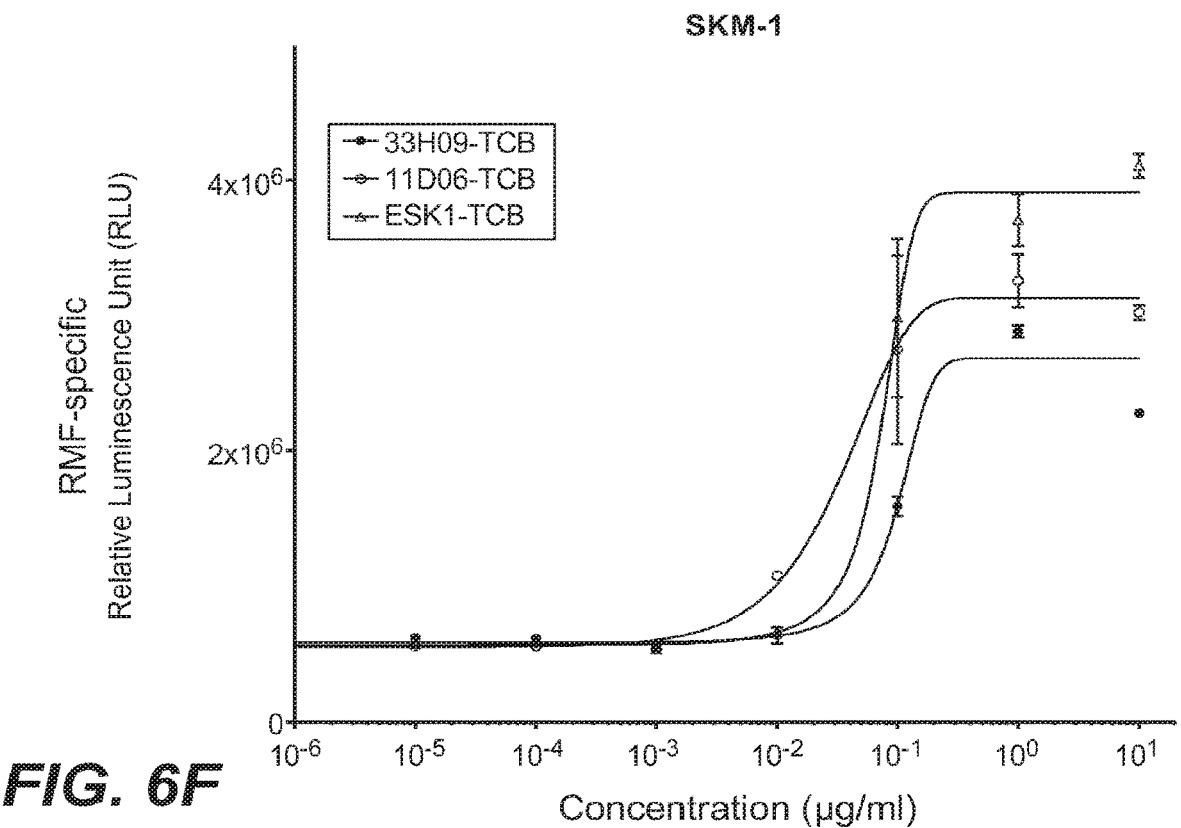
Figure 6G:
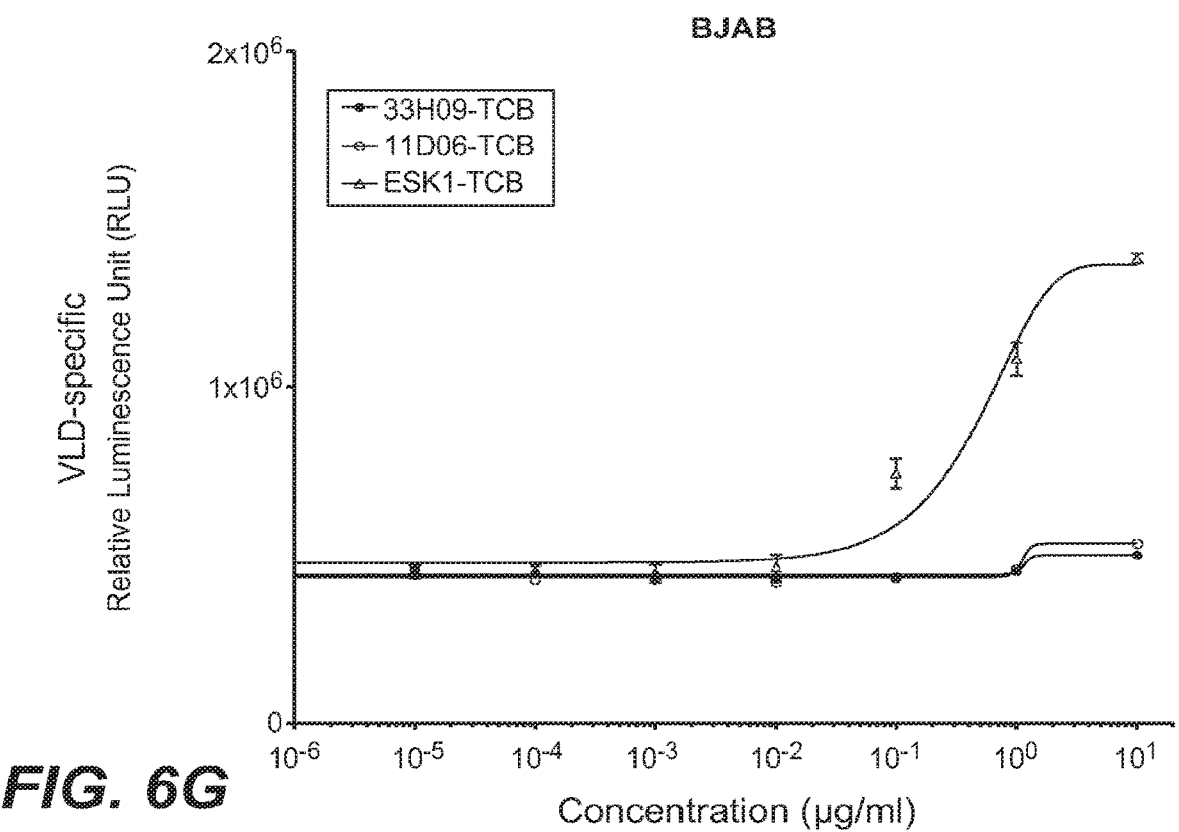

We also compared our selected TCBs with ESK1-TCB for their killing activity of the tumor target cells. Interestingly, though ESK1-TCB achieved similar potency in mediating killing of SKM-1 cells as compared to 11D06-TCB and 33H09-TCB, it also induced killing on HLA-A2$^+$WT-1$^-$ BJAB cells, indicating that ESK1-TCB binding is not restricted to HLA-A2/WT1$_{RMF}$ complex (FIGS. 6F, 6G).

We tested the killing of multiple tumor cell lines that are HLA-A2+WT1+. Based on the EC$_{50}$ value for the killing, cell lines were categorized into those that were killed with an EC$_{50}$ of <1 µM (marked in Table 4 with "++"), those that were killed with an EC$_{50}$ of >1 µM and <5 µM (marked in Table 4 with "+"), and those that were essentially not killed (marked in Table 4 with "no").

All together, the selected TCBs 11D06-TCB and 33H09-TCB mediated T cell cytotoxicity on 6 out of 13 HLA-A2$^+$ WT1$^+$ cell lines. The lack of killing on the other cell lines was likely due to the low expression of WT1 presented on the cell surface by MHC L. Table 4 shows the results for 11D06-TCB. The results for 33H09-TCB were similar (with BC values being slightly higher than for 11D06-TCB).

TABLE 4

Killing of WT1+ cell lines by selected TCBs.

| Cell line name | HLA-A2 | WT1 | Disease of Tissue Origin | Killing by by 11D06-TCB (RMF-specific) | EC50 (uM) in vitro killing by 11D06-TCB | K-Ras mutation |
|---|---|---|---|---|---|---|
| SKM-1 | + | + | Acute myeloid leukemia | ++ | 0.09-0.35 | Yes |
| T98G | + | + | Glioblastoma | ++ | 0.8-1.7 | No |
| MDA-MB-231 | + | + | Breast adenocarcinoma | ++ | 0.5-2.8 | Yes |
| SW620 | + | + | Colorectal adenocarcinoma | + | 4.8 | Yes |
| SW480 | + | + | Colorectal adenocarcinoma | + | 2.9 | Yes |
| SET-2 | + | + | Essential thrombocytopenia | (+)* if treated with Decitabine | (0.005) | No |
| CTV-1 | + | + | Leukemia, acute myeloid | No | | No |
| BV173 | + | + | Acute leukemia, chronic myeloid | No | | No |
| A-375 | + | + | Melanoma | No | | No |
| LN-18 | + | + | Glioblastoma | No | | No |
| U-266 | + | + | Myeloma | No | | No |
| OVCAR3 | + | + | Ovarian carcinoma | No | | No |
| Nalm6 | + | + | B cell precursor leukemia | No | | No |

Example 8. T Cell Activation Mediated by HLA-A2/WT1 x CD3 Bispecific Antibodies ("TCBs") Upon Binding to WT1$^+$ Cell Lines A prerequisite of TCB-mediated cytotoxicity on WT1$^+$ target cells is that T cells are activated to acquire effector function. We measured the activation status of T cells by flow cytometry in the co-culture of T cells and HLA-A2$^+$ WT1$^-$ cells SKM-1 or HLA-A2$^+$WT1$^-$ cells BJAB in the presence of the two selected TCBs, 33H09-TCB and 11D06-TCB, during the in vitro killing assay as described in Example 7. Cells were harvested after 18 hours of co-incubation, and stained with antibodies against CD3 (Biolegend Cat. No. 300321), CD25 (Biolegend Cat. No. 302606) and CD69 (Biolegend Cat. No. 310914) to measure T cell activation by flow cytometry.

Figure 7A:
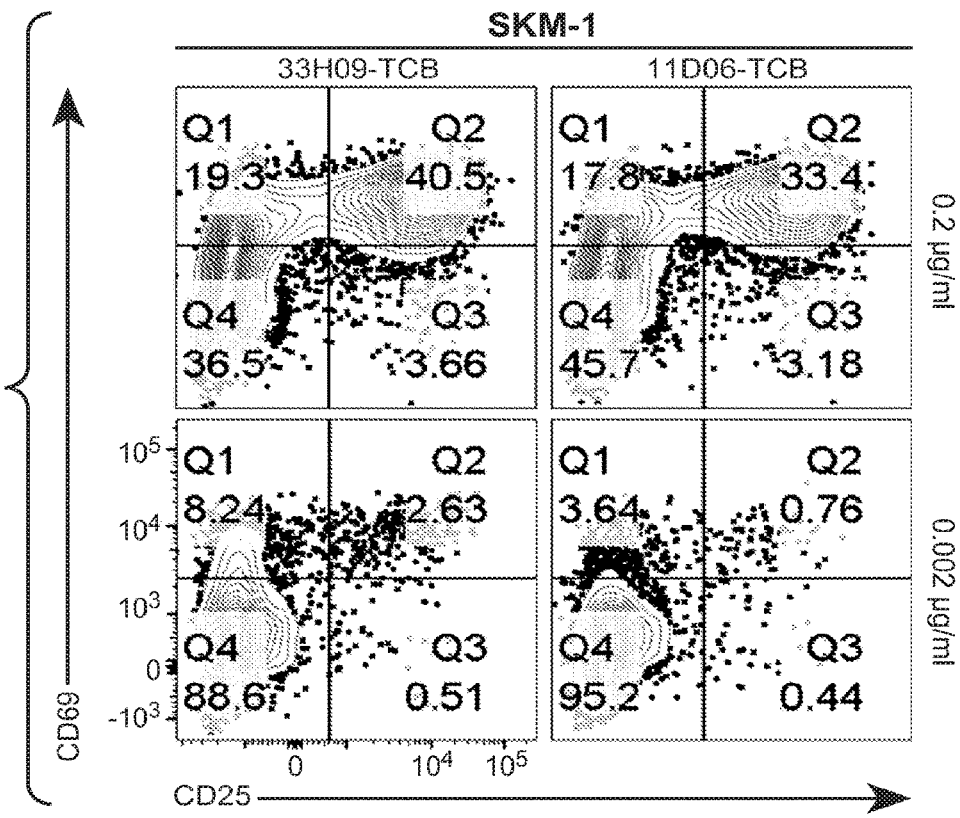
FIGS. 7A-B. Activation of T cells by HLA-A2/WT1 x CD3 bispecific antibodies (TCBs) upon binding to HLA-A2+WT1+ tumor cell lines. (A) SKM-1 cells, (B) BJAB cells.
Figure 7B:
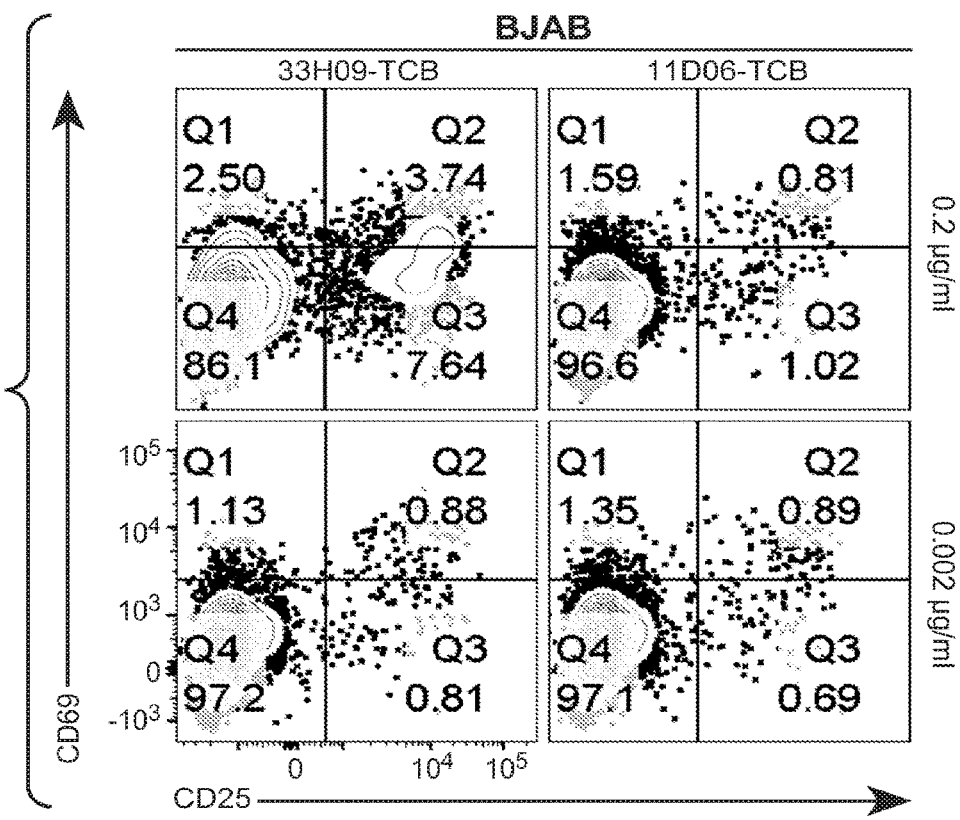

As shown in FIGS. 7A-B, both TCBs induced up-regulation of CD69 and CD25 on CD3$^+$ T cells upon binding to SKM-1 cells, but not BJAB cells, indicating that the specific recognition by TCBs of HLA-A2/WT1$_{RMF}$ complex presented by SKM-1 cells triggers CD3-mediated activation of T cells, eventually leading to the specific lysis of target cells.

Figure 8A:
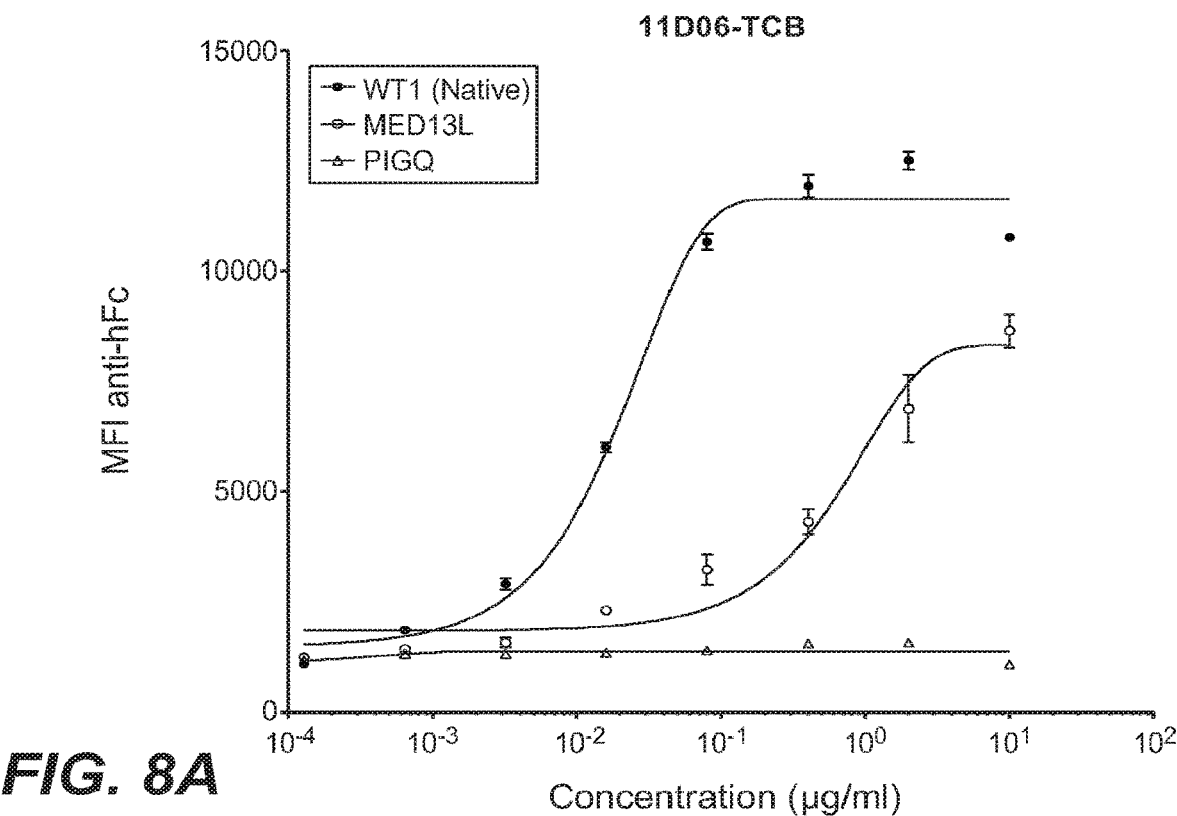
FIGS. 8A-F. No binding to off-target peptides by selected HLA-A2/WT1 x CD3 bispecific antibodies (TCBs). (A-C) Binding to peptide-pulsed T2 cells by (A) 11D06-TCB, (B) 33H09-TCB, (C) ESK1-TCB. (D-E) Activation of T cells upon binding to peptide-pulsed T2 cells by (D) 11D06-TCB and (E) 33H09-TCB. (F) Overview of peptides.
Figure 8B:
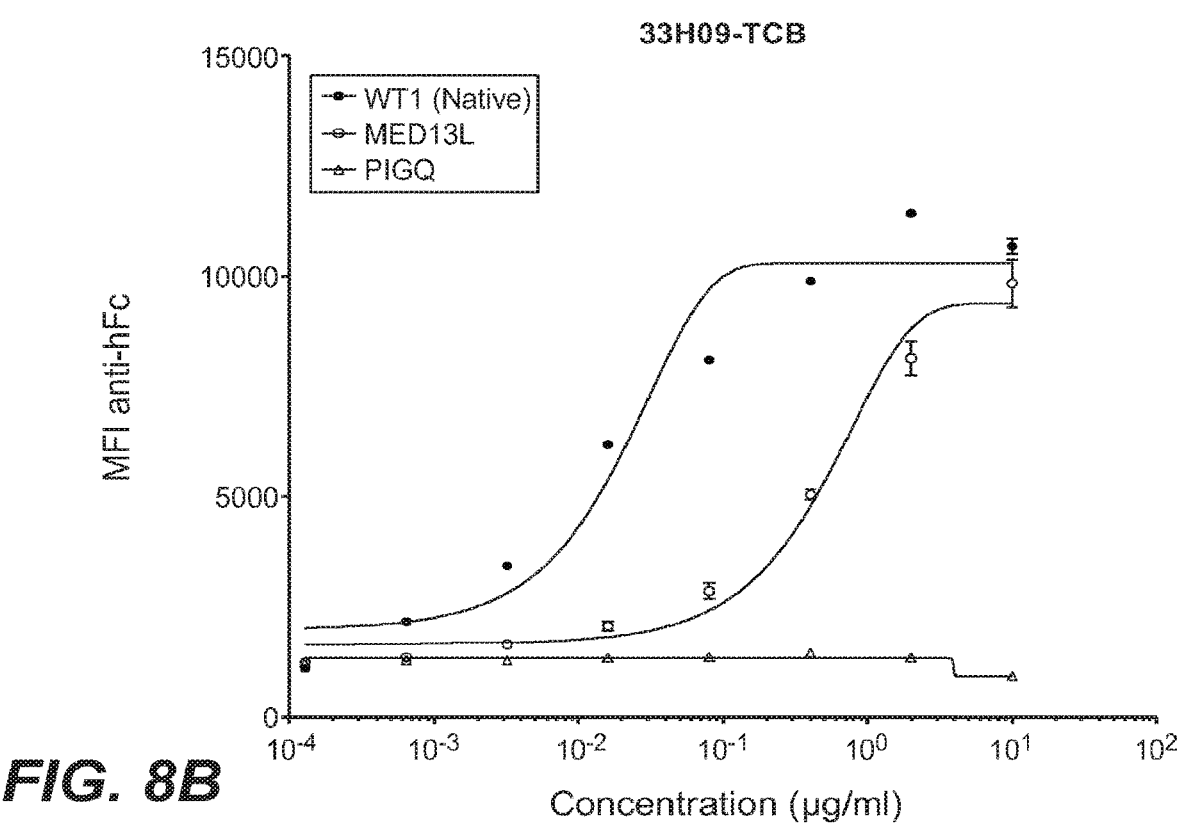
Figure 8C:
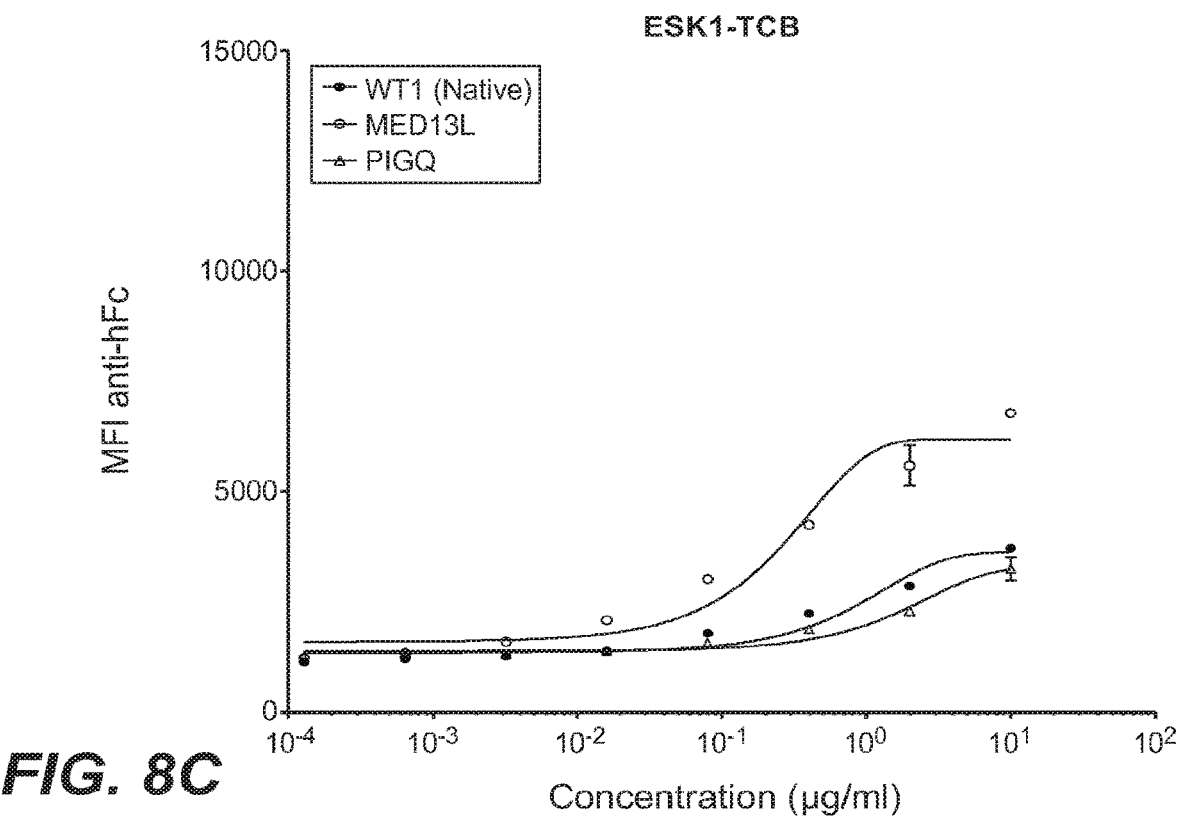
Figure 8D:
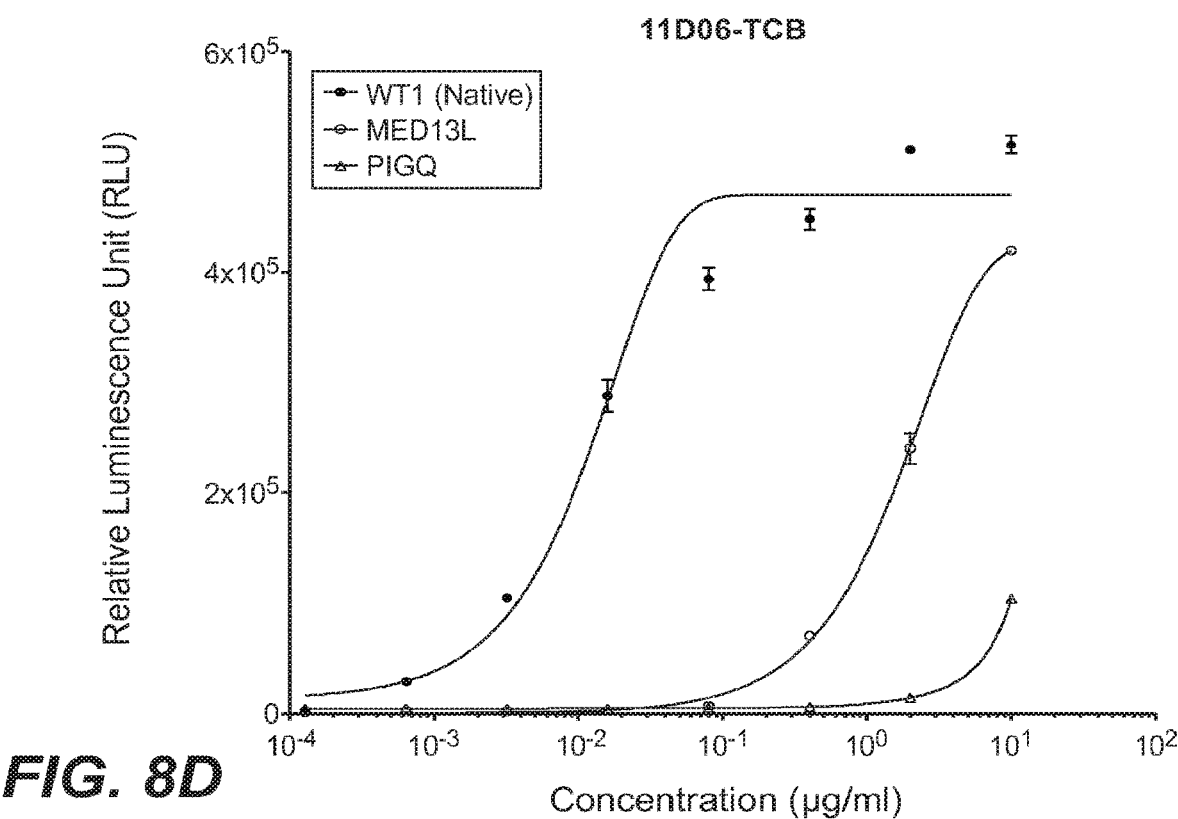
Figures 8E, 8F:
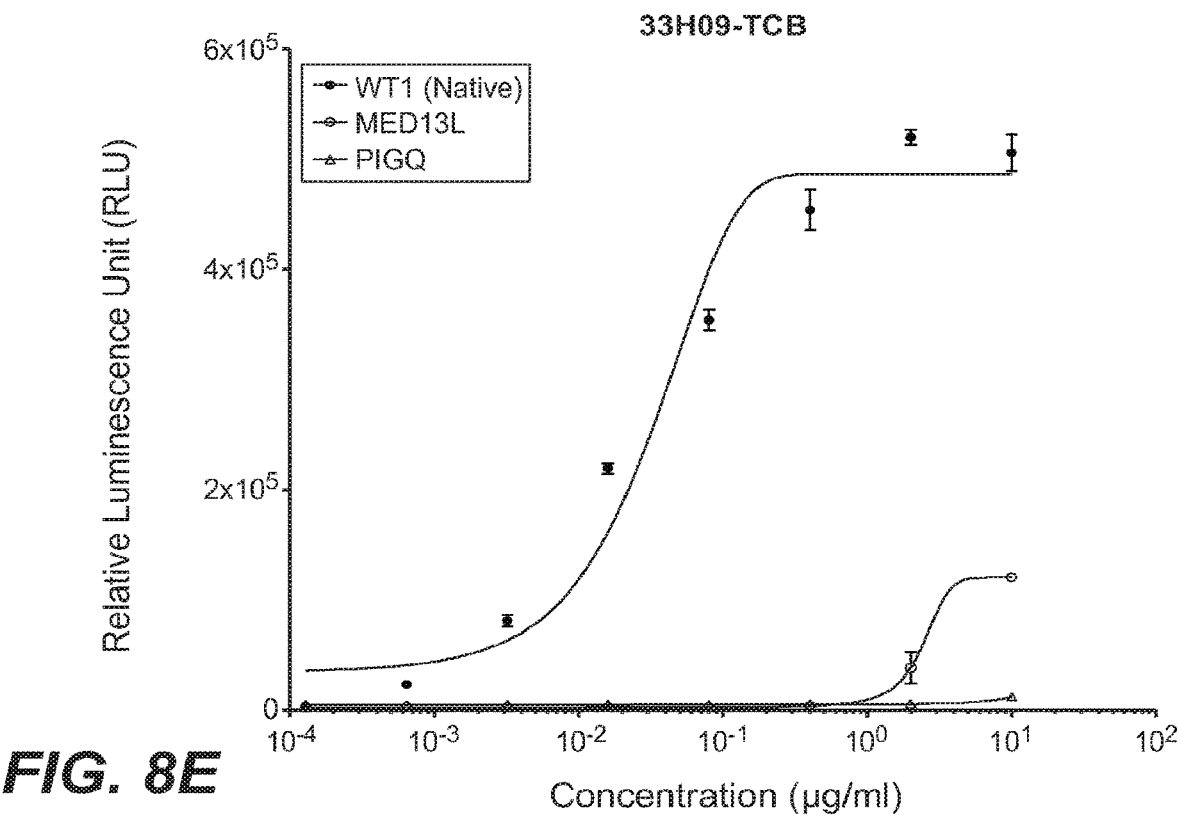

Example 9. No Binding of Selected HLA-A2/WT1 x CD3 Bispecific Antibodies ("TCBs") to Reported Off-Target Peptides A major potential risk in developing T cell receptor (TCR)-like antibodies is the cross-reactivity of the antibody with peptide homologues presented from proteins expressed by normal tissue. As it was reported by Ataie et al. (J Mol Biol. (2016) 428:194-205) that ESK1 antibody binds to sequence-similar peptides derived from protein MED13L and PIGQ, we tested our TCBs for their cross-reactivity to these two peptides. The sequences of these peptides are shown in FIG. 8F, and SEQ ID NOs 79 and 80. In a flow cytometry-based binding assay, as described in Example 4, we found that both 11D06-TCB and 33H09-TCB do not bind to PIGQ peptide. The binding to MED 13L peptide by both TCBs is nearly 100 fold less as compared to the native WT1 RMF peptide (FIGS. 8A, 8B). Although ESK1-TCB binds to RMF peptide in a low affinity, it binds to PIGQ peptide in a similar manner and even more strongly to MED13L (FIG. 8C), consistent with the reported binding activity of the ESK1 IgG (Ataie et al., J Mol Biol. (2016) 428:194-205).

We also tested cross-reactivity using the NFAT-reporter assay as described in Example 5. In line with the binding data, the strength of NFAT activation on Jurkat cells upon binding to MED13L and PIGQ is at least 100 fold weaker than the activation upon binding to WT1 RMF peptide by 11D06-TCB and 33H09-TCB (FIGS. 8 D, 8E).

Example 10. No Binding of Selected HLA-A2/WT1 x CD3 Bispecific Antibodies ("TCBs") to Unidentified Off-Target Peptides Cross-reactivity against homologous peptides (sharing key recognition residues) derived from normal tissue may cause serious and not readily predictable toxicities by TCR-like antibody or TCR-based T cell therapy (see e.g. Linette et al, Blood (2013) 122:863-71; reporting fatal toxicity of MAGE A3-TCR-therapy due to off-target reactivity against a protein expressed by cardiac tissue). Specificity of these agents is therefore critical. To thoroughly define specificity of our antibodies, based on the crystal structure data which confirms the positions in the RMF peptide involved in binding of 11D06 (see Example 15), we extended our search for potential off-target peptides with similar amino acid sequence as WT1 RMF peptide (SEQ ID NO: 78) by masking RxxPNxxYx in the peptidome databases (Swissprot and TrEMBL). We found additional 25 peptides derived from different proteins which all have high predicted affinity to HLA-A2 (Table 5). We then tested the cross-reactivity of our selected TCBs on the peptide-pulsed T2 cells using the NFAT-reporter assay (peptide 1-6) or T cell cytotoxicity assay (peptide 7-25), as described above.

Figure 9A:
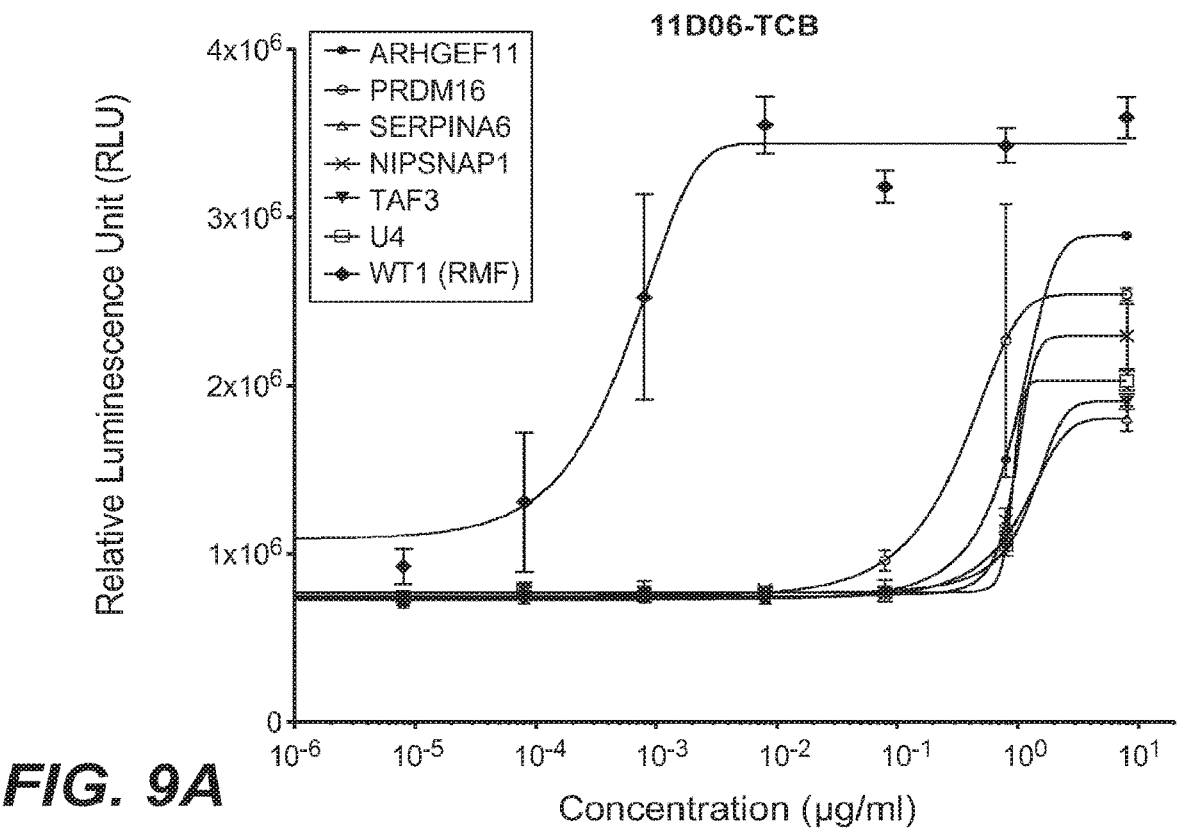
FIGS. 9A-G. No binding to additional off-target peptides by selected HLA-A2/WT1 x CD3 bispecific antibodies (TCBs). (A-B) Activation of T cells upon binding to peptide-pulsed T2 cells by (A) 11D06-TCB and (B) 33H09-TCB. The 6 indicated off-target peptides were tested along with the RMF peptide. (C-G) Killing of peptide-pulsed T2 cells by (C, E) 11D06-TCB, (D, F) 33H09-TCB and (G) ESK1-TCB. The 19 indicated off-target peptides were tested along with the RMF and VLD peptides.
Figure 9B:
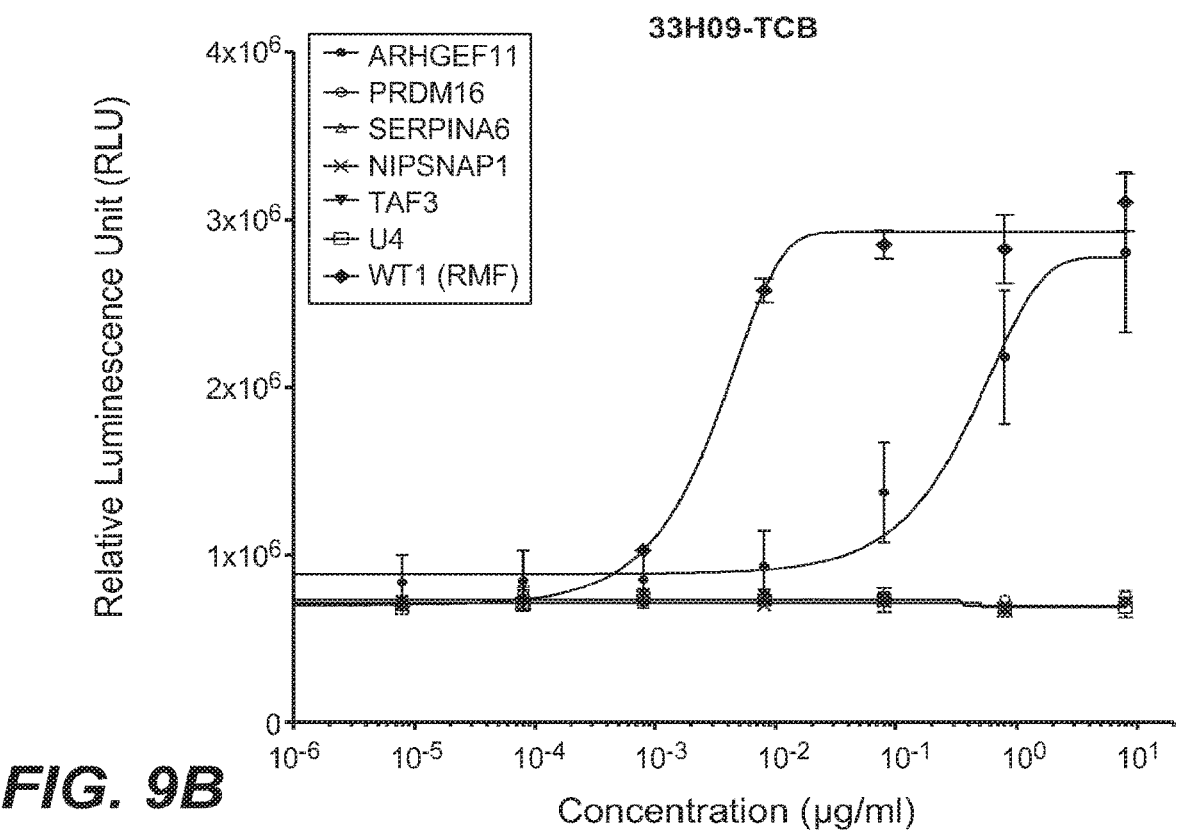
Figure 9C:
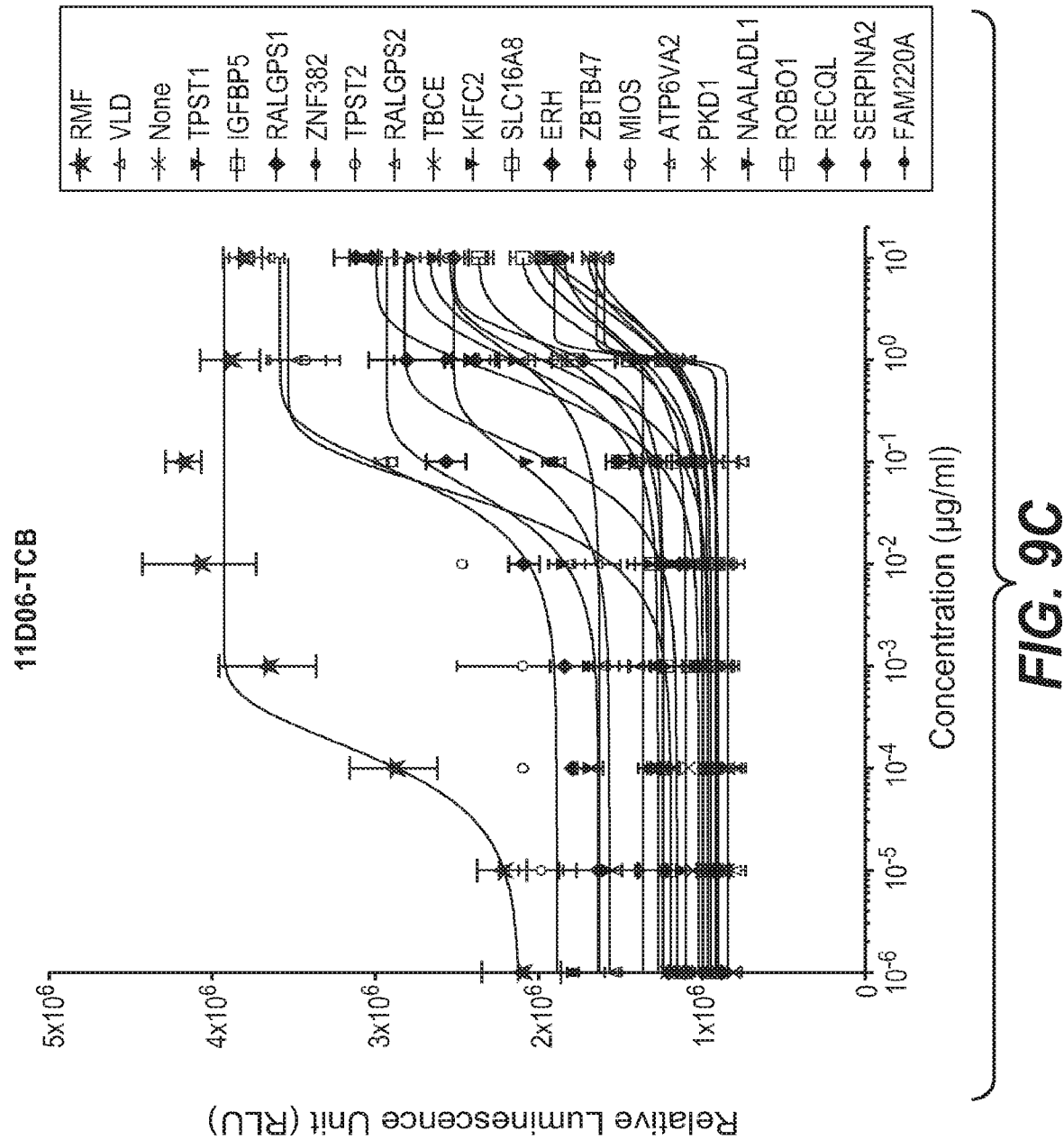
Figure 9D:
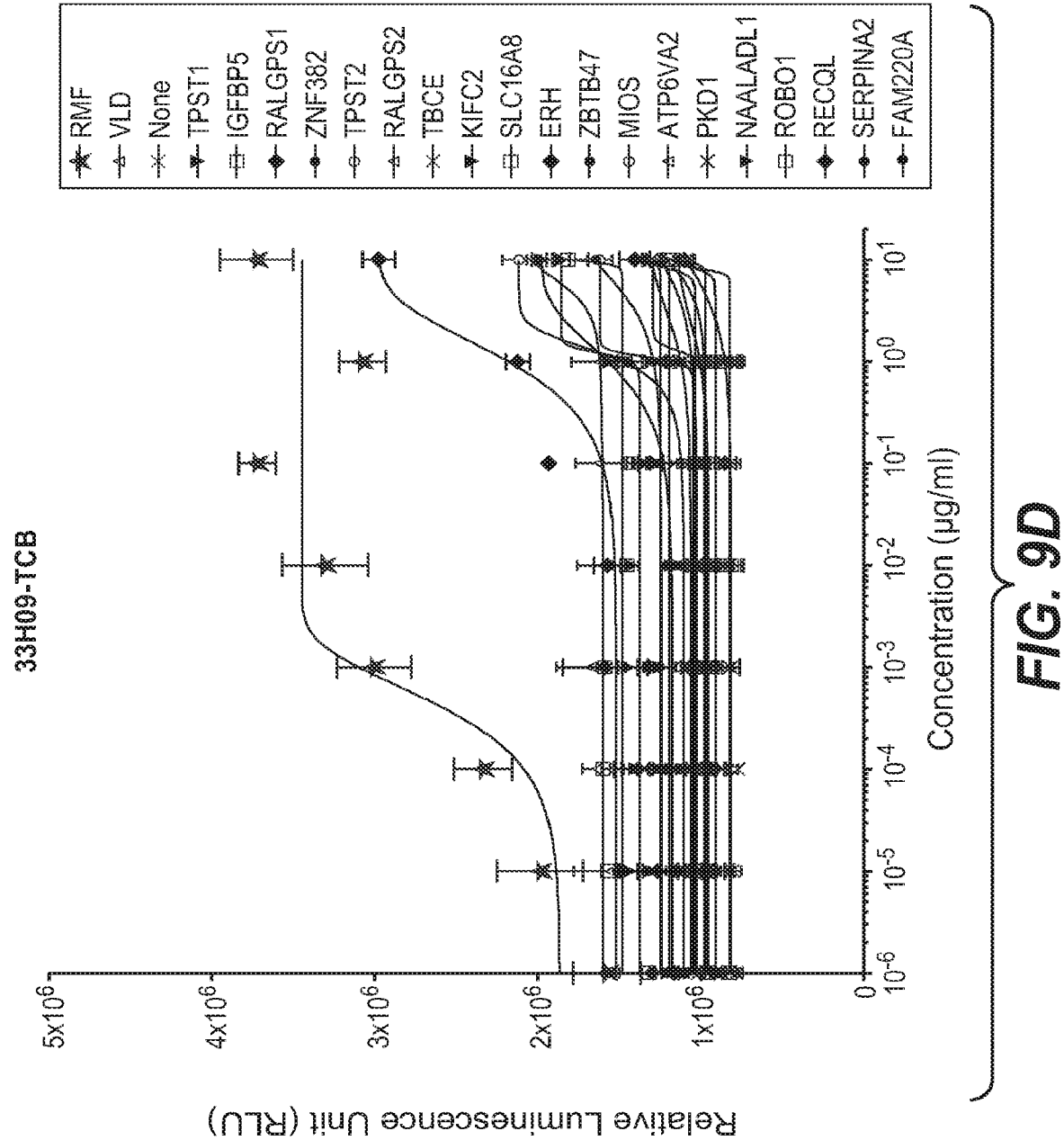
Figure 9E:
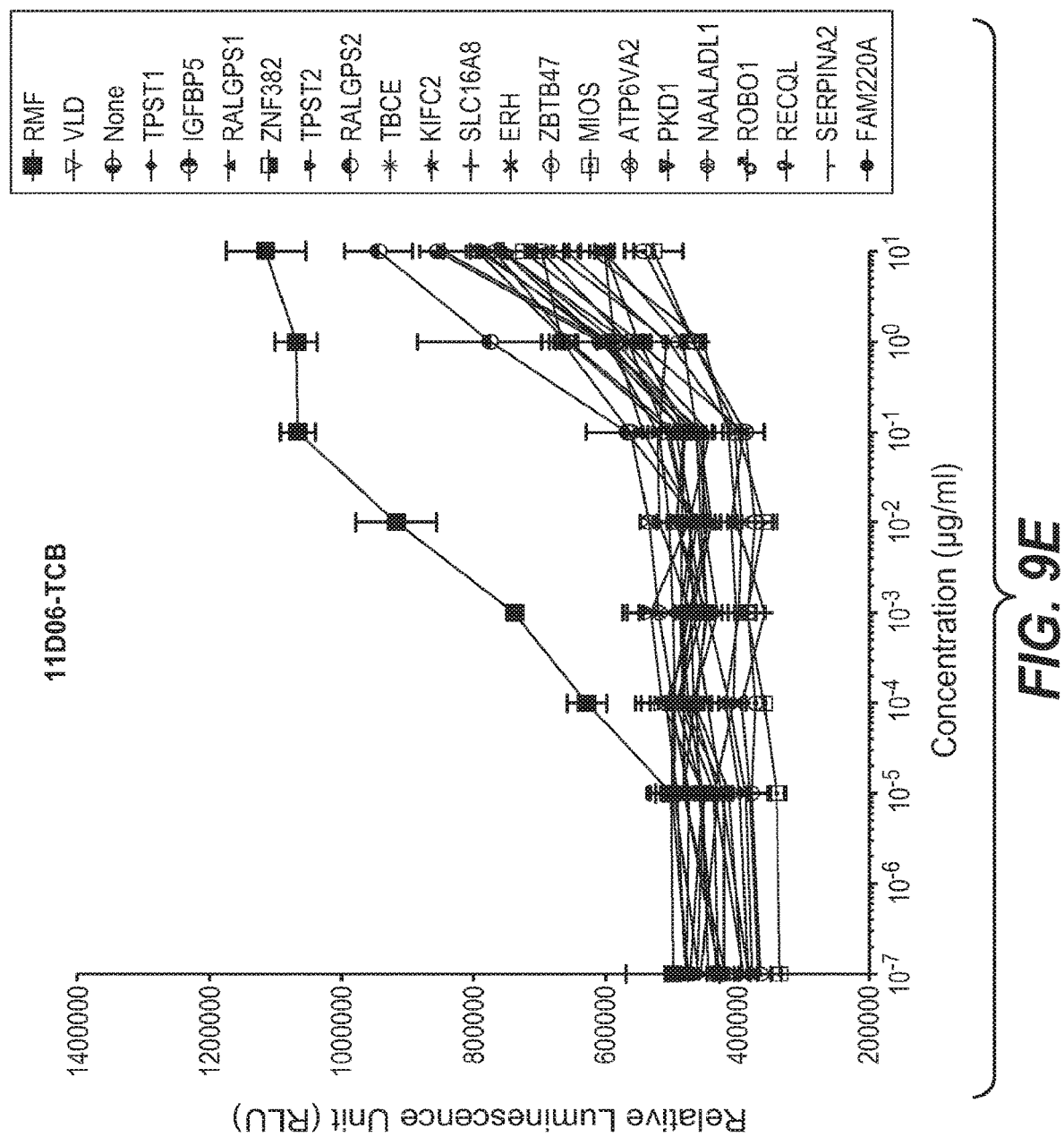
Figure 9F:
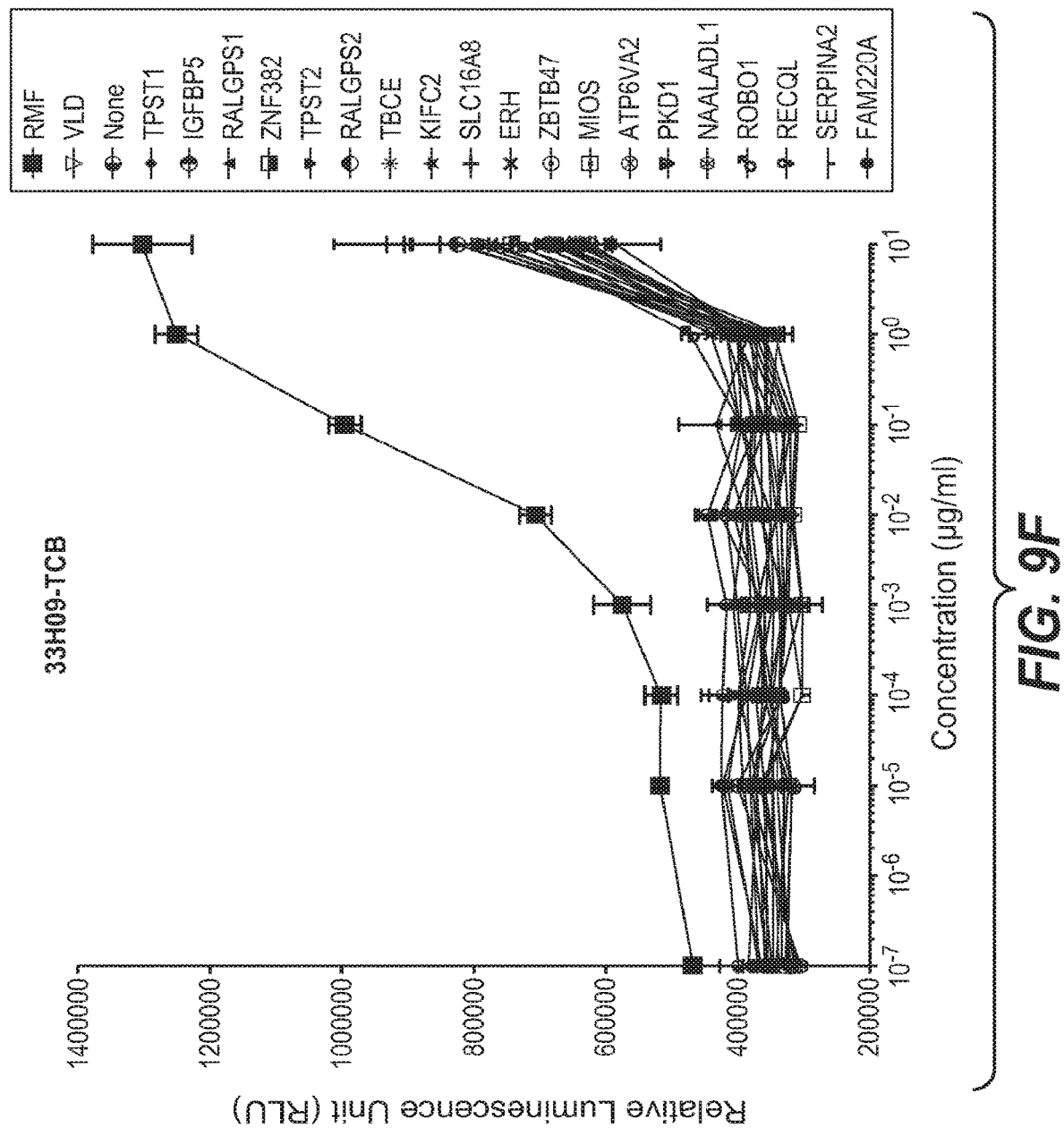
Figure 9G:
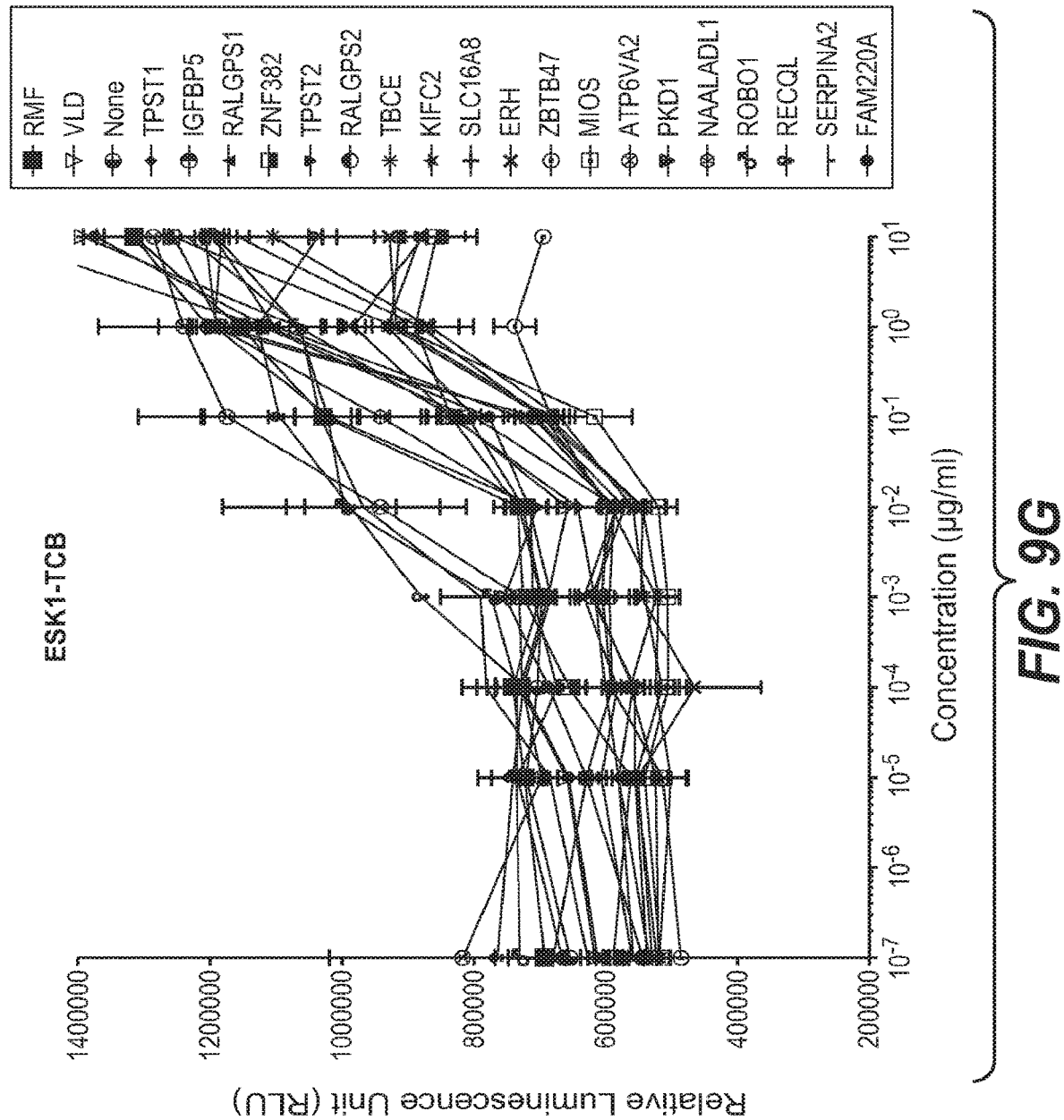

For the first 6 peptides tested, there was no cross-reactivity to any of the 6 peptides by 11D06-TCB. 33H09-TCB showed some recognition to ARHGEF11, but the degree of NFAT-activation was >100 fold lower as compared to native RMF peptide (FIGS. 9A, 9B). Similarly, the cross-reactivity to the other 19 off-target peptides was at least 100 fold lower than to the native RMF peptide, as measured by direct T cell killing of peptide-pulsed T2 cells (FIGS. 9 C, 9D). This result was confirmed in a second experiment, wherein also ESK1-TCB was tested (FIGS. 9 E-G).

Taken together, we confirmed that 11D06 and 33H09 (but not the ESK1-like binder) show specificity to the WT1 RMF peptide, and not to the potential off-target peptides detected in the peptidome.

TABLE 5

Additional, newly identified off-target peptides.

| Peptide | Peptide sequence | Gene name | SEQ ID NO |
|---|---|---|---|
| 1 | RLFPNLPEL | ARHGEF11 | 81 |
| 2 | RMFPNKYSL | PRDM16 | 82 |
| 3 | AMDPNAAYV | SERPINA6 | 83 |
| 4 | RMGPNIYEL | NIPSNAP1 | 84 |
| 5 | NMPPNFPYI | TAF3 | 85 |
| 6 | YTIPNHPYL | U4 | 86 |
| 7 | RLFPNAKFL | TPST1 | 87 |
| 8 | RMVPRAVYL | IGFBP5 | 88 |
| 9 | KMVPSIPYL | RALGPS1 | 89 |
| 10 | RIFPSYSYL | ZNF382 | 90 |
| 11 | RLFPNSKFL | TPST2 | 91 |
| 12 | KMTPCIPYL | RALGPS2 | 92 |
| 13 | SMFPSLKYL | TBCE | 93 |
| 14 | RLLPSAPTL | KIFC2 | 94 |
| 15 | RLRPHVPYL | SLC16A8 | 95 |
| 16 | RMNPNSPSI | ERH | 96 |
| 17 | RVFNNRWYL | ZBTB47 | 97 |
| 18 | RLQLNNPYL | MIOS | 98 |
| 19 | RMFFNGRYI | ATP6V0A2 | 99 |
| 20 | RLSPNRPPL | PKD1 | 100 |
| 21 | ETFPNSWYL | NAALADL1 | 101 |
| 22 | GLKPNAIYL | ROBO1 | 102 |
| 23 | RQFPNASLI | RECQL | 103 |
| 24 | YIFPNCPFL | SERPINA2 | 104 |
| 25 | RLRINFPYL | FAM220A | 105 |

Example 11. No Cytotoxicity on CD34$^+$ Stem Cells Mediated by Selected HLA-A2/WT1 x CD3 Bispecific Antibodies ("TCBs")

It has been reported that CD34$^+$ hematopoietic stem cells are WT1 positive (Ramani and Cowell, J. Path (1996) 179:162-8), therefore it can potentially be harmful if the TCBs would bind them. To study whether CD34$^+$ cells endogenously present the RMF peptide, we obtained HLA-A2$^+$ bone marrow derived CD34$^+$ cells from 3 donors from Lonza, and tested our selected TCBs in a killing assay as described above in Example 7. Whereas 11D06-TCB and 33H09-TCB mediate potent killing on SKM-1 cells, they had no killing activity on the CD34$^+$ stem cells, indicating that these stem cells may not present the RMF peptide in the context of HLA-A2 (FIGS. 10A-B).

Figure 11A:
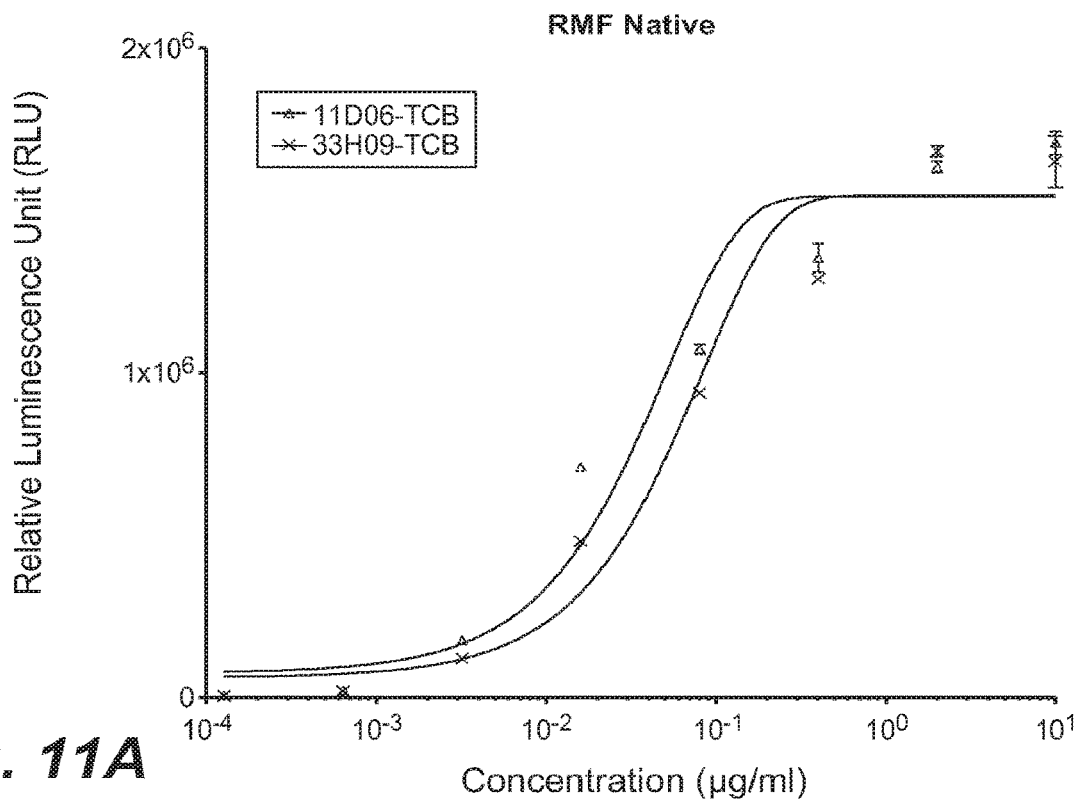
FIGS. 11A-N. Identification by alanine scan of binding residues in RMF peptide for selected HLA-A2/WT1 x CD3 bispecific antibodies (TCBs). (A) RMF native peptide, (B) RMF R1Y peptide, (C) RMF R1A peptide, (D) RMF M2A peptide, (E) RMF F3A peptide, (F) RMF P4A peptide, (G) RMF N5A peptide, (H) RMF A6G peptide, (I) RMF P7A peptide, (J) RMF Y8A peptide, (K) RMF L9A peptide. (L) Overview of peptides. (M) Fold change of $EC_{50}$ relative to $EC_{50}$ for the RMF native peptide. (N) Critical contact residues.
Figure 11B:
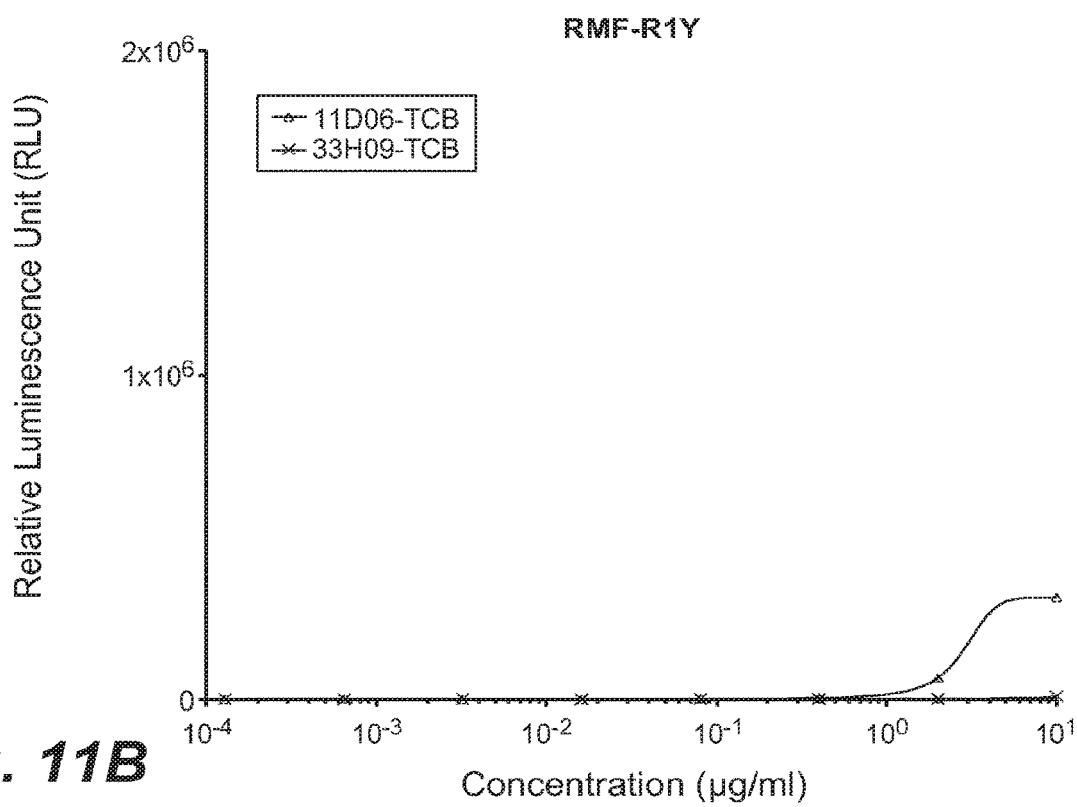
Figure 11C:
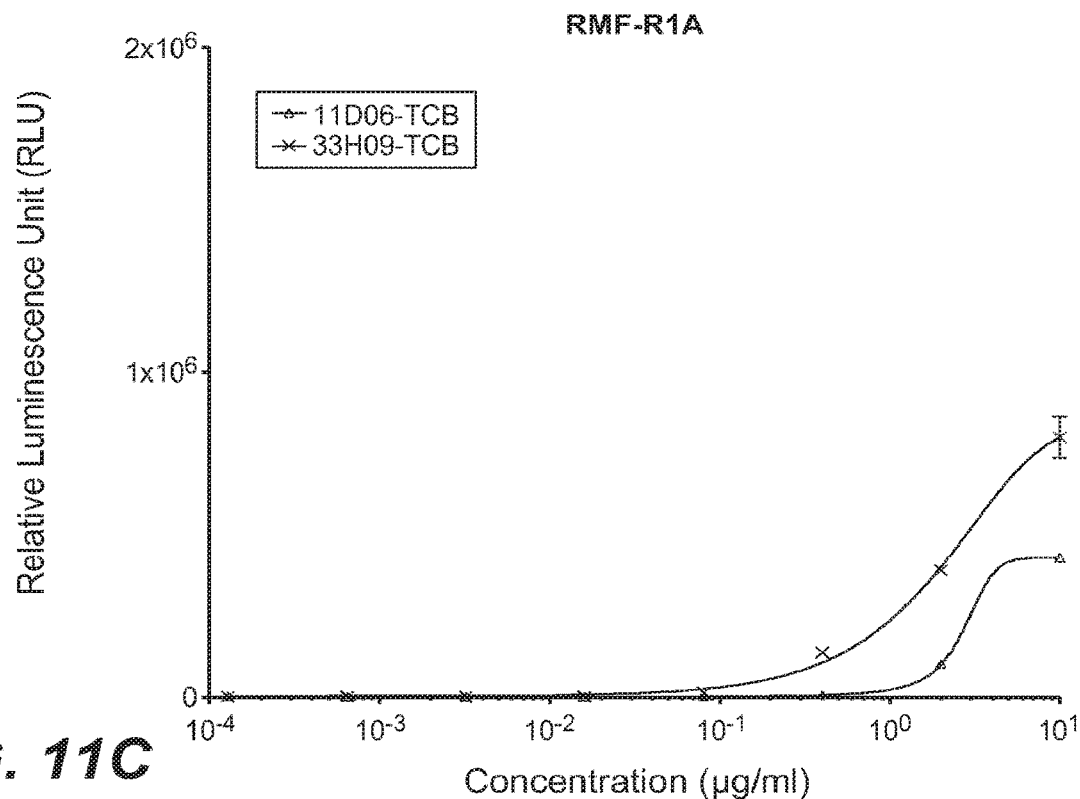
Figure 11D:
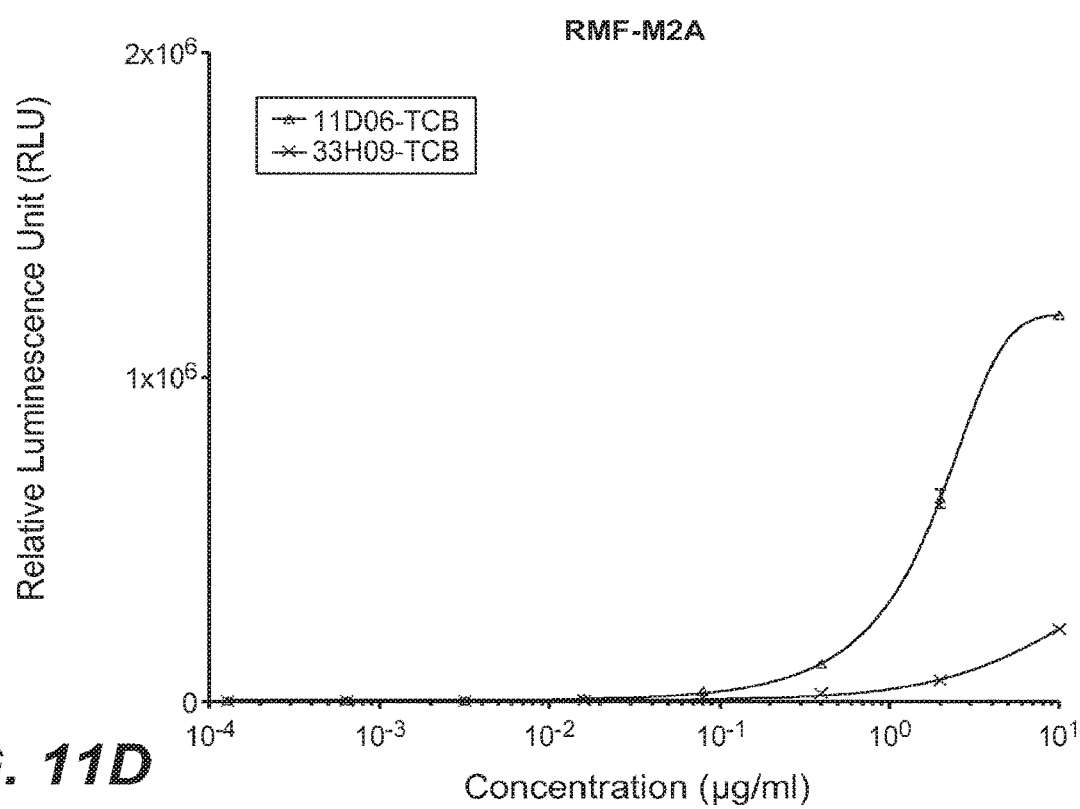
Figure 11E:
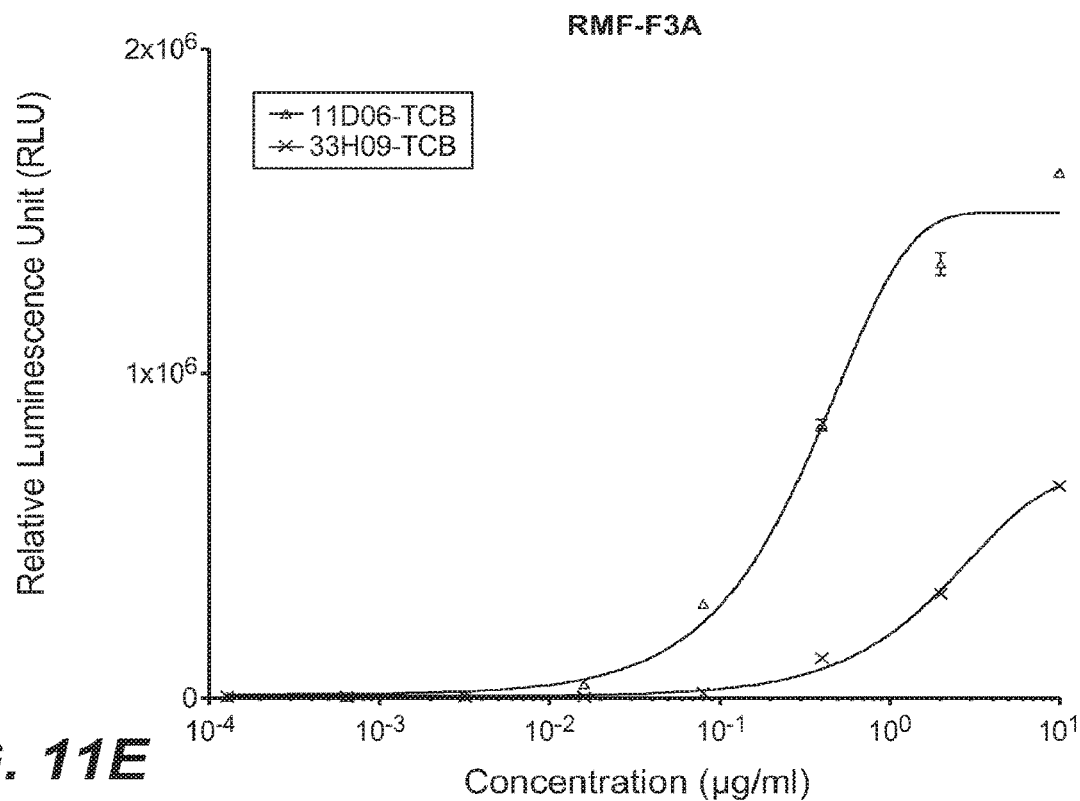
Figure 11F:
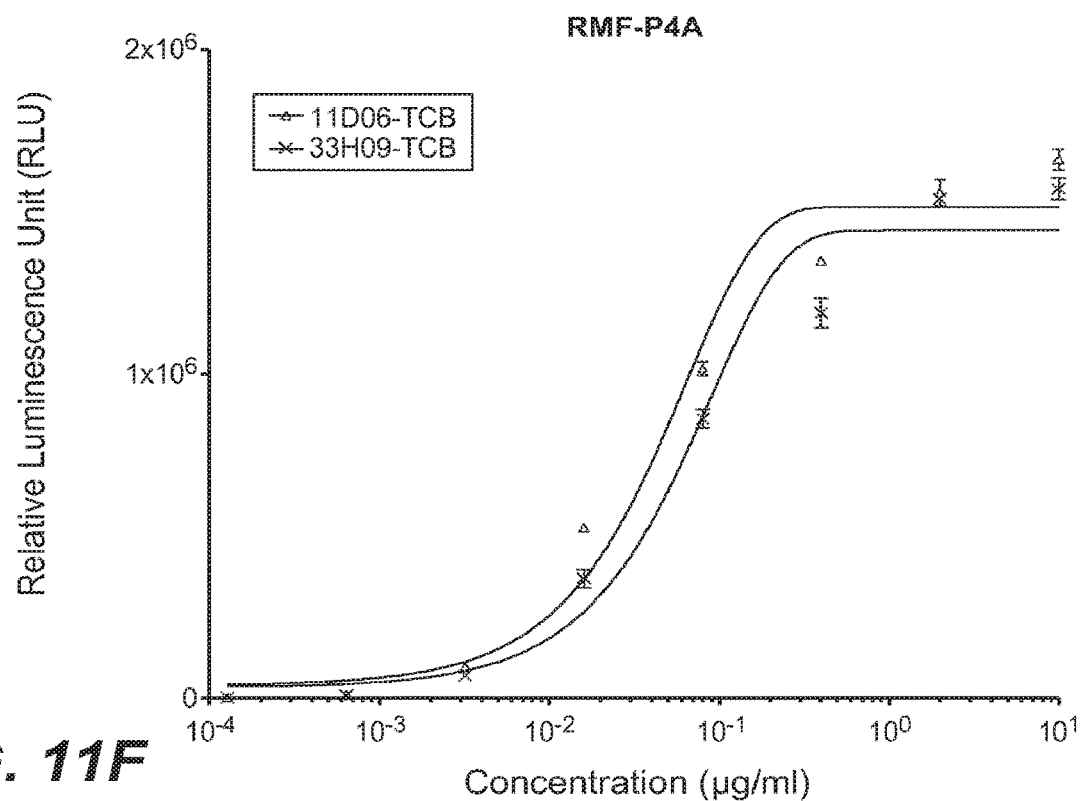
Figure 11G:
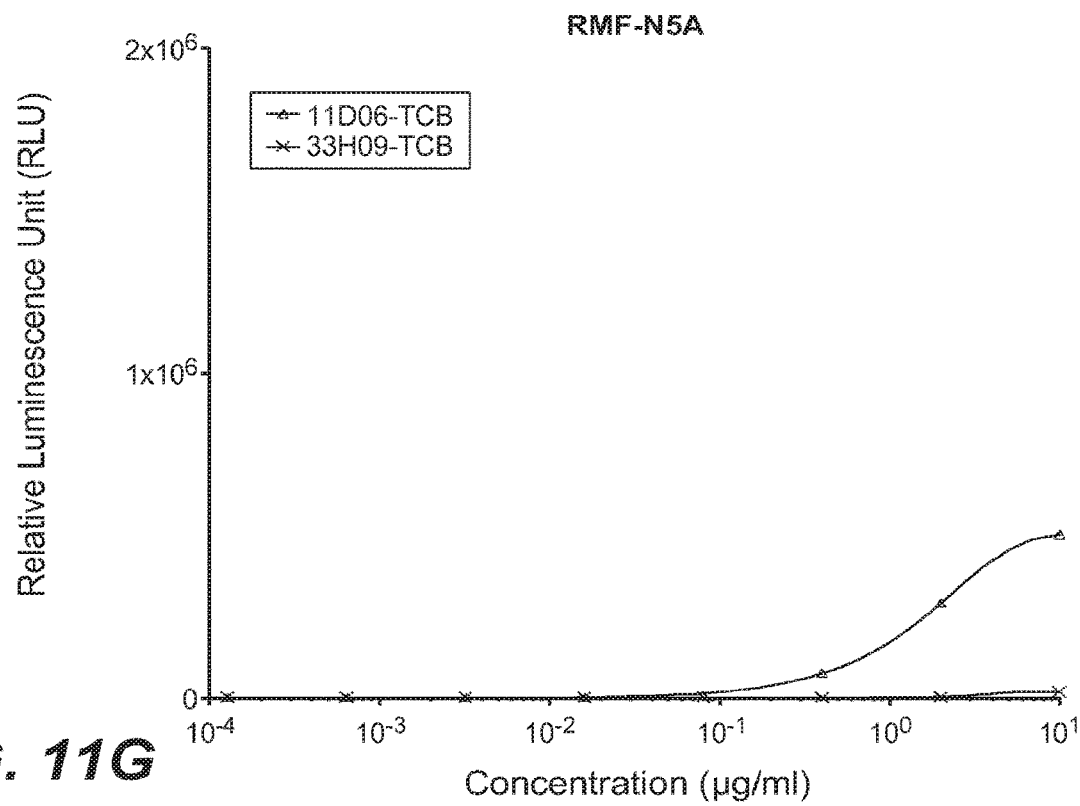
Figure 11H:
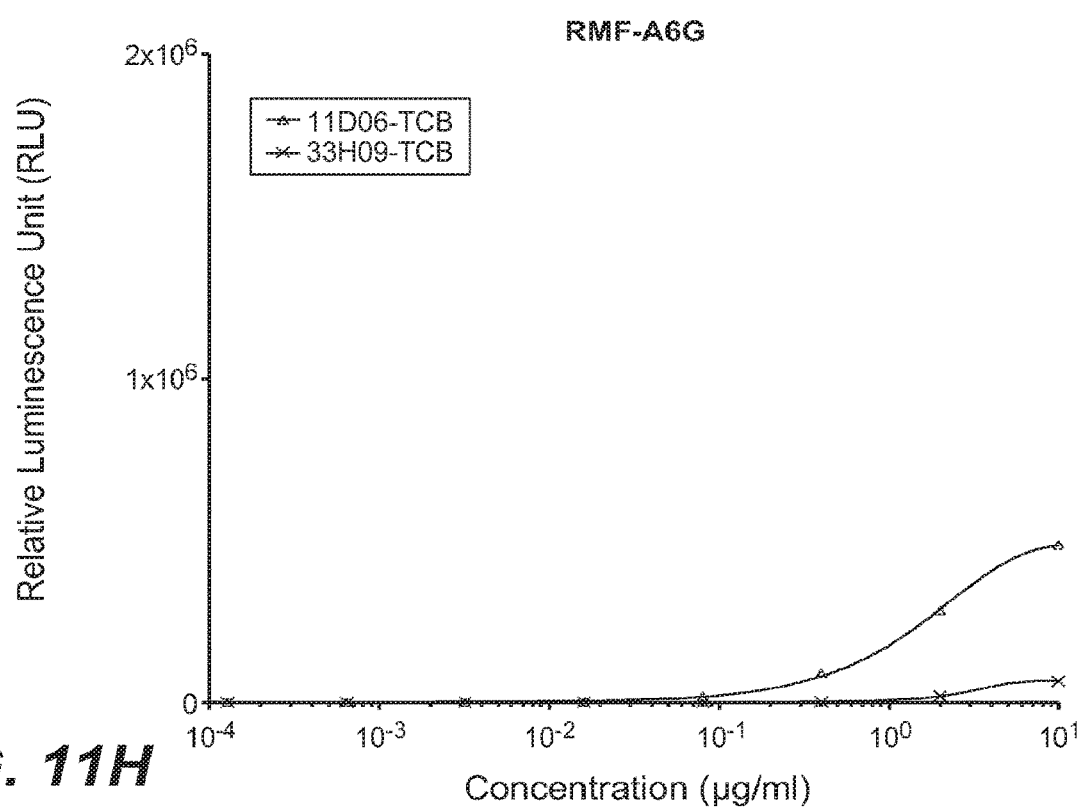
Figure 11I:
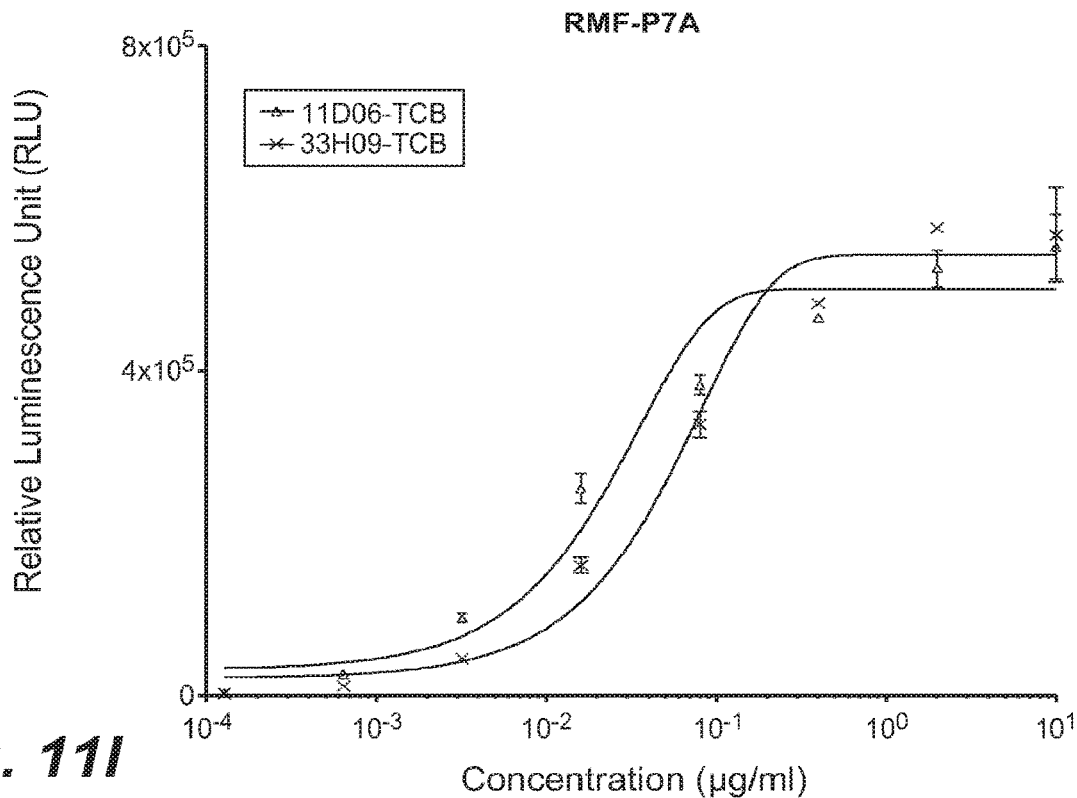
Figure 11J:
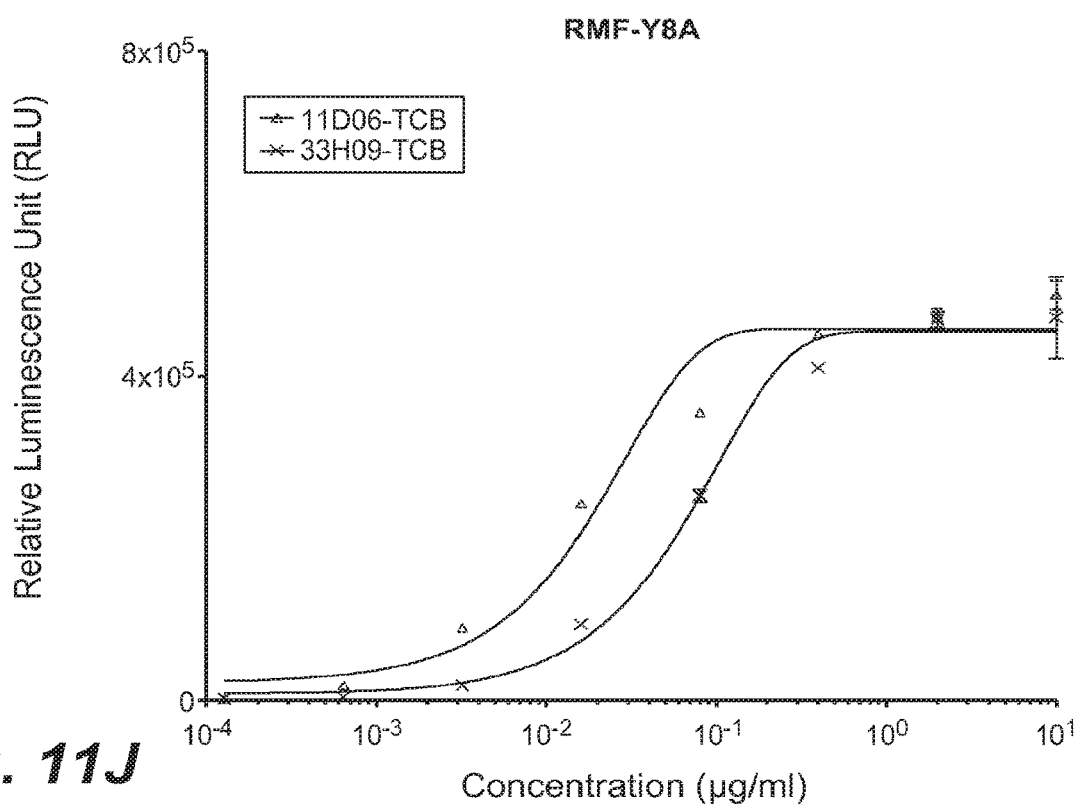
Figures 11K, 11L, 11M, 11N:
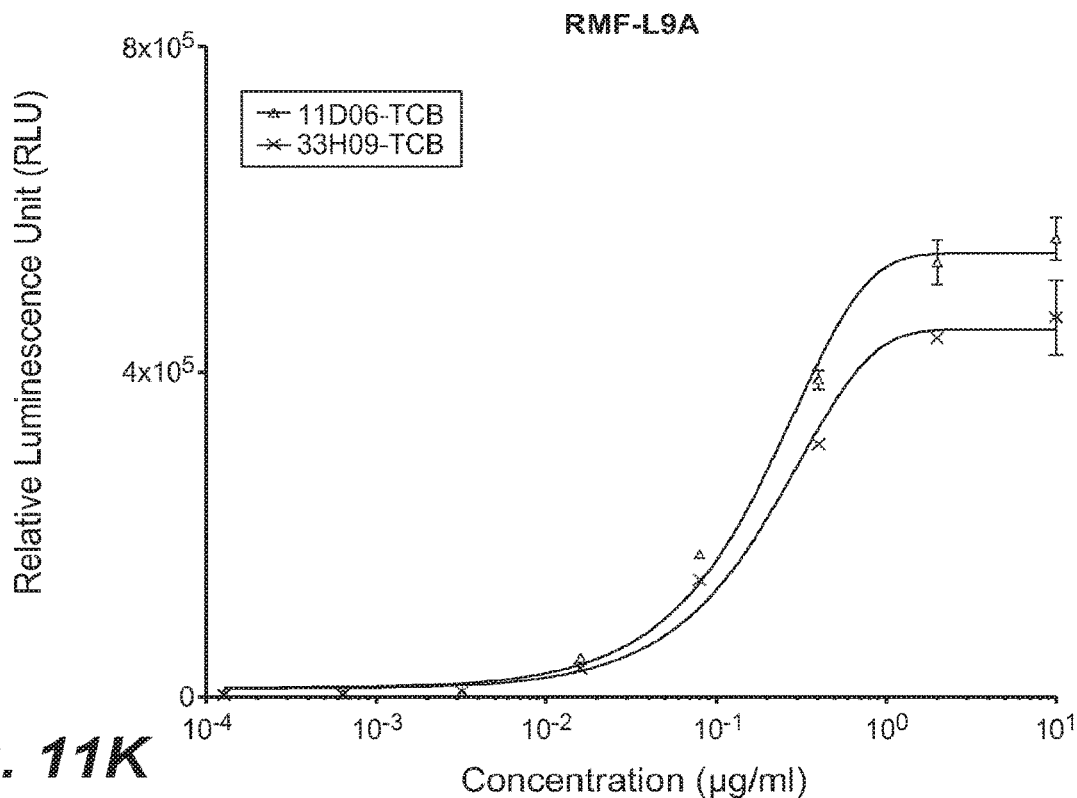

Example 12. Definition of Binding Residues of Selected HLA-A2/WT1 x CD3 Bispecific Antibodies ("TCBs") by Alanine Scan Assay It is clear that our TCBs have different binding to RMF peptide and functional activity as compared to ESK1-TCB. To characterize the potential binding motifs of the RMF peptide by the TCBs, we set up an alanine scan assay using peptide arrays derived from native sequences by individually replacing each amino acid with an alanine, and measured the NFAT-reporter signal by T2 cells pulsed with these peptides (FIGS. 11 A-L.). Data are presented as RLU across increasing concentrations of TCB. We plotted the fold change of EC50 relative to the EC50 for the native peptide, and considered a fold change of >10 as significant, meaning the respective amino acid residue of the RMF peptide might be critical for recognition by the 11D06-TCB and 33H09-TCB (FIG. 11M). We concluded that both 11D06-TCB and 33H09-TCB have critical contact with residues R1, F3, N5 and A6 (FIG. 11N), while ESK1 was shown to have close contact to RMF peptide R1, P4 and N5 (Ataie et al., J Mol Biol. (2016) 428:194-205).

Figure 12:
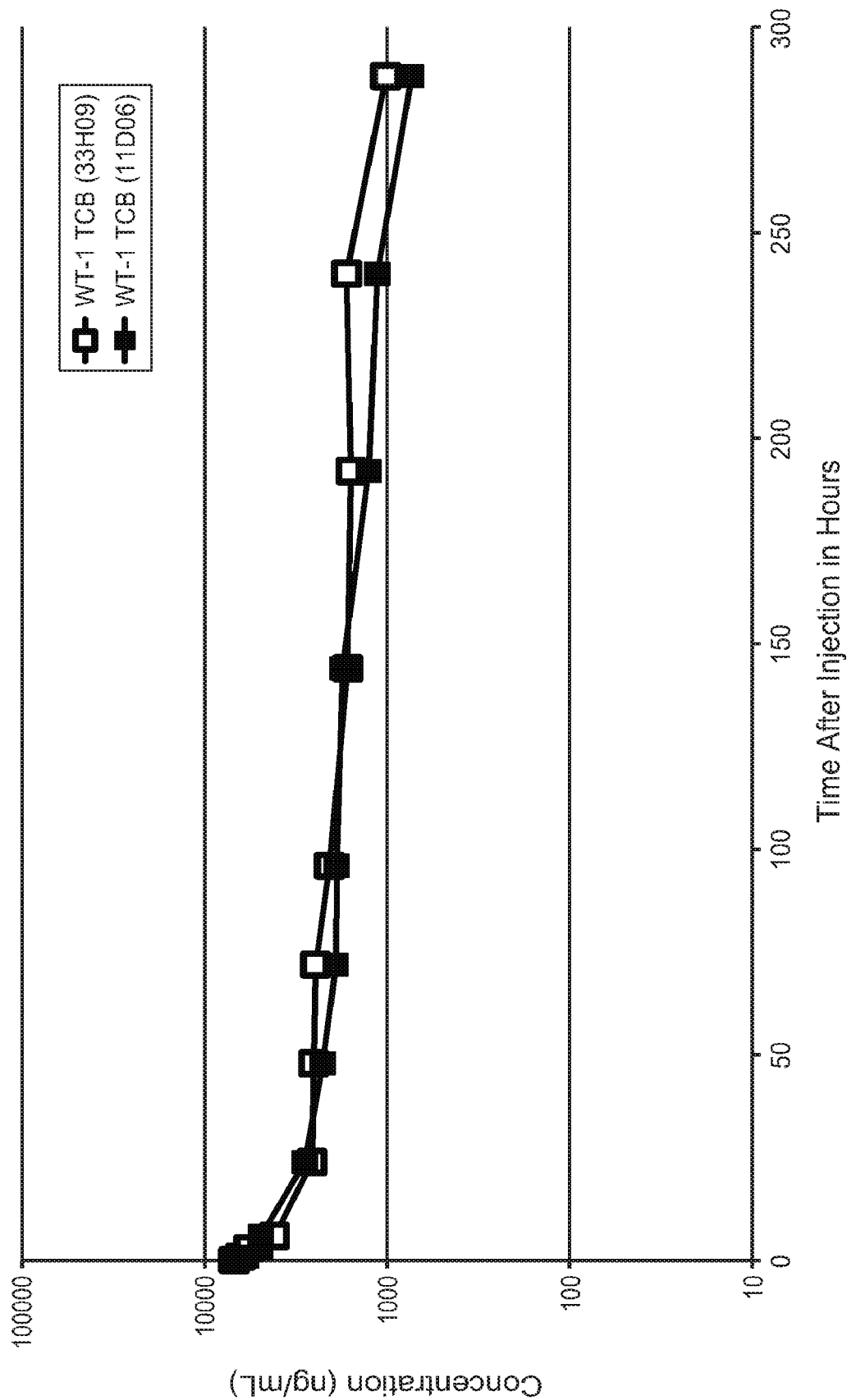
FIG. 12. Pharmacokinetic profile of HLA-A2/WT1 x CD3 bispecific antibodies (11D06-TCB and 33H09-TCB) after single injection in NSG mice.

Example 13. Pharmacokinetic Profile of HLA-A2/WT1 x CD3 Bispecific Antibodies ("TCBs") After Single Injection in NSG Mice A single dose of 0.5 mg/kg of 33H09-TCB or 11D06-TCB was injected into NSG mice. All mice were injected i.v. with 200 µl of the appropriate solution. To obtain the proper amount of compounds per 200 µl, the stock solution was diluted with histidine buffer. Three mice per time point were bled at 10 min, 1 hr, 3 hrs, 6 hrs, 24 hrs, 48 hrs, 72 hrs, 96 hrs, 6 days, 8 days, 10 days and 12 days. The injected compound was analyzed in serum samples by ELISA. Biotinylated anti-huCD3-CDR antibody (Roche Diagnostics, Penzberg, Germany), test sample, digoxigenin-labelled anti-huFc antibody and anti-digoxigenin detection antibody (peroxidase (POD)) were added stepwise to a 96-well streptavidin-coated microtiter plate and incubated after every step for 1 h at room temperature. The plate was washed three times after each step to remove unbound substances. Finally, the peroxidase-bound complex is visualized by adding ABTS (2,2'-azino-bis(3-ethylbenzthiazoline-6-sulfonic acid) substrate solution to form a colored reaction product. The reaction product intensity, which was photometrically determined at 405 nm (with reference wavelength at 490 nm), is proportional to the analyte concentration in the serum. The result (FIG. 12) showed a stable PK-behaviour for both clones tested which suggested a once weekly schedule for subsequent efficacy studies.

Example 14. Efficacy Study with HLA-A2/WT1 x CD3 Bispecific Antibodies ("TCBs") in SKM-1 Xenograft in Humanized Mice The first efficacy study of HLA-A2/WT1 x CD3 bispecific antibodies was aimed at comparing two different WT1 binders (11D06 and 33H09) in terms of efficacy in a human acute myeloid leukemia (AML) xenograft (SKM-1; HLA-A2+, WT-1+) in fully humanized NSG mice.

SKM-1 cells (human AML) were originally obtained from ATCC and deposited in the Roche Glycart internal cell bank. The cells were cultured in RPMI+10% FCS+1% glutamine in a water-saturated atmosphere at 5% $CO_2$. In vitro passage 15 was used for subcutaneous injection at a viability of 98% with Matrigel (1:1 ratio).

Female NSG mice, age 4-5 weeks at start of the experiment (Jackson Laboratory) were maintained under specific-pathogen-free condition with daily cycles of 12 h light/12 h darkness according to committed guidelines (GV-Solas; Felasa; TierschG). The experimental study protocol was reviewed and approved by local government. After arrival, animals were maintained for one week to get accustomed to the new environment and for observation. Continuous health monitoring was carried out on a regular basis.

Figures 13A, 13B:
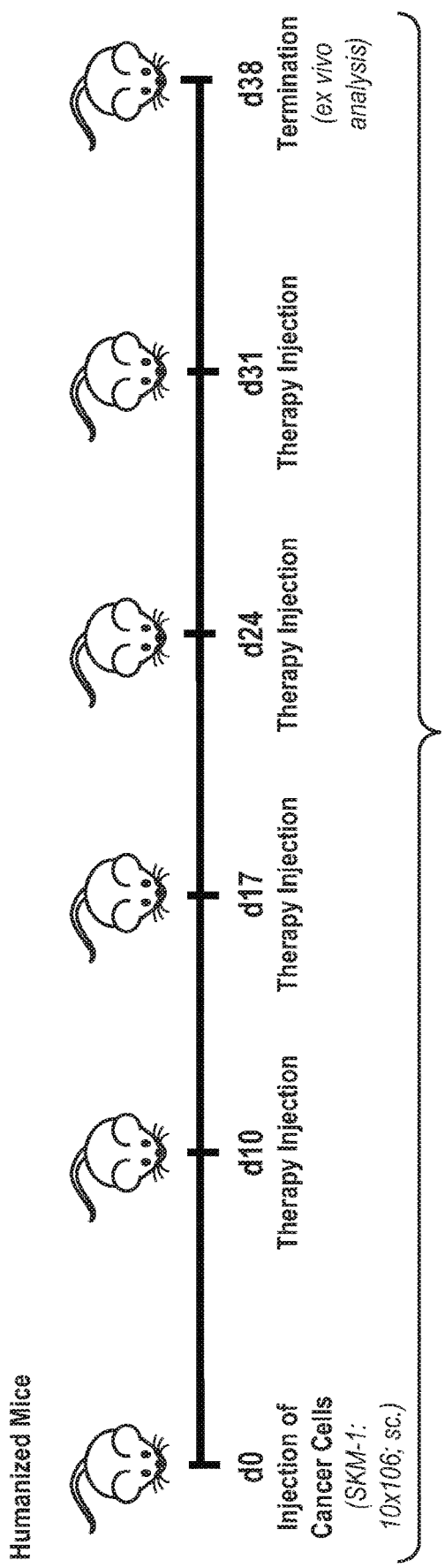
FIGS. 13A-G. Efficacy study with HLA-A2/WT1 x CD3 bispecific antibodies ("TCBs") in SKM-1 xenograft in humanized mice. (A) Study design. (B) Treatment groups. (C) Tumor growth kinetics (mean) in all treatment groups. (D) Single tumor growth kinetics in the vehicle group. (E) Single tumor growth kinetics in the 11D06-TCB group. (F) Single tumor growth kinetics in the 33H09-TCB group. (G) Statistics. Calculations based on day 38 (vehicle as control group). Tumor growth inhibition (TGI): TGI>100→tumor regression, TGI=100→tumor stasis. Treatment to control ratio (TCR): TCR=1→no effect, TCR=0→complete regression.
Figure 13C:
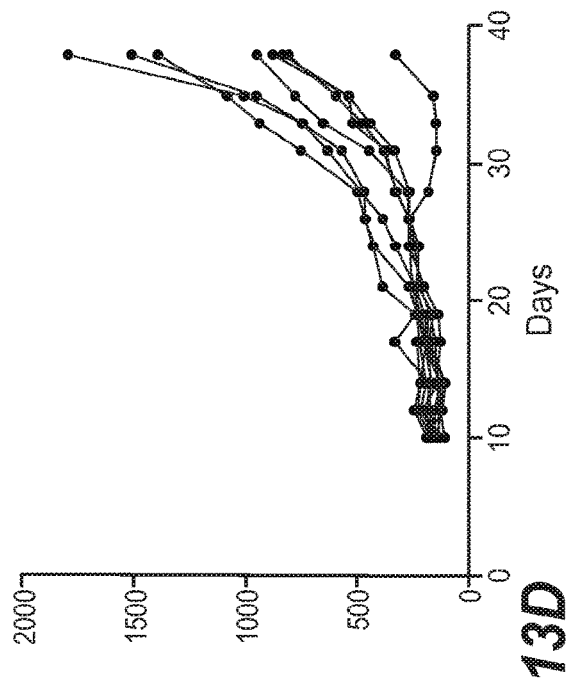
Figure 13D:
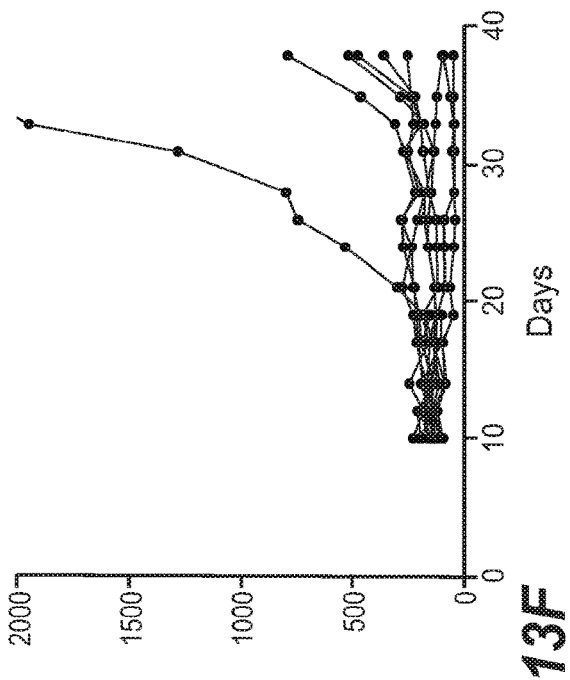
Figure 13E:
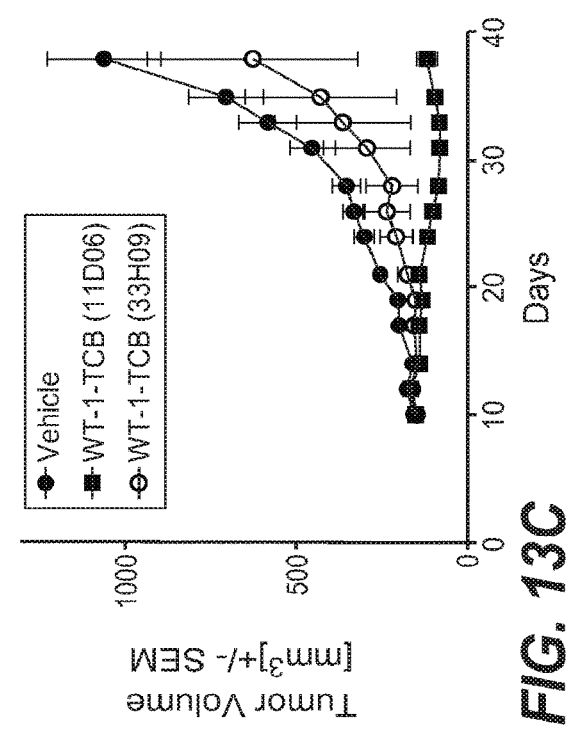
Figure 13F:
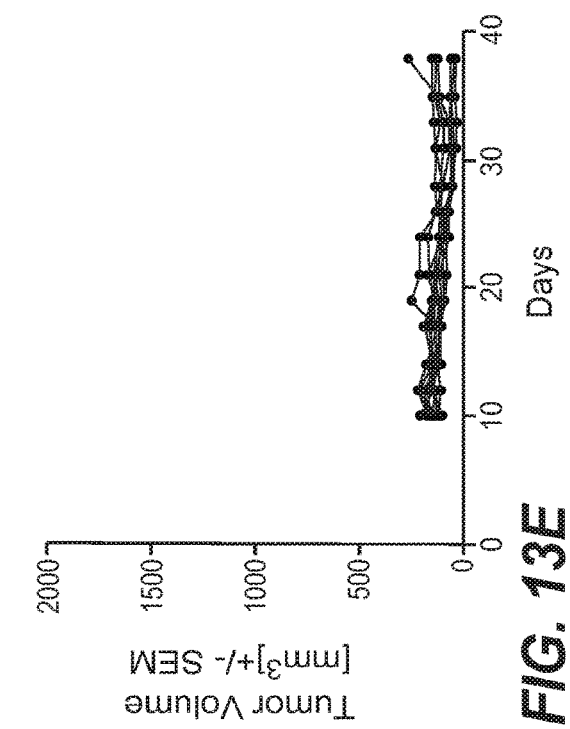

Female NSG mice were injected i.p. with 15 mg/kg of busulfan followed one day later by an i.v. injection of $1\times10^5$ human hematopoietic stem cells isolated from cord blood. At week 14-16 after stem cell injection mice were bled sublingual and blood was analyzed by flow cytometry for successful humanization. Efficiently engrafted mice were randomized according to their human T cell frequencies into the different treatment groups. At that time, mice were injected with SKM-1 tumor cells s.c. as illustrated in FIG. 13A and treated once weekly with the compounds or histidine buffer (vehicle) when tumor size reached approximately 150 $mm^3$ (day 10). All mice were injected i.v. with 200 µl of the appropriate solution. To obtain the proper amount of compounds per 200 µl, the stock solutions were diluted with histidine buffer when necessary. Tumor growth was measured three times weekly using a caliper and tumor volume was calculated as follows:

$$T_v:(W^2/2)\times L$$

(W: Width, L: Length)

Tumor growth Inhibition (TGI) as well as Tumor to control ratio (TCR) were calculated as follows:

$$TGI: \frac{100-Av(T\_treatment^{[day\ x]} - T\_treatment^{[baseline]})}{Av(T\_Vehicle^{[day\ x]} - T\_Vehicle^{[baseline]})}*100$$

$$TCR: \frac{Av(T\_treatment^{[day\ x]})}{Av(T\_Vehicle^{[day\ x]})}$$

Figures 13G, 14A, 14B, 14C:
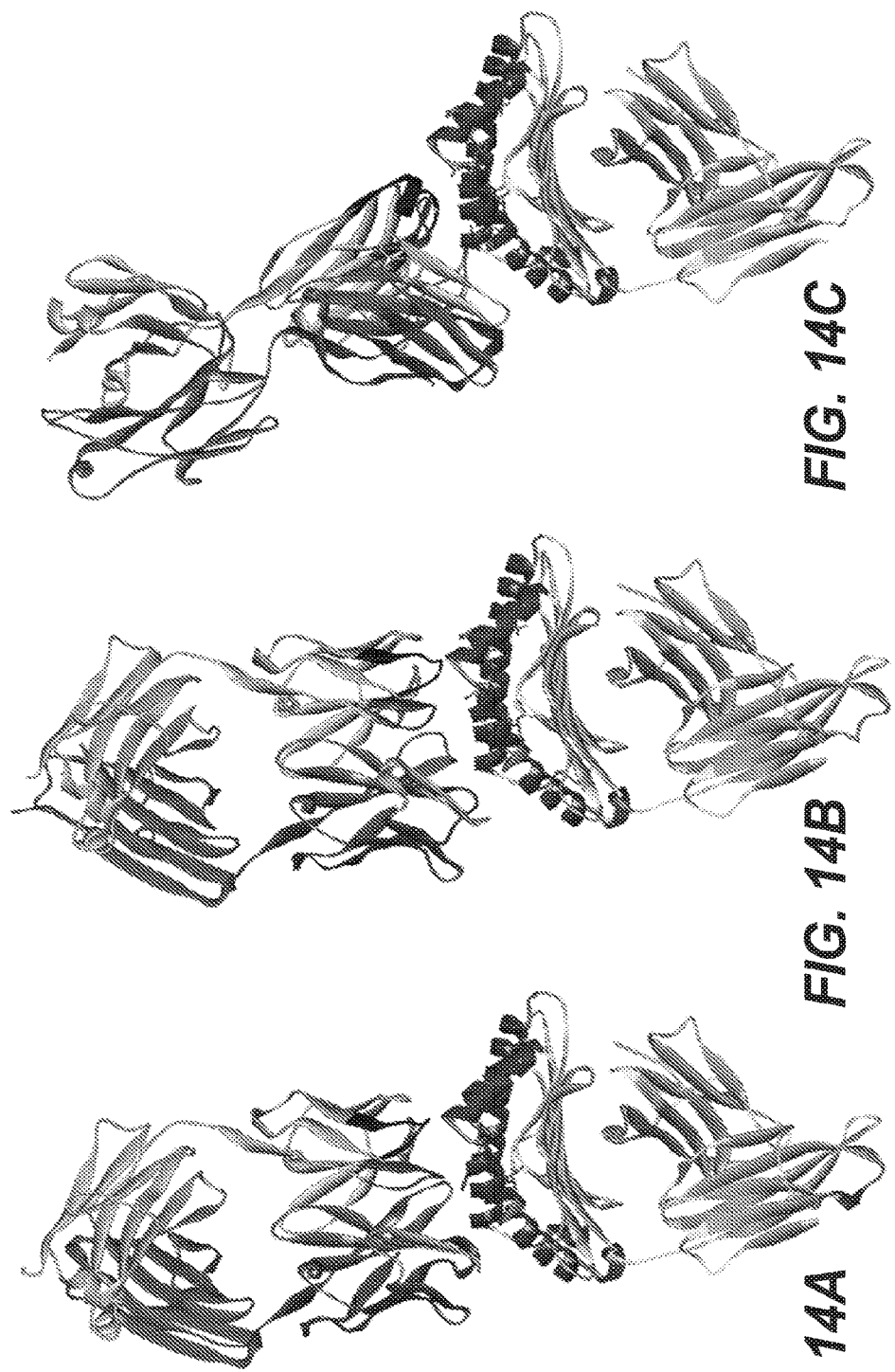
FIGS. 14A-C. Overview of crystal structures of HLA-A2/WT1 antibody-pMHC complexes. The antibodies (Fab fragments) are shown on top, with the heavy chain colored dark gray and the light chain colored light gray. Crystallized solvent atoms are not shown. (A) 1.98 Å resolution crystal structure of 5C01 Fab in complex with HLA-A02/VLD pMHC. Fab-pMHC contact area: ≈476 Å$^2$, peptide contribution: ≈68 Å$^2$. (B) 2.60 Å resolution crystal structure of 11D06 Fab in complex with HLA-A02/RMF pMHC. Fab-pMHC contact area: ≈397 Å$^2$, peptide contribution: ≈107 Å$^2$. (C) 3.05 Å resolution crystal structure of ESK1 Fab in complex with HLA-A02/RMF pMHC (published, PDB ID 4WUU). Fab-pMHC contact area: ≈505 Å$^2$, peptide contribution: ≈60 Å$^2$.

FIGS. 13A-G shows the tumor growth kinetics (mean) in all treatment groups (FIG. 13C) as well as the single tumor growth kinetics in each group (FIGS. 13 D-F). As shown, both TCBs exhibit tumor growth inhibition, with clone 11D06 showing the strongest tumor growth inhibition with a TGI of 101.3 (FIG. 13G).

Example 15. Crystal Structure of HLA-A2/WT1 Antibody/pMHC Complexes

Fab fragments were prepared by incubation of antibodies for 72 hours at 25° C. in 50 mM Tris pH 8.0, 150 mM NaCl with 1.05 U plasmin (Roche, Cat. No. 602361) per mg. Cleaved Fc was separated from Fab fragments using a 4.5 mL CaptureSelect CH1-affinity column (BAC BV, Cat. No. 191.3120) equilibrated with 50 mM Tris, 100 mM glycine, 150 mM NaCl, pH 8.0. Fab fragments were eluted from the column with 50 mM Tris, 100 mM glycine, 150 mM NaCl, pH 2.0 and neutralized with 0.5M sodium phosphate pH8.0 before loading on a size exclusion column S75 (GE Healthcare) equilibrated with 20 mM Tris, 150 mM NaCl, pH 7.4. Quality control was performed by doing analytical size exclusion (column Tosoh, TSK-Gel G3000SWXL, on an Agilent HPLC 1200 system) and CE-SDS (Caliper LabChip GXII, Perkin Elmer) under non-reducing and reduced conditions. Purified Fab fragments were frozen in liquid nitrogen and stored at −80° C.

Crystallization, Data Collection and Structure Determination of the 5C01 Antibody/pMHC Complex Crystallization. The antibody/pMHC complex (Fab 5C01 HLA-A02/WT1$_{VLD}$ pMHC) was prepared by mixing a 1.2-fold molar excess of HLA-A2/WT1 Fab fragment based on the 5C01 binder (Fab 5C01) with HLA-A2/WT1$_{VLD}$ peptide complex (HLA-A02/WT1$_{VLD}$ PMHC). After 1 hour incubation at 4° C. the mixture was concentrated to 10 mg/ml. Initial crystallization trials were performed in sitting drop vapor diffusion setups at 21° C. Crystals appeared within 1 day out of 0.2 M sodium-tartrate, 20% polyethyleneglycol (PEG) 3350 with 10%2-methyl-2,4-pentanediol (MPD) added to the crystallization droplet to improve crystal quality. Crystals were harvested directly from the screening plate without any further optimization step.

Data collection and structure determination. For data collection crystals were flash frozen at 100K in precipitant solution containing 15% glycerol. Diffraction data were collected at a wavelength of 1.0000 Å using a PILATUS 6M detector at the beamline X10SA of the Swiss Light Source (Villigen, Switzerland). Data were processed with XDS (Kabsch, W. Acta Cryst. D66, 133-144 (2010)) and scaled with SADABS (BRUKER). The crystals of the complex belong to space group P21212 with cell axes of a=158.94 Å, b=49.12 Å, c=128.63 Å and diffract to a resolution of 1.98 Å. The structure was determined by molecular replacement with PHASER (McCoy, A. J, Grosse-Kunstleve, R. W., Adams, P. D., Storoni, L. C., and Read, R. J. *J. Appl. Cryst.* 40, 658-674 (2007)) using the coordinates of the crystal structure with Protein Data Bank (PDB) entry 4NO5 and an in house Fab structure as search models. Difference electron density was used to place peptide and to change amino acids according to the sequence differences by real space refinement. Structures were refined with programs from the CCP4 suite (Collaborative Computational Project, Number 4 *Acta Cryst. D*50, 760-763 (1994)) and BUSTER (Bricogne, G., Blanc, E., Brandl, M., Flensburg, C., Keller, P., Paciorek, W., Roversi, P., Sharff, A., Smart, O. S., Vonrhein, C., Womack, T. O. (2011). Buster version 2.9.5 Cambridge, United Kingdom: Global Phasing Ltd). Manual rebuilding was done with COOT (Emsley, P., Lohkamp, B., Scott, W. G. and Cowtan, K. *Acta Cryst D*66, 486-501 (2010)).

Data collection and refinement statistics are summarized in Table 6.

TABLE 6

Data collection and refinement statistics for Fab 5C01 HLA-A02/WT1$_{VLD}$ pMHC.

| | 5C01-HLA-A02/WT1$_{VLD}$ pMHC |
|---|---|
| Data collection | |
| Space group | P2$_1$2$_1$2 |
| Cell dimensions | |
| a, b, c (Å) | 158.94, 49.12, 128.63 |
| (°) | 90, 90, 90 |
| Resolution (Å) | 1.98 |
| R$_{sym}$ or R$_{merge}$ | 0.11 |
| I/σI | 12.01 (0.53) |
| Completeness (%) | 99.9 (99.9) |
| Redundancy | 6.61 (6.76) |
| Refinement | |
| Resolution (Å) | 48.9-1.98 |
| No. reflections | 71103 |
| R$_{work}$/R$_{free}$ | 19.12/24.01 |

TABLE 6-continued

Data collection and refinement statistics for Fab 5C01 HLA-A02/WT1$_{VLD}$ pMHC.

| | 5C01-HLA-A02/WT1$_{VLD}$ pMHC |
|---|---|
| No. atoms | |
| Protein | 6374 |
| Water | 528 |
| B-factors | |
| Protein | 66.32 |
| Water | 59.27 |
| R.m.s. deviations | |
| Bond lengths (Å) | 0.010 |
| Bond angles (°) | 1.07 |

*Values in parentheses are for highest-resolution shell.

Structure of Fab 5C01 in Complex with HLA-A02/WT1$_{VLD}$

Figure 15:
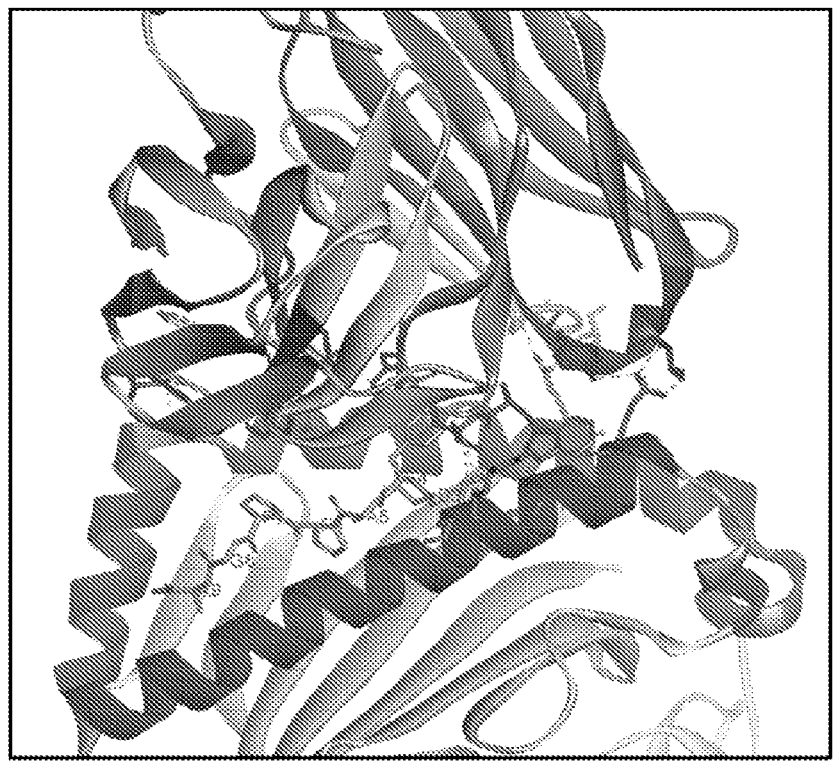
FIG. 15. Close-up view on the 5C01 Fab-HLA-A2/WT1$_{VLD}$ pMHC binding interface. Essential chemical interactions between Fab and pMHC as identified by BIOVIA Discovery Studio 4.5 are highlighted. Solvent atoms are not shown.

In order to characterize the interaction details of the VLD peptide with Fab 5C01, the binding epitope and paratope of 5C01 with HLA-A02, we determined the crystal structure of the complex of 5C01 with HLA-A02/WT1$_{VLD}$ pMHC at a resolution of 1.98 Å (FIG. 14A). The structure reveals Fab 5C01 to bind to pMHC by main contributions of the CDR1 and CDR3 of the light chain and by all CDRs of the heavy chain. From the VLD peptide (SEQ ID NO: 77), the side chains of residues Val1, Phe4 and Pro7 are in direct contact to the Fab. All other side chains of the peptide point towards the HLA-A02 molecule. Contribution of the peptide to the contact surface area is ~68 A2 whereas a total Fab-pMHC contact area of ~476 Å$^2$ is observed. A close-up of the Fab 5C01-pMHC interface is shown in FIG. 15.

Figure 16:
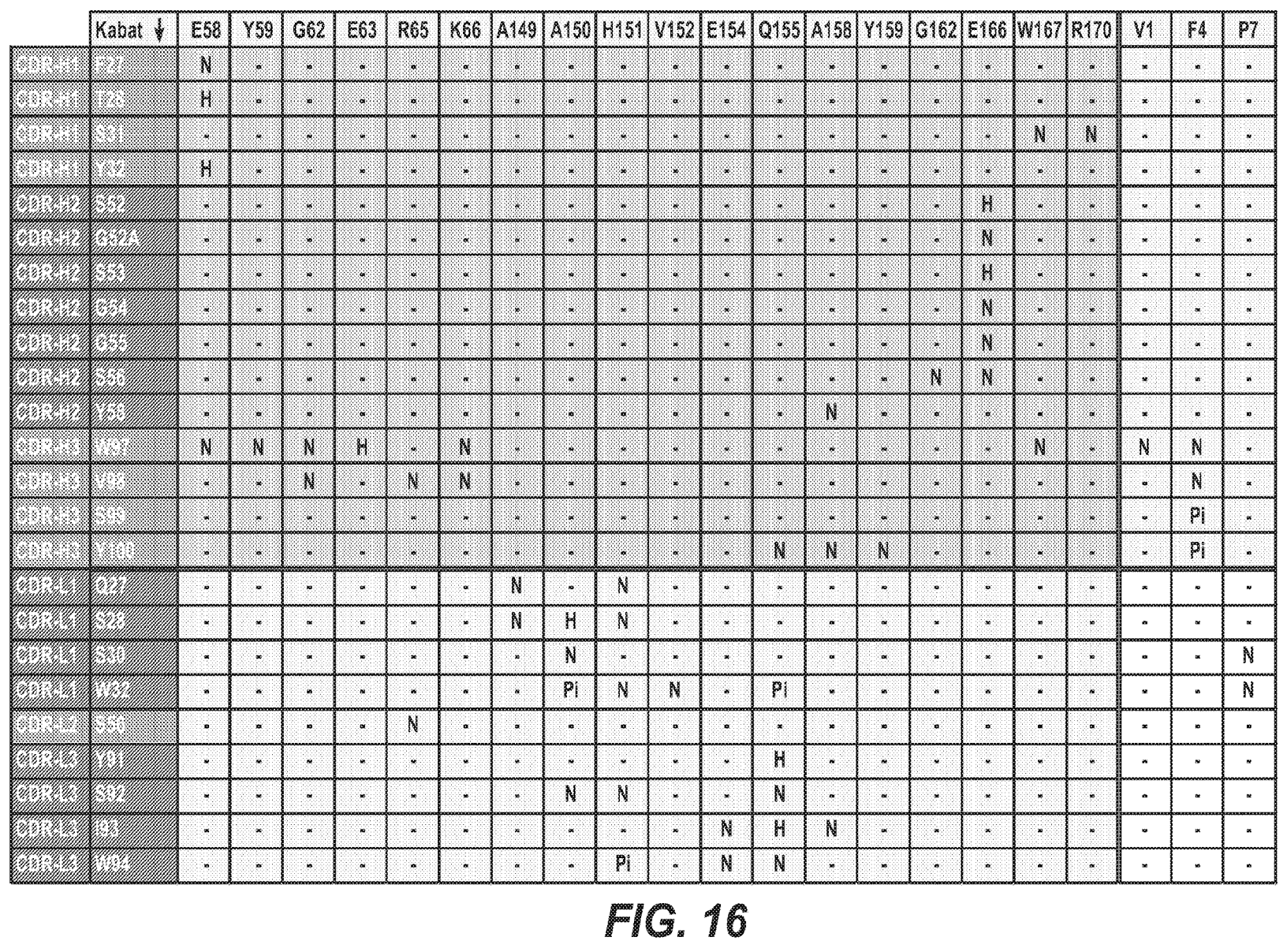

Analysis of the binding interface with the program PISA (E. Krissinel and K. Henrick (2007), J. Mol. Biol. 372, 774-797) reveals an interaction pattern of Fab 5C01 with the HLA-A02 via 8 hydrogen bonds, Pi-Pi interactions and van der Waals contacts. Side chain hydrogen bonds are formed between residues of heavy chain CDR3 (Trp97) and CDR2 (Ser52, Ser53) with Glu63 and Glu166 of HLA-A02. Further hydrogen bonds are established by light chain backbone atoms of Tyr91 and Ile93 with Gln155. The complex is in addition stabilized via formation of Pi—Pi interactions of light chain residues Trp32 and Trp94 with HLA-A02 side chains of Gln155 and His151. The N-terminal valine of the VLD peptide entertains hydrogen bonds through the backbone nitrogen to Tyr171 of HLA-A02. Its side chain is oriented towards a pocket formed by Glu63 and Trp167 of HLA-A02 and Trp97 of the heavy chain of Fab 5C01. In addition Phe4 of the peptide makes edge to face interactions with Tyr100 of the heavy chain. A schematic Fab 5C01-pMHC interaction matrix summarizing the contacts is shown in FIG. 16.

Crystallization, Data Collection and Structure Determination of the 11D06 Antibody/pMHC Complex Crystallization. The antibody/pMHC complex (Fab 11D06 HLA-A02/WT1$_{RMF}$ PMHC) was prepared by mixing a 1:1 molar amount of HLA-A2/WT1 Fab fragment based on the 11D06 binder (Fab 11D06) with HLA-A2/WT1$_{RMF}$ peptide complex (HLA-A02/WT1$_{RMF}$ PMHC). After 4 hours of incubation at 21° C. the mixture was concentrated to 20 mg/ml. Initial crystallization trials were performed in sitting drop vapor diffusion setups at 21° C. Crystals appeared within 4 days out of 0.1 M Tris pH 8.0, 20% PEG 4000. Crystals were harvested directly from the screening plate without any further optimization step.

Data collection and structure determination. Data was collected, processed and scaled as described above. The crystals of the complex belong to space group P2$_1$ with cell axes of a=54.11 Å, b=67.00 Å, c=139.36 Å with β=90.57° and diffract to a resolution of 2.64 Å. The structure was determined by molecular replacement with PHASER using the coordinates of an in house Fab and MHC complex structure as search model. Difference electron density was used to place peptide and to change amino acids according to the sequence differences by real space refinement. Structure refinement and manual rebuilding were done as described above.

Data collection and refinement statistics are summarized in Table 7.

TABLE 7

Data collection and refinement statistics for 11D06 HLA-A02/WT1$_{RMF}$ pMHC.

|  | 11D06 HLA-A02/WT1$_{RMF}$ pMHC |
|---|---|
| Data collection |  |
| Space group | P2$_1$ |
| Cell dimensions |  |
| a, b, c (Å) | 54.11, 67.00, 139.36 |
| (°) | 90, 90.57, 90 |
| Resolution (Å) | 2.64 |
| R$_{sym}$ or R$_{merge}$ | 0.10 |
| I/σI | 13.10 (0.82) |
| Completeness (%) | 99.9 (99.8) |
| Redundancy | 3.79 (3.85) |
| Refinement |  |
| Resolution (Å) | 48.3-2.64 |
| No. reflections | 29606 |
| R$_{work}$/R$_{free}$ | 17.10/23.00 |
| No. atoms |  |
| Protein | 6395 |
| Water | 250 |
| B-factors |  |
| Protein | 67.52 |
| Water | 57.46 |
| R.m.s. deviations |  |
| Bond lengths (Å) | 0.010 |
| Bond angles (°) | 1.20 |

*Values in parentheses are for highest-resolution shell.

Structure of Fab 11D06 in Complex with HLA-A02/RMF pMHC

Figure 17:
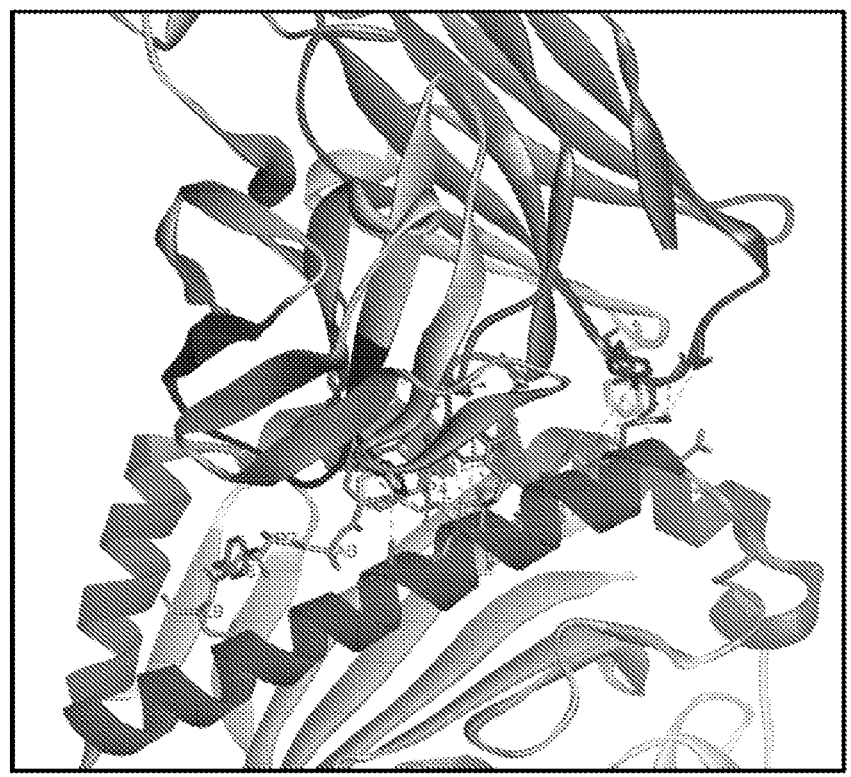
FIG. 17. Close-up view on the 11D06 Fab-HLA-A2/WT1$_{RMF}$ pMHC binding interface. Essential chemical interactions between Fab and pMHC as identified by BIOVIA Discovery Studio 4.5 are highlighted. Solvent atoms are not shown.

We determined the crystal structure of the complex of Fab 11D06 with HLA-A02/RMF pMHC at a resolution of 2.64 Å (FIG. 14B). The structure shows Fab 11D06 binds to pMHC by contributions of all CDRs. RMF peptide (SEQ ID NO: 78) side chains of residues Arg1, Met2, Pro4, Asn5, Ala6 and Tyr8 are in direct contact to light and heavy chain of the Fab. The remaining side chains of the peptide point towards the HLA-A02 molecule. Contribution of the peptide to the contact surface area is ~107 A2. The total Fab-pMHC contact area corresponds to ~397 Å$^2$. A close-up of the Fab 11D06-pMHC interface is shown in FIG. 17.

Figure 18:
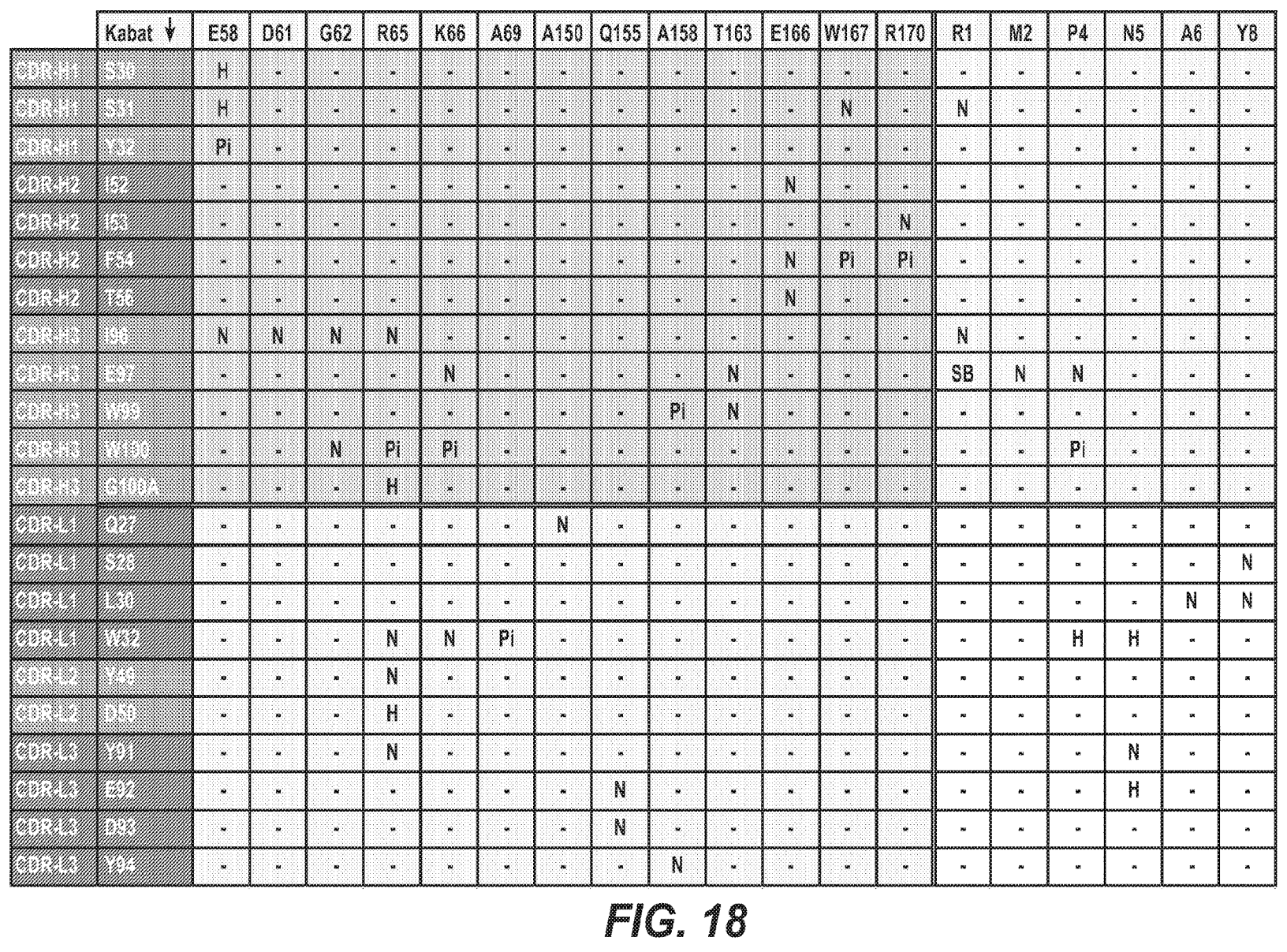

Analysis of the binding interface with the program PISA reveals an interaction pattern of Fab 11D06 with HLA-A02 via 4 hydrogen bonds, numerous Pi-Pi interactions and van der Waals contacts. Hydrogen bonds are observed between residues of heavy chain CDR1 (Ser30, Ser31) and CDR3 (Gly100A) with Glu58 and Arg65 of HLA-A02. Further hydrogen bonds are established by light chain residue Asp50 with HLA-A02 Arg65. Beside others, Trp100 of the heavy chain provides van der Waals and Pi-Pi contacts to Arg65 and Lys66 of the HLA-A02 and to Pro4 of the RMF peptide. The N-terminal arginine of the RMF peptide points with its side chain into a polar pocket formed by Ser31, Glu97 and the backbone carbonyl of Ile96 of the heavy chain of 11D06. Additional polar contacts to 11D06 and HLA-A02 are entertained by the RMF peptide residue Asn5 which is part of a hydrogen bonding network to Trp32 of light chain CDR1, Glu92 of light chain CDR3 together with Gln155 of the HLA-A02. A schematic Fab 11D06-pMHC interaction matrix summarizing the contacts is shown in FIG. 18.

Figure 19:
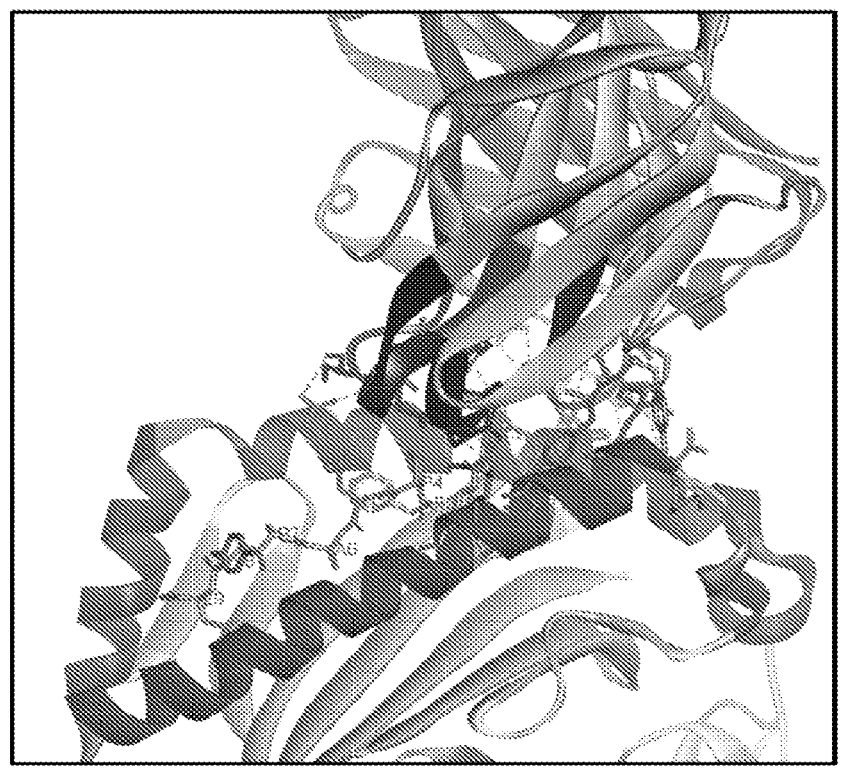
FIG. 19. Close-up view on the ESK1 Fab-HLA-A2/WT1$_{RMF}$ pMHC binding interface (PDB ID 4WUU). Essential chemical interactions between Fab and pMHC as identified by BIOVIA Discovery Studio 4.5 are highlighted. Solvent atoms are not shown.

3D Structure of ESK1 Retrieved from the Public Database:

For comparison, the publicly available crystal structure of antibody (Fab) ESK1 binding to HLA-A02/RMF pMHC (PDB ID 4WUU;

http://www.rcsb.org/pdb/explore/explore.do?structureId=4WUU) was analyzed analogously with regard to its Fab-pMHC contacts. FIG. 14C shows the Fab ESK1 with HLA-A02/RMF pMHC crystal structure from the same angle (aligned on the HLA-A02 part) as the crystal structures of Fab 5C01 with HLA-A02/VLD pMHC and Fab 11D06 with HLA-A02/RMF pMHC (FIGS. 14 A and B). A close-up of the Fab ESK1-pMHC interface is shown in FIG. 19, and a schematic Fab ESK1-pMHC interaction matrix summarizing the contacts is shown in FIG. 20.

The structural comparison reveals that 5C01 and particularly 11D06 cover and bind to a larger fraction of the respective WT1 peptide than ESK1, which forms specific contacts exclusively with the N-terminal Arg of the RMF peptide while the remainder of the binding interface is provided by HLA-A02. Based on these observations one can conclude that 5C01 and 11D06 should be less likely to tolerate off-target peptides than ESK1 as they create significantly more steric hindrance for peptides with non-VLD or non-RMF-like sidechains on the exposed positions.

All graphical representations of the crystal structures were created with BIOVIA Discovery Studio 4.5, Dassault Systèmes BIOVIA.

Epitope and Paratope Residues (5 Å Radius)

A summary of the epitope and paratope for the binders 5C01, 11D06 and ESK1 is shown below. Epitope and paratope (definition based on 5 Å neighborhood radius) residues are highlighted in bold italic script. CDR residues are highlighted with grey background.

HLA-A02

5C01 GSHSMRYFFTSVSRPGRGEPRFIAVGYVDDTQFVRFDSDAASQRMEPRAPWIEQEGP*EYW*

11D06 GSHSMRYFFTSVSRPGRGEPRFIAVGYVDDTQFVRFDSDAASQRMEPRAPWIEQ*EGPEYW*

ESK1 GSHSMRYFFTSVSRPGRGEPRFIAVGYVDDTQFVRFDSDAASQRMEPRAPWIEQ*EGPEYW*

-continued 1-60

5C01 DGETRKVKAHSQTHRVDLGTLRGYYNQSEAGSHTVQRMYGCDVGSDWRFLRGYHQYAYDG

11D06 DGETRKVKAHSQTHRVDLGTLRGYYNQSEAGSHTVQRMYGCDVGSDWRFLRGYHQYAYDG

ESK1 DGETRKVKAHSQTHRVDLGTLRGYYNQSEAGSHTVQRMYGCDVGSDWRFLRGYHQYAYDG 61-120

5C01 KDYIALKEDLRSWTAADMAAQTTKHKWEAAHVAEQLRAYLEGTCVEWLRRYLENGKETLQ

11D06 KDYIALKEDLRSWTAADMAAQTTKHKWEAAHVAEQLRAYLEGTCVEWLRRYLENGKETLQ

ESK1 KDYIALKEDLRSWTAADMAAQTTKHKWEAAHVAEQLRAYLEGTCVEWLRRYLENGKETLQ 121-180
5C01 RTDAPKTHMTHHAVSDHEATLRCWALSFYPAEITLTWQRDGEDQTQDTELVETRPAGDGT
11D06 RTDAPKTHMTHHAVSDHEATLRCWALSFYPAEITLTWQRDGEDQTQDTELVETRPAGDGT
ESK1 RTDAPKTHMTHHAVSDHEATLRCWALSFYPAEITLTWQRDGEDQTQDTELVETRPAGDGT
181-240
5C01 FQKWAAVVVPSGQEQRYTCHVQHEGLPKPLTRWE
11D06 FQKWAAVVVPSGQEQRYTCHVQHEGLPKPLTRWE
ESK1 FQKWAAVVVPSGQEQRYTCHVQHEGLPKPLTRWE
241-275
Peptide

5C01 VLDFAPPGA

11D06 RMFPNAPYL

ESK1 RMFPNAPYL 1-9
Fab Heavy Chain

5C01 EVQLLESGGGLVQPGGSLRLSCAASGFTISSYAMSWVRQAPGKGLEWVSAISGSGGSTIY

11D06 QVQLVQSGAEVKKPGSSVKVSCKASGGTFSSYAISWVRQAPGQGLEWMGGIIPIFGTANY

ESK1 QMQLVQSGAEVKEPGESLRISCKGSGYSFTNPWISWVRQMPGKGLEWMGRVDPGYSYSTY

1-60

5C01 ADSVKGRFTISRDNSKNTLYLQMNSLRAEDTAVYYCAKGWV SYAFDYWGQGTLVTVS

11D06 AQKFQGRVTITADKSTSTAYMELSSLRSEDTAVYYCARSIELW WGGFDYWGQGTTVTVS

ESK1 SPSFQGHVTISADKSTSTAYLQWNSLKASDTAMYYCARVQYSGYYDWFDPWGQGTLVTVS 61-120
5C01 SASTKGPSVFPLAPSSKSTSGGTAALGCLVKDYFPEPVTVSWNSGALTSGVHTFPAVLQS
11D06 SASTKGPSVFPLAPSSKSTSGGTAALGCLVKDYFPEPVTVSWNSGALTSGVHTFPAVLQS
ESK1 SASTKGPSVFPLAPSSKSTSGGTAALGCLVKDYFPEPVTVSWNSGALTSGVHTFPAVLQS
121-180
5C01 SGLYSLSSVVTVPSSSLGTQTYICNVNHKPSNTKVDKKVEPKSC
11D06 SGLYSLSSVVTVPSSSLGTQTYICNVNHKPSNTKVDKKVEPKSC
ESK1 SGLYSLSSVVTVPSSSLGTQTYICNVNHKPSNTKVDKRVEPKS

181-224
Fab Light Chain

```
5C01  DIQMTQSPSTLSASVGDRVTITCRAS Q SIS SWLAWYQQKPGKAPKLLIYDASSLES

11D06 DIQMTQSPSTLSASVGDRVTITCRAS Q SIS SWLAWYQQKPGKAPKLLIYDASSLES

ESK1  QAVVTQP PSASGTPGQRVTISCSG SSSNIGSN TVNWYQQVPGTAPKLLIYSNNQRPS
```

1-60

```
5C01  GVPSRFSGSGSGTEFTLTISSLQPDDFATYYCQQYSI WTPYTFGQGTKVEIKRTVAAPS

11D06 GVPSRFSGSGSGTEFTLTIGSLQPDDFATYYCQQYS DYTTTGQGTKVEIKRTVAAPS

ESK1  GVPDRFSGSKSGTSASLAISGLQSEDEADYYCAAWDSLNGVVFGGGTKLTVLGQPKANP
```

61-120
```
5C01  VFIFPPSDEQLKSGTASVVCLLNNFYPREAKVQWKVDNALQSGNSQESVTEQDSKDSTYS
11D06 VFIFPPSDEQLKSGTASVVCLLNNFYPREAKVQWKVDNALQSGNSQESVTEQDSKDSTYS
ESK1  TVTLFPPSSEELQANKATLVCLISDFYPGAVTVAWKADGSPVKAGVETTKPSKQSNNKYA
```
121-180
```
5C01  LSSTLTLSKADYEKHKVYACEVTHQGLSSPVTKSFNRGEC
11D06 LSSTLTLSKADYEKHKVYACEVTHQGLSSPVTKSFNRGEC
ESK1  ASSYLSLTPEQWKSHRSYSCQVTHEGSTVEKTVAPTECS
```
181-220

Residues Involved in Chemical Interactions

A summary of the residues involved in chemical interaction for the binders 5C01, 11D06 and ESK1 is shown below.

Residues involved in specific chemical interactions (compare FIGS. 16, 18 and 20) are highlighted in bold italic script. CDR residues are highlighted with grey background.

HLA-A02

```
5C01  GSHSMRYFFTSVSRPGRGEPRFIAVGYVDDTQFVRFDSDAASQRMEPRAPWIEQEGPEYW

11D06 GSHSMRYFFTSVSRPGRGEPRFIAVGYVDDTQFVRFDSDAASQRMEPRAPWIEQEGPEYW

ESK1  GSHSMRYFFTSVSRPGRGEPRFIAVGYVDDTQFVRFDSDAASQRMEPRAPWIEQEGPEYW
```

1-60

```
5C01  DGETRKVKAHSQTHRVDLGTLRGYYNQSEAGSHTVQRMYGCDVGSDWRFLRGYHQYAYDG

11D06 DGETRKVKAHSQTHRVDLGTLRGYYNQSEAGSHTVQRMYGCDVGSDWRFLRGYHQYAYDG

ESK1  DGETRKVKAHSQTHRVDLGTLRGYYNQSEAGSHTVQRMYGCDVGSDWRFLRGYHQYAYDG
```

61-120

```
5C01  KDYIALKEDLRSWTAADMAAQTTKHKWEAAHVAEQLRAYLEGTCVEWLRRYLENGKETLQ

11D06 KDYIALKEDLRSWTAADMAAQTTKHKWEAAHVAEQLRAYLEGTCVEWLRRYLENGKETLQ

ESK1  KDYIALKEDLRSWTAADMAAQTTKHKWEAAHVAEQLRAYLEGTCVEWLRRYLENGKETLQ
```

121-180
5C01  RTDAPKTHMTHHAVSDHEATLRCWALSFYPAEITLTWQRDGEDQTQDTELVETRPAGDGT
11D06 RTDAPKTHMTHHAVSDHEATLRCWALSFYPAEITLTWQRDGEDQTQDTELVETRPAGDGT
ESK1  RTDAPKTHMTHHAVSDHEATLRCWALSFYPAEITLTWQRDGEDQTQDTELVETRPAGDGT
181-240
5C01  FQKWAAVVVPSGQEQRYTCHVQHEGLPKPLTLRWE
11D06 FQKWAAVVVPSGQEQRYTCHVQHEGLPKPLTLRWE
ESK1  FQKWAAVVVPSGQEQRYTCHVQHEGLPKPLTLRWE
241-275
Peptide

5C01  VLDFAPPGA

11D06 RMFPNAPYL

ESK1  RMFPNAPYL 1-9
Fab Heavy Chain

5C01  EVQLLESGGGLVQPGGSLRLSCAASGFTFSSFAMSWVRQAPGKGLEWVSAISGSGGSTYY

11D06 QVQLVQSGAEVKKPGSSVKVSCKASGGTFSSYAISWVRQAPGQGLEWMGGIIPIFGTANY

ESK1  QMQLVQSGAEVKEPGESLRISCKGSGYSFTNFWISWVRQMPGKGLEWMGRVDPGYSTSTY 1-60

5C01  ADSVKGRFTISRDNSKNTLYLQMNSLRAEDTAVYYCAKGSWY STAFDYWGQGTLVTVS

11D06 AQKFQGRVTITADKSTSTAYMELSSLRSEDTAVYYCARSIELW WGFFDYWGQGTTVTVS

ESK1  SPSFQGRVTISADKSTSTAYLQWNSLKASDTAMYYCARVQYSGYYDWFDPWGQGTLVTVS 61-120
5C01  SASTKGPSVFPLAPSSKSTSGGTAALGCLVKDYFPEPVTVSWNSGALTSGVHTFPAVLQS
11D06 SASTKGPSVFPLAPSSKSTSGGTAALGCLVKDYFPEPVTVSWNSGALTSGVHTFPAVLQS
ESK1  SASTKGPSVFPLAPSSKSTSGGTAALGCLVKDYFPEPVTVSWNSGALTSGVHTFPAVLQS
121-180
5C01  SGLYSLSSVVTVPSSSLGTQTYICNVNHKPSNTKVDKKVEPKSC
11D06 SGLYSLSSVVTVPSSSLGTQTYICNVNHKPSNTKVDKKVEPKSC
ESK1  SGLYSLSSVVTVPSSSLGTQTYICNVNHKPSNTKVDKRVEPKS
181-224
Fab Light Chain

5C01  DIQMTQSPSTLSASVGDRVTITCRAS Q SIS SWLAWYQQKPGKAPKLLIYDASSLES

11D06 DIQMTQSPSTLSASVGDRVTITCRAS Q SIS SWLAWYQQKPGKAPKLLIYDASSLES

ESK1  QAVVTQP PSASGTPGQRVTISCSG SSSNIGSN TVNWYQQVPGTAPKLLIYSNNQRPS 1-60

5C01  GVPSRFSGSGSGTEFTLTISSLQPDDFATYYCQQYSI WPPYTTGQGTKVEIKRTVAAPS

11D06 GVPSRFSGSGSGTEFTLTIGSLQPDDFATYYCQQYE DYTTFGQGTKVEIKRTVAAPS

ESK1  GVPDRFSGSKSGTSASLAISGLQSEDEADYYCAAWDDSLNSYVFGGGTKLTVLGQPKANP

```
61-120
5C01  VFIFPPSDEQLKSGTASVVCLLNNFYPREAKVQWKVDNALQSGNSQESVTEQDSKDSTYS
11D06 VFIFPPSDEQLKSGTASVVCLLNNFYPREAKVQWKVDNALQSGNSQESVTEQDSKDSTYS
ESK1  TVTLFPPSSEELQANKATLVCLISDFYPGAVTVAWKADGSPVKAGVETTKPSKQSNNKYA
121-180
5C01  LSSTLTLSKADYEKHKVYACEVTHQGLSSPVTKSFNRGEC
11D06 LSSTLTLSKADYEKHKVYACEVTHQGLSSPVTKSFNRGEC
ESK1  ASSYLSLTPEQWKSHRSYSCQVTHEGSTVEKTVAPTECS
181-220
```

Example 16. Comparison of HLA-A2/WT1 x CD3 Bispecific Antibodies ("TCBs") with Different CD3 Binders We compared the potency of killing activities of 11D06-TCB with different CD3 binders, using SKM-1 cells in an assay as described above (Example 7). CH2527 is the CD3 binder of the TCBs used in the previous experiments (see SEQ ID NOs 121 and 122 for the VH and VL sequences). V9 is a CD3 binder described Rodrigues et al., Int J Cancer Suppl (1992) 7, 45-50, and WO 1992/22653 (see SEQ ID NOs 136 and 137 for the VH and VL sequences), and 40G5C is described in WO 2015/095392 (see SEQ ID NOs 184 and 185 ("hu40G5c") of WO 2015/095392 for the VH and VL sequences).

The affinity of CD3 binders CH2527, 40G5C and V9 are shown in Table 8.

Figure 21:
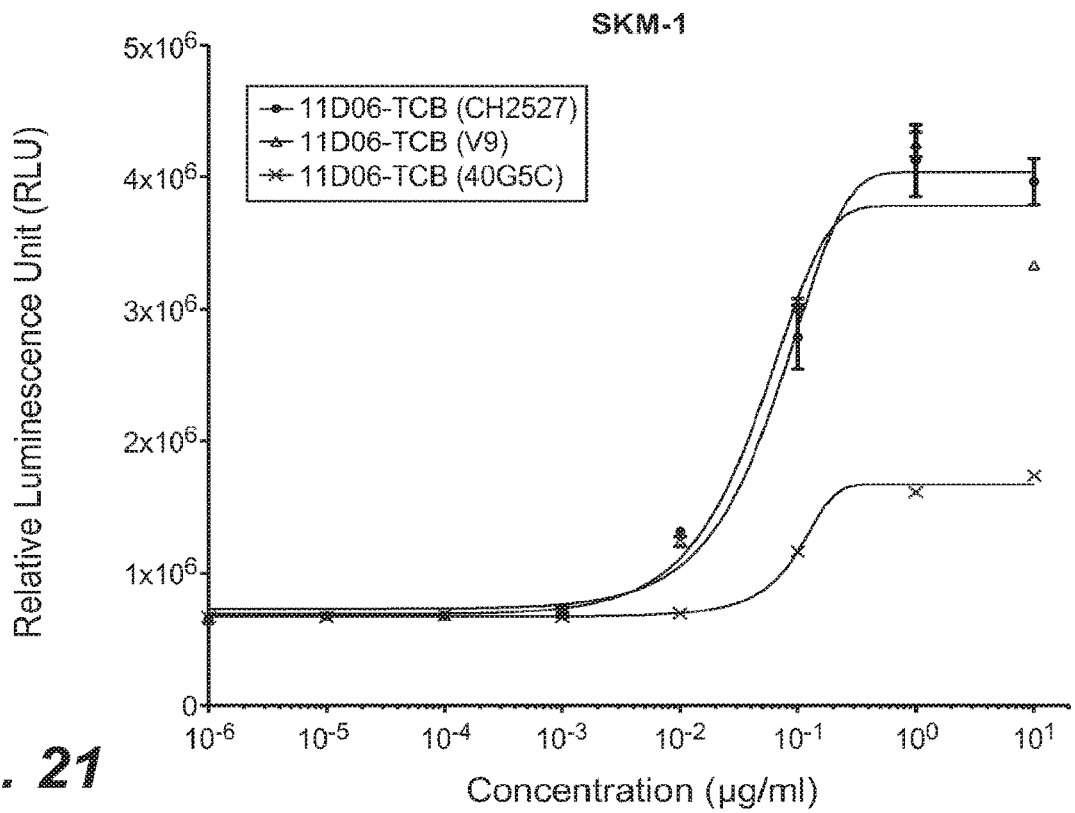
FIG. 21. Killing of HLA-A2+/WT1+SKM-1 cells mediated by HLA-A2/WT1 x CD3 bispecific antibodies with different CD3 binders.

As shown in FIG. 21, we observed that 11D06-TCB (CH2527) showed the same potency of T cell-mediated killing on HLA-A2$^+$WT1$^+$SKM-1 cell lines as 11D06-TCB (V9), whereas 11D06-TCB (40G5C) showed strongly reduced killing potency.

TABLE 8

Affinities of CD3 binders compared in this experiment.

| CD3 clone | Cross-reactivity | Affinity (Kd) [nM] |
|---|---|---|
| CH2527 | Hu-Cyno | 85-130 |
| 40G5C | Hu-Cyno | 390-460 |
| V9 | Hu only | 35-50 |

Example 17. T Cell Cytotoxicity Mediated by HLA-A2/WT1 x CD3 Bispecific Antibodies ("TCBs") Upon Binding to RMF Peptide-Pulsed T2 Cells The killing activity of 11D06-TCB (V9) (see SEQ ID NOs 123, 125, 139, 140 for full sequences) was compared to analogous TCBs with different HLA/WT1 binders ("Aali" and "Daniel", see WO 2017/060201, SEQ ID NOs 5 (VH) and 6 (VL) and SEQ ID NOs 35 (VH) and 36 (VL), respectively). The ESK1-TCB and the untargeted DP47-TCB were also included as controls. The experiment was performed as described in Example 6. The RMF peptide-pulsed cells (100 µl, 2×10$^5$ cells/ml) were co-cultured with 50 µl of T cells (2×10$^6$ cells/ml), and with serial dilutions of TCB (50 µl) for 24 hours at 37° C. with 5% CO$_2$.

Figure 22:
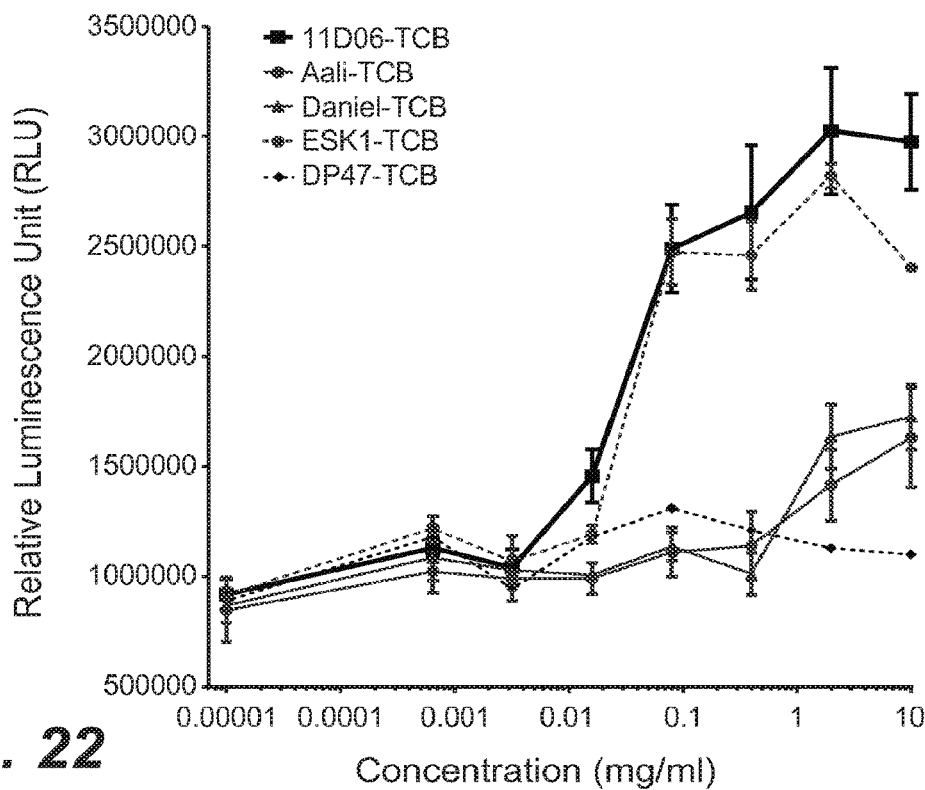
FIG. 22. Killing of RMF peptide-pulsed T2 cells mediated by HLA-A2/WT1 x CD3 bispecific antibodies (TCBs).
Figure 23A:
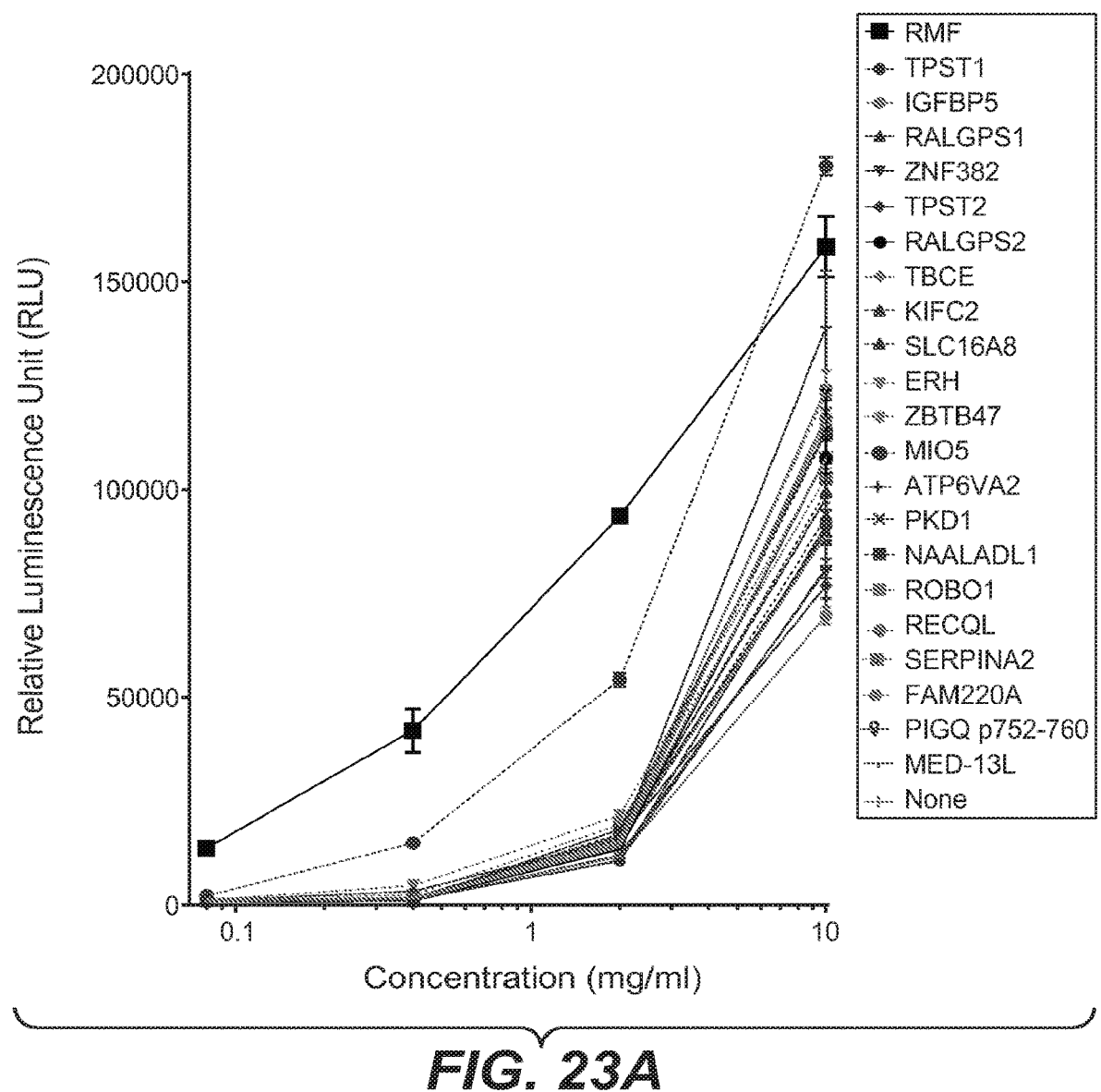
FIGS. 23A-D. Assessment of binding to off-target peptides by HLA-A2/WT1 x CD3 bispecific antibodies (TCBs) Aali-TCB (A), Daniel-TCB (B), ESK1-TCB (C) and 11D06-TCB (D).
Figure 23B:
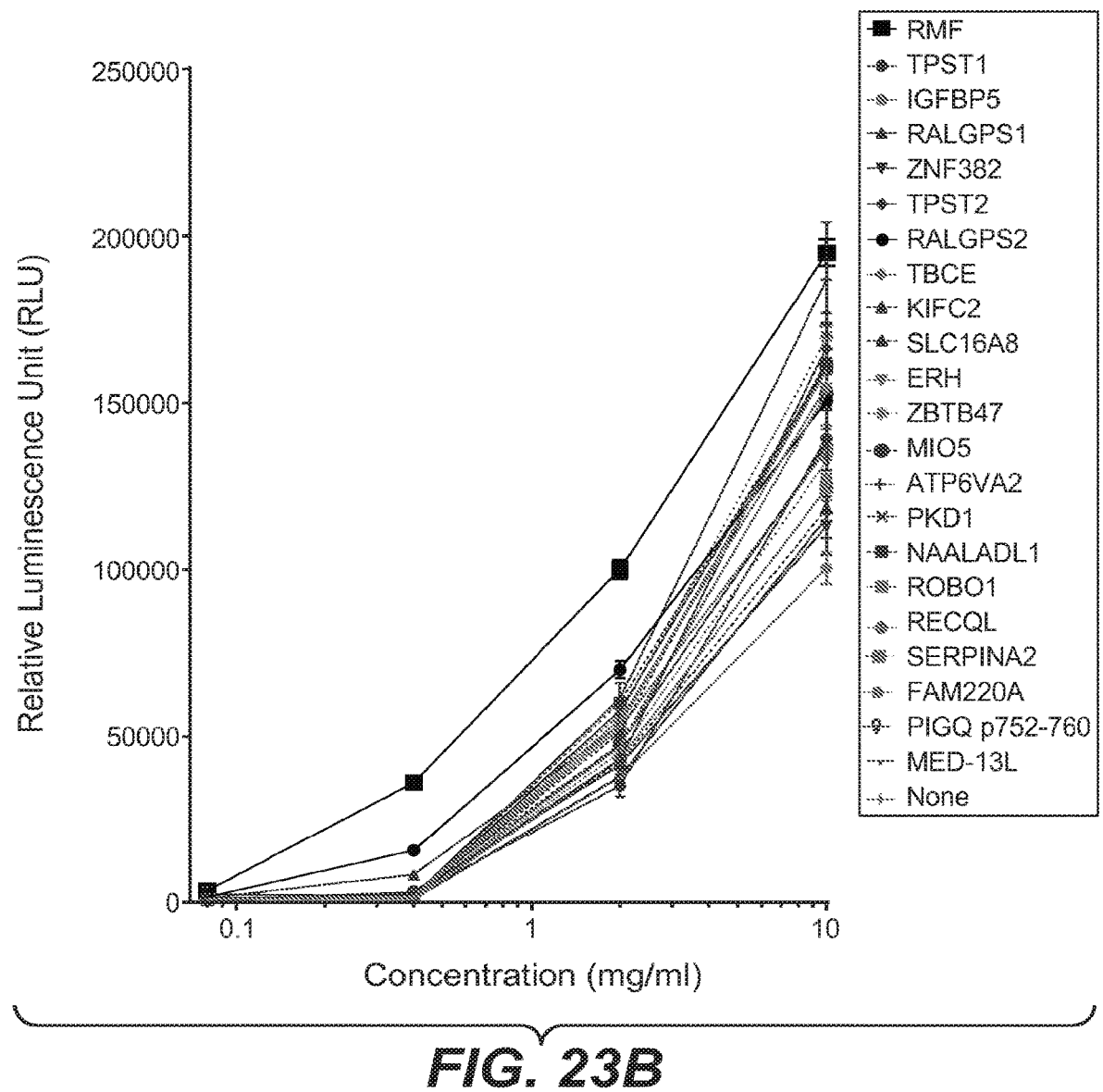
Figure 23C:
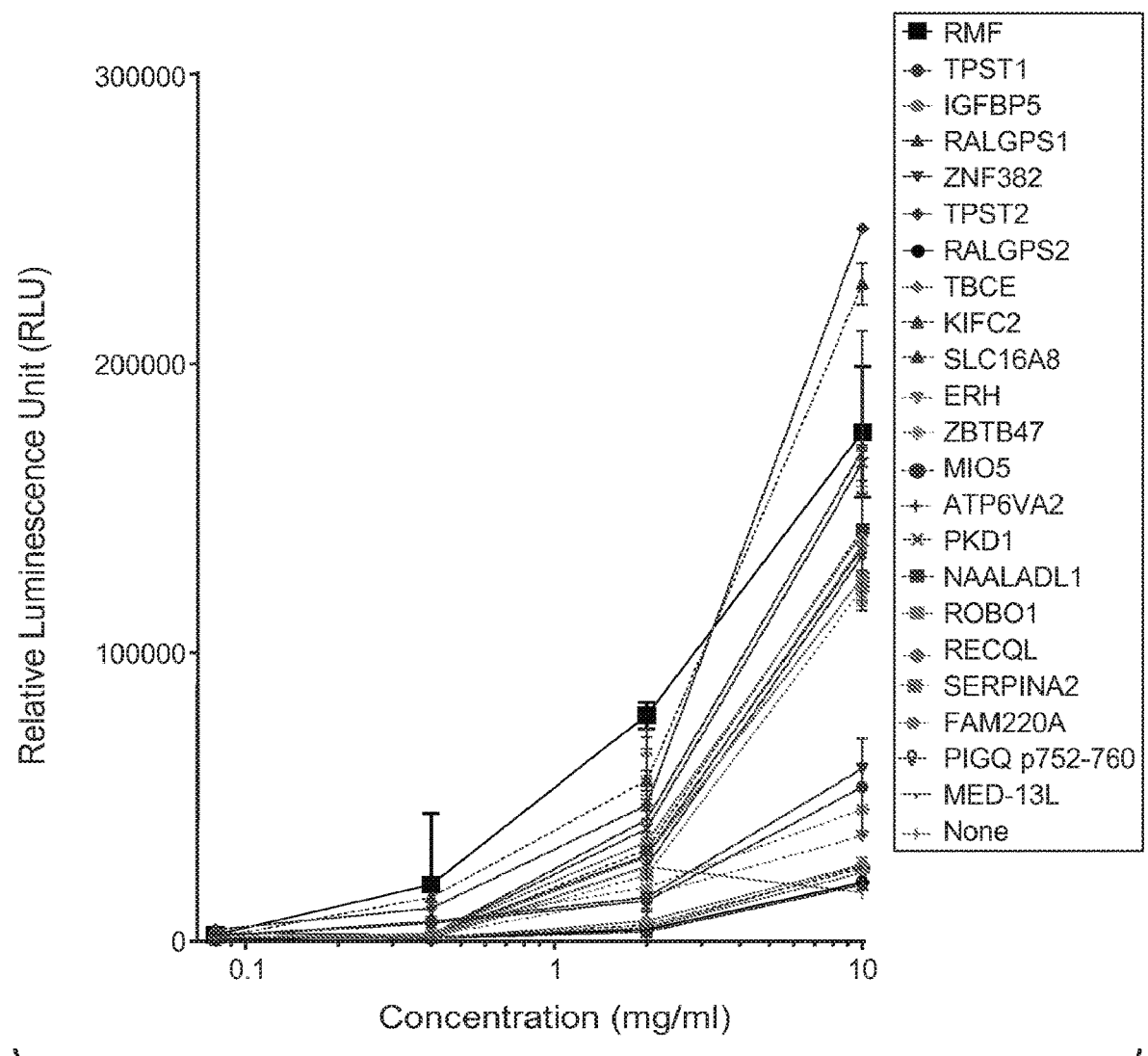
Figure 23D:
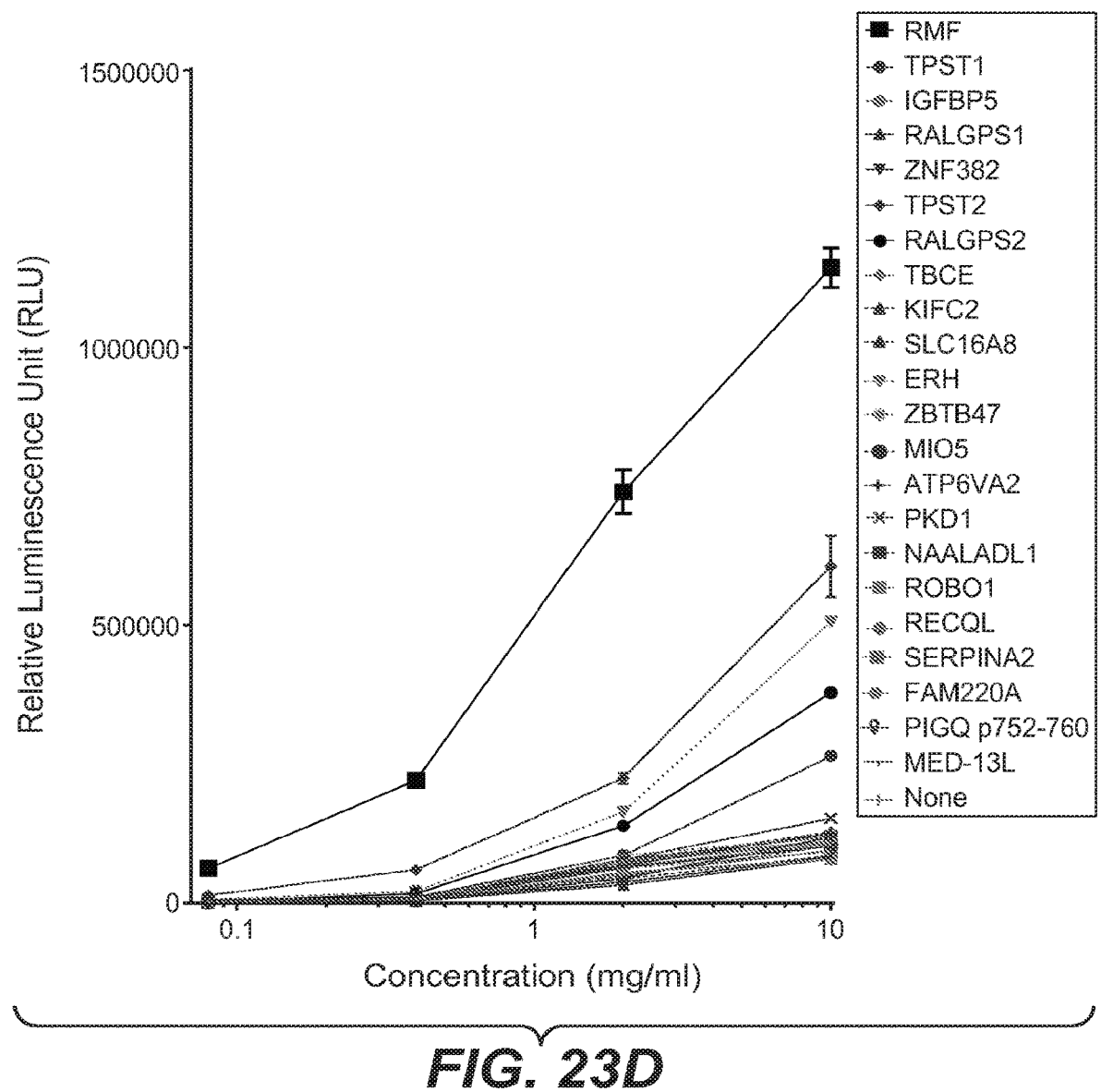

FIG. 22 shows the TCB-mediated specific T cell killing of RMF-expressing target cells. We found that 11D06-TCB and ESK1-TCB mediated potent killing on RMF peptide-pulsed T2 cells, whereas the TCBs based on the HLA/WT1 binders "Aali" and "Daniel" (Aali-TCB and Daniel-TCB) showed weak killing of RMF-pulsed cells only at the highest concentrations.

Example 18. No Binding of Selected HLA-A2/WT1 x CD3 Bispecific Antibodies ("TCBs") to Off-Target Peptides We also compared the cross-reactivity of 11D06-TCB (V9), Aali-TCB, Daniel-TCB and ESK1-TCB with the off-target peptides described in Examples 9 and 10.

For this experiment, Jurkat NFAT reporter cells expressing an anti-PGLALA chimeric antigen receptor (CAR) were used (CAR J assay, see PCT application claiming priority from European patent application no. EP17209201.7, incorporated herein by reference in its entirety). The anti-PGLALA CAR recognizes the P329G L234A L235A ("PGLALA", EU numbering) mutations in the Fc region of the TCBs. Peptide-pulsed T2 cells as described above were used as target cells. The principle of the assay is to co-culture the Jurkat-NFAT engineered effector cells with target cells. Only upon simultaneous binding of the TCBs to the CAR (via the PGLALA mutation) and the target antigen, the NFAT promoter is activated and leads to increasing luciferase expression in the Jurkat effector cells. Upon addition of an adequate substrate, active Firefly Luciferase leads to emission of luminescence, which can be measured as a signal of CAR-mediated activation.

Briefly, target cells were harvested and viability determined. 20 000 target cells/well were plated in a round-bottom, 96-well-plate (Greiner bio-one, #650180) in 100 µl medium. Non-pulsed T2 cells were used as negative control. 50 µl/well of diluted TCB were added to the target cells. Subsequently, Jurkat-NFAT reporter cells were harvested and viability assessed, resuspended in cell culture medium and added to tumor cells at 100 000 cells/well (50 µl/well) to obtain a final effector-to-target (E:T) ratio of 5:1 and a final volume of 200 µl per well. Cells were incubated for 20 h at 37° C. in a humidified incubator. At the end of the incubation time, the plates were adapted to room temperature (about 15 min). 125 µl of media/well was removed from the top and 25 µl/well of One-Glo Luciferase (Promega #E6120) was added, and mixed. 100 ul/well of the mixture was then transferred to 96 well flat bottom plate (Greiner bio-one, #655098) and the plate was incubated for 15 min in the dark before luminescence was detected using Perkin Elmer.

As shown in FIGS. 23A-D, Aali-TCB (A), Daniel-TCB (B) and ESK1-TCB (C) resulted in weaker activation of Jurkat NFAT reporter cell line (corresponding to weaker killing shown in FIG. 22) and moreover, a smaller window between recognition of RMF peptide and other off-target peptides comparing to 11D06-TCB (V9) (D).

Example 19. Pharmacokinetic Profile of HLA-A2/WT1 x CD3 Bispecific Antibody (11D06-TCB (V9)) after Single Injection in NSG Mice A single dose of 1 mg/kg of 11D06-TCB (V9) was injected into humanized and tumor-bearing NSG mice. Mice were injected i.v. with 200 μl of TCB, diluted with histidine buffer. Three mice per time point were bled at 10 min, 6 h, 24 h, 72 h and 7 days. The injected compound was analyzed in serum samples by ELISA as described in Example 13.

Figure 24:
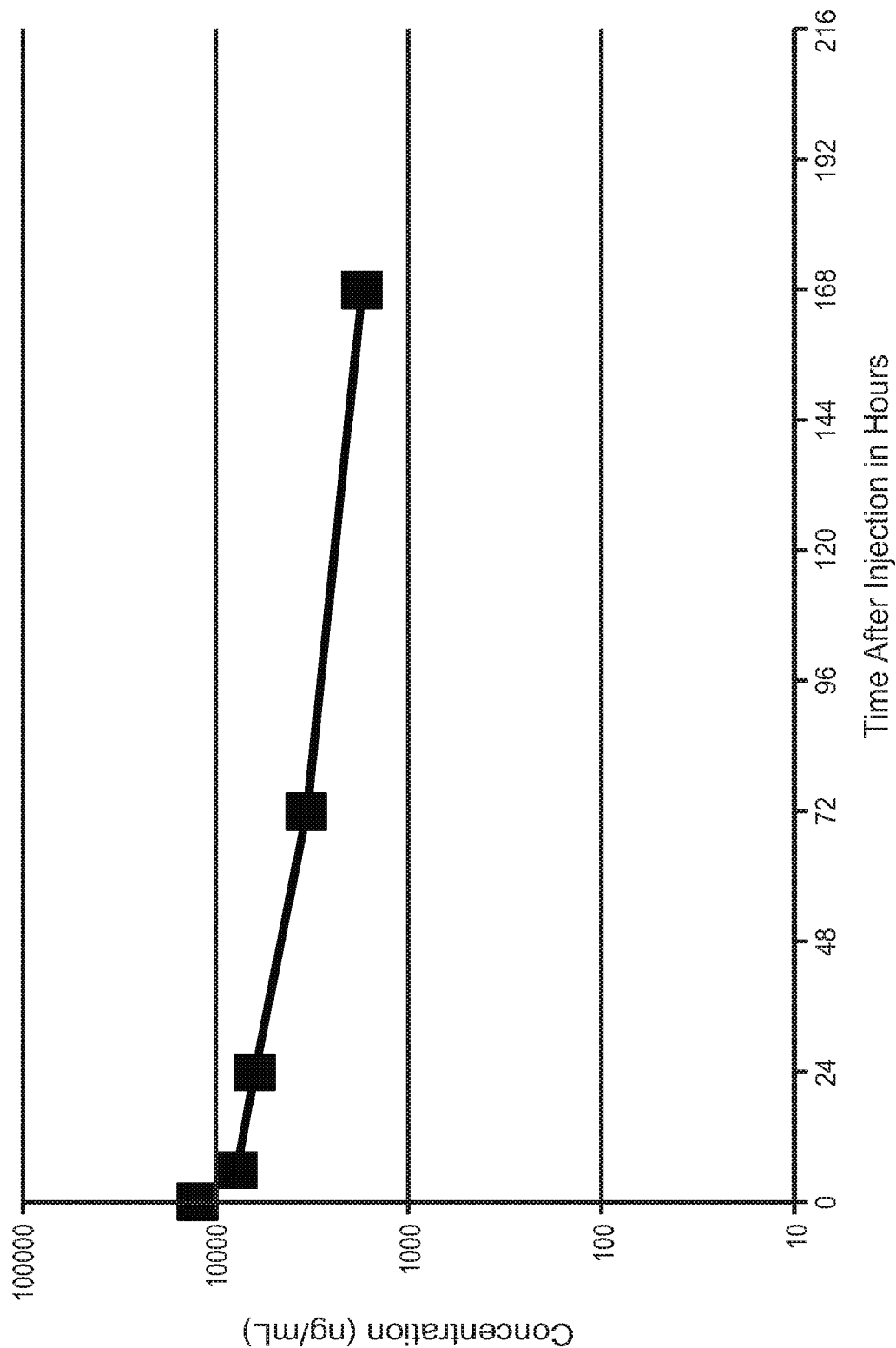
FIG. 24. Pharmacokinetic profile of HLA-A2/WT1 x CD3 bispecific antibody 11D06-TCB (V9) after single injection in NSG mice.

The result (FIG. 24) showed a stable PK-behaviour for the tested TCB, which suggested a once weekly schedule for subsequent efficacy studies.

Example 20. Efficacy Study with HLA-A2/WT1 x CD3 Bispecific Antibody (11D06-TCB (V9)) in SKM-1 Xenograft in Humanized Mice This efficacy study was aimed to evaluate the efficacy of 11D06-TCB (V9) in a human AML xenograft (SKM-1) in fully humanized NSG mice. The experiment was performed as described in Example 14.

FIGS. 25A-D shows the tumor growth kinetics (mean, FIG. 25A) as well as the single tumor growth kinetics in each group (FIGS. 25 B, C). As shown, the TCB exhibits tumor growth inhibition a TGI of 78 at study day 48 (FIG. 25D).

Example 21. Comparison of HLA-A2/WT1 x CD3 Bispecific Antibodies ("TCBs") with Different Molecular Formats We compared the activity of 11D06-TCB (V9) with an analogous molecule in a "1+1 CrossMab" format (as depicted in FIG. 1A). Activity was monitored using a cell-based functional assay which detects TCB-mediated activation of a reporter cell line (Jurkat NFAT) in the presence of target cells in a dose-dependent manner. The assay was performed essentially as described in Example 5 above, using as target cells CHO-K1 cells expressing a HLA-A02/WT1$_{RMF}$ PMHC complex. Reporter cell activation occurs upon simultaneous binding of the TCB to the HLA-A02/WT1$_{RMF}$ pMHC complex on target cells and to the CD3E unit of T cell receptor (TCR) on reporter cells, which leads to hyper-clustering of CD3 and thereby to TCR activation. Subsequent initiation of corresponding intracellular signaling pathways results in activation of transcription factor NFAT which induces expression of a NFAT-driven luciferase reporter gene. Activity of luciferase reporter is measured upon addition of substrate by luminescence readout.

Figure 26:
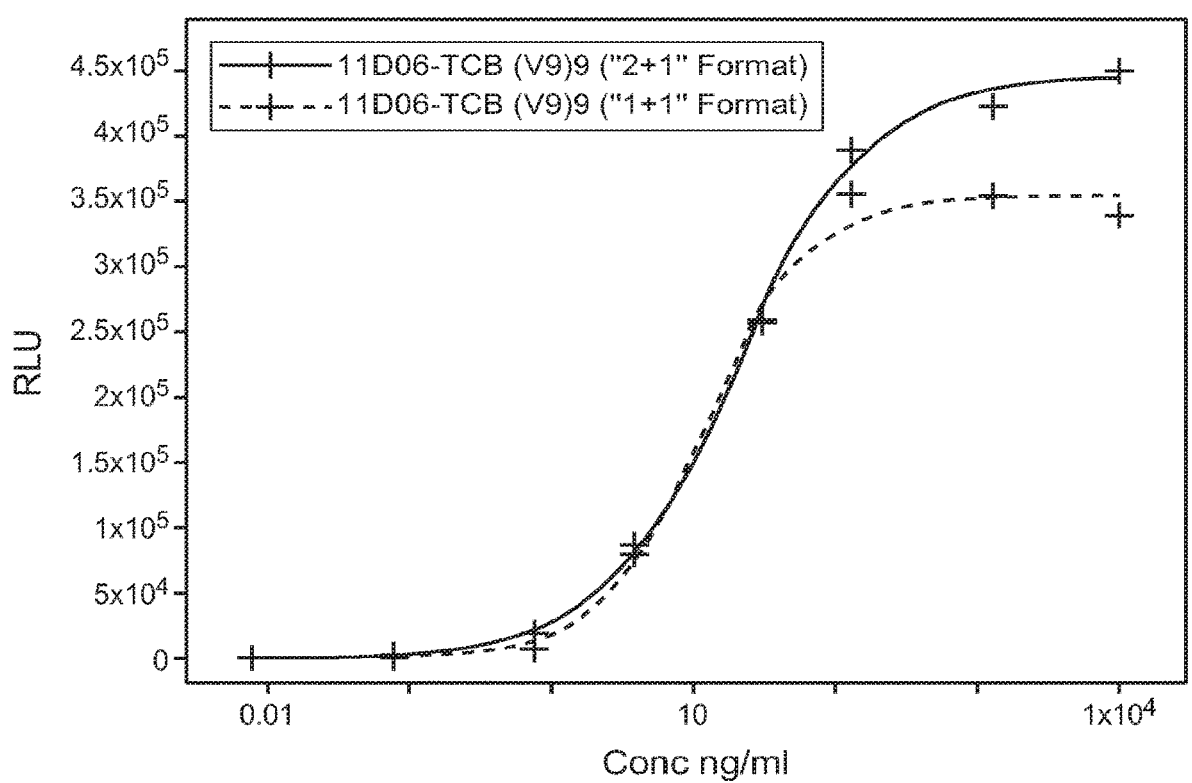
FIG. 26. Activation of T cells by HLA-A2/WT1 x CD3 bispecific antibodies (TCBs) upon binding to CHO-K1 cells expressing a HLA-A02/WT1$_{RMF}$ pMHC complex (NFAT reporter assay). Solid line: 11D06-TCB (V9) ("2+1" format). Dashed line: analogous molecule (11D06 and V9 binders) in "1+1 CrossMab" format.

The result of this experiment is shown in FIG. 26. Relative light units (RLU) reflecting target-dependent reporter cell activation are plotted against antibody concentration. As can be seen in FIG. 26, the molecule in the "1+1" format showed a lower activity than the "2+1" format in this assay.

Amino Acid Sequences

| | Sequence | SEQ ID NO |
|---|---|---|
| 11D06 HCDR1 | SYAIS | 1 |
| 11D06 HCDR2 | GIIPIFGTANYAQKFQG | 2 |
| 11D06 HCDR3 | SIELWWGGFDY | 3 |
| 11D06 LCDR1 | RASQSISSWLA | 4 |
| 11D06 LCDR2 | DASSLES | 5 |
| 11D06 LCDR3 | QQYEDYTT | 6 |
| 11D06 VH | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARSIELWWGGFDYWGQGTTVTVSS | 7 |
| 11D06 VL | DIQMTQSPSTLSASVGDRVTITCRASQSISSWLAWYQQKPG KAPKLLIYDASSLESGVPSRFSGSGSGTEFTLTIGSLQPDDFA TYYCQQYEDYTTFGQGTKVEIK | 8 |
| 33H09 HCDR1 | SYAIS | 9 |
| 33H09 HCDR2 | GIIPIFGTANYAQKFQG | 10 |
| 33H09 HCDR3 | GSYDLFSLDY | 11 |
| 33H09 LCDR1 | RASQSISSWLA | 12 |
| 33H09 LCDR2 | DASSLES | 13 |

| | Amino Acid Sequences | |
|---|---|---|
| | Sequence | SEQ ID NO |
| 33H09 LCDR3 | QQYYDGIT | 14 |
| 33H09 VH | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARGSYDLFSLDYWGQGTTVTVSS | 15 |
| 33H09 VL | DIQMTQSPSTLSASVGDRVTITCRASQSISSWLAWYQQKPG KAPKLLIYDASSLESGVPSRFSGSGSGTEFTLTISSLQPDDFA TYYCQQYYDGITFGQGTKVEIK | 16 |
| 13B04 HCDR1 | SYYWS | 17 |
| 13B04 HCDR2 | YIYYSGSTNYNPSLKS | 18 |
| 13B04 HCDR3 | VSYNGLDY | 19 |
| 13B04 LCDR1 | RASQSISSWLA | 20 |
| 13B04 LCDR2 | DASSLES | 21 |
| 13B04 LCDR3 | QQYNMWNPVT | 22 |
| 13B04 VH | EVQLLESGPGLVKPSETLSLTCTVSGGSISSYYWSWIRQPPG KGLEWIGYIYYSGSTNYNPSLKSRVTISVDTSKNQFSLKLSS VTAADTAVYYCARVSYNGLDYWGQGTLVTVSS | 23 |
| 13B04 VL | DIQMTQSPSTLSASVGDRVTITCRASQSISSWLAWYQQKPG KAPKLLIYDASSLESGVPSRFSGSGSGTEFTLTISSLQPDDFA TYYCQQYNMWNPVTFGQGTKVEIK | 24 |
| 11B09 HCDR1 | SYAIS | 25 |
| 11B09 HCDR2 | GIIPIFGTANYAQKFQG | 26 |
| 11B09 HCDR3 | VPGRWYGAMDY | 27 |
| 11B09 LCDR1 | RASQSISSWLA | 28 |
| 11B09 LCDR2 | DASSLES | 29 |
| 11B09 LCDR3 | QQEDDYPLT | 30 |
| 11B09 VH | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARVPGRWYGAMDYWGQGTTVTVSS | 31 |
| 11B09 VL | DIQMTQSPSTLSASVGDRVTITCRASQSISSWLAWYQQKPG KAPKLLIYDASSLESGVPSRFSGSGSGTEFTLTISSLQPDDFA TYYCQQEDDYPLTFGQGTKVEIK | 32 |
| 33F05 HCDR1 | SYYWS | 33 |
| 33F05 HCDR2 | YIYYSGSTNYNPSLKS | 34 |
| 33F05 HCDR3 | SYYEAFDY | 35 |
| 33F05 LCDR1 | QGDSLRSYYAS | 36 |

-continued

Amino Acid Sequences

| | Sequence | SEQ ID NO |
|---|---|---|
| 33F05 LCDR2 | GKNNRPS | 37 |
| 33F05 LCDR3 | NSPDMNGNAV | 38 |
| 33F05 VH | QVQLQESGPGLVKPSETLSLTCTVSGGSINSYYWSIRQPP GKGLEWIGYIYYSGSTNYNPSLKSRVTISVDTSKNQFSLKLS SVTAADTAVYYCARSYYEAFDYWGQGTLVTVSS | 39 |
| 33F05 VL | SSELTQDPAVSVALGQTVRITCQGDSLRSYYASWYQQKPG QAPVLVIYGKNNRPSGIPDRFSGSSSGNTASLTITGAQAEDE ADYYCNSPDMNGNAVFGGGTKLTVL | 40 |
| 5E11 HCDR1 | SYAIS | 41 |
| 5E11 HCDR2 | GIIPIFGTANYAQKFQG | 42 |
| 5E11 HCDR3 | SSYDLYSFDY | 43 |
| 5E11 LCDR1 | RASQSISSWLA | 44 |
| 5E11 LCDR2 | DASSLES | 45 |
| 5E11 LCDR3 | QQYSFPPMIT | 46 |
| 5E11 VH | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARSSYDLYSFDYWGQGTTVTVSS | 47 |
| 5E11 VL | DIQMTQSPSTLSASVGDRVTITCRASQSISSWLAWYQQKPG KAPKLLIYDASSLESGVPSRFSGSGSGTEFTLTISSLQPDDFA TYYCQQYSFPPMITFGQGTKVEIK | 48 |
| 13E08 HCDR1 | SYAMS | 49 |
| 13E08 HCDR2 | AISGSGGSTYYADSVKG | 50 |
| 13E08 HCDR3 | TYPYTGSFDY | 51 |
| 13E08 LCDR1 | RASQSISSWLA | 52 |
| 13E08 LCDR2 | DASSLES | 53 |
| 13E08 LCDR3 | QQNYNYPPT | 54 |
| 13E08 VH | EVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKTYPYTGSFDYWGQGTLVTVSS | 55 |
| 13E08 VL | DIQMTQSPSTLSASVGDRVTITCRASQSISSWLAWYQQKPG KAPKLLIYDASSLESGVPSRFSGSGSGTEFTLTISSLQPDDFA TYYCQQNYNYPPTFGQGTKVEIK | 56 |
| 5C01 HCDR1 | SYAMS | 57 |
| 5C01 HCDR2 | AISGSGGSTYYADSVKG | 58 |
| 5C01 HCDR3 | GSWVSYAFDY | 59 |
| 5C01 LCDR1 | RASQSISSWLA | 60 |
| 5C01 LCDR2 | DASSLES | 61 |
| 5C01 LCDR3 | QQYSIWFPYT | 62 |
| 5C01 VH | EVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKGSWVSYAFDYWGQGTLVTVSS | 63 |

-continued

Amino Acid Sequences

| | Sequence | SEQ ID NO |
|---|---|---|
| 5C01 VL | DIQMTQSPSTLSASVGDRVTITCRASQSISSWLAWYQQKPG KAPKLLIYDASSLESGVPSRFSGSGSGTEFTLTISSLQPDDFA TYYCQQYSIWFPYTFGQGTKVEIK | 64 |
| 11G06 HCDR1 | SYAIS | 65 |
| 11G06 HCDR2 | GIIPIFGTANYAQKFQG | 66 |
| 11G06 HCDR3 | TGPYYGAFDY | 67 |
| 11G06 LCDR1 | RASQSISSWLA | 68 |
| 11G06 LCDR2 | DASSLES | 69 |
| 11G06 LCDR3 | QQGFRGYT | 70 |
| 11G06 VH | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARTGPYYGAFDYWGQGTTVTSS | 71 |
| 11G06 VL | DIQMTQSPSTLSASVGDRVTITCRASQSISSWLAWYQQKPG KAPKLLIYDASSLESGVPSRFSGSGSGTEFTLTISSLQPDDFA TYYCQQGFRGYTFGQGTKVEIK | 72 |
| ESK1 VH | QMQLVQSGAEVKEPGESLRISCKGSGYSFTNFWISWVRQM PGKGLEWMGRVDPGYSYSTYSPSFQGHVTISADKSTSTAY LQWNSLKASDTAMYYCARVQYSGYYDWFDPWGQGTLVT VSS | 73 |
| ESK1 VL | QAWTQPPSASGTPGQRVTISCSGSSSNIGSNTVNWYQQVPG TAPKLLIYSNNQRPSGVPDRFSGSKSGTSASLAISGLQSEDE ADYYCAAWDDSLNGWVFGGGTKLTVL | 74 |
| Untargeted VH | EVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKGSGFDYWGQGTLVTVSS | 75 |
| Untargeted VL | EIVLTQSPGTLSLSPGERATLSCRASQSVSSSYLAWYQQKP GQAPRLLIYGASSRATGIPDRFSGSGSGTDFTLTISRLEPEDF AVYYCQQYGSSPLTFGQGTKVEIK | 76 |
| VLD peptide | VLDFAPPGA | 77 |
| RMF peptide | RMFPNAPYL | 78 |
| MED13L | RMFPTPPSL | 79 |
| PIGQ | RMFPGEVAL | 80 |
| ARHGEF11 | RLFPNLPEL | 81 |
| PRDM16 | RMFPNKYSL | 82 |
| SERPINA6 | AMDPNAAYV | 83 |
| NIPSNAP1 | RMGPNIYEL | 84 |
| TAF3 | NMPPNFPYI | 85 |
| U4 | YTIPNHPYL | 86 |
| TPST1 | RLFPNAKFL | 87 |
| IGFBP5 | RMVPRAVYL | 88 |
| RALGPS1 | KMVPSIPYL | 89 |

Amino Acid Sequences

| | Sequence | SEQ ID NO |
|---|---|---|
| ZNF382 | RIFPSYSYL | 90 |
| TPST2 | RLFPNSKFL | 91 |
| RALGPS2 | KMTPCIPYL | 92 |
| TBCE | SMFPSLKYL | 93 |
| KIFC2 | RLLPSAPTL | 94 |
| SLC16A8 | RLRPHVPYL | 95 |
| ERH | RMNPNSPSI | 96 |
| ZBTB47 | RVFNNRWYL | 97 |
| MIOS | RLQLNNPYL | 98 |
| ATP6V0A2 | RMFFNGRYI | 99 |
| PKD1 | RLSPNRPPL | 100 |
| NAALADL1 | ETFPNSWYL | 101 |
| ROBO1 | GLKPNAIYL | 102 |
| RECQL | RQFPNASLI | 103 |
| SERPINA2 | YIFPNCPFL | 104 |
| FAM220A | RLRINFPYL | 105 |
| Human WT1 | MGSDVRDLNALLPAVPSLGGGGCALPVSGAAQWAPVLD FAPPGASAYGSLGGPAPPPAPPPPPPPPHSFIKQEPSWGGA EPHEEQCLSAFTVHFSGQFTGTAGACRYGPFGPPPPSQASS GQARMFPNAPYLPSCLESQPAIRNQGYSTVTFDGTPSYGHT PSHHAAQFPNHSFKHEDPMGQQGSLGEQQYSVPPPVYGCH TPTDSCTGSQALLLRTPYSSDNLYQMTSQLECMTWNQMNL GATLKGVAAGSSSSVKWTEGQSNHSTGYESDNHTTPILCG AQYRIHTHGVFRGIQDVRRVPGVAPTLVRSASETSEKRPFM CAYPGCNKRYFKLSHLQMHSRKHTGEKPYQCDFKDCERR FSRSDQLKRHQRRHTGVKPFQCKTCQRKFSRSDHLKTHTR THTGKTSEKPFSCRWPSCQKKFARSDELVRHHNMHQRNM TKLQLAL | 106 |
| Human CD3 | MQSGTHWRVLGLCLLSVGVWGQDGNEEMGGITQTPYKVS ISGTTVILTCPQYPGSEILWQHNDKNIGGDEDDKNIGSDEDH LSLKEFSELEQSGYYVCYPRGSKPEDANFYLYLRARVCENC MEMDVMSVATIVIVDICITGGLLLLVYYWSKNRKAKAKPV TRGAGAGGRQRGQNKERPPPVPNPDYEPIRKGQRDLYSGL NQRRI | 107 |
| Cynomolgus CD3 | MQSGTRWRVLGLCLLSIGVWGQDGNEEMGSITQTPYQVSI SGTTVILTCSQHLGSEAQWQHNGKNKEDSGDRLFLPEFSE MEQSGYYVCYPRGSNPEDASHHLYLKARVCENCMEMDV MAVATIVIVDICITLGLLLLVYYWSKNRKAKAKPVTRGAG AGGRQRGQNKERPPPVPNPDYEPIRKGQQDLYSGLNQRRI | 108 |
| hIgG1 Fc region | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWE SNGQPENNYKTTPPVLDSDGSFFLYSKLTVDKSRWQQGNV FSCSVMHEALHNHYTQKSLSLSP | 109 |
| linker | GGGGSGGGGS | 110 |
| linker | DGGGGSGGGGS | 111 |
| Human kappa CL domain | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC | 112 |

| Sequence | | SEQ ID NO |
|---|---|---|
| Human lambda CL domain | QPKAAPSVTLFPPSSEELQANKATLVCLISDFYPGAVTVAW KADSSPVKAGVETTTPSKQSNNKYAASSYLSLTPEQWKSH RSYSCQVTHEGSTVEKTVAPTECS | 113 |
| Human IgG1 heavy chain constant region (CH1-CH2-CH3) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKN QVSLTCLVKGFYPSDIAVEWESNGQPENNYKTTPPVLDSD GSFFLYSKLTVDKSRWQQGNVFSCSVMHEALHNHYTQKS LSLSP | 114 |
| CD3 HCDR1 | TYAMN | 115 |
| CD3 HCDR2 | RIRSKYNNYATYYADSVKG | 116 |
| CD3 HCDR3 | HGNFGNSYVSWFAY | 117 |
| CD3 LCDR1 | GSSTGAVTTSNYAN | 118 |
| CD3 LCDR2 | GTNKRAP | 119 |
| CD3 LCDR3 | ALWYSNLWV | 120 |
| CD3 VH | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSS | 121 |
| CD3 VL | QAVVTQEPSLTVSPGGTVTLTCGSSTGAVTTSNYANWVQE KPGQAFRGLIGGTNKRAPGTPARFSGSLLGGKAALTLSGAQ PEDEAEYYCALWYSNLWVFGGGTKLTVL | 122 |
| WT1 11D06 VH-CH1(EE)-Fc(hole, PGLALA) | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARSIELWWGGFDYWGQGTTVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKC KVSNKALGAPIEKTISKAKGQPREPQVCTLPPSRDELTKNQ VSLSCAVKGFYPSDIAVEWESNGQPENNYKTTPPVLDSDGS FFLVSKLTVDKSRWQQGNVFSCSVMHEALHNHYTQKSLSL SP | 123 |
| WT1 11D06 VH-CH1(EE)-CD3 VL-CH1-Fc(knob, PGLALA) | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARSIELWWGGFDYWGQGTTVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDGGGGSGGGGSQAVVTQEPSL TVSPGGTVTLTCGSSTGAVTTSNYANWVQEKPGQAFRGLI GGTNKRAPGTPARFSGSLLGGKAALTLSGAQPEDEAEYYC ALWYSNLWVFGGGTKLTVLSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEPK SCDKTHTCPPCPAPEAAGGPSVFLFPPKPKDTLMISRTPEVT CVVVDVSHEDPEVKFNWYVDGVEVHNAKTKPREEQYNST YRVVSVLTVLHQDWLNGKEYKCKVSNKALGAPIEKTISKA KGQPREPQVYTLPPCRDELTKNQVSLWCLVKGFYPSDIAV EWESNGQPENNYKTTPPVLDSDGSFFLYSKLTVDKSRWQQ GNVFSCSVMHEALHNHYTQKSLSLSP | 124 |
| WT1 11D06 VL-CL(RK) | DIQMTQSPSTLSASVGDRVTITCRASQSISSWLAWYQQKPG KAPKLLIYDASSLESGVPSRFSGSGSGTEFTLTIGSLQPDDFA TYYCQQYEDYTTFGQGTKVEIKRTVAAPSVFIFPPSDRKLK SGTASVVCLLNNFYPREAKVQWKVDNALQSGNSQESVTE QDSKDSTYSLSSTLTLSKADYEKHKVYACEVTHQGLSSPVT KSFNRGEC | 125 |

Amino Acid Sequences

| | Sequence | SEQ ID NO |
|---|---|---|
| WT1 33H09 VH-CH1(EE)-Fc(hole, PGLALA) | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARGSYDLFSLDYWGQGTTVTVSSAS TKGPSVFPLAPSSKSTSGGTAALGCLVEDYFPEPVTVSWNS GALTSGVHTFPAVLQSSGLYSLSSVVTVPSSSLGTQTYICNV NHKPSNTKVDEKVEPKSCDKTHTCPPCPAPEAAGGPSVFLF PPKPKDTLMISRTPEVTCVVVDVSHEDPEVKFNWYVDGVE VHNAKTKPREEQYNSTYRVVSVLTVLHQDWLNGKEYKCK VSNKALGAPIEKTISKAKGQPREPQVCTLPPSRDELTKNQV SLSCAVKGFYPSDIAVEWESNGQPENNYKTTPPVLDSDGSF FLVSKLTVDKSRWQQGNVFSCSVMHEALHNHYTQKSLSLS P | 126 |
| WT1 33H09 VH-CH1(EE)-CD3 VL-CH1-Fc(knob, PGLALA) | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARGSYDLFSLDYWGQGTTVTVSSAS TKGPSVFPLAPSSKSTSGGTAALGCLVEDYFPEPVTVSWNS GALTSGVHTFPAVLQSSGLYSLSSVVTVPSSSLGTQTYICNV NHKPSNTKVDEKVEPKSCDGGGSGGGGSQAVVTQEPSLT VSPGGTVTLTCGSSTGAVTTSNYANWVQEKPGQAFRGLIG GTNKRAPGTPARFSGSLLGGKAALTLSGAQPEDEAEYYCA LWYSNLWVFGGGTKLTVLSSASTKGPSVFPLAPSSKSTSGG TAALGCLVKDYFPEPVTVSWNSGALTSGVHTFPAVLQSSG LYSLSSVVTVPSSSLGTQTYICNVNHKPSNTKVDKKVEPKS CDKTHTCPPCPAPEAAGGPSVFLFPPKPKDTLMISRTPEVTC VVVDVSHEDPEVKFNWYVDGVEVHNAKTKPREEQYNSTY RVVSVLTVLHQDWLNGKEYKCKVSNKALGAPIEKTISKAK GQPREPQVYTLPPCRDELTKNQVSLWCLVKGFYPSDIAVE WESNGQPENNYKTTPPVLDSDGSFFLYSKLTVDKSRWQQG NVFSCSVMHEALHNHYTQKSLSLSP | 127 |
| WT1 33H09 VL-CL(RK) | DIQMTQSPSTLSASVGDRVTITCRASQSISSWLAWYQQKPG KAPKLLIYDASSLESGVPSRFSGSGSGTEFTLTISSLQPDDFA TYYCQQYYDGITFGQGTKVEIKRTVAAPSVFIFPPSDRKLKS GTASVVCLLNNFYPREAKVQWKVDNALQSGNSQESVTEQ DSKDSTYSLSSTLTLSKADYEKHKVYACEVTHQGLSSPVTK SFNRGEC | 128 |
| CD3 VH-CL | EVQLLESGGGLVQPGGSLRLSCAASGFTFSTYAMNWVRQA PGKGLEWVSRIRSKYNNYATYYADSVKGRFTISRDDSKNT LYLQMNSLRAEDTAVYYCVRHGNFGNSYVSWFAYWGQG TLVTVSSASVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC | 129 |
| CD3 HCDR1 (V9) | GYTMN | 130 |
| CD3 HCDR2 (V9) | LINPYKGVSTYNQKFKD | 131 |
| CD3 HCDR3 (V9) | SGYYGDSDWYFDV | 132 |
| CD3 LCDR1 (V9) | RASQDIRNYLN | 133 |
| CD3 LCDR2 (V9) | YTSRLES | 134 |
| CD3 LCDR3 (V9) | QQGNTLPWT | 135 |
| CD3 VH (V9) | EVQLVESGGGLVQPGGSLRLSCAASGYSFTGYTMNWVRQ APGKGLEWVALINPYKGVSTYNQKFKDRFTISVDKSKNTA YLQMNSLRAEDTAVYYCARSGYYGDSDWYFDVWGQGTL VTVSS | 136 |
| CD3 VL (V9) | DIQMTQSPSSLSASVGDRVTITCRASQDIRNYLNWYQQKPG KAPKLLIYYTSRLESGVPSRFSGSGSGTDYTLTISSLQPEDFA TYYCQQGNTLPWTFGQGTKVEIK | 137 |
| HLA-A2 | GSHSMRYFFTSVSRPGRGEPRFIAVGYVDDTQFVRFDSDAA SQRMEPRAPWIEQEGPEYWDGETRKVKAHSQTHRVDLGT | 138 |

-continued

Amino Acid Sequences

| | Sequence | SEQ ID NO |
|---|---|---|
| | LRGYYNQSEAGSHTVQRMYGCDVGSDWRFLRGYHQYAY DGKDYIALKEDLRSWTAADMAAQTTKHKWEAAHVAEQL RAYLEGTCVEWLRRYLENGKETLQRTDAPKTHMTHHAVS DHEATLRCWALSFYPAEITLTWQRDGEDQTQDTELVETRP AGDGTFQKWAAVVVPSGQEQRYTCHVQHEGLPKPLTLRW E | |
| WT1 11D06 VH-CH1(EE)- CD3 (V9) VL- CH1-Fc(knob, PGLALA) | QVQLVQSGAEVKKPGSSVKVSCKASGGTFSSYAISWVRQA PGQGLEWMGGIIPIFGTANYAQKFQGRVTITADKSTSTAYM ELSSLRSEDTAVYYCARSIELWWGGFDYWGQGTTVTVSSA STKGPSVFPLAPSSKSTSGGTAALGCLVEDYFPEPVTVSWN SGALTSGVHTFPAVLQSSGLYSLSSVVTVPSSSLGTQTYICN VNHKPSNTKVDEKVEPKSCDGGGGSGGGGSDIQMTQSPSS LSASVGDRVTITCRASQDIRNYLNWYQQKPGKAPKLLIYYT SRLESGVPSRFSGSGSGTDYTLTISSLQPEDFATYYCQQGNT LPWTFGQGTKVEIKSSASTKGPSVFPLAPSSKSTSGGTAALG CLVKDYFPEPVTVSWNSGALTSGVHTFPAVLQSSGLYSLSS VVTVPSSSLGTQTYICNVNHKPSNTKVDKKVEPKSCDKTH TCPPCPAPEAAGGPSVFLFPPKPKDTLMISRTPEVTCVVVDV SHEDPEVKFNWYVDGVEVHNAKTKPREEQYNSTYRVVSV LTVLHQDWLNGKEYKCKVSNKALGAPIEKTISKAKGQPRE PQVYTLPPCRDELTKNQVSLWCLVKGFYPSDIAVEWESNG QPENNYKTTPPVLDSDGSFFLYSKLTVDKSRWQQGNVFSC SVMHEALHNHYTQKSLSLSP | 139 |
| CD3 (V9) VH-CL | EVQLVESGGGLVQPGGSLRLSCAASGYSFTGYTMNWVRQ APGKGLEWVALINPYKGVSTYNQKFKDRFTISVDKSKNTA YLQMNSLRAEDTAVYYCARSGYYGDSDWYFDVWGQGTL VTVSSASVAAPSVFIFPPSDEQLKSGTASVVCLLNNFYPREA KVQWKVDNALQSGNSQESVTEQDSKDSTYSLSSTLTLSKA DYEKHKVYACEVTHQGLSSPVTKSFNRGEC | 140 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating an HLA-A2/WT1-expressing cancer in an individual, comprising administering to said individual a therapeutically effective amount of a composition comprising an antibody that binds to HLA-A2/WT1, wherein the antibody comprises a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6 in a pharmaceutically acceptable form.

2. The method of claim 1, wherein the antibody comprises a VH comprising an amino acid sequence that is at least 95%, identical to the amino acid sequence of SEQ ID NO: 7, and a VL comprising an amino acid sequence that is at least 95% identical to the amino acid sequence of SEQ ID NO: 8.

3. The method of claim 1, wherein the antibody is an IgG antibody.

4. The method of claim 3, wherein the antibody is an IgG$_1$ antibody.

5. The method of claim 1, wherein the antibody is a full-length antibody.

6. The method of claim 1, wherein the antibody is an antibody fragment selected from the group of that is an Fv molecule, a scFv molecule, a Fab molecule, or a F(ab')$_2$ molecule.

7. The method of claim 1, wherein the antibody is a multispecific antibody.

8. A method of treating an HLA-A2/WT1-expressing cancer in an individual, comprising administering to said individual a therapeutically effective amount of a composition comprising a bispecific antigen binding molecule, said bispecific antigen binding molecule comprising
(a) a first antigen binding moiety that binds to a first antigen, wherein the first antigen is HLA-A2/WT1 and the first antigen binding moiety comprises a heavy chain variable region (VH) comprising a heavy chain complementary determining region (HCDR) 1 of SEQ ID NO: 1, a HCDR 2 of SEQ ID NO: 2, and a HCDR 3 of SEQ ID NO: 3, and a light chain variable region (VL) comprising a light chain complementarity determining region (LCDR) 1 of SEQ ID NO: 4, a LCDR 2 of SEQ ID NO: 5 and a LCDR 3 of SEQ ID NO: 6, and
(b) a second antigen binding moiety which specifically binds to a second antigen.

9. The method of claim 8, wherein the first antigen binding moiety comprises a VH comprising an amino acid sequence that is at least 95% identical to the amino acid sequence of SEQ ID NO: 7, and a VL comprising an amino acid sequence that is at least 95% identical to the amino acid sequence of SEQ ID NO: 8.

10. The method of claim 8, wherein the second antigen is CD3.

11. The method of claim 10, wherein the second antigen binding moiety comprises
    (i) a VH comprising a HCDR 1 of SEQ ID NO: 115, a HCDR 2 of SEQ ID NO: 116, and a HCDR 3 of SEQ ID NO: 117, and a VL comprising a LCDR 1 of SEQ ID NO: 118, a LCDR 2 of SEQ ID NO: 119 and a LCDR 3 of SEQ ID NO: 120; or
    (ii) a VH comprising a HCDR 1 of SEQ ID NO: 130, a HCDR 2 of SEQ ID NO: 131, and a HCDR 3 of SEQ ID NO: 132, and a VL comprising a LCDR 1 of SEQ ID NO: 133, a LCDR 2 of SEQ ID NO: 134 and a LCDR 3 of SEQ ID NO: 135.

12. The method of claim 11, wherein the second antigen binding moiety comprises
    (i) a VH comprising an amino acid sequence that is at least 95% identical to the amino acid sequence of SEQ ID NO: 121, and a VL comprising an amino acid sequence that is at least 95% identical to the amino acid sequence of SEQ ID NO: 122; or
    (ii) a VH comprising an amino acid sequence that is at least 95% identical to the amino acid sequence of SEQ ID NO: 136, and a VL comprising an amino acid sequence that is at least 95% identical to the amino acid sequence of SEQ ID NO: 137.

13. The method of claim 8, wherein the first and/or the second antigen binding moiety is a Fab molecule.

14. The method of claim 8, wherein the second antigen binding moiety is a Fab molecule wherein the variable domains VL and VH or the constant domains CL and CH1 of the Fab light chain and the Fab heavy chain are replaced by each other.

15. The method of claim 8, wherein the first antigen binding moiety is a Fab molecule wherein in the constant domain CL the amino acid at position 124 as numbered according to Kabat is substituted independently by lysine (K), arginine (R) or histidine (H) and the amino acid at position 123 as numbered according to Kabat is substituted independently by lysine (K), arginine (R) or histidine (H), and in the constant domain CH1 the amino acid at position 147 as numbered according to Kabat EU index is substituted independently by glutamic acid (E), or aspartic acid (D) and the amino acid at position 213 as numbered according to Kabat EU index is substituted independently by glutamic acid (E), or aspartic acid (D).

16. The method of claim 8, wherein the first and the second antigen binding moiety are fused to each other via a peptide linker.

17. The method of claim 8, wherein the first and the second antigen binding moiety are each a Fab molecule and wherein either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety.

18. The method of claim 8, wherein said bispecific antigen binding molecule comprises a third antigen binding moiety.

19. The method of claim 18, wherein the third antigen binding moiety is identical to the first antigen binding moiety.

20. The method of claim 8, wherein said bispecific antigen binding molecule comprises an Fc domain composed of a first and a second subunit.

21. The method of claim 20, wherein the first, the second and, where present, a third antigen binding moiety are each a Fab molecule; and wherein either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain;
    and wherein the third antigen binding moiety, where present, is fused at the C-terminus of the Fab heavy chain to the N-terminus of the second subunit of the Fc domain.

22. The method of claim 20, wherein the Fc domain is an IgG Fc domain.

23. The method of claim 20, wherein the Fc domain is a human Fc domain.

24. The method of claim 20, wherein an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

25. The method of claim 20, wherein the Fc domain comprises one or more amino acid substitution that reduces binding to an Fc receptor and/or effector function.

26. The method of claim 20, wherein the Fc domain comprises one or more amino acid substitution that reduces binding to an Fc receptor and/or effector function.

27. The method of claim 20, wherein the Fc domain is a human IgG1 Fc domain.

28. The method of claim 27, wherein in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V), in each case as numbered according to Kabat EU index.

29. The method of claim 28, wherein in the second subunit of the Fc domain, the threonine residue at position 366 is replaced with a serine residue (T366S) and the leucine residue at position 368 is replaced with an alanine residue (L368A), in each case as numbered according to Kabat EU index.

30. The method of claim 28, wherein in the first subunit of the Fc domain the serine residue at position 354 is replaced with a cysteine residue (S354C), as numbered according to Kabat EU index.

31. The method of claim 28, wherein in the first subunit of the Fc domain the glutamic acid residue at position 356 is replaced with a cysteine residue (E356C), as numbered according to Kabat EU index.

32. The method of claim 30 or 31, wherein in the second subunit of the Fc domain the tyrosine residue at position 349 is replaced by a cysteine residue (Y349C), as numbered according to Kabat EU index.

33. The method of claim 25 wherein said one or more amino acid substitution is at a position selected from the group consisting of E233, L234, L235, N297, P331 and P329, in each case as numbered according to Kabat EU index.

34. The method of claim 20, wherein each subunit of said Fc domain comprises the amino acid substitutions L234A, L235A and P329G, in each case as numbered according to Kabat EU index.

35. The method of claim 8, wherein said bispecific antigen binding molecule comprises
(a) a first and a third antigen binding moiety that binds to a first antigen; wherein the first antigen is HLA-A2/WT1 and wherein the first and the third antigen binding moiety are each a (conventional) Fab molecule comprising a heavy chain variable region comprising the amino acid sequence of SEQ ID NO: 7 and a light chain variable region comprising the amino acid sequence of SEQ ID NO: 8;
(b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 136 and a light chain variable region comprising the amino acid sequence of SEQ ID NO: 137;
(c) a human IgG1 Fc domain composed of a first and a second subunit;
wherein
(i) in the constant domain CL of the first and the third antigen binding moiety under a) the amino acid at position 124 as numbered according to Kabat is substituted by lysine (K) and the amino acid at position 123 as numbered according to Kabat is substituted by arginine (R), and wherein in the constant domain CH1 of the first and the third antigen binding moiety under a) the amino acid at position 147 as numbered according to Kabat EU index is substituted by glutamic acid (E) according to Kabat EU index) and the amino acid at position 213 as numbered according to Kabat EU index is substituted by glutamic acid (E);
(ii) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c); and
(iii) the first subunit of the Fc domain comprises amino acid substitutions S354C and T366W, and the second subunit of the Fc domain comprises amino acid substitutions Y349C, T366S, L368A and Y407V, and each subunit of the Fc domain further comprises the amino acid substitutions L234A, L235A and P329G in each case as numbered according to Kabat EU index.

36. The method of claim 8, wherein said bispecific antigen binding molecule comprises an amino acid sequence that is at least 95% identical to the sequence of SEQ ID NO: 123, a polypeptide comprising an amino acid sequence that is at least 95% identical to the sequence of SEQ ID NO: 125, a polypeptide comprising an amino acid sequence that is at least 95% identical to the sequence of SEQ ID NO: 139, and a polypeptide comprising an amino acid sequence that is at least 95% identical to the sequence of SEQ ID NO: 140.

37. The method of claim 1, wherein the antibody comprises a VH comprising the amino acid sequence of SEQ ID NO: 7, and a VL comprising the amino acid sequence of SEQ ID NO: 8.

38. The method of claim 8, wherein the first antigen binding moiety comprises a VH comprising the amino acid sequence of SEQ ID NO: 7, and a VL comprising the amino acid sequence of SEQ ID NO: 8.

39. The method of claim 10, wherein said antigen is CD3E.

40. The method of claim 12, wherein the second antigen binding moiety comprises
(i) a VH comprising the amino acid sequence of SEQ ID NO: 121, and a VL comprising the amino acid sequence of SEQ ID NO: 122; or
(ii) a VH comprising the amino acid sequence of SEQ ID NO: 136, and a VL comprising the amino acid sequence of SEQ ID NO: 137.

\* \* \* \* \*